(12) United States Patent
Cha et al.

(10) Patent No.: US 10,193,076 B2
(45) Date of Patent: Jan. 29, 2019

(54) AMINE COMPOUND AND ORGANIC LIGHT EMITTING ELEMENT COMPRISING SAME

(71) Applicant: LG Chem, Ltd., Seoul (KR)

(72) Inventors: Yongbum Cha, Daejeon (KR); Sung Kil Hong, Daejeon (KR); Jin Joo Kim, Daejeon (KR)

(73) Assignee: LG Chem, Ltd. (KR)

( * ) Notice: Subject to any disclaimer, the term of this patent is extended or adjusted under 35 U.S.C. 154(b) by 0 days.

(21) Appl. No.: 15/543,304

(22) PCT Filed: Oct. 12, 2016

(86) PCT No.: PCT/KR2016/011420
§ 371 (c)(1),
(2) Date: Jul. 13, 2017

(87) PCT Pub. No.: WO2017/073932
PCT Pub. Date: May 4, 2017

(65) Prior Publication Data
US 2017/0365788 A1      Dec. 21, 2017

(30) Foreign Application Priority Data

Oct. 26, 2015   (KR) .................. 10-2015-0149012
Oct. 10, 2016   (KR) .................. 10-2016-0130723

(51) Int. Cl.
*H01L 51/50*       (2006.01)
*H01L 51/00*       (2006.01)
(Continued)

(52) U.S. Cl.
CPC ........ *H01L 51/0061* (2013.01); *C07C 13/567* (2013.01); *C07C 211/54* (2013.01); *C07D 209/82* (2013.01); *C07D 209/86* (2013.01);
*C07D 403/10* (2013.01); *C07D 405/12* (2013.01); *C07D 409/12* (2013.01); *C09K 11/06* (2013.01); *H01L 51/00* (2013.01); *H01L 51/006* (2013.01); *H01L 51/0072* (2013.01);
(Continued)

(58) Field of Classification Search
None
See application file for complete search history.

(56) References Cited

U.S. PATENT DOCUMENTS

2003/0137239 A1*   7/2003   Matsuura ............ H01L 51/5016
                                                                        313/503
2004/0251816 A1    12/2004  Leo et al.
(Continued)

FOREIGN PATENT DOCUMENTS

EP    1623970 A1    2/2006
EP    2930168 A1    10/2015
(Continued)

OTHER PUBLICATIONS

Search Report from International Application No. PCT/KR2016/011420, dated Jan. 2, 2017.
(Continued)

*Primary Examiner* — Gregory D Clark
(74) *Attorney, Agent, or Firm* — Lerner, David, Littenberg, Krumholz & Mentlik, LLP

(57) ABSTRACT

The present specification provides an amine compound of Chemical Formula 1 and an organic light emitting device including the same.

20 Claims, 1 Drawing Sheet

(51) Int. Cl.
*C07D 209/86* (2006.01)
*C07D 405/12* (2006.01)
*C07D 409/12* (2006.01)
*C07C 211/54* (2006.01)
*C07D 403/10* (2006.01)
*C07D 209/82* (2006.01)
*C07C 13/567* (2006.01)
*C09K 11/06* (2006.01)

(52) U.S. Cl.
CPC .......... *H01L 51/0077* (2013.01); *H01L 51/50* (2013.01); *H01L 51/0052* (2013.01); *H01L 51/0054* (2013.01); *H01L 51/0073* (2013.01); *H01L 51/0074* (2013.01); *H01L 51/5012* (2013.01); *H01L 51/5016* (2013.01); *H01L 51/5056* (2013.01); *H01L 51/5088* (2013.01); *H01L 51/5096* (2013.01)

(56) References Cited

U.S. PATENT DOCUMENTS

| | | | |
|---|---|---|---|
| 2007/0018569 A1* | 1/2007 | Kawamura | C07C 211/61 313/504 |
| 2009/0167161 A1 | 7/2009 | Yabunouchi et al. | |
| 2015/0065730 A1 | 3/2015 | Montenegro et al. | |
| 2015/0179940 A1* | 6/2015 | Mujica-Fernaud | H01L 51/0052 252/519.21 |
| 2015/0303379 A1 | 10/2015 | Lee et al. | |
| 2015/0318484 A1 | 11/2015 | Buesing et al. | |
| 2015/0325795 A1 | 11/2015 | Lee et al. | |
| 2016/0190466 A1 | 6/2016 | Pfister et al. | |

FOREIGN PATENT DOCUMENTS

| | | | |
|---|---|---|---|
| JP | 2004339134 A | 12/2004 | |
| JP | 2010-114180 | * 5/2010 | ............. H01L 51/50 |
| JP | 2015513530 A | 5/2015 | |
| JP | 2015530364 A | 10/2015 | |
| KR | 20130135039 A | 12/2013 | |
| KR | 20140073412 A | 6/2014 | |
| KR | 20150010387 A | 1/2015 | |
| KR | 20150089427 A | 8/2015 | |
| WO | 2003012890 A2 | 2/2003 | |
| WO | 2009084268 A1 | 7/2009 | |
| WO | 2014079527 A1 | 5/2014 | |
| WO | 2015009102 A1 | 1/2015 | |
| WO | 2015022051 A1 | 2/2015 | |

OTHER PUBLICATIONS

Written Opinion of the International Searching Authority from PCT/KR2016/011420, dated Jan. 23, 2017.

* cited by examiner

[FIG. 1]
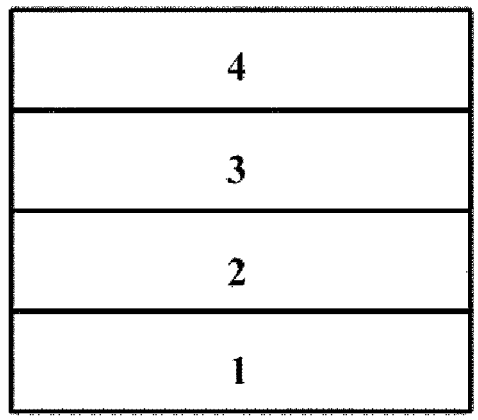
[FIG. 2]
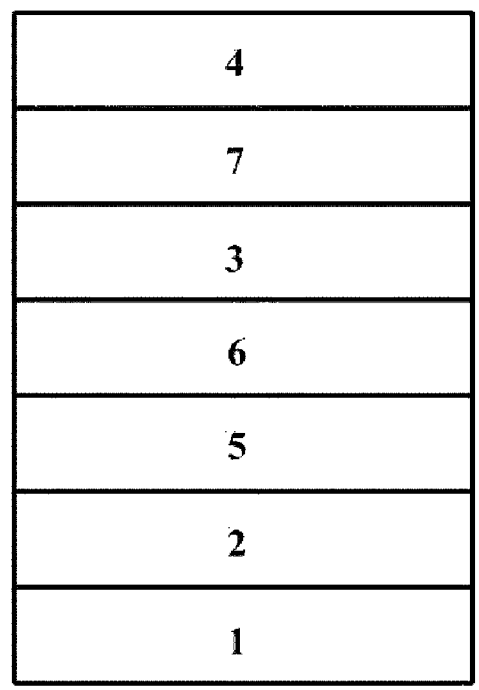

AMINE COMPOUND AND ORGANIC LIGHT EMITTING ELEMENT COMPRISING SAME

CROSS-REFERENCE TO RELATED APPLICATIONS

The present application is a national phase entry under 35 U.S.C. § 371 of International Application No. PCT/KR2016/011420 filed Oct. 12, 2016, published on May 4, 2017, which claims priority from Korean Patent Application No. 10-2015-0149012, filed Oct. 26, 2015, and Korean Patent Application No. 10-2016-0130723, filed Oct. 10, 2016, all of which are incorporated herein by reference.

TECHNICAL FIELD

The present specification relates to an amine compound and an organic light emitting device including the same.

BACKGROUND ART

An organic light emission phenomenon generally refers to a phenomenon converting electrical energy to light energy using an organic material. An organic light emitting device using an organic light emission phenomenon normally has a structure including an anode, a cathode, and an organic material layer therebetween. Herein, the organic material layer is often formed in a multilayer structure formed with different materials in order to increase efficiency and stability of the organic light emitting device, and for example, may be formed with a hole injection layer, a hole transfer layer, a light emitting layer, an electron transfer layer, an electron injection layer and the like. When a voltage is applied between the two electrodes in such an organic light emitting device structure, holes and electrons are injected to the organic material layer from the anode and the cathode, respectively, and when the injected holes and electrons meet, excitons are formed, and light emits when these excitons fall back to the ground state.

Development of new materials for such an organic light emitting device has been continuously required.

DISCLOSURE

Technical Problem

The present specification describes an amine compound and an organic light emitting device including the same.

Technical Solution

One embodiment of the present specification provides a compound represented by the following Chemical Formula 1:

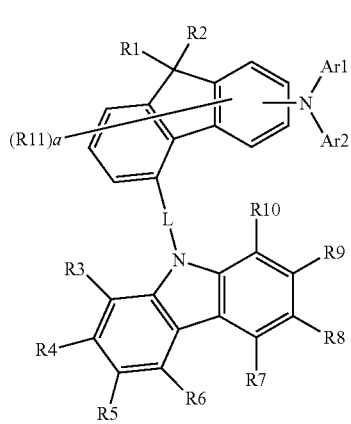

[Chemical Formula 1]

In Chemical Formula 1,

R1 and R2 are the same as or different from each other, and each independently a substituted or unsubstituted alkyl group; or a substituted or unsubstituted aryl group, Ar1 and Ar2 are the same as or different from each other, and each independently a substituted or unsubstituted aryl group; or a substituted or unsubstituted heterocyclic group, or bond to each other to form a substituted or unsubstituted ring, L is a direct bond, or a substituted or unsubstituted arylene group, R3 to R11 are the same as or different from each other, and each independently hydrogen; deuterium; a halogen group; a nitrile group; a nitro group; a hydroxyl group; a carbonyl group; an ester group; an imide group; a substituted or unsubstituted amine group; a substituted or unsubstituted silyl group; a substituted or unsubstituted boron group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted aralkyl group; a substituted or unsubstituted aralkenyl group; a substituted or unsubstituted alkylaryl group; a substituted or unsubstituted alkylamine group; a substituted or unsubstituted aralkylamine group; a substituted or unsubstituted heteroarylamine group; a substituted or unsubstituted arylamine group; a substituted or unsubstituted arylheteroarylamine group; a substituted or unsubstituted arylphosphine group; a substituted or unsubstituted phosphine oxide group; a substituted or unsubstituted aryl group; or a substituted or unsubstituted heterocyclic group, or may bond to an adjacent group to form a substituted or unsubstituted ring, and a is an integer of 0 to 6, and when a is an integer of 2 or greater, R11s are the same as or different from each other.

Another embodiment of the present specification provides an organic light emitting device including a first electrode; a second electrode provided opposite to the first electrode; and one or more organic material layers provided between the first electrode and the second electrode, wherein one or more layers of the organic material layers include the compound of Chemical Formula 1.

Advantageous Effects

Compounds described in the present specification can be used as a material of an organic material layer of an organic light emitting device. Compounds according to at least one embodiment are capable of enhancing efficiency, low driving voltage and/or enhancing lifespan properties in an organic light emitting device. Particularly, compounds described in the present specification can be used as a material of hole injection, hole transfer, hole injection and hole transfer, light emission, electron transfer or electron injection. In addition, compounds described in the present specification can be preferably used as a material of a light emitting layer, electron transfer or electron injection. More preferably, when using compounds described in the present specification as a material of hole injection, hole transfer and electron suppression layer, properties of low voltage, high efficiency and/or long lifespan are exhibited.

DESCRIPTION OF DRAWINGS

FIG. 1 illustrates an organic light emitting device formed with a substrate (1), an anode (2), a light emitting layer (3) and a cathode (4).

FIG. 2 illustrates an organic light emitting device formed with a substrate (1), an anode (2), a hole injection layer (5), a hole transfer layer (6), a light emitting layer (3), an electron transfer layer (7) and a cathode (4).

REFERENCE NUMERAL

1: Substrate
2: Anode
3: Light Emitting Layer
4: Cathode
5: Hole Injection Layer
6: Hole Transfer Layer
7: Electron Transfer Layer

[MODE FOR DISCLOSURE]

Hereinafter, the present specification will be described in more detail.

One embodiment of the present specification provides a compound represented by Chemical Formula 1.

Examples of the substituents are described below, however, the substituents are not limited thereto.

In the present specification, the term "substituted or unsubstituted" means being substituted with one or more substituents selected from the group consisting of deuterium; a halogen group; a nitrile group; a nitro group; a hydroxyl group; a carbonyl group; an ester group; an imide group; an amine group; a phosphine oxide group; an alkoxy group; an aryloxy group; an alkylthioxy group; an arylthioxy group; an alkylsulfoxy group; an arylsulfoxy group; a silyl group unsubstituted or substituted with an alkyl group; a boron group; an alkyl group; a cycloalkyl group; an alkenyl group; an aryl group; an aralkyl group; an aralkenyl group; an alkylaryl group; an alkylamine group; an aralkylamine group; a heteroarylamine group; an arylamine group; an arylphosphine group; and a heterocyclic group, or being unsubstituted, or being substituted with a substituent linking two or more substituents among the substituents illustrated above, or being unsubstituted. For example, "a substituent linking two or more substituents" may include a biphenyl group. In other words, a biphenyl group may be an aryl group, or interpreted as a substituent linking two phenyl groups.

In the present specification, the expression "substituted or unsubstituted" may mean being preferably substituted with one or more substituents selected from the group consisting of deuterium; a halogen group; a nitrile group; an alkyl group; a trimethylsilyl group; an aryl group; and a heterocyclic group, or being unsubstituted.

In the present specification, an "adjacent" group may mean a substituent substituting an atom directly linked to an atom substituted by the corresponding substituent, a substituent sterically most closely positioned to the corresponding substituent, or another substituent substituting an atom substituted by the corresponding substituent. For example, two substituents substituting ortho positions in a benzene ring, and two substituents substituting the same carbon in an aliphatic ring may be interpreted as groups "adjacent" to each other.

In the present specification, the number of carbon atoms of the carbonyl group is not particularly limited, but is preferably from 1 to 40. Specifically, compounds having structures as below may be included, however, the carbonyl group is not limited thereto.

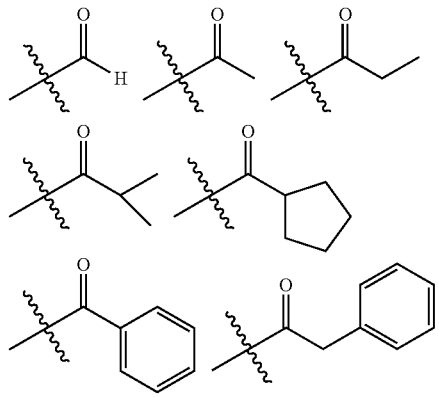

In the present specification, in the ester group, the oxygen of the ester group may be substituted with a linear, branched or cyclic alkyl group having 1 to 25 carbon atoms, or an aryl group having 6 to 25 carbon atoms. Specifically, compounds having the following structural formulae may be included, however, the ester group is not limited thereto.

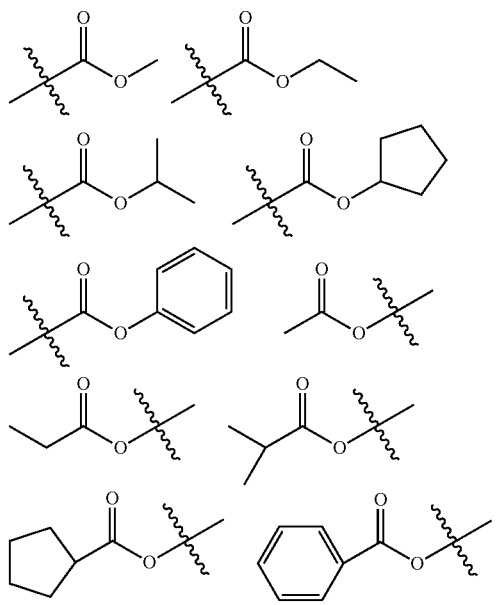

In the present specification, the number of carbon atoms of the imide group is not particularly limited, but is preferably from 1 to 25. Specifically, compounds having structures as below may be included, however, the imide group is not limited thereto.

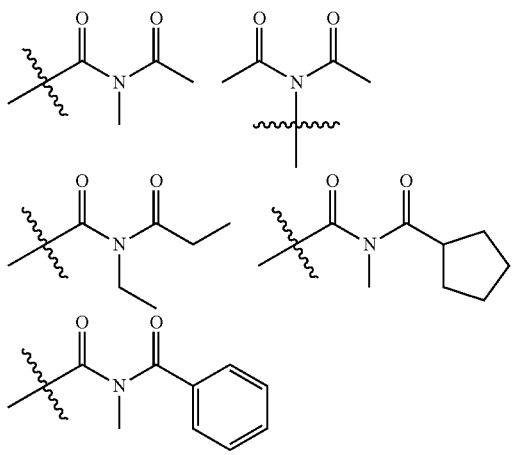

In the present specification, the silyl group may be represented by the chemical formula of —SiRR'R", and R, R' and R" may each be hydrogen; a substituted or unsubstituted alkyl group; or a substituted or unsubstituted aryl group. Specific examples of the silyl group may include a trimethylsilyl group, a triethylsilyl group, a t-butyldimethylsilyl group, a vinyldimethylsilyl group, a propyldimethylsilyl group, a triphenylsilyl group, a diphenylsilyl group, a phenylsilyl group and the like, but are not limited thereto.

In the present specification, the boron group may be represented by the chemical formula of —BRR', and R and R' may each be hydrogen; a substituted or unsubstituted alkyl group; or a substituted or unsubstituted aryl group. Specific examples of the boron group may include a trimethylboron group, a triethylboron group, a t-butyldimethylboron group, a triphenylboron group, a phenylboron group and the like, but are not limited thereto.

In the present specification, examples of the halogen group may include fluorine, chlorine, bromine or iodine.

In the present specification, the alkyl group may be linear or branched, and the number of carbon atoms is not particularly limited, but is preferably from 1 to 40. According to one embodiment, the number of carbon atoms of the alkyl group is from 1 to 20. According to another embodiment, the number of carbon atoms of the alkyl group is from 1 to 10. According to still another embodiment, the number of carbon atoms of the alkyl group is from 1 to 6. Specific examples of the alkyl group may include methyl, ethyl, propyl, n-propyl, isopropyl, butyl, n-butyl, isobutyl, tert-butyl, sec-butyl, 1-methylbutyl, 1-ethylbutyl, pentyl, n-pentyl, isopentyl, neopentyl, tert-pentyl, hexyl, n-hexyl, 1-methylpentyl, 2-methylpentyl, 4-methyl-2-pentyl, 3,3-dimethylbutyl, 2-ethylbutyl, heptyl, n-heptyl, 1-methylhexyl, cyclopentylmethyl, cyclohexylmethyl, octyl, n-octyl, tert-octyl, 1-methylheptyl, 2-ethylhexyl, 2-propylpentyl, n-nonyl, 2,2-dimethylheptyl, 1-ethylpropyl, 1,1-dimethylpropyl, isohexyl, 4-methylhexyl, 5-methylhexyl and the like, but are not limited thereto.

In the present specification, the alkenyl group may be linear or branched, and although not particularly limited thereto, the number of carbon atoms is preferably from 2 to 40. According to one embodiment, the number of carbon atoms of the alkenyl group is from 2 to 20. According to another embodiment, the number of carbon atoms of the alkenyl group is from 2 to 10. According to still another embodiment, the number of carbon atoms of the alkenyl group is from 2 to 6. Specific examples thereof may include vinyl, 1-propenyl, isopropenyl, 1-butenyl, 2-butenyl, 3-butenyl, 1-pentenyl, 2-pentenyl, 3-pentenyl, 3-methyl-1-butenyl, 1,3-butadienyl, allyl, 1-phenylvinyl-1-yl, 2-phenylvinyl-1-yl, 2,2-diphenylvinyl-1-yl, 2-phenyl-2-(naphthyl-1-yl)vinyl-1-yl, 2,2-bis(diphenyl-1-yl)vinyl-1-yl, a stilbenyl group, a styrenyl group and the like, but are not limited thereto.

In the present specification, the cycloalkyl group is not particularly limited, but preferably has 3 to 60 carbon atoms, and according to one embodiment, the number of carbon atoms of the cycloalkyl group is from 3 to 30. According to another embodiment, the number of carbon atoms of the cycloalkyl group is from 3 to 20. According to still another embodiment, the number of carbon atoms of the cycloalkyl group is from 3 to 6. Specific examples thereof may include cyclopropyl, cyclobutyl, cyclopentyl, 3-methylcyclopentyl, 2,3-dimethylcyclopentyl, cyclohexyl, 3-methylcyclohexyl, 4-methylcyclohexyl, 2,3-dimethylcyclohexyl, 3,4,5-trimethylcyclohexyl, 4-tert-butylcyclohexyl, cycloheptyl, cyclooctyl and the like, but are not limited thereto.

In the present specification, the alkoxy group is not particularly limited, but preferably has 1 to 40 carbon atoms. According to one embodiment, the number of carbon atoms of the alkoxy group is from 1 to 10. According to another embodiment, the number of carbon atoms of the alkoxy group is from 1 to 6. Specific examples of the alkoxy group may include a methoxy group, an ethoxy group, a propoxy group, an isobutyloxy group, a sec-butyloxy group, a pentyloxy group, an iso-amyloxy group, a hexyloxy group and the like, but are not limited thereto.

In the present specification, the number of carbon atoms of the amine group is not particularly limited, but is preferably from 1 to 30. Specific examples of the amine group may include a methylamine group, a dimethylamine group, an ethylamine group, a diethylamine group, a phenylamine group, a naphthylamine group, a biphenylamine group, an anthracenylamine group, a 9-methylanthracenylamine group, a diphenylamine group, a phenylnaphthylamine group, a ditolylamine group, a phenyltolylamine group, a triphenylamine group and the like, but are not limited thereto.

In the present specification, examples of the arylamine group include a substituted or unsubstituted monoarylamine group, a substituted or unsubstituted diarylamine group, or a substituted or unsubstituted triarylamine group. The aryl group in the arylamine group may be a monocyclic aryl group or a multicyclic aryl group. The arylamine group including two or more aryl groups may include monocyclic aryl groups, multicyclic aryl groups, or both monocyclic aryl groups and multicyclic aryl groups. Specific examples of the arylamine group may include phenylamine, naphthylamine, biphenylamine, anthracenylamine, 3-methylphenylamine, 4-methylnaphthylamine, 2-methylbiphenylamine, 9-methylanthracenylamine, a diphenylamine group, a phenylnaphthylamine group, a ditolylamine group, a phenyltolylamine group, carbazole, a triphenylamine group and the like, but are not limited thereto.

In the present specification, examples of the heteroarylamine group include a substituted or unsubstituted monoheteroarylamine group, a substituted or unsubstituted diheteroarylamine group, or a substituted or unsubstituted triheteroarylamine group. The heteroaryl group in the heteroarylamine group may be a monocyclic heterocyclic group or a multicyclic heterocyclic group. The heteroarylamine group including two or more heterocyclic groups may include monocyclic heterocyclic groups, multicyclic heterocyclic groups, or both monocyclic heterocyclic groups and multicyclic heterocyclic groups.

In the present specification, the arylheteroarylamine group means an amine group substituted with an aryl group and a heterocyclic group.

In the present specification, examples of the arylphosphine group include a substituted or unsubstituted monoarylphosphine group, a substituted or unsubstituted diarylphosphine group, or a substituted or unsubstituted triarylphosphine group. The aryl group in the arylphosphine group may be a monocyclic aryl group or a multicyclic aryl group. The arylphosphine group including two or more aryl groups may include monocyclic aryl groups, multicyclic aryl groups, or both monocyclic aryl groups and multicyclic aryl groups.

In the present specification, the aryl group is not particularly limited, but preferably has 6 to 60 carbon atoms, and may be a monocyclic aryl group or a multicyclic aryl group. According to one embodiment, the number of carbon atoms of the aryl group is from 6 to 30. According to one embodiment, the number of carbon atoms of the aryl group is from 6 to 20. Examples of the monocyclic aryl group may include a phenyl group, a biphenyl group, a terphenyl group and the like, but are not limited thereto. Examples of the multicyclic aryl group may include a naphthyl group, an anthracenyl group, a phenanthryl group, a pyrenyl group, a perylenyl group, a chrysenyl group, a fluorenyl group, a triphenylene group and the like, but are not limited thereto.

In the present specification, the fluorenyl group may be substituted, and two of the substituents may bond to each other to form a spiro structure.

When the fluorenyl group is substituted,

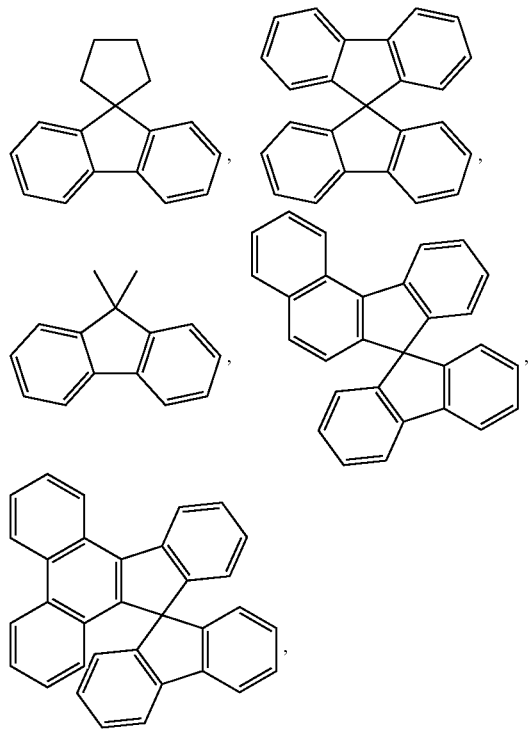

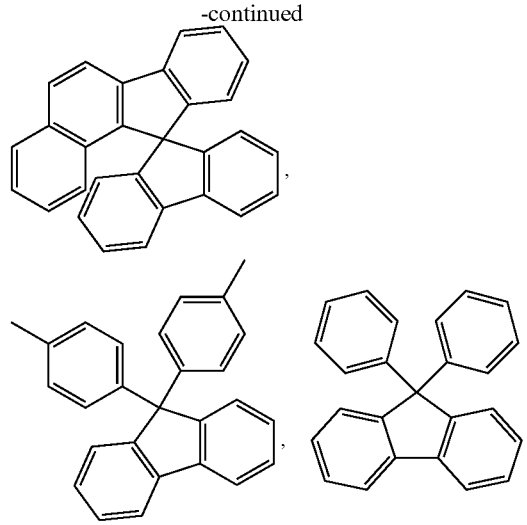

and the like may be included. However, the structure is not limited thereto.

In the present specification, the heterocyclic group is a heterocyclic group including one or more of N, O, S, Si and Se as a heteroatom, and although not particularly limited thereto, the number of carbon atoms is preferably from 2 to 60. Examples of the heterocyclic group may include a thiophene group, a furan group, a pyrrole group, an imidazole group, a triazole group, an oxazole group, an oxadiazole group, a triazole group, a pyridyl group, a bipyridyl group, a pyrimidyl group, a triazine group, a triazole group, an acridyl group, a pyridazine group, a pyrazinyl group, a quinolinyl group, a quinazoline group, a quinoxalinyl group, a phthalazinyl group, a pyridopyrimidinyl group, a pyridopyrazinyl group, a pyrazinopyrazinyl group, an isoquinoline group, an indole group, a carbazole group, a benzoxazole group, a benzimidazole group, a benzothiazole group, a benzocarbazole group, a benzothiophene group, a dibenzothiophene group, a benzofuranyl group, a phenanthroline group, a thiazolyl group, an isoxazolyl group, a thiadiazolyl group, a benzothiazolyl group, a phenoxazinyl group, a phenothiazinyl group, a dibenzofuranyl group and the like, but are not limited thereto. The heterocyclic group includes an aliphatic heterocyclic group and an aromatic heterocyclic group.

In the present specification, the descriptions on the heterocyclic group provided above may be used on the heteroaryl group except that the heteroaryl group is an aromatic group.

In the present specification, the descriptions on the aryl group provided above may be used on the aryl group in the aryloxy group, the arylthioxy group, the arylsulfoxy group, the arylphosphine group, the aralkyl group, the aralkylamine group, the aralkenyl group, the alkylaryl group, the arylamine group and the arylheteroarylamine group.

In the present specification, the descriptions on the alkyl group provided above may be used on the alkyl group in the alkylthioxy group, the alkylsulfoxy group, the aralkyl group, the aralkylamine group, the alkylaryl group and the alkylamine group.

In the present specification, the descriptions on the heterocyclic group provided above may be used on the heteroayl group in the heteroaryl group, the heteroarylamine group and the arylheteroarylamine group.

In the present specification, the descriptions on the alkenyl group provided above may be used on the alkenyl group in the aralkenyl group.

In the present specification, the descriptions on the aryl group provided above may be used on the arylene group except that the arylene group is divalent.

In the present specification, the descriptions on the heterocyclic group provided above may be used on the heteroarylene group except that the heteroarylene group is divalent.

According to one embodiment of the present specification, L is a direct bond, or a phenylene group, a biphenylylene group, a terphenylene group, a quaterphenylene group, a naphthylene group, a fluorenylene group unsubstituted or substituted with an alkyl group or an aryl group, a phenanthrenylene group and the like. L may be represented by the following structural formulae.

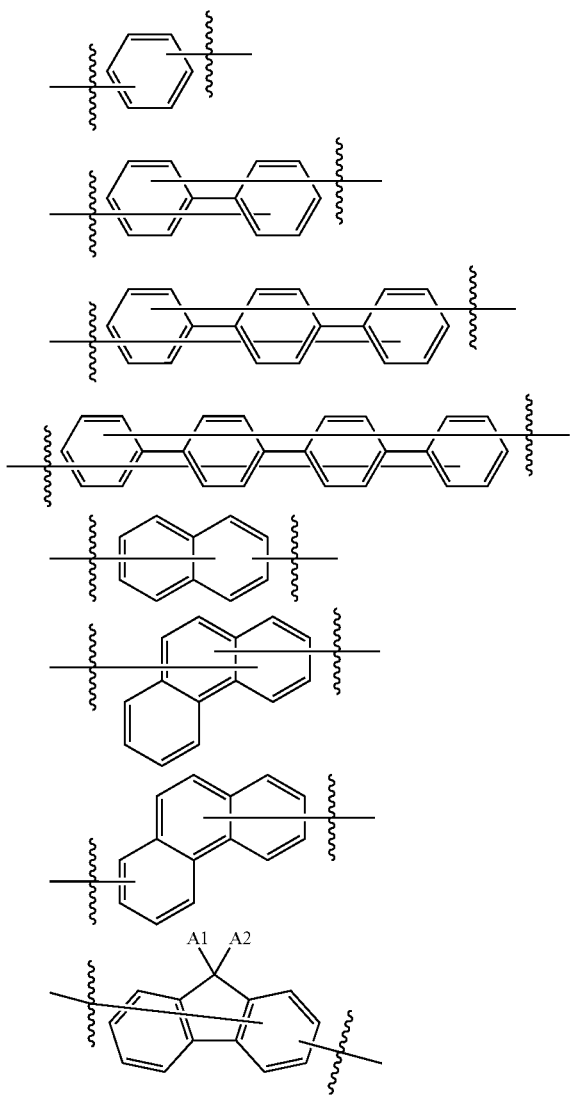

In the structural formulae,

A1 and A2 are the same as or different from each other, and each independently hydrogen; a substituted or unsubstituted alkyl group; or a substituted or unsubstituted aryl group.

According to one embodiment of the present specification, L is a direct bond or a phenylene group.

According to one embodiment of the present specification, Chemical Formula 1 may be represented by the following Chemical Formula 2.

[Chemical Formula 2]

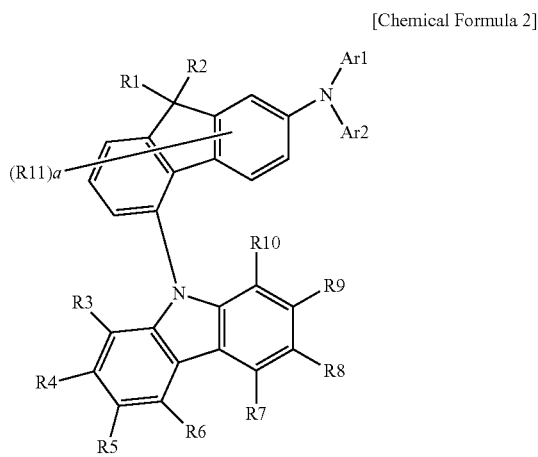

In Chemical Formula 2, definitions of substituents are the same as in Chemical Formula 1.

According to one embodiment of the present specification, Chemical Formula 1 may be represented by the following Chemical Formula 3.

[Chemical Formula 3]

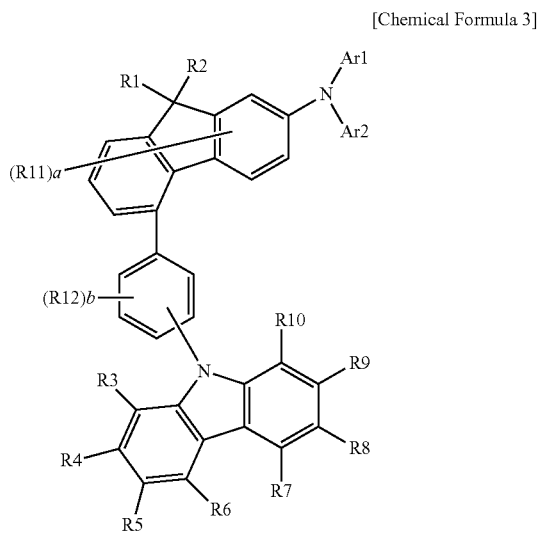

In Chemical Formula 3, definitions of R1 to R11, a, Ar1 and Ar2 are the same as in Chemical Formula 1, R12 may be the same as or different from R11, has the same definition as R11, b is an integer of 0 to 4, and when b is an integer of 2 or greater, R12s are the same as or different from each other.

According to one embodiment of the present specification, Chemical Formula 3 may be represented by the following Chemical Formula 4.

[Chemical Formula 4]

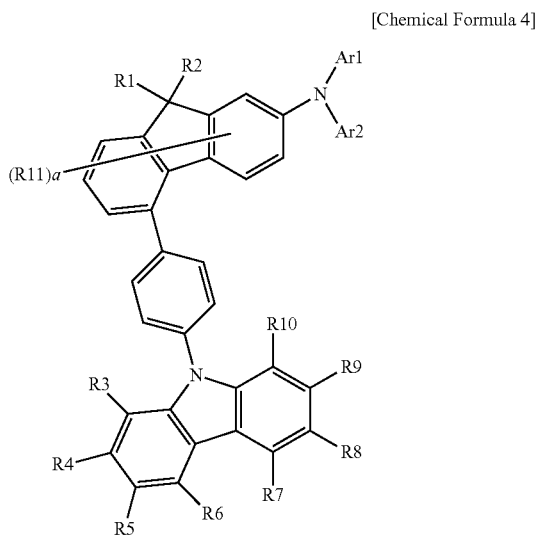

In Chemical Formula 4, definitions of substituents are the same as in Chemical Formula 1.

According to one embodiment of the present specification, Ar1 and Ar2 are the same as or different from each other, and each independently a substituted or unsubstituted phenyl group; a substituted or unsubstituted biphenyl group; a substituted or unsubstituted terphenyl group; a substituted or unsubstituted quaterphenyl group; a substituted or unsubstituted naphthyl group; a substituted or unsubstituted fluorenyl group; a substituted or unsubstituted phenanthrenyl group; a substituted or unsubstituted carbazole group; a substituted or unsubstituted benzocarbazole group; a substituted or unsubstituted dibenzofuran group; or a substituted or unsubstituted dibenzothiophene group.

According to one embodiment of the present specification, Ar1 and Ar2 are the same as or different from each other, and each independently a phenyl group unsubstituted or substituted with deuterium, a halogen group, a nitrile group, a silyl group, an alkyl group, a naphthyl group, a dialkylfluorenyl group, a phenanthrenyl group, a carbazole group or a benzocarbazole group; a biphenyl group; a terphenyl group; a quaterphenyl group; a naphthyl group; a fluorenyl group unsubstituted or substituted with an alkyl group or an aryl group; a phenanthrenyl group; a carbazole group unsubstituted or substituted with an aryl group; a dibenzofuran group unsubstituted or substituted with an aryl group; or a dibenzothiophene group unsubstituted or substituted with an aryl group.

According to one embodiment of the present specification, Ar1 and Ar2 are the same as or different from each other, and each independently a phenyl group unsubstituted or substituted with deuterium, a naphthyl group, a dialkylfluorenyl group or a phenanthrenyl group; a biphenyl group; a terphenyl group; a quaterphenyl group; a naphthyl group; a fluorenyl group unsubstituted or substituted with an alkyl group or an aryl group; a phenanthrenyl group; a carbazole group unsubstituted or substituted with an aryl group; a dibenzofuran group; or a dibenzothiophene group.

According to one embodiment of the present specification, Ar1 and Ar2 are the same as or different from each other, and each independently a phenyl group unsubstituted or substituted with deuterium, a naphthyl group, a dimethylfluorenyl group or a phenanthrenyl group; a biphenyl group; a terphenyl group; a quaterphenyl group; a naphthyl group; a fluorenyl group unsubstituted or substituted with a methyl group or a phenyl group; a phenanthrenyl group; a carbazole group unsubstituted or substituted with a phenyl group or a biphenyl group; a dibenzofuran group; or a dibenzothiophene group.

According to one embodiment of the present specification, Ar1 and Ar2 are the same as or different from each other, and may be each independently selected from among the following structural formulae, but are not limited thereto.

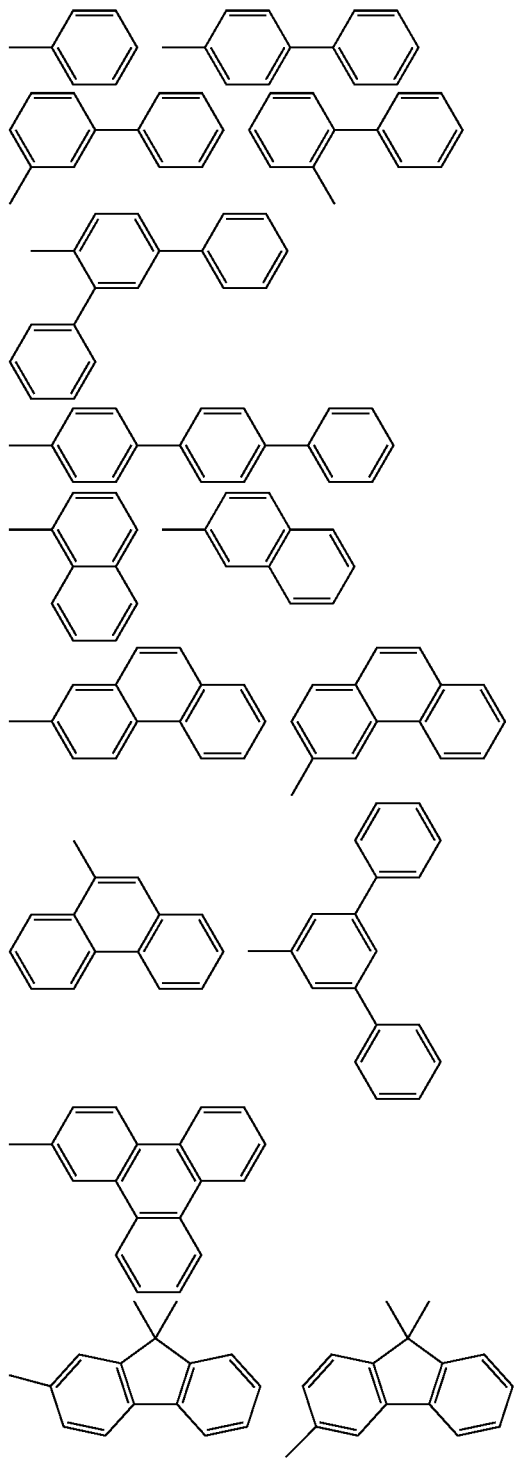

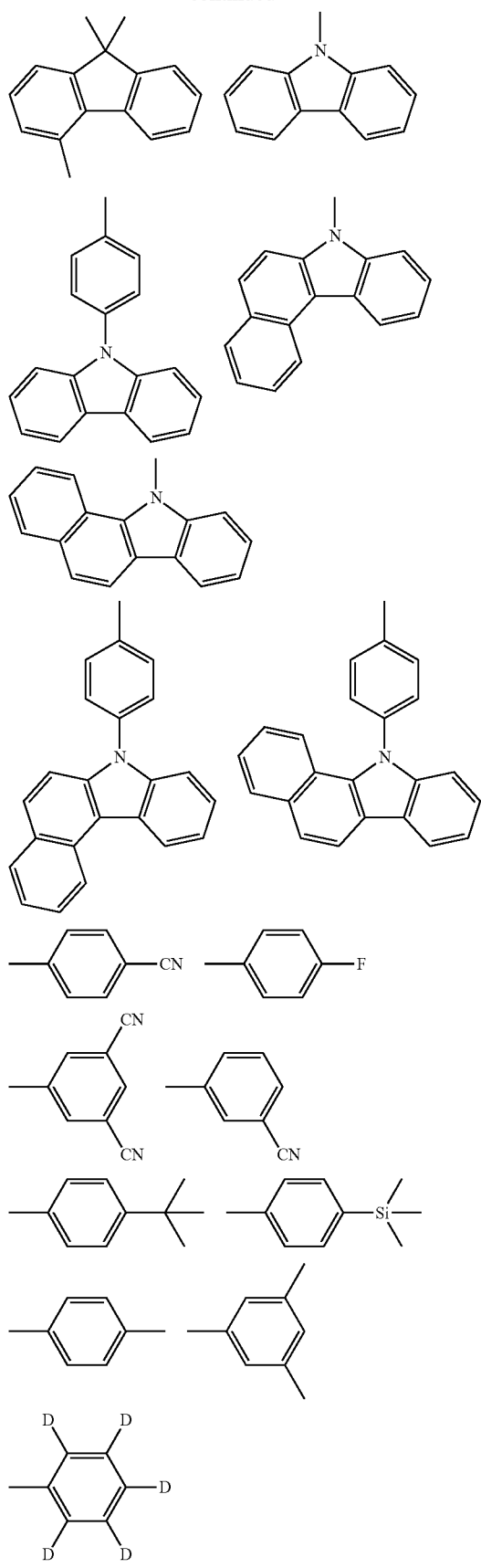
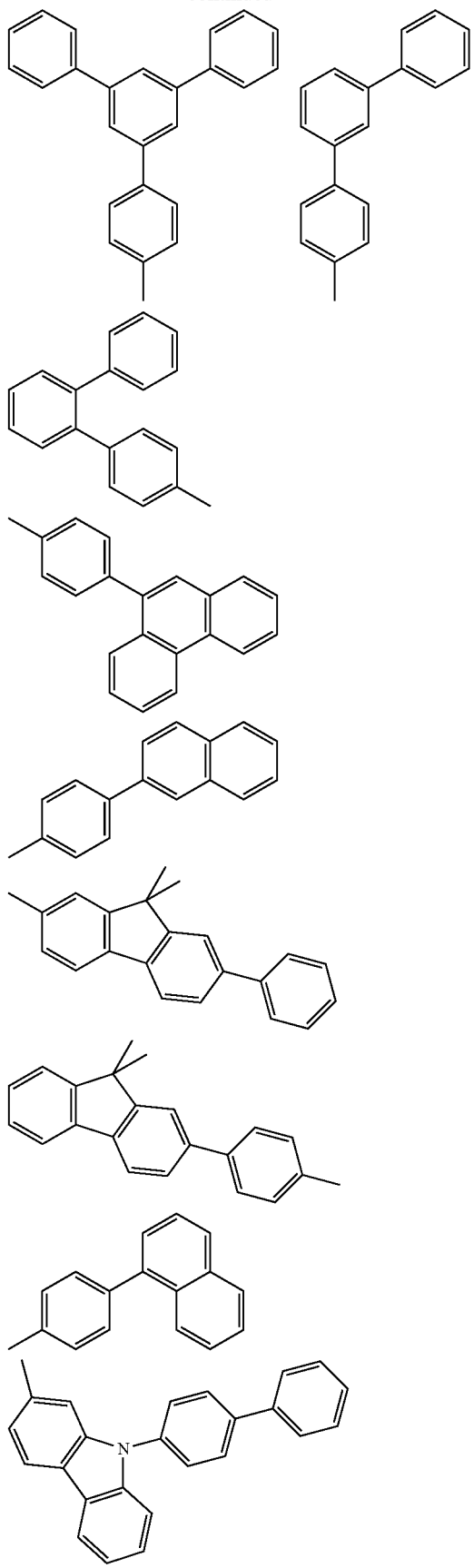

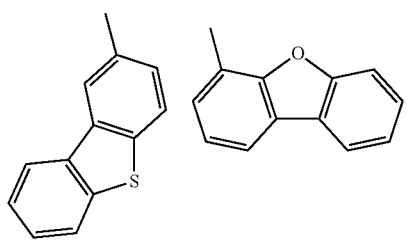
According to one embodiment of the present specification, Ar1 and Ar2 are the same as or different from each other, and may be each independently selected from among the following structural formulae, but are not limited thereto.
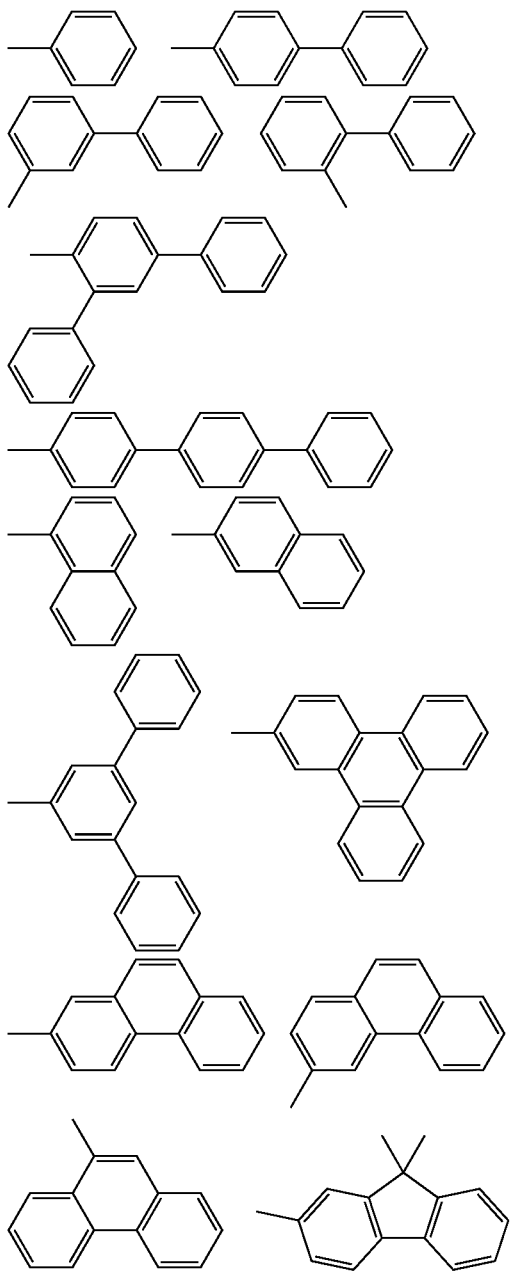
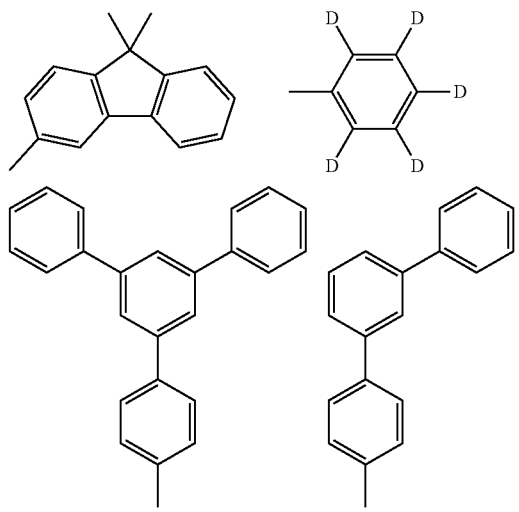
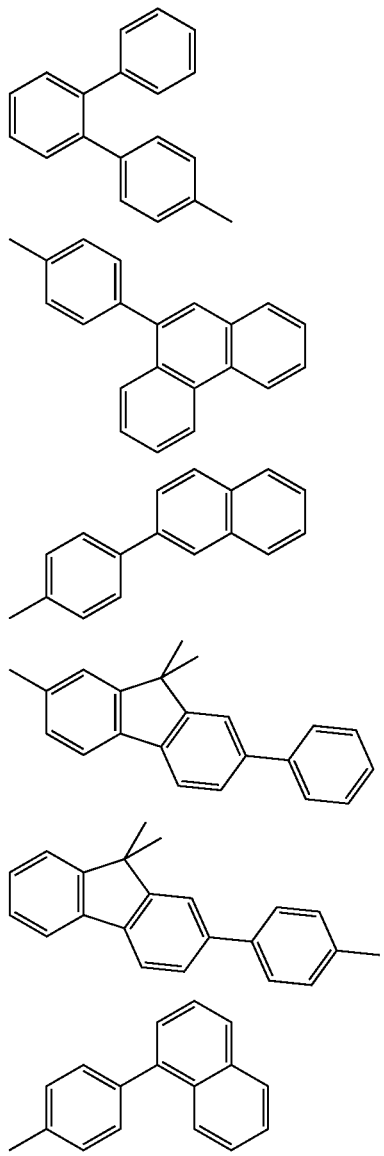

-continued

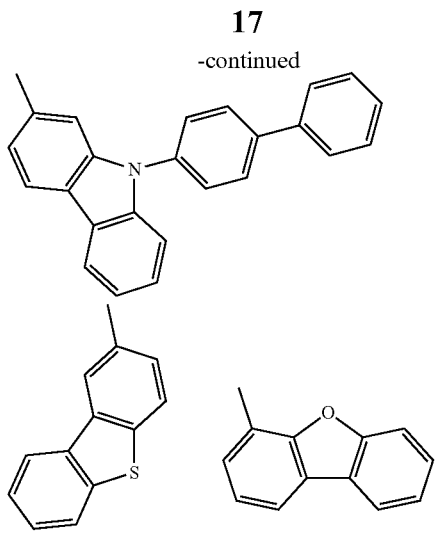

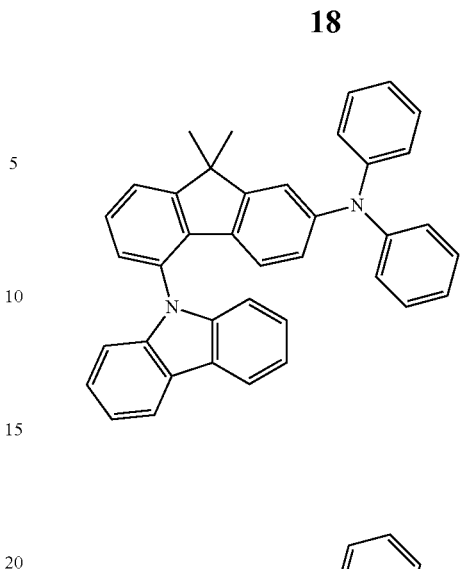

According to one embodiment of the present specification, Ar1 and Ar2 are the same as or different from each other, each independently a substituted or unsubstituted aryl group, and bond to each other.

According to one embodiment of the present specification, Ar1 and Ar2 are the same as or different from each other, each independently a substituted or unsubstituted phenyl group; a substituted or unsubstituted biphenyl group; or a substituted or unsubstituted naphthyl group, and bond to each other to form a substituted or unsubstituted carbazole structure; a substituted or unsubstituted benzocarbazole structure; or a substituted or unsubstituted dibenzocarbazole structure.

According to one embodiment of the present specification, Ar1 and Ar2 are the same as or different from each other, each independently a phenyl group; a biphenyl group; or a naphthyl group, and bond to each other to form a carbazole structure; a benzocarbazole structure; or a benzocarbazole structure.

According to one embodiment of the present specification, R1 and R2 are the same as or different from each other, and each independently an alkyl group; an aryl group; or an aryl group substituted with an alkyl group.

According to one embodiment of the present specification, R1 and R2 are the same as or different from each other, and each independently a methyl group; a phenyl group; or a phenyl group substituted with a methyl group.

According to one embodiment of the present disclosure, R3 to R10 are each hydrogen.

According to one embodiment of the present disclosure, R3 and R4 bond to each other to form a substituted or unsubstituted benzene ring.

According to one embodiment of the present disclosure, R3 and R4 bond to each other to form a benzene ring, and R5 to R10 are hydrogen.

According to one embodiment of the present disclosure, R5 and R6 bond to each other to form a substituted or unsubstituted a benzene ring.

According to one embodiment of the present disclosure, R5 and R6 bond to each other to form a benzene ring, and R3, R4, R7 to R10 are each hydrogen.

According to one embodiment of the present disclosure, the compound of Chemical Formula 1 may be any one selected from among the following compounds.

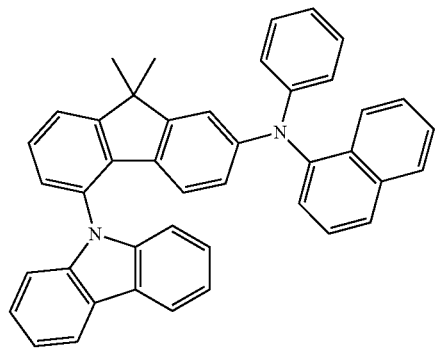

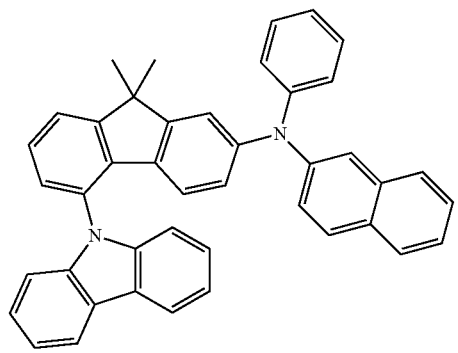

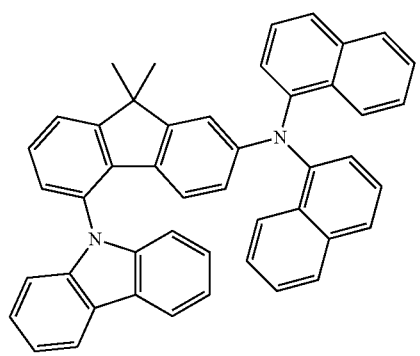

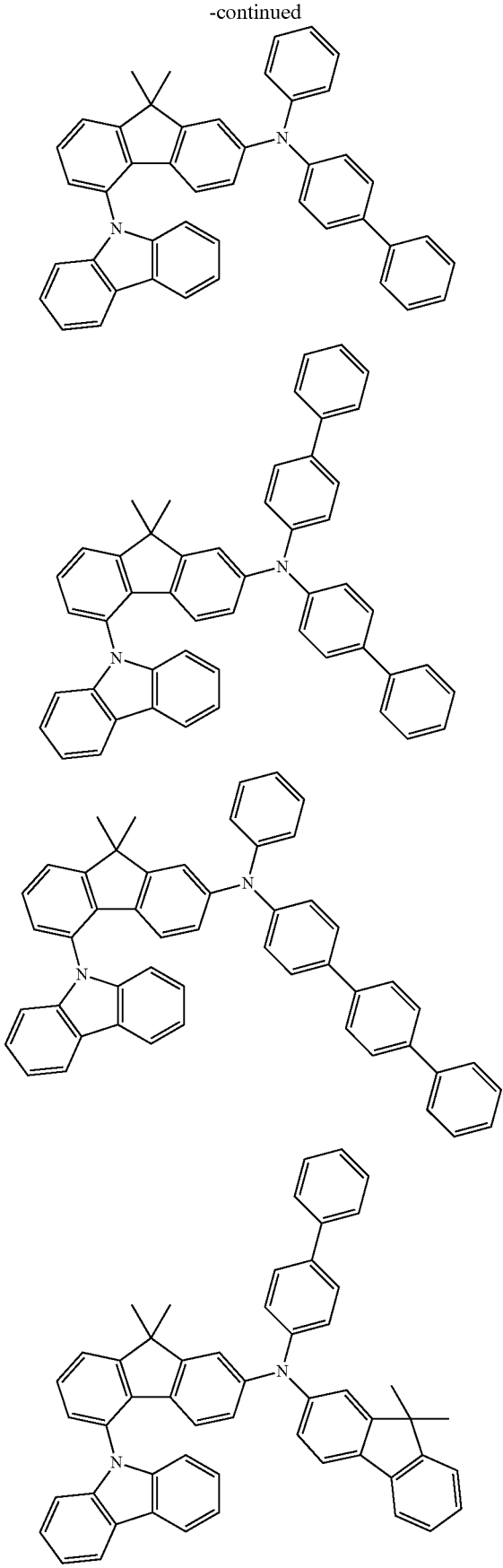
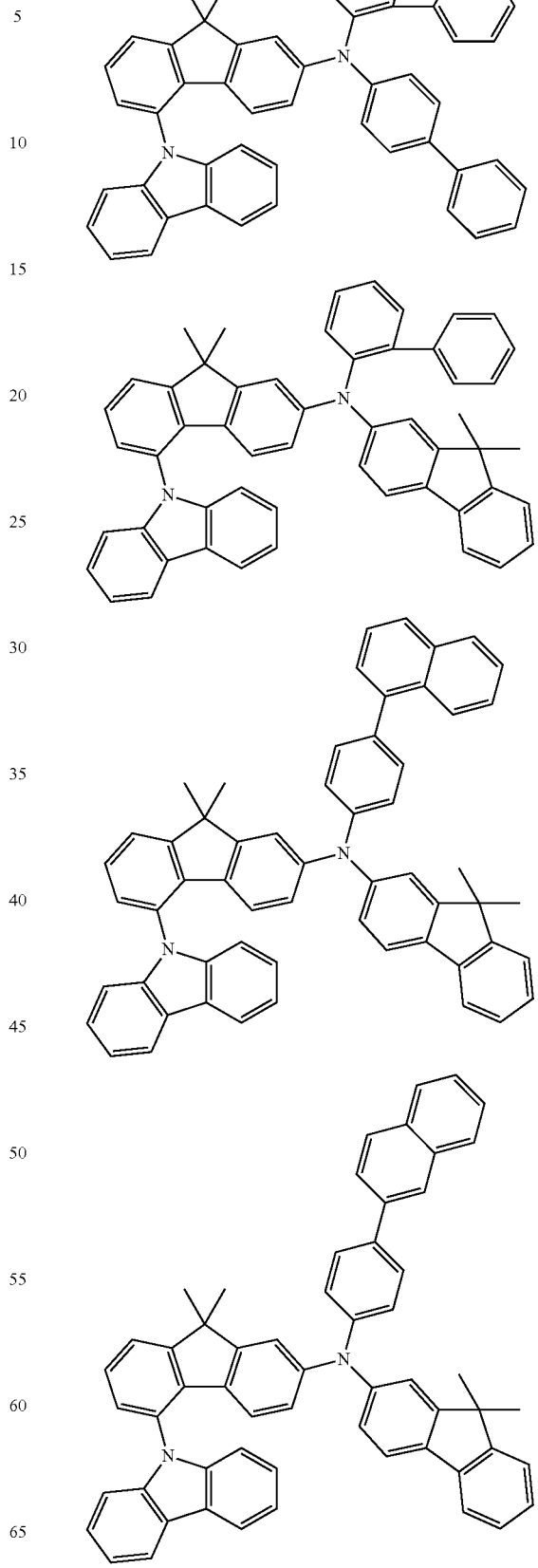

-continued
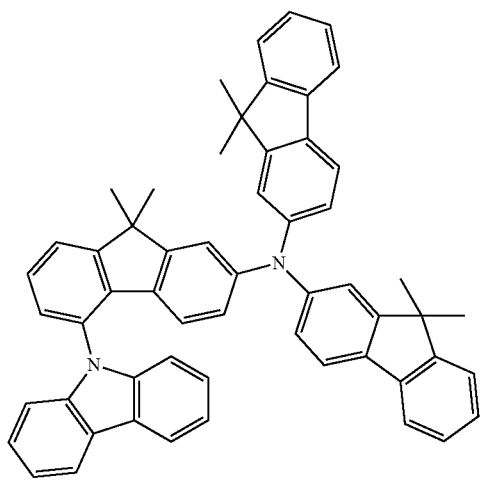
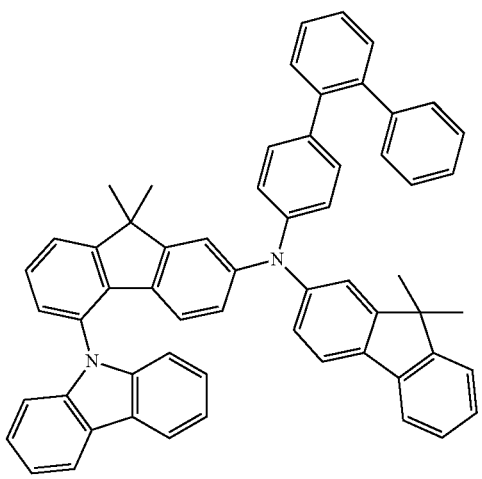
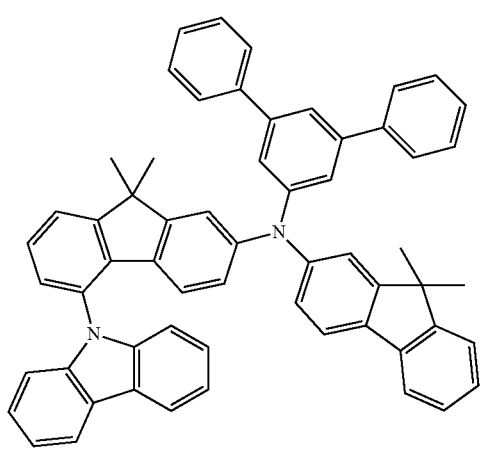
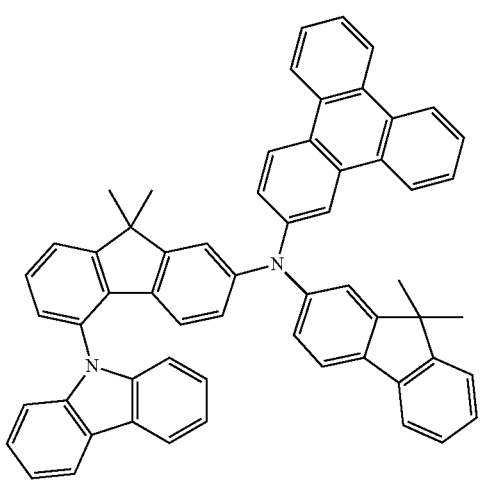
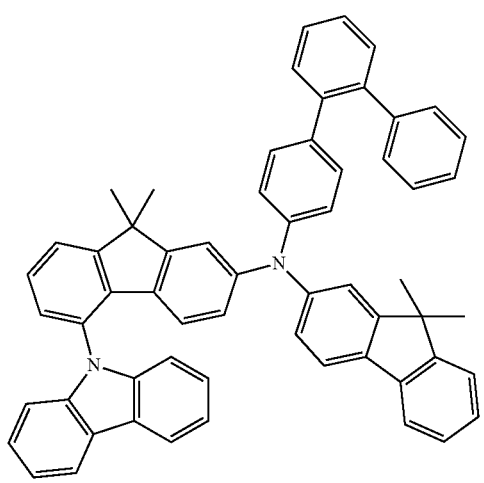
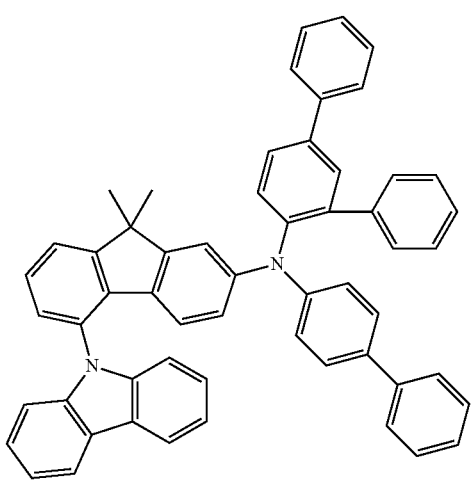

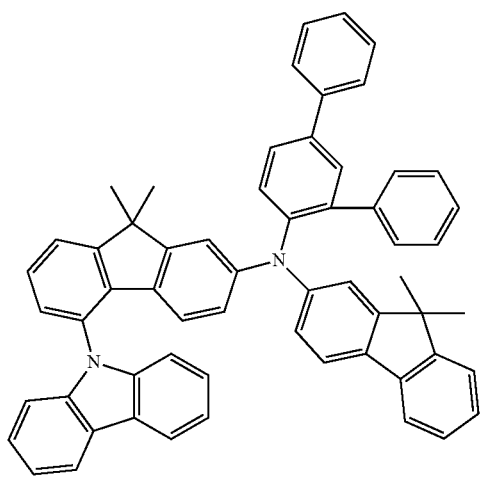
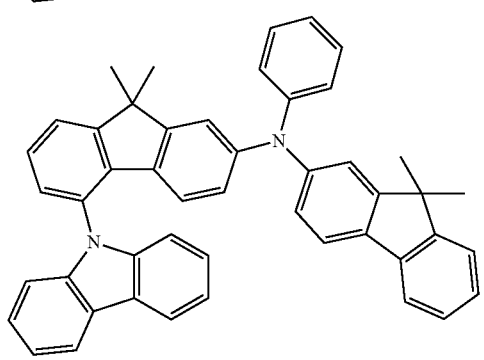
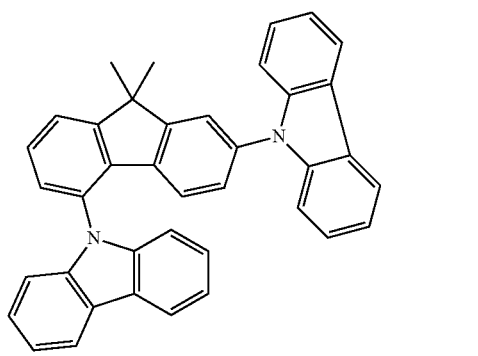
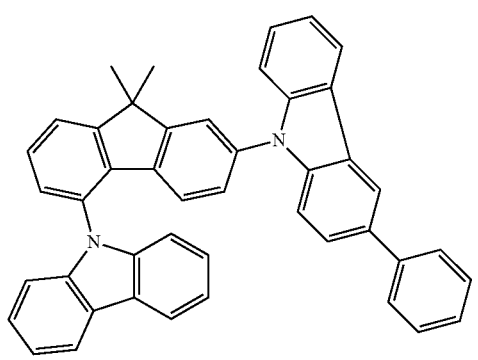
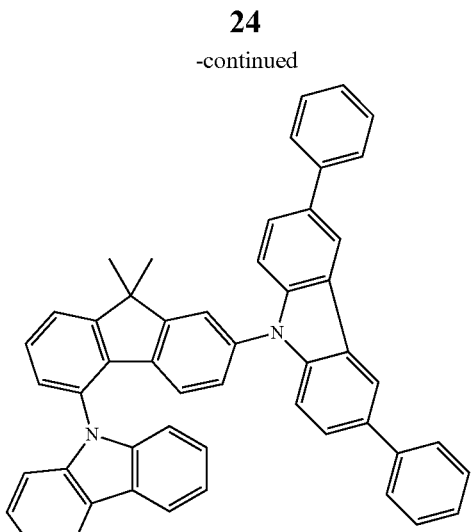
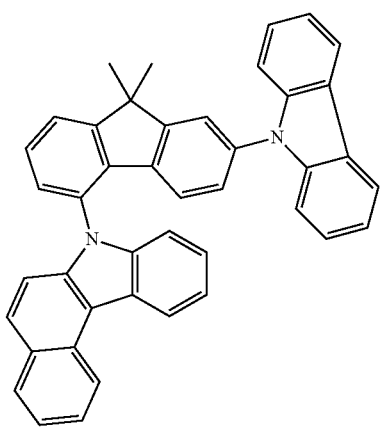
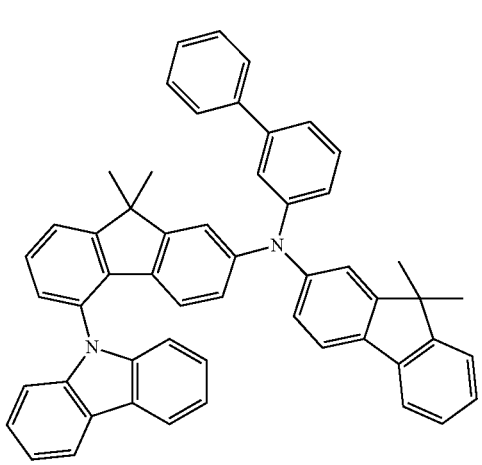

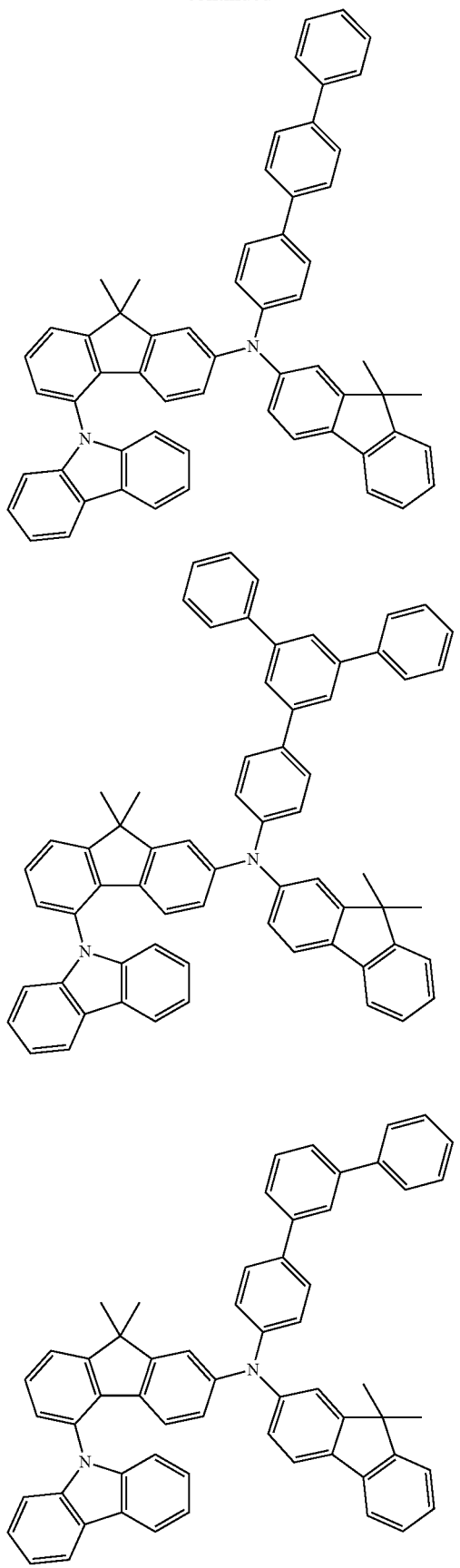
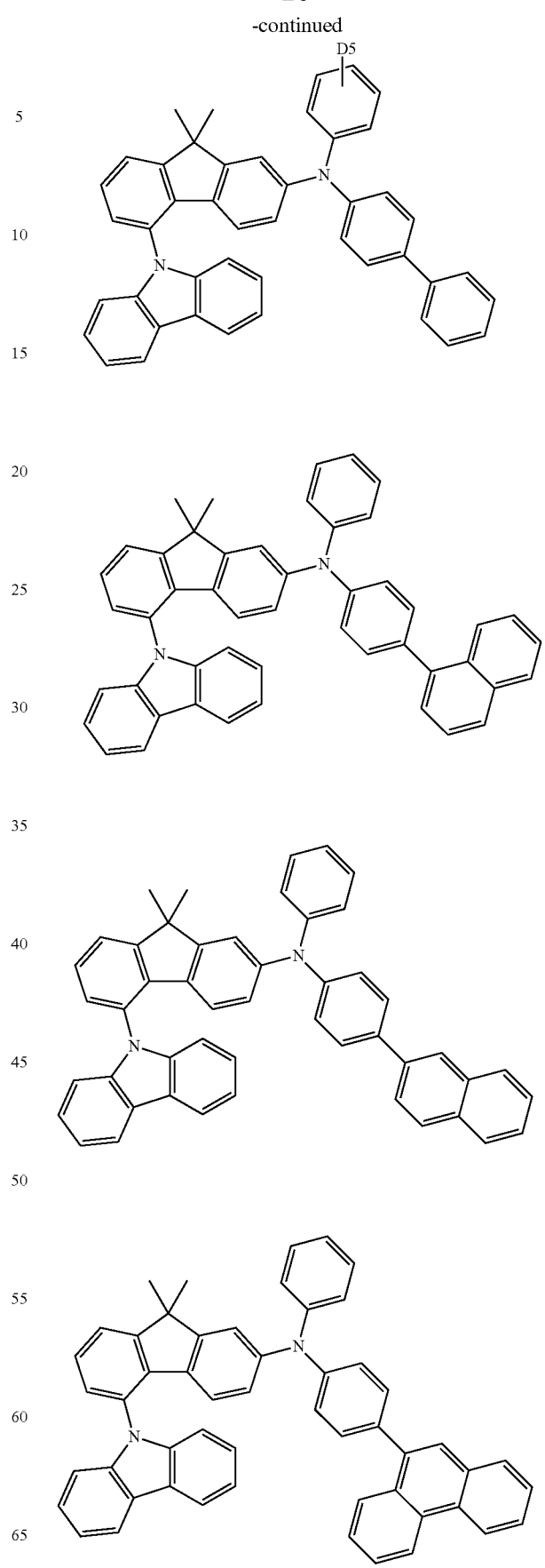

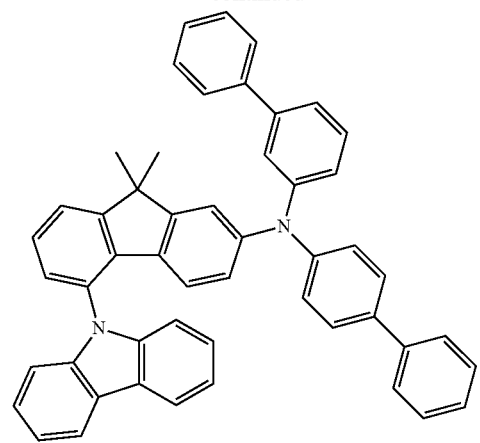
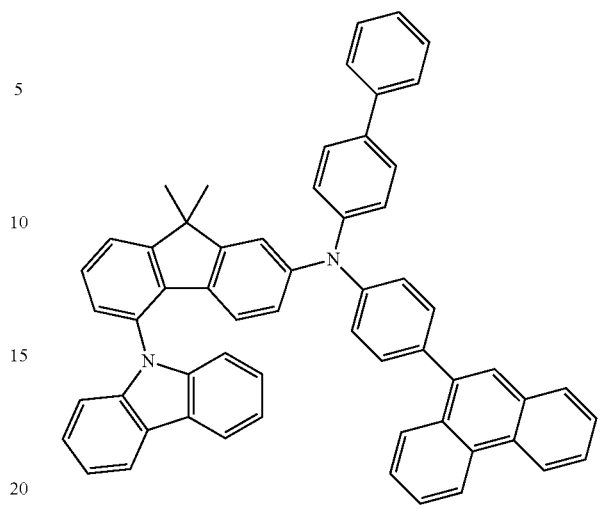
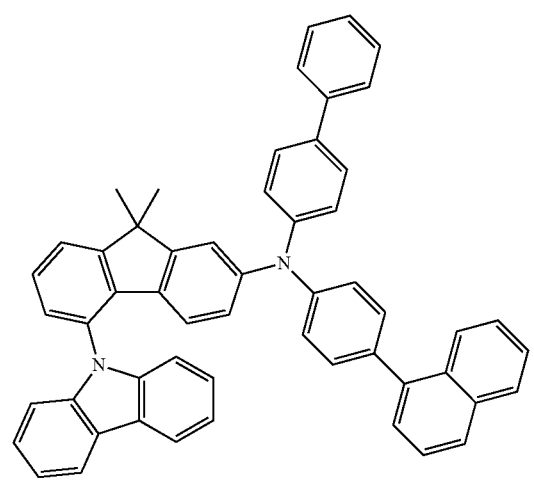
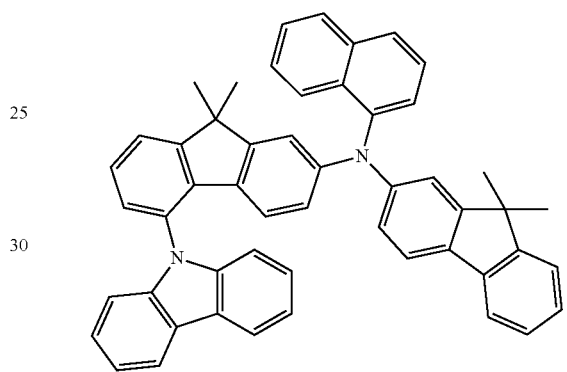
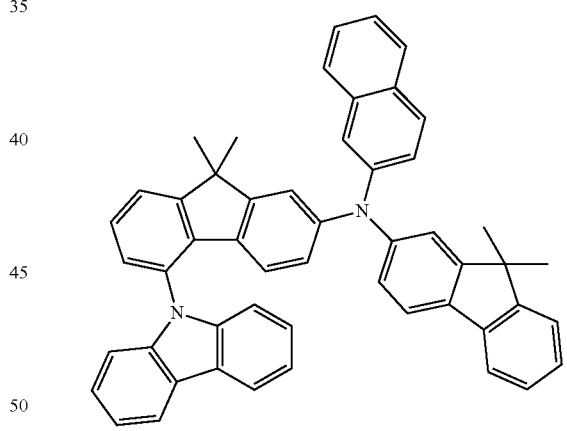
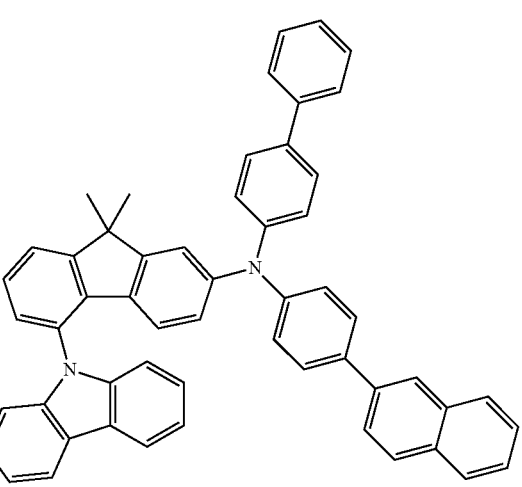
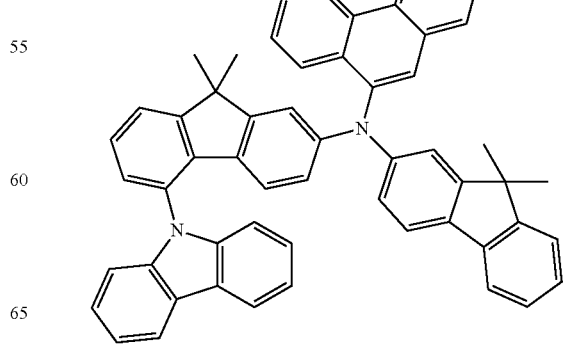

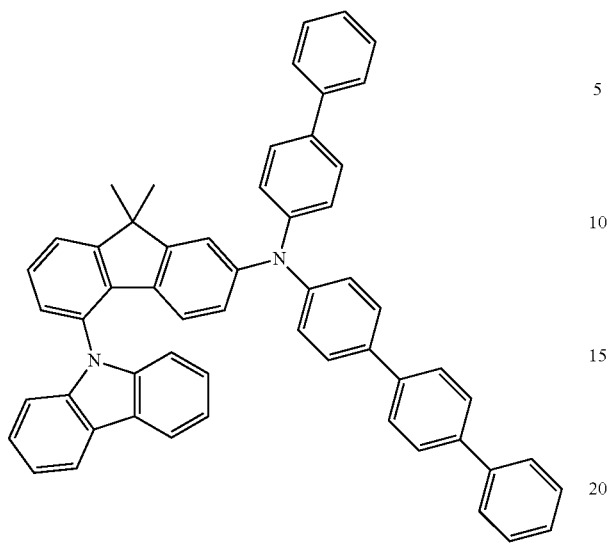
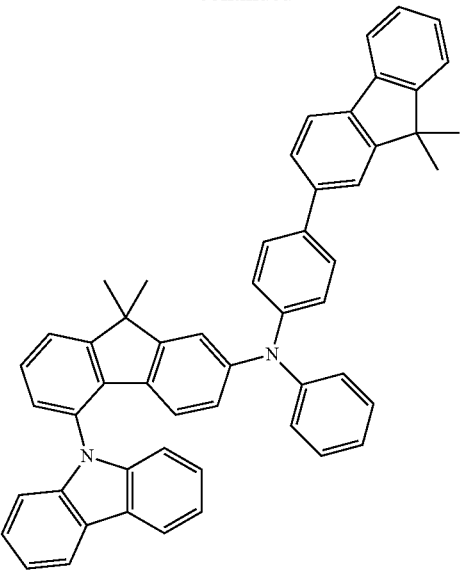
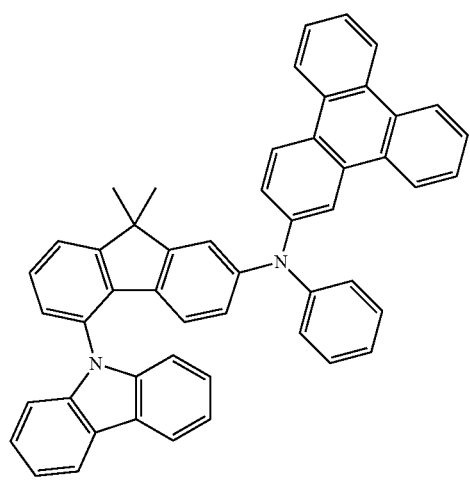
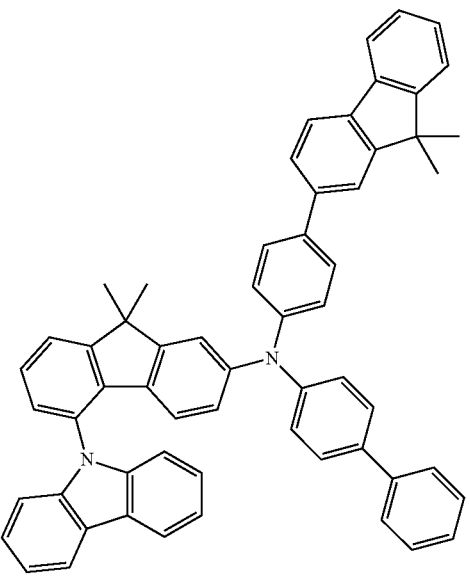
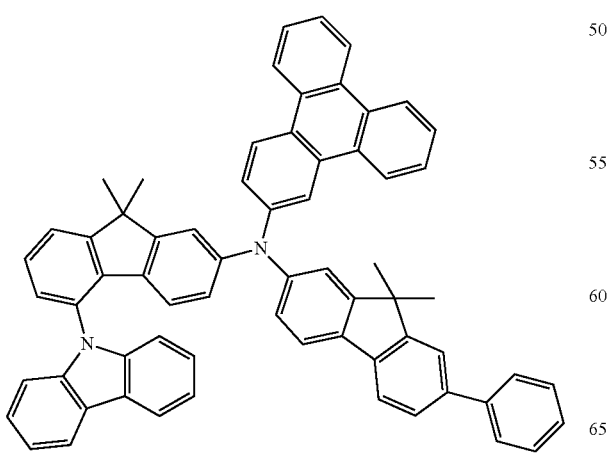
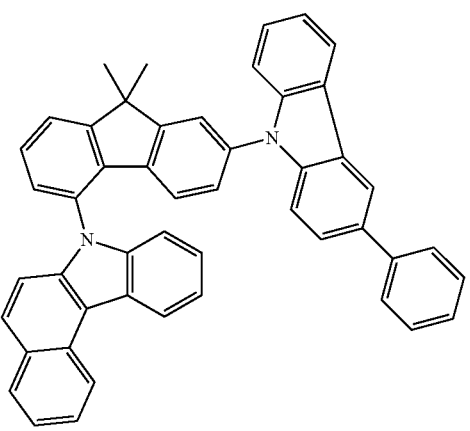

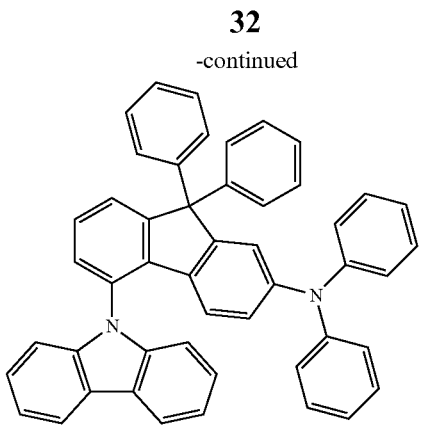
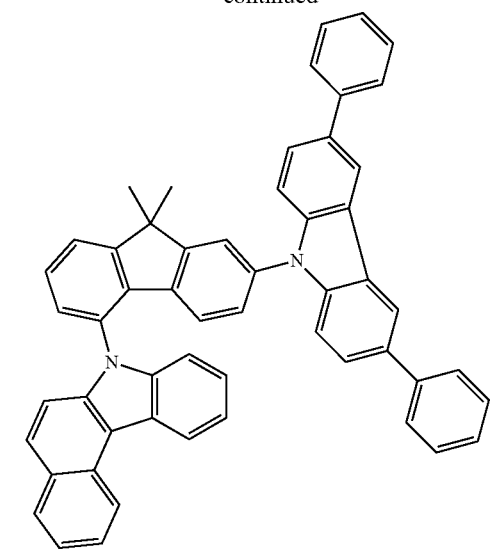
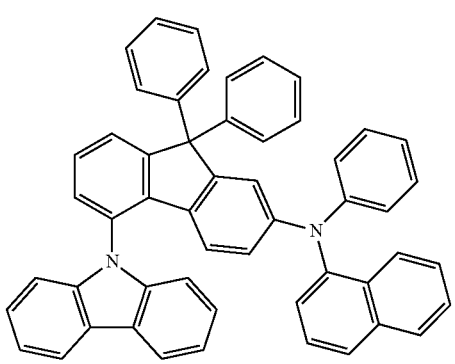
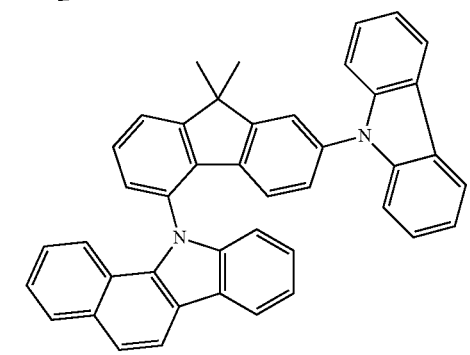
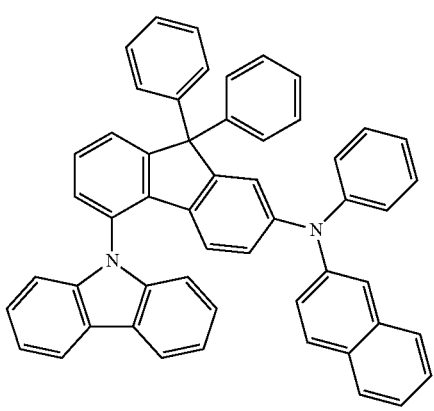
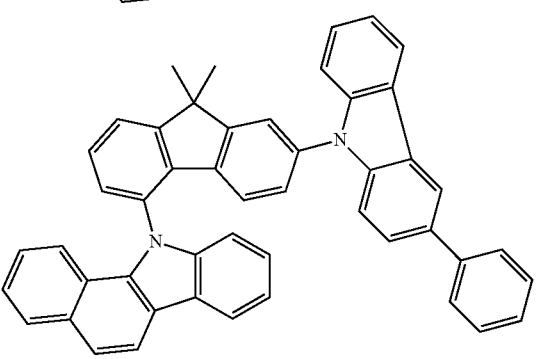
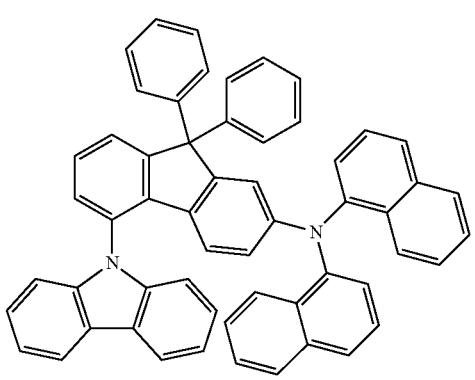
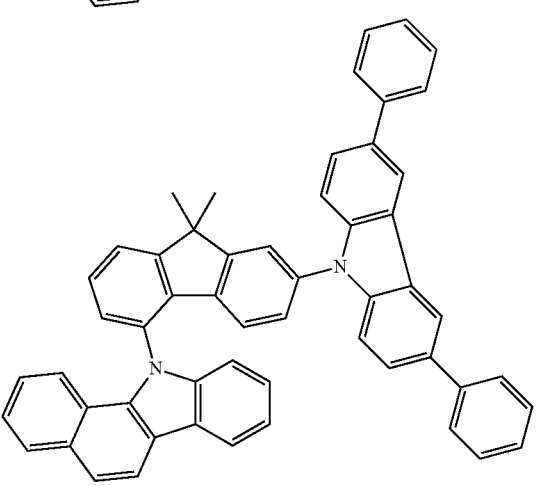

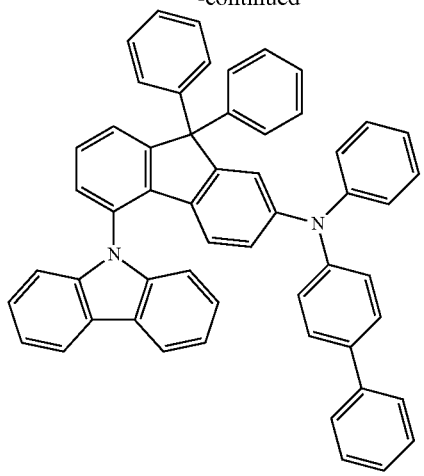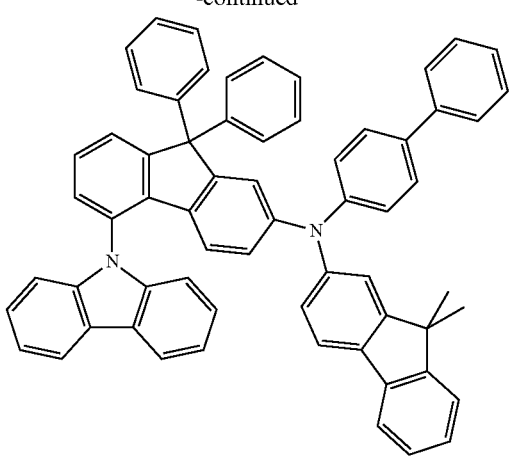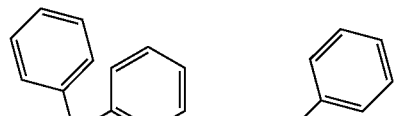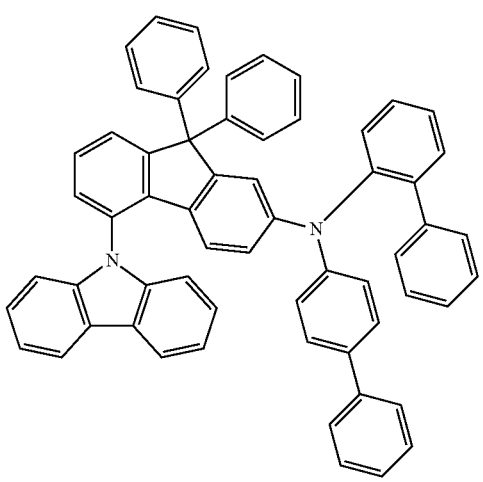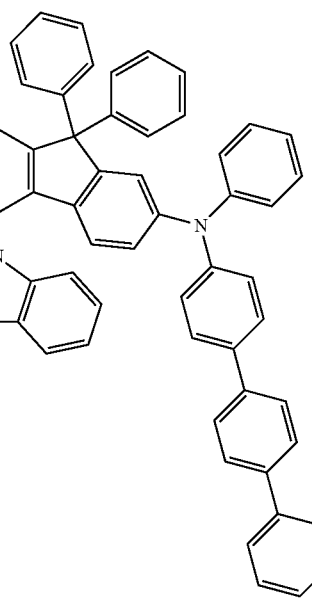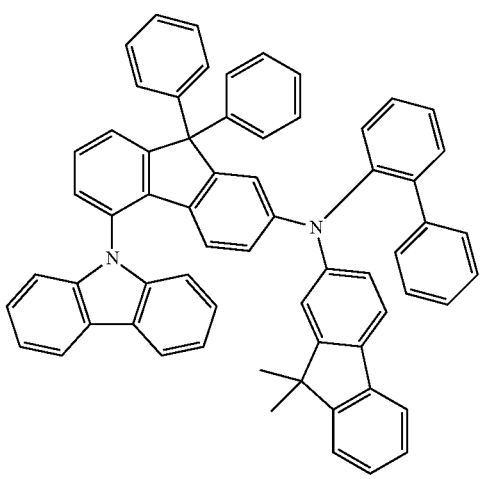

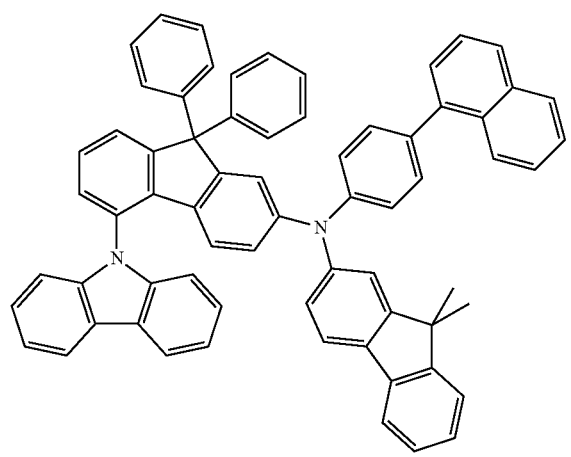
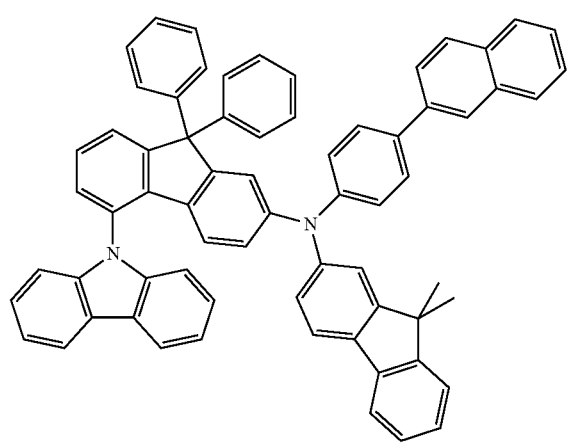
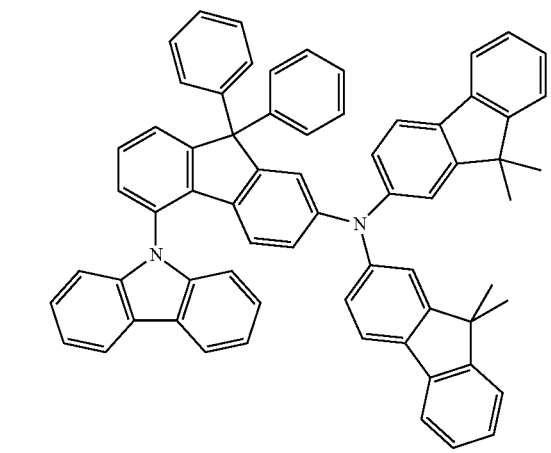
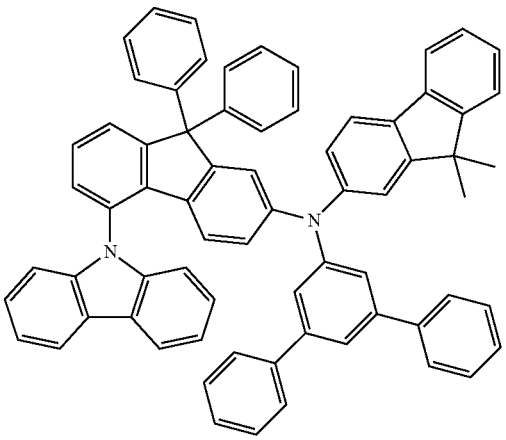
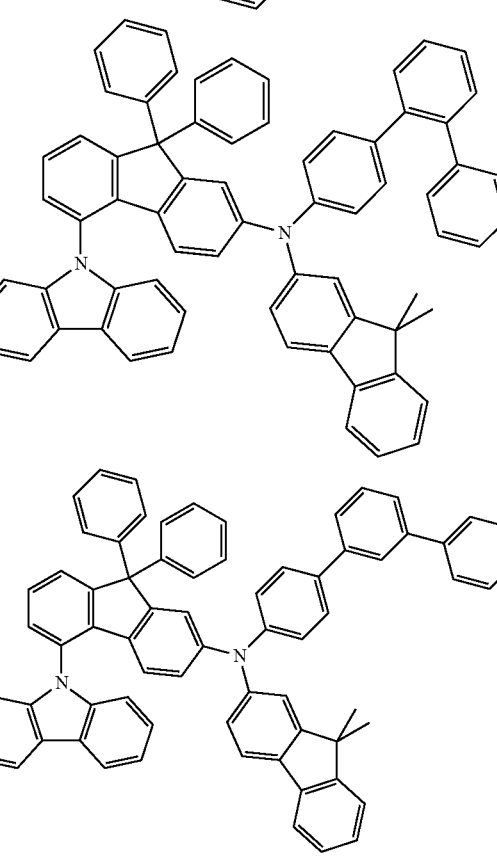
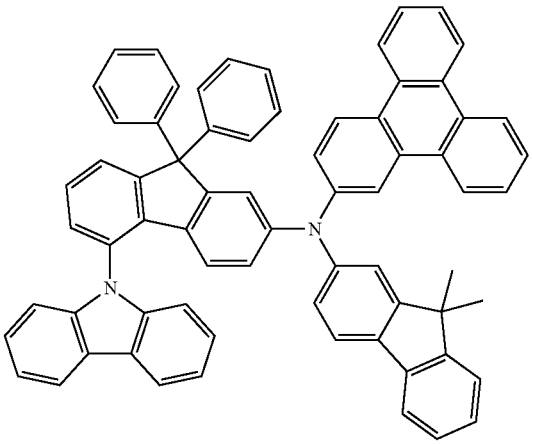

37
-continued
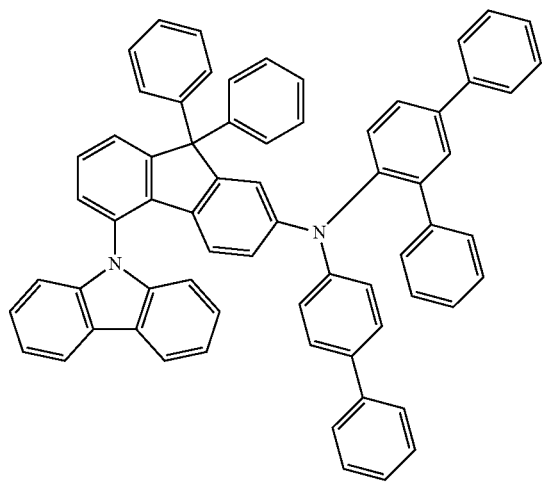
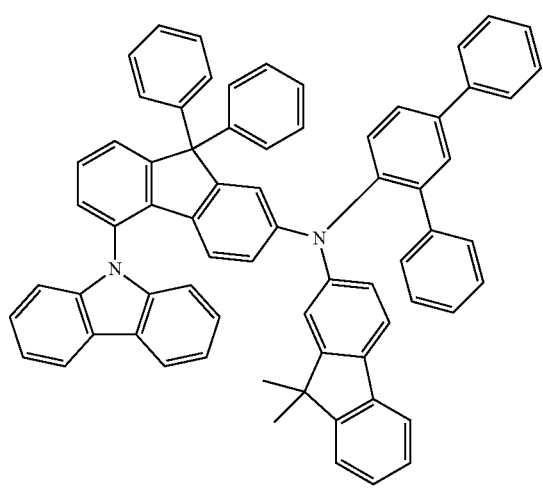
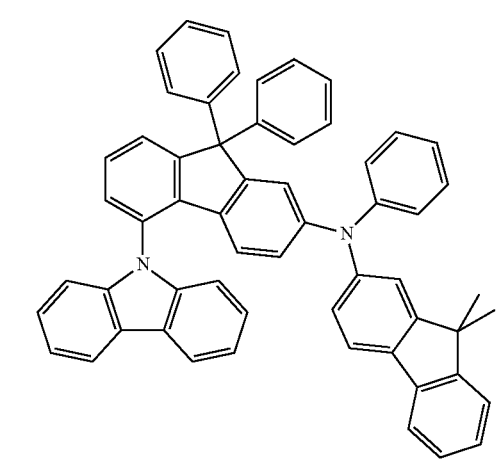
38
-continued
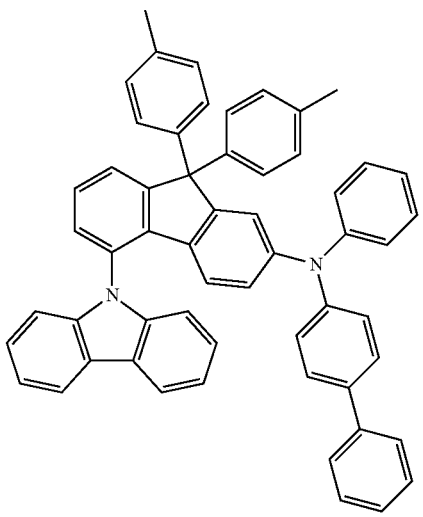
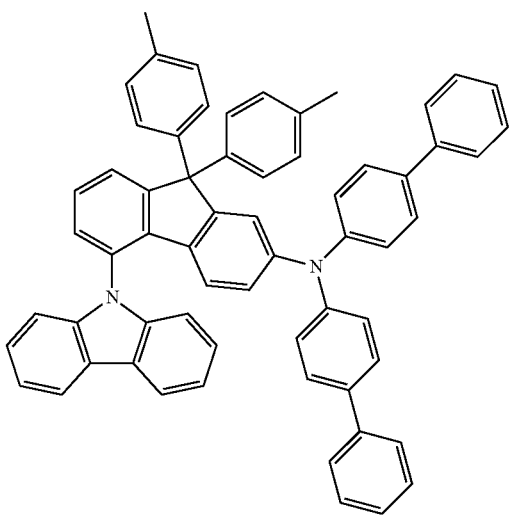
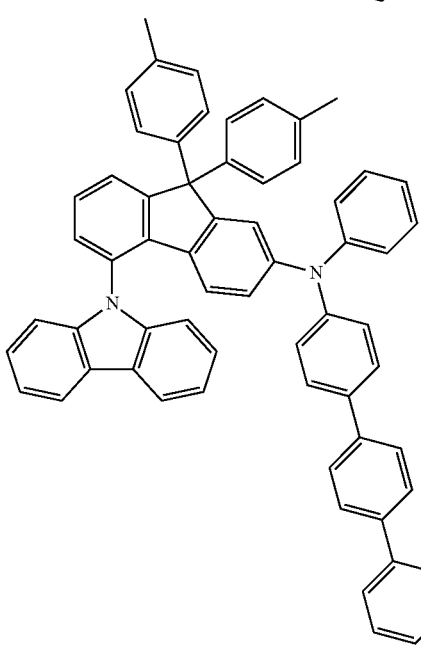

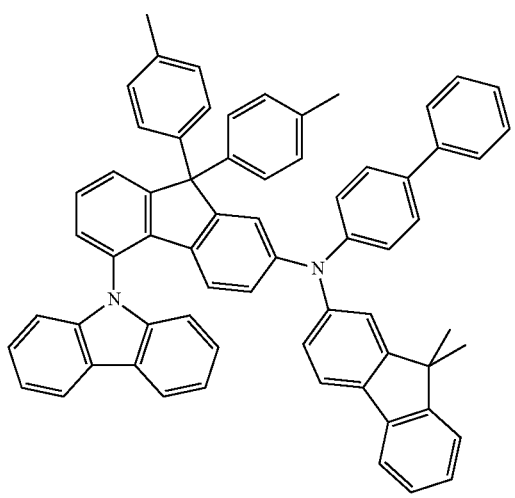
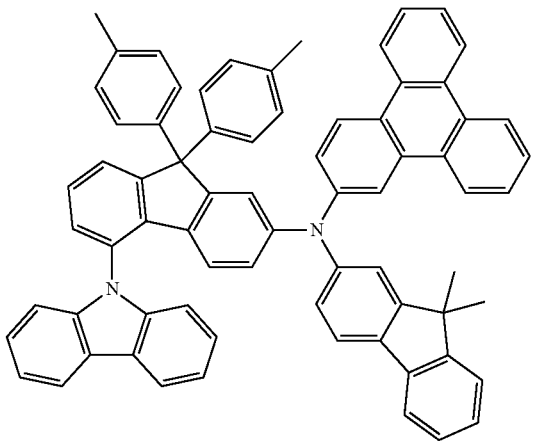
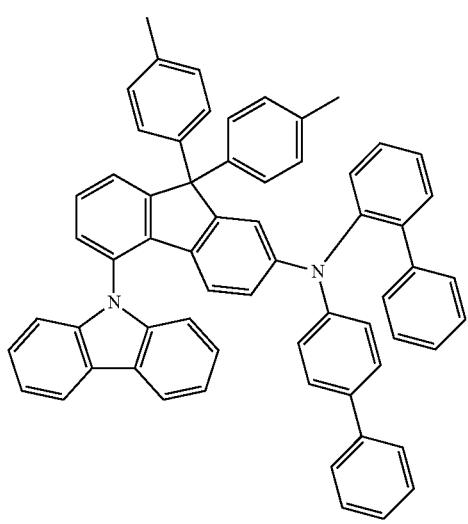
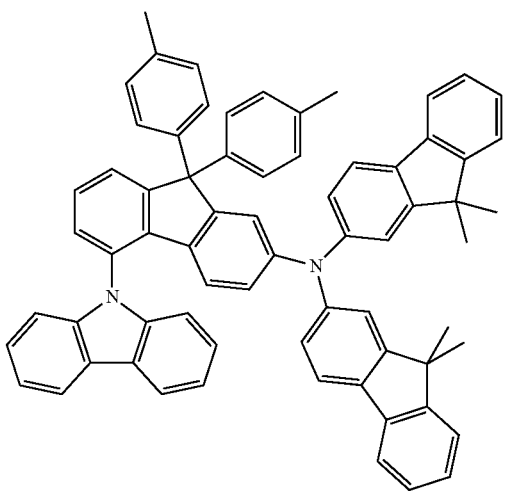
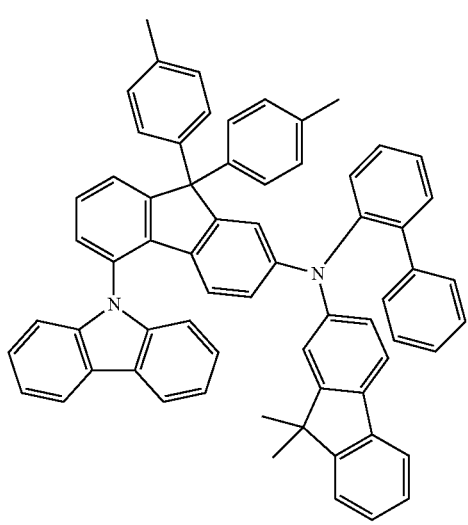
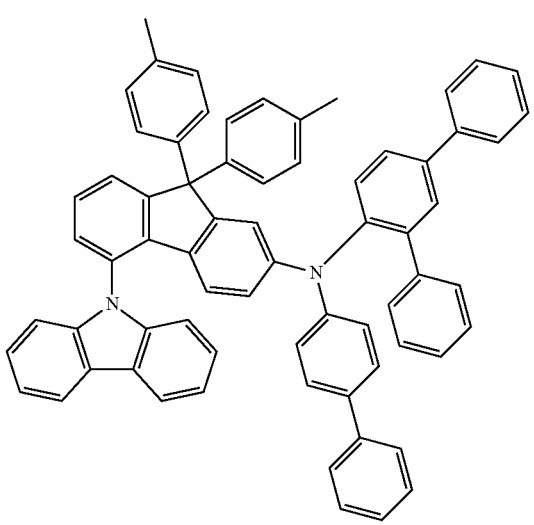

41
-continued
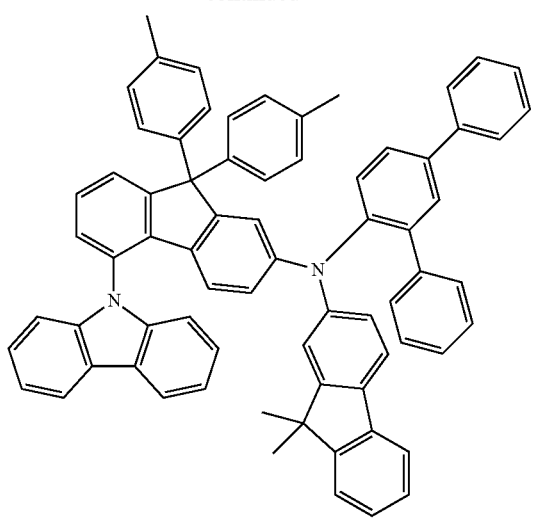
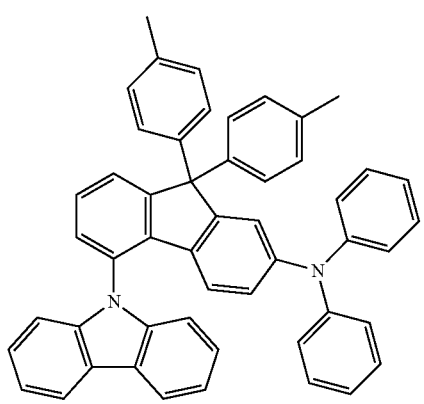
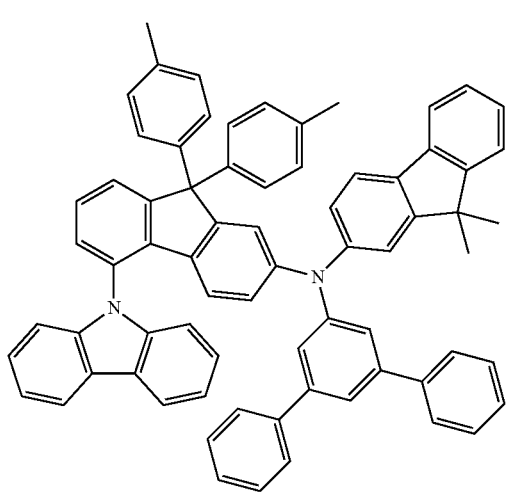
42
-continued
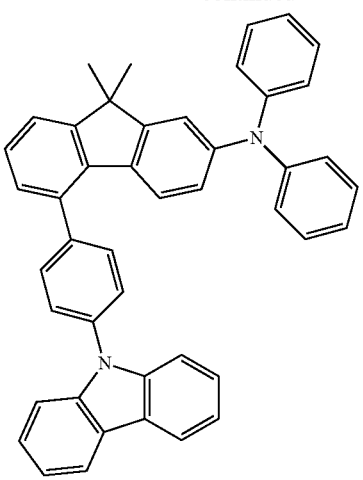
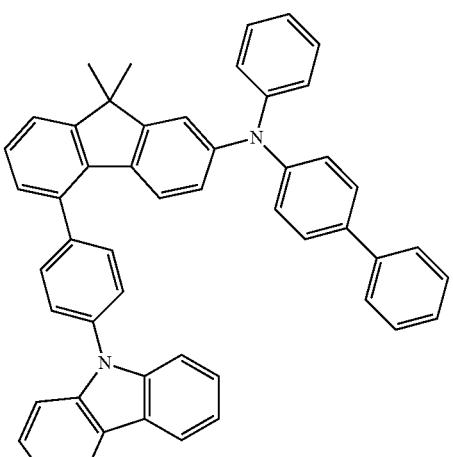
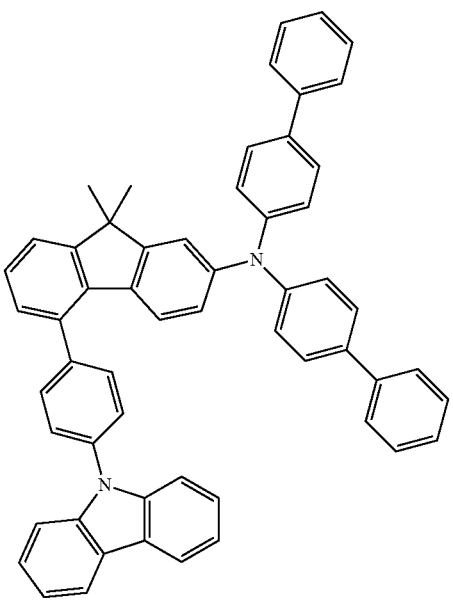

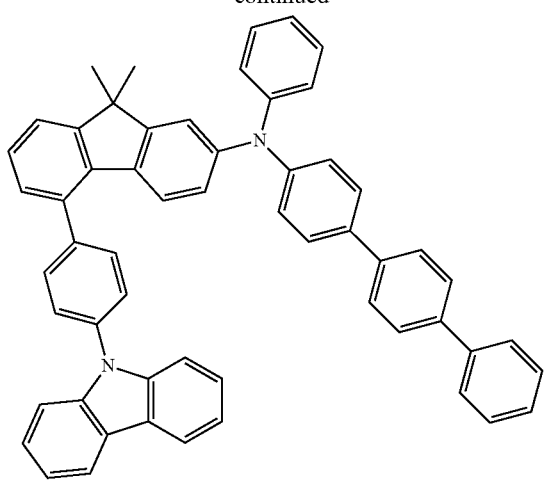
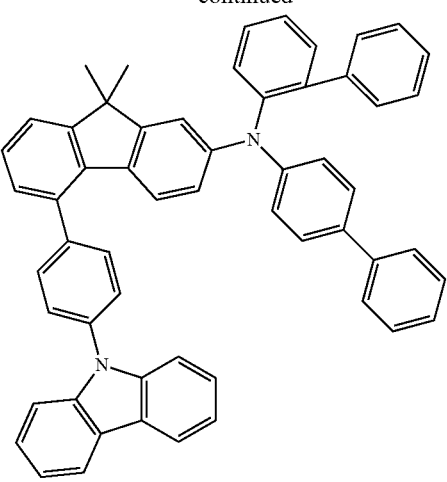
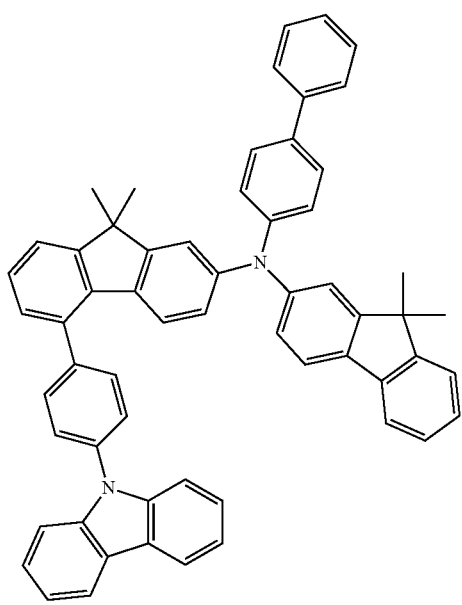
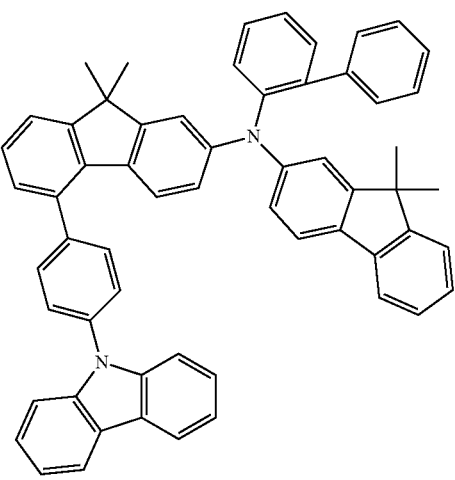
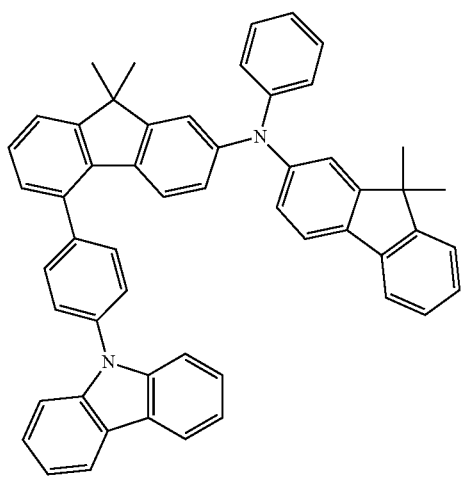
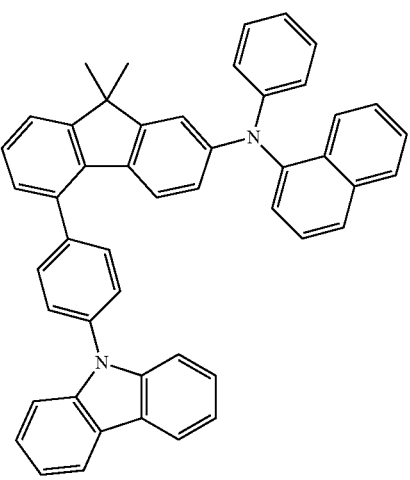

45
-continued
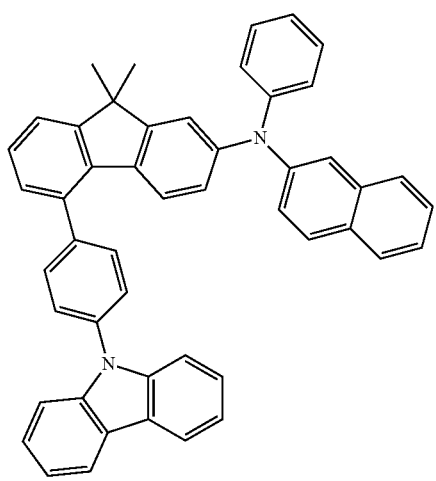
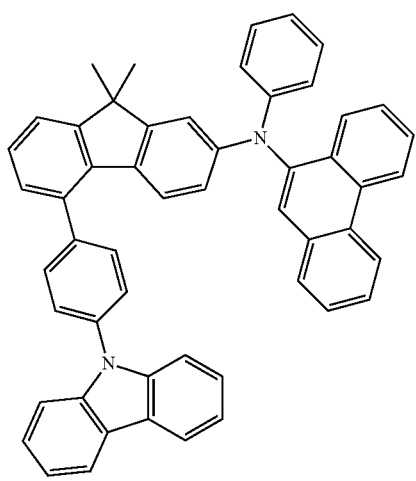
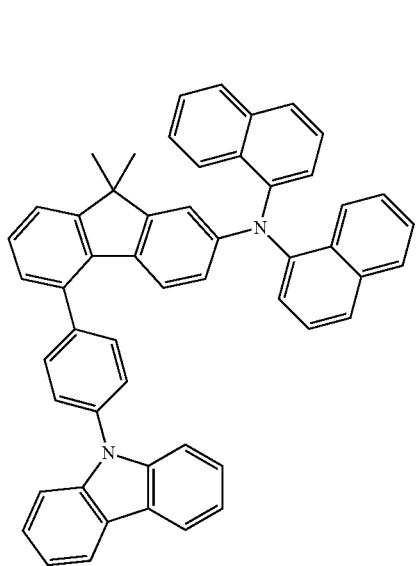
46
-continued
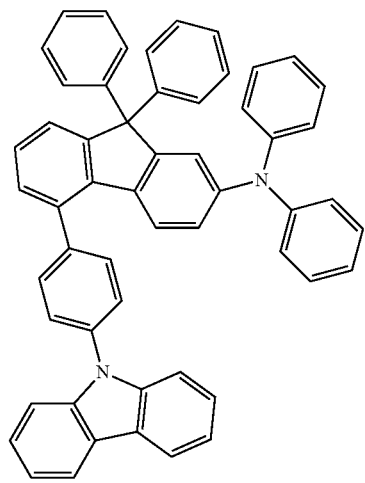
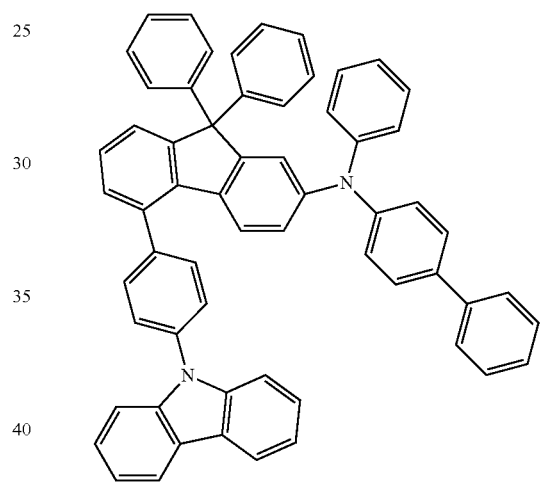
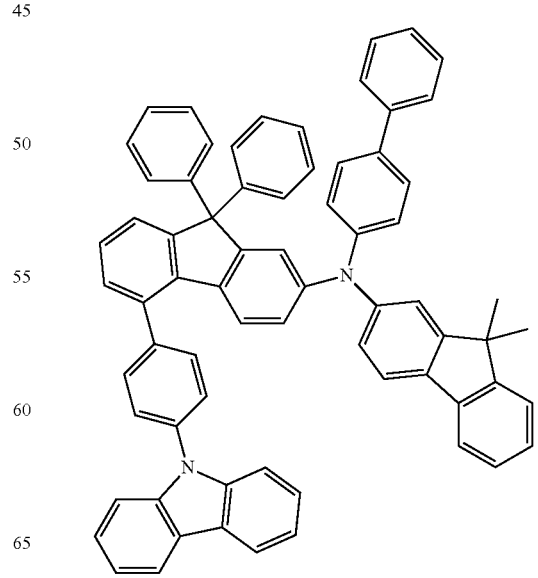

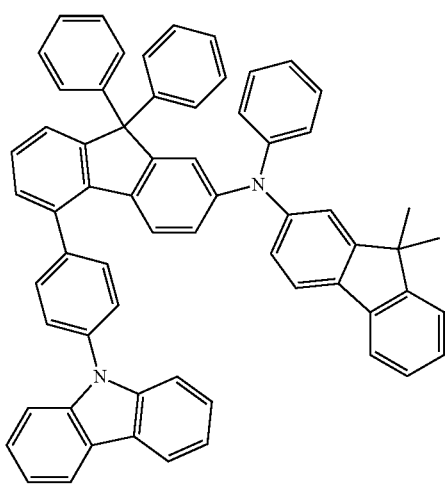
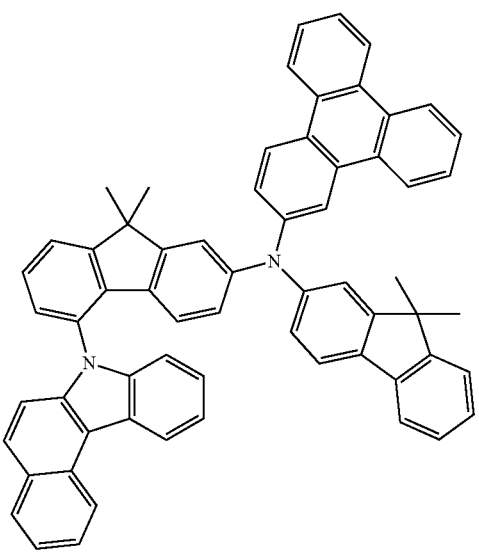
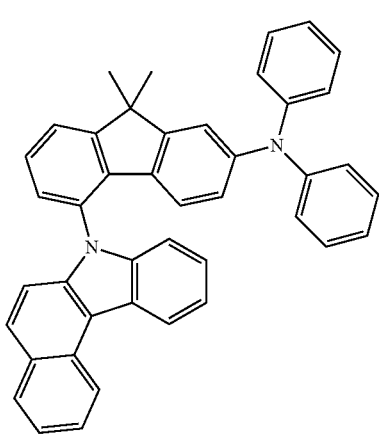
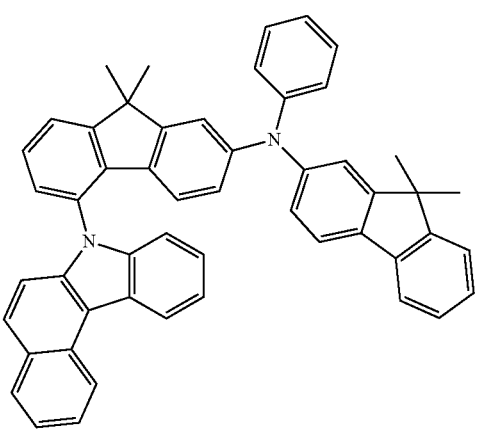
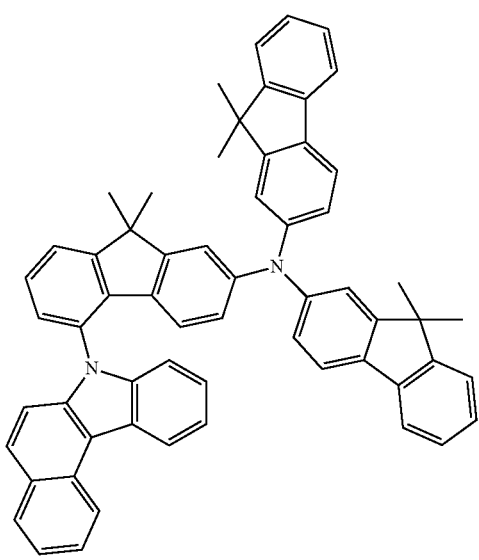
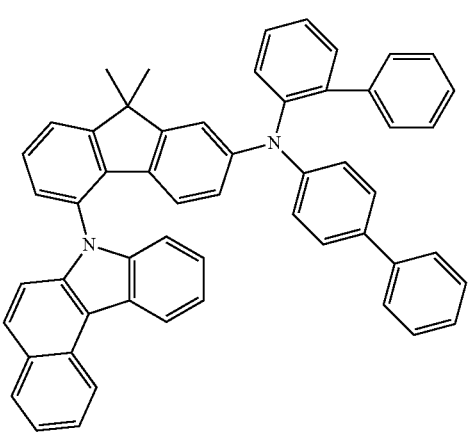

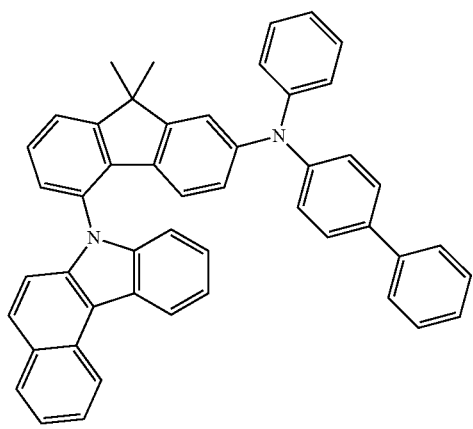
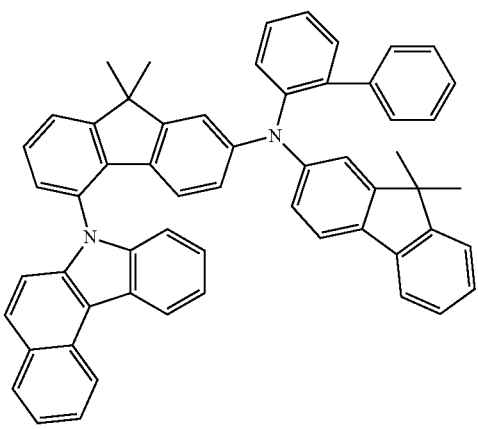
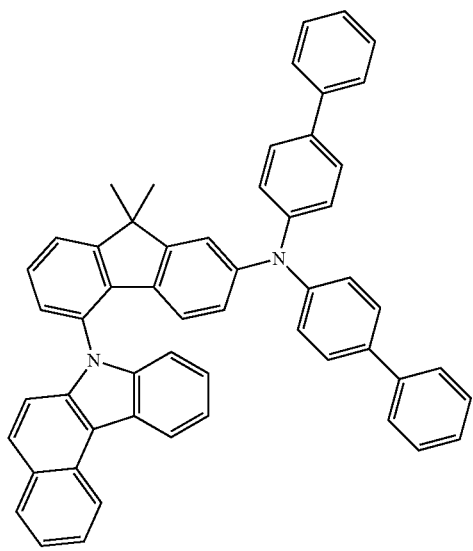
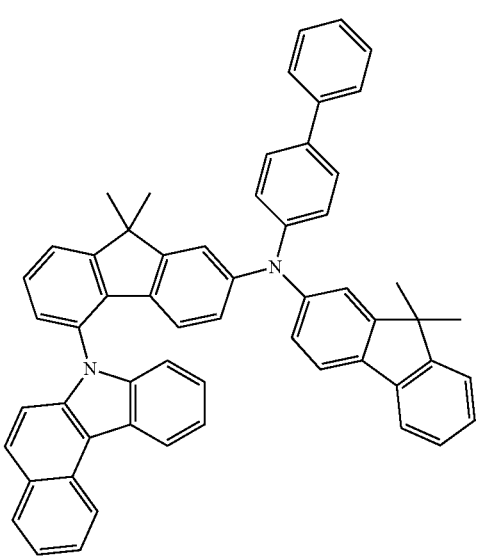
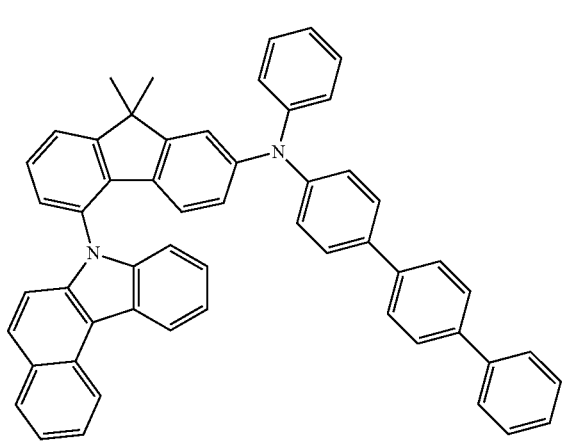
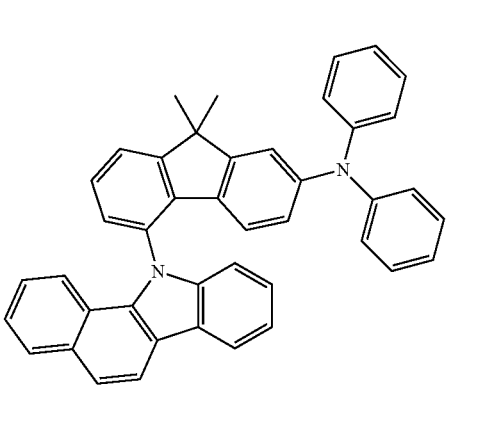

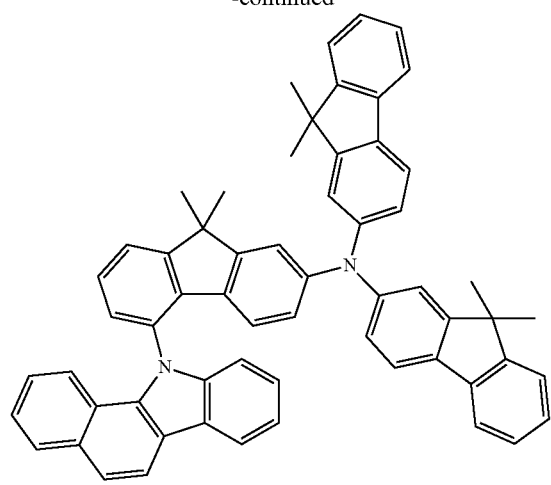
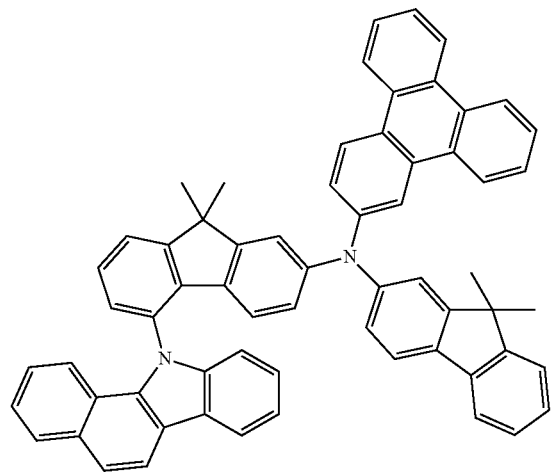
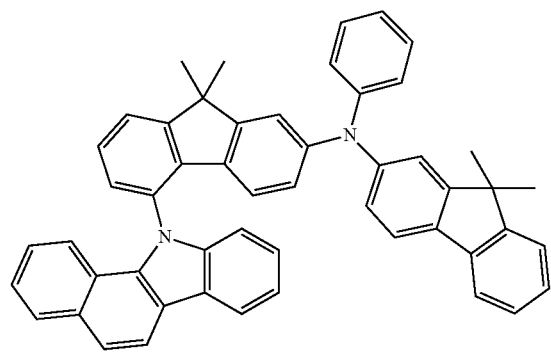
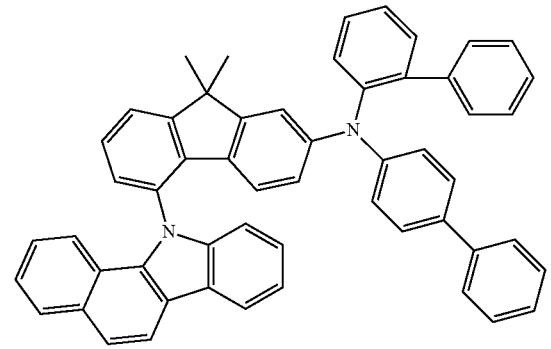
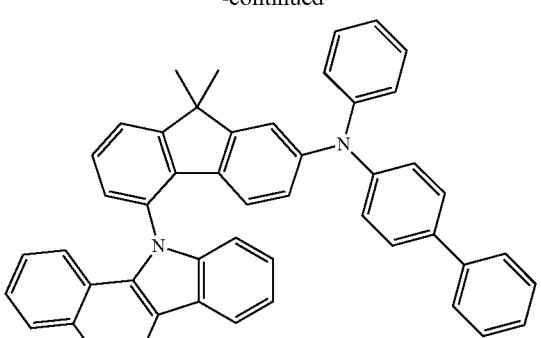
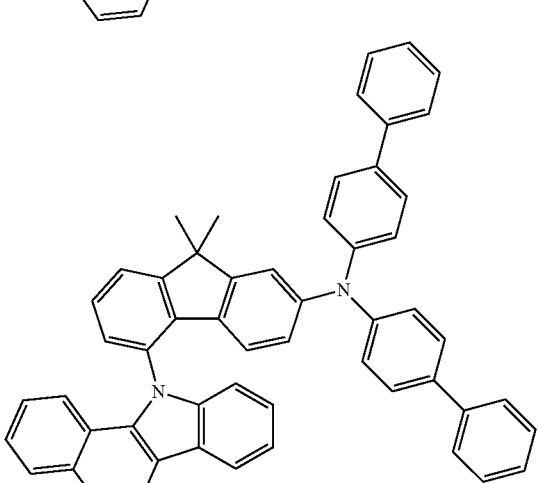

53
-continued
54
-continued
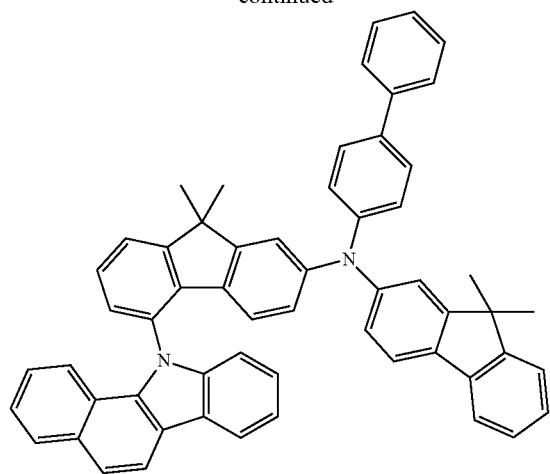
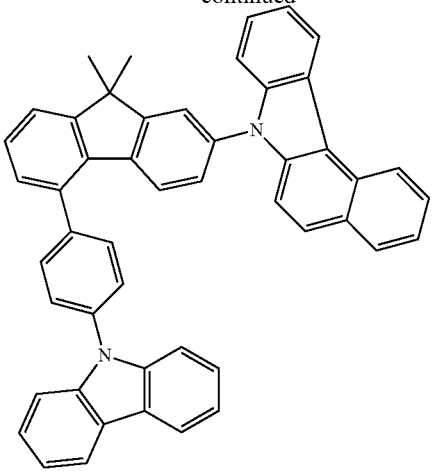
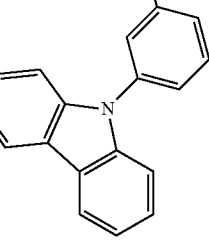
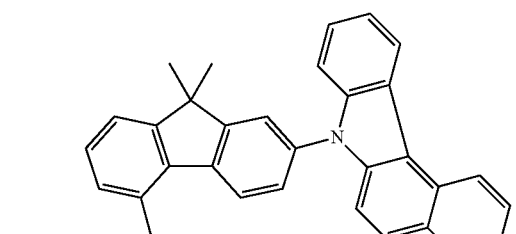
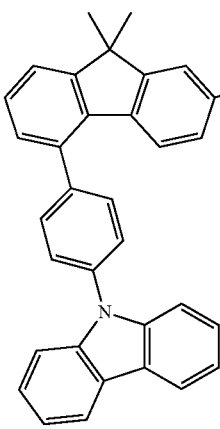

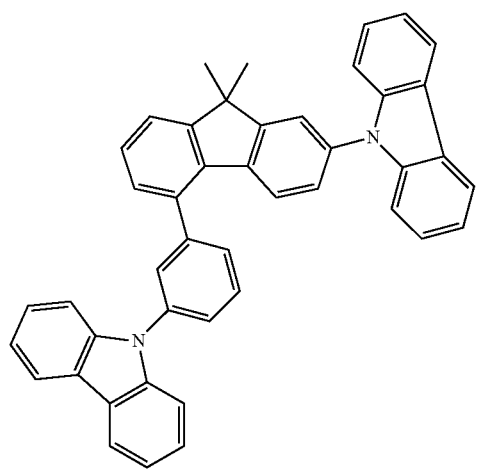
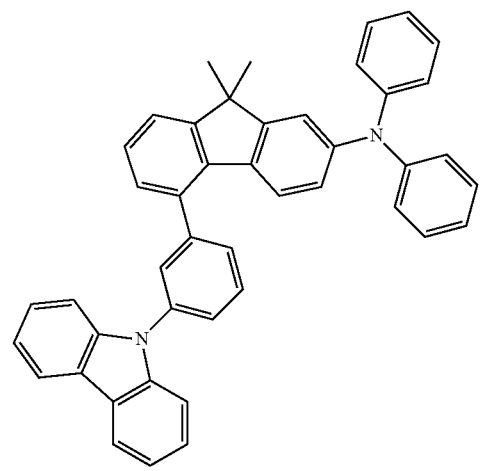
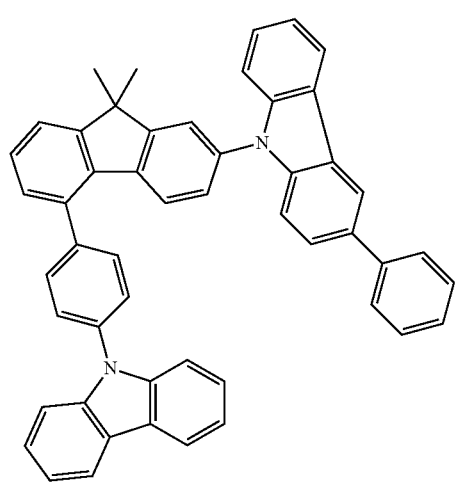
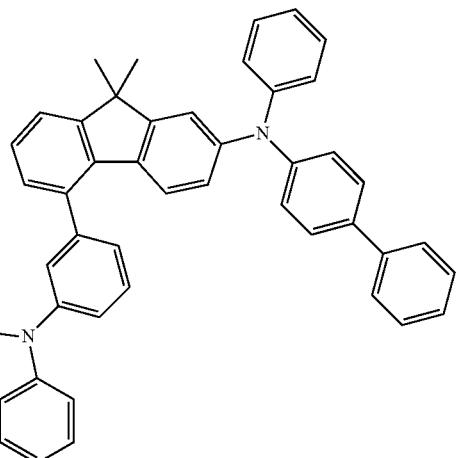
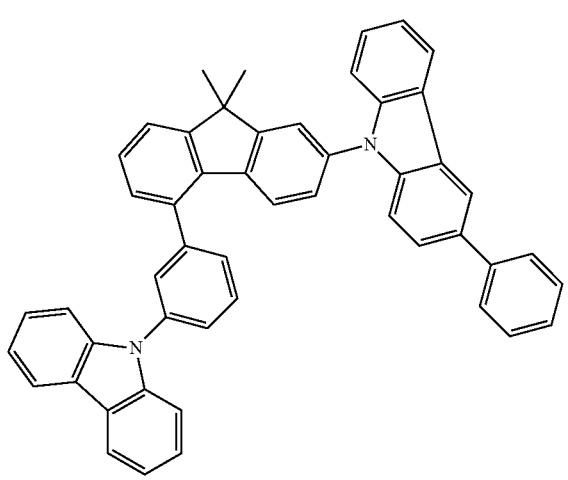
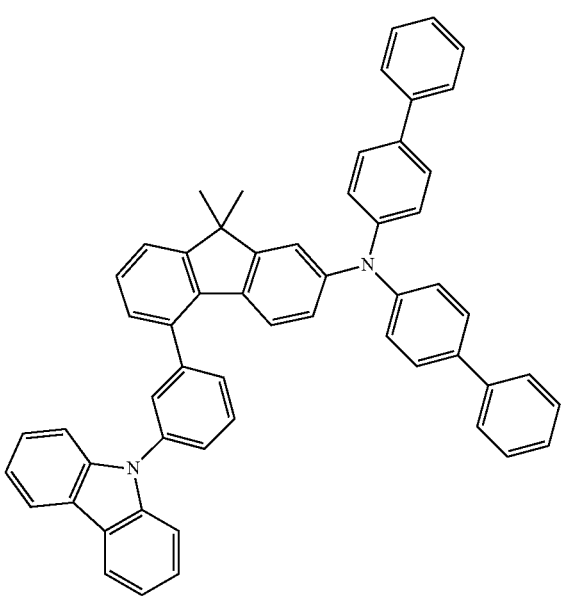

57
-continued
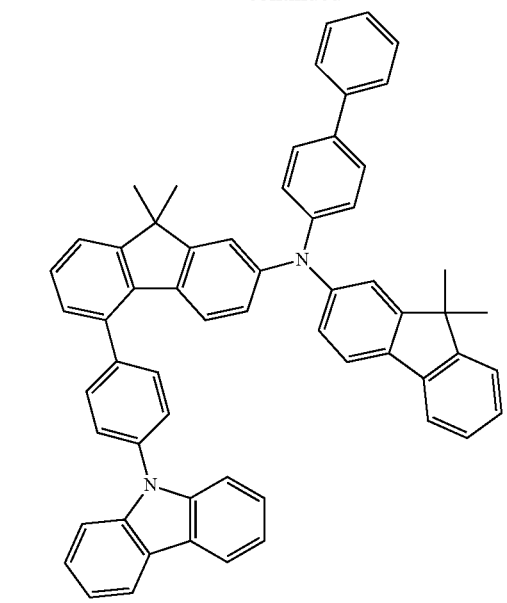
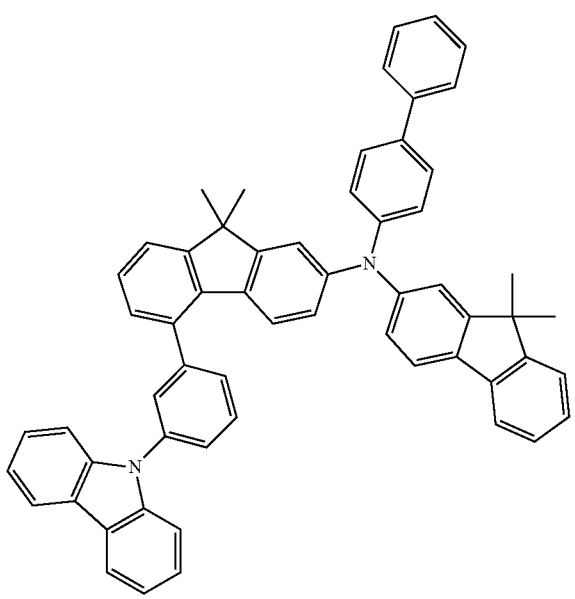
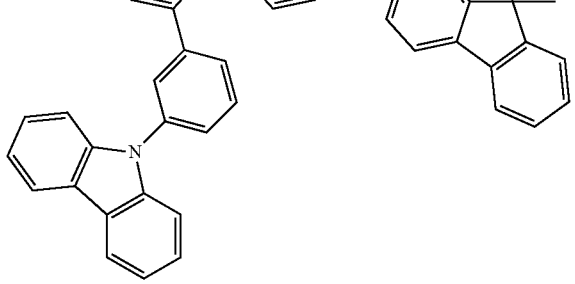
58
-continued
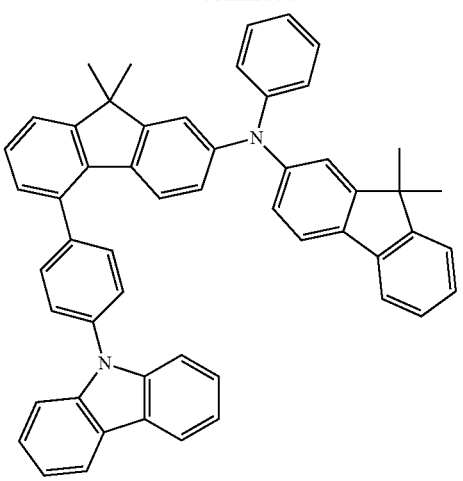
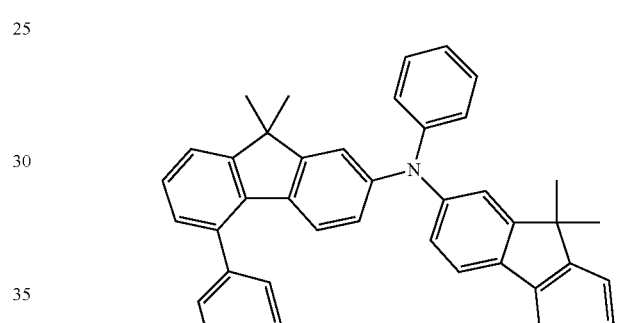
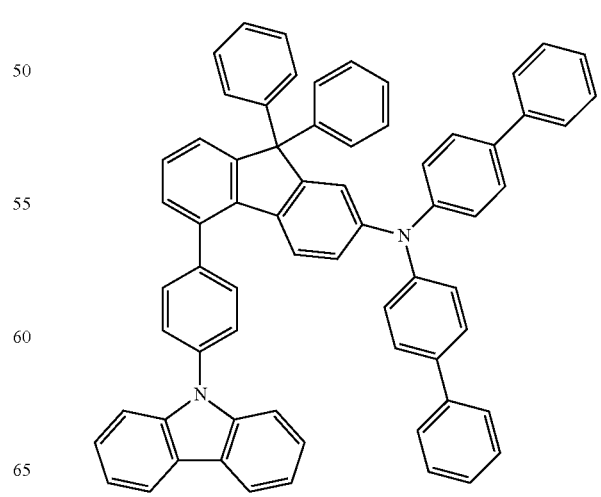

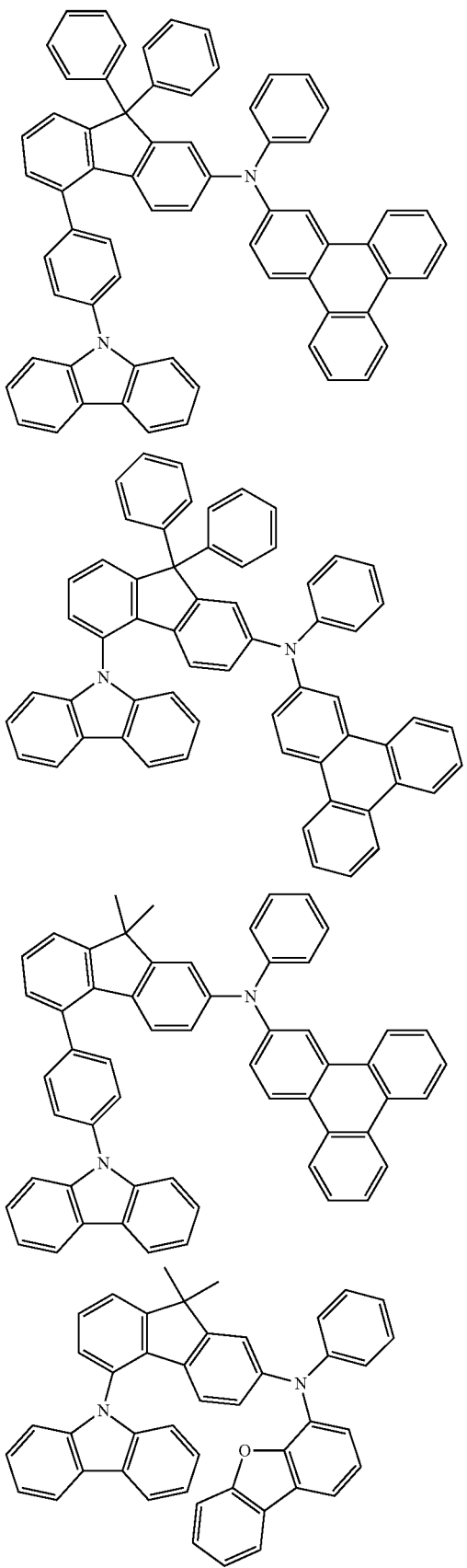
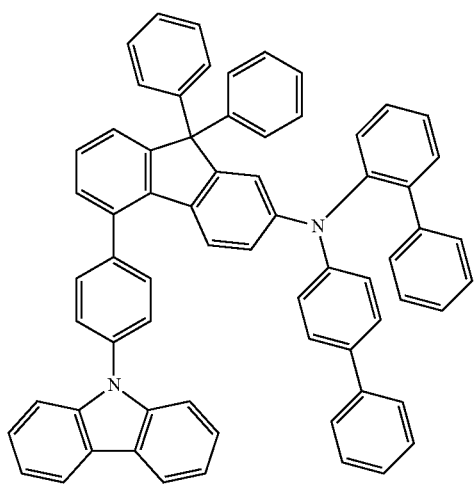

61
-continued
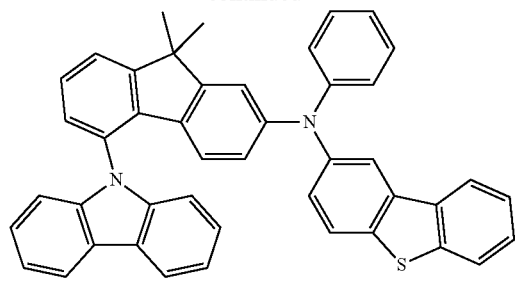
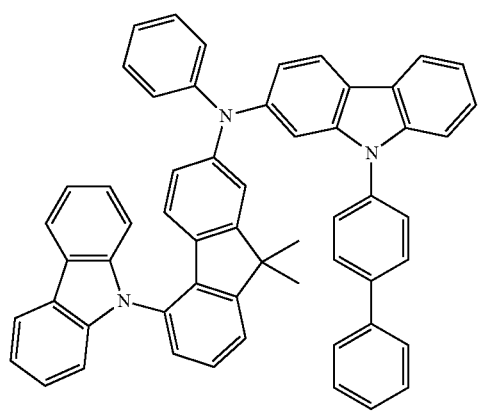
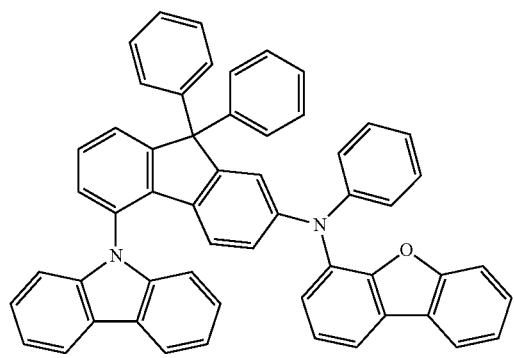
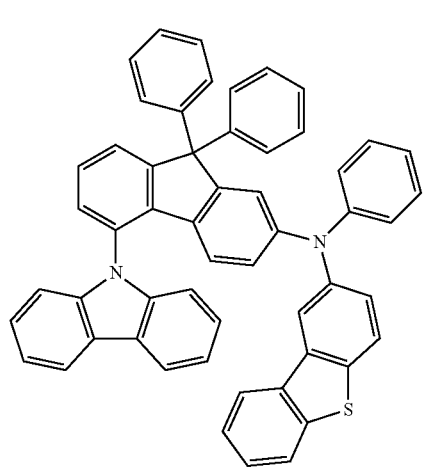
62
-continued
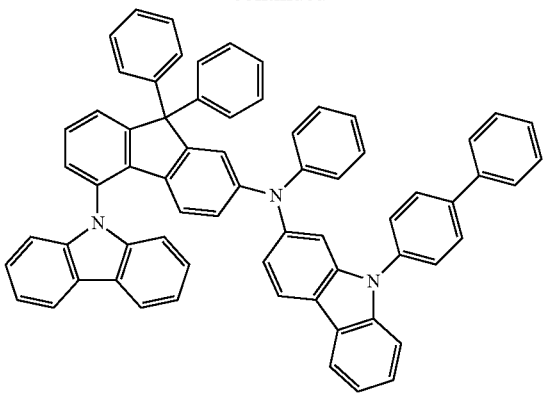
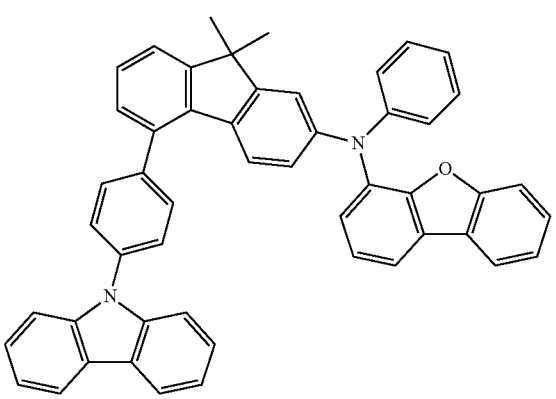
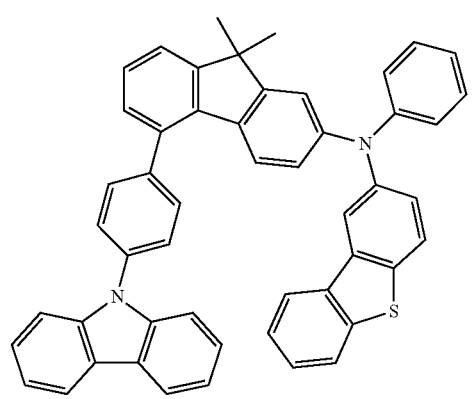
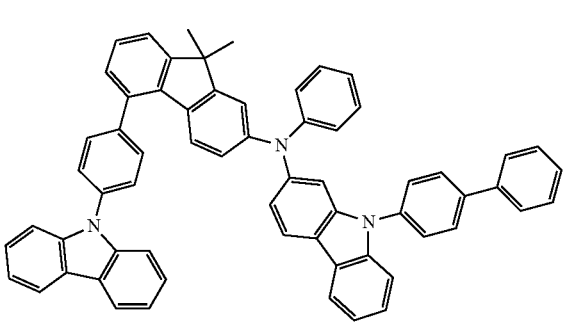

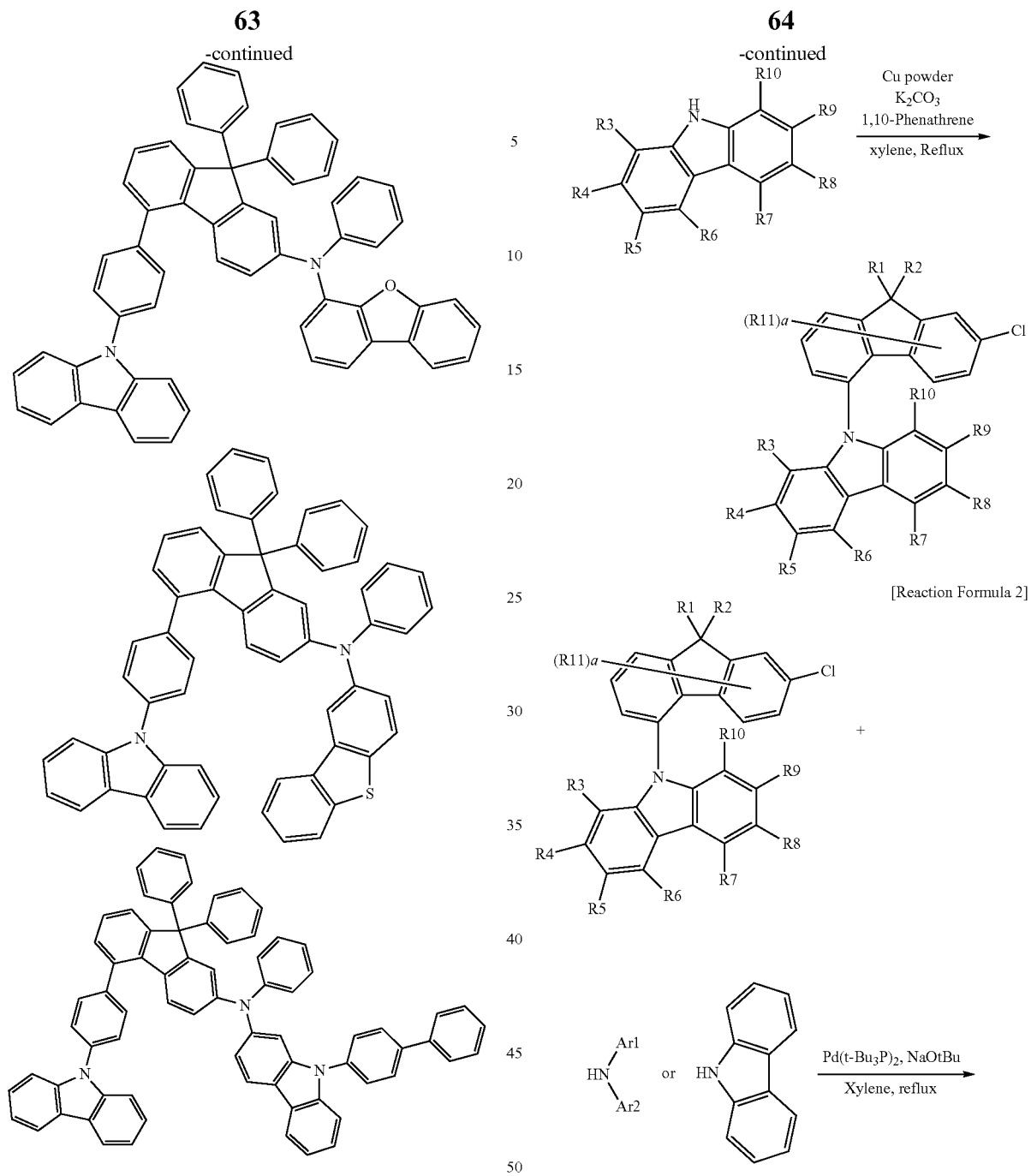
According to one embodiment, the compound of Chemical Formula 1 may be prepared through the following Reaction Formulae 1 and 2, or through Reaction Formulae 3 and 4. Reaction conditions may be modified as necessary based on those known in the art.
[Reaction Formula 1]
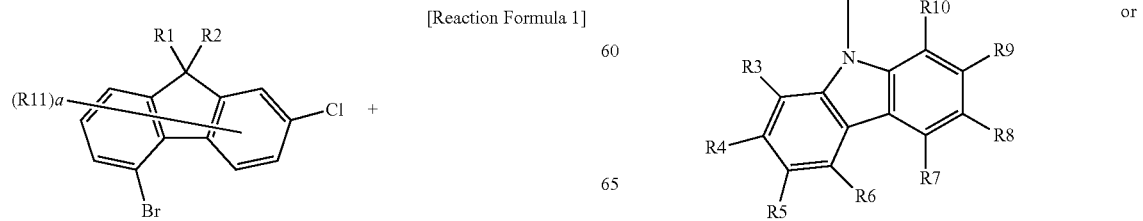

-continued
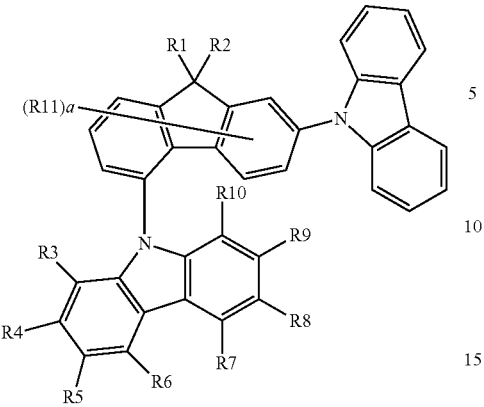
[Reaction Formula 3]
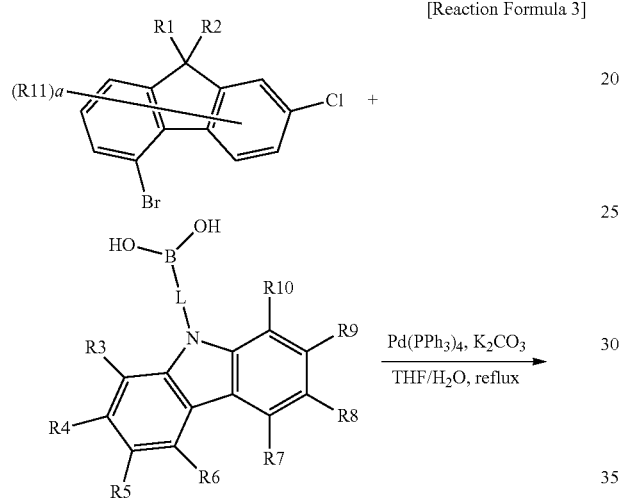
[Reaciton Formula 4]
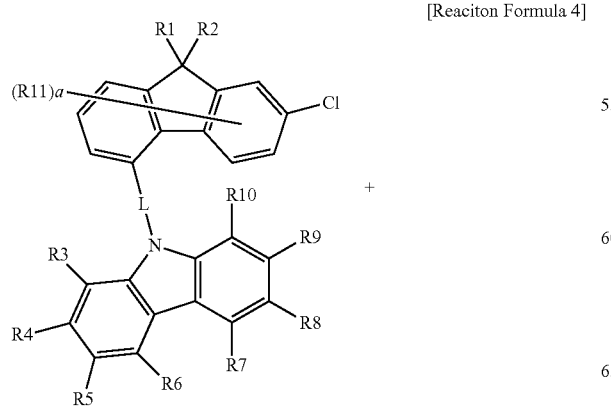
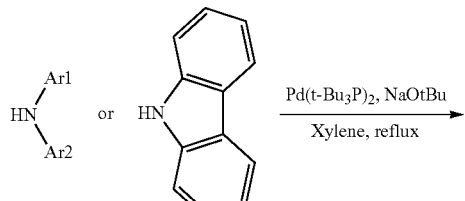
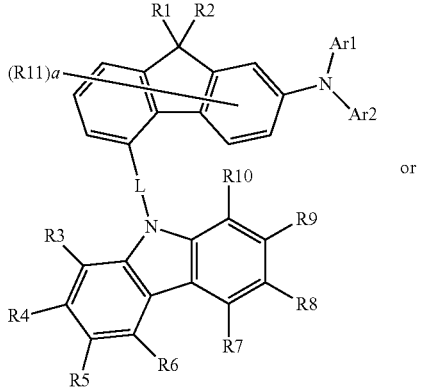
or
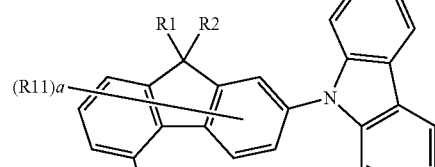
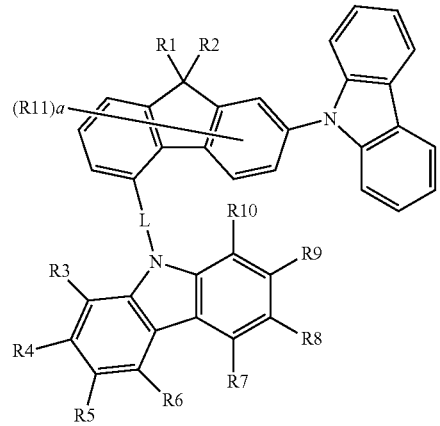
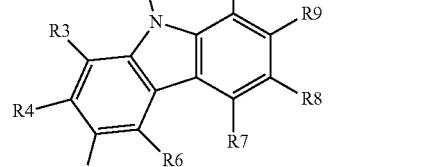
In the reaction formulae, definitions of substituents are the same as in Chemical Formula 1. For example, Compounds A, B, C and D as below may be prepared through Reaction Formulae 1 and 3.
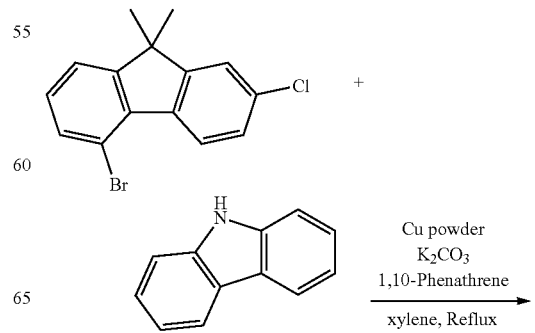

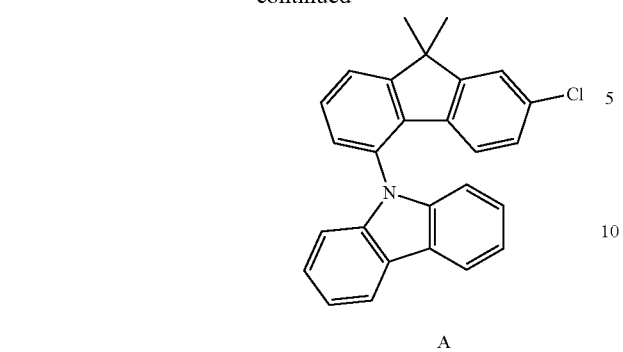

A

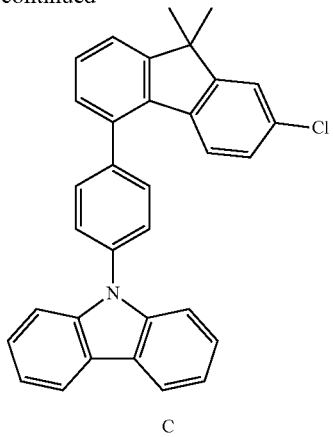

C

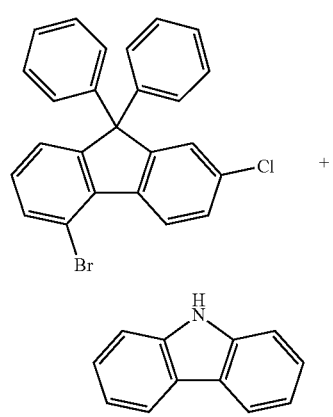

+

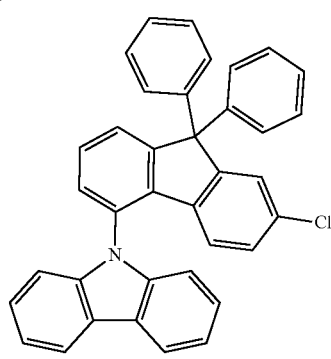

Cu powder
K₂CO₃
1,10-Phenathrene
―――――――→
xylene, Reflux

B

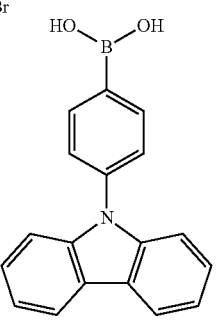

+

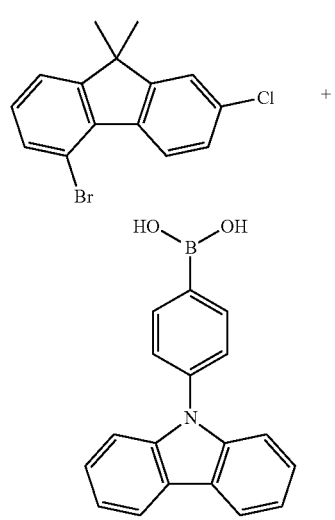

Pd(PPh₃)₄, K₂CO₃
―――――――→
THF/H₂O, reflux

Pd(PPh₃)₄, K₂CO₃
―――――――→
THF/H₂O, reflux

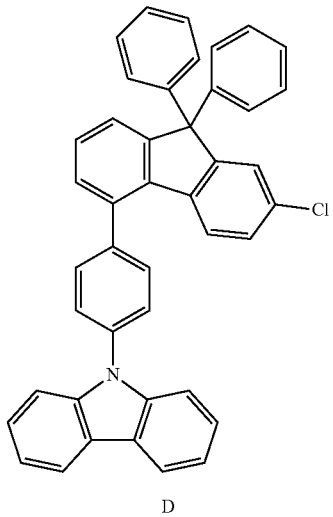

D

In addition, the present specification provides an organic light emitting device including the compound represented by Chemical Formula 1.

One embodiment of the present specification provides an organic light emitting device including a first electrode; a second electrode provided opposite to the first electrode; and one or more organic material layers provided between the first electrode and the second electrode, wherein one or more layers of the organic material layers include the compound of Chemical Formula 1.

The organic material layer of the organic light emitting device of the present specification may be formed in a single layer structure, but may be formed in a multilayer structure in which two or more organic material layers are laminated. For example, the organic light emitting device of the present disclosure may have a structure including a hole injection layer, a hole transfer layer, a light emitting layer, an electron transfer layer, an electron injection layer and the like as the organic material layer. However, the structure of the organic light emitting device is not limited thereto, and may include less numbers of organic material layers.

In one embodiment of the present specification, the organic material layer includes a hole injection layer, a hole transfer layer or a layer carrying out hole injection and transfer at the same time, and the hole injection layer, the hole transfer layer, or the layer carrying out hole injection and transfer at the same time includes the compound of Chemical Formula 1.

In another embodiment, the organic material layer includes an electron suppression layer, and the electron suppression layer includes the compound of Chemical Formula 1.

In another embodiment, the organic material layer includes a light emitting layer, and the light emitting layer includes the compound of Chemical Formula 1.

In another embodiment, the organic light emitting device may be an organic light emitting device having a structure of consecutively laminating an anode, one or more organic material layers and a cathode on a substrate (normal type).

In another embodiment, the organic light emitting device may be an organic light emitting device having a reverse structure of consecutively laminating a cathode, one or more organic material layers and an anode on a substrate (inverted type).

For example, structures of an organic light emitting device according to one embodiment of the present specification are illustrated in FIG. 1 and FIG. 2.

FIG. 1 illustrates an organic light emitting device formed with a substrate (1), an anode (2), a light emitting layer (3) and a cathode (4). In such a structure, the compound may be included in the light emitting layer.

FIG. 2 illustrates an organic light emitting device formed with a substrate (1), an anode (2), a hole injection layer (5), a hole transfer layer (6), a light emitting layer (3), an electron transfer layer (7) and a cathode (4). In such a structure, the compound may be included in one or more layers of the hole injection layer, the hole transfer layer, the light emitting layer and the electron transfer layer.

According to one embodiment of the present specification, the organic material layer includes a light emitting layer, and the light emitting layer may include a compound represented by the following Chemical Formula 5,

[Chemical Formula 5]

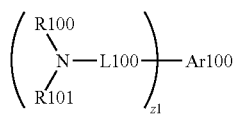

In Chemical Formula 5, z1 is an integer of 1 or greater, and when z1 is 2 or greater, structures in the parentheses are the same as or different from each other, Ar100 is a substituted or unsubstituted monovalent or higher benzofluorene group; a substituted or unsubstituted monovalent or higher fluoranthene group; a substituted or unsubstituted monovalent or higher pyrene group; or a substituted or unsubstituted monovalent or higher chrysene group, L100 is a direct bond; a substituted or unsubstituted arylene group; or a substituted or unsubstituted heteroarylene group, and R100 and R101 are the same as or different from each other, and each independently a substituted or unsubstituted aryl group; a substituted or unsubstituted alkyl group; a substituted or unsubstituted silyl group; a substituted or unsubstituted arylalkyl group; or a substituted or unsubstituted heterocyclic group, or may bond to each other to form a substituted or unsubstituted ring.

According to one embodiment of the present specification, the light emitting layer includes the compound represented by Chemical Formula 5 as a dopant of the light emitting layer.

According to one embodiment of the present specification, L100 is a direct bond.

According to one embodiment of the present specification, z1 is 2.

According to one embodiment of the present specification, Ar100 is a divalent pyrene group unsubstituted or substituted with deuterium, a methyl group, an ethyl group, an iso-propyl group or a tert-butyl group; or a divalent chrysene group unsubstituted or substituted with deuterium, a methyl group, an ethyl group, an iso-propyl group or a tert-butyl group.

According to one embodiment of the present specification, Ar100 is a divalent pyrene group unsubstituted or substituted with deuterium, a methyl group, an ethyl group, an iso-propyl group or a tert-butyl group.

According to one embodiment of the present specification, Ar100 is a divalent pyrene group.

According to one embodiment of the present specification, R100 and R101 are the same as or different from each other, and each independently a substituted or unsubstituted aryl group having 6 to 60 carbon atoms; or a substituted or unsubstituted heterocyclic group having 2 to 60 carbon atoms.

According to one embodiment of the present specification, R100 and R101 are the same as or different from each other, and each independently an aryl group having 6 to 60 carbon atoms unsubstituted or substituted with deuterium, an alkyl group, a nitrile group, an aryl group, an alkylsilyl group or an alkylgermanium group; or a heterocyclic group having 2 to 60 carbon atoms unsubstituted or substituted with deuterium, an alkyl group, a nitrile group, an aryl group, an alkylsilyl group or an alkylgermanium group.

According to one embodiment of the present specification, R100 and R101 are the same as or different from each other, and each independently an aryl group having 6 to 60 carbon atoms unsubstituted or substituted with deuterium, a methyl group, an ethyl group, an iso-propyl group, a tert-butyl group, a nitrile group, a phenyl group, a trimethylsilyl group or a trimethylgermanium group; or a heterocyclic group having 2 to 60 carbon atoms unsubstituted or substituted with deuterium, a methyl group, an ethyl group, an iso-propyl group, a tert-butyl group, a nitrile group, a phenyl group, a trimethylsilyl group or a trimethylgermanium group.

According to one embodiment of the present specification, R100 and R101 are the same as or different from each other, and each independently a phenyl group unsubstituted or substituted with deuterium, a methyl group, an ethyl group, an iso-propyl group, a tert-butyl group, a nitrile group, a phenyl group, a trimethylsilyl group or a trimethylgermanium group; a biphenyl group unsubstituted or substituted with deuterium, a methyl group, an ethyl group, an iso-propyl group, a tert-butyl group, a nitrile group, a phenyl group, a trimethylsilyl group or a trimethylgermanium group; a terphenyl group unsubstituted or substituted with deuterium, a methyl group, an ethyl group, an iso-propyl group, a tert-butyl group, a nitrile group, a phenyl group, a trimethylsilyl group or a trimethylgermanium group; or a dibenzofuran group unsubstituted or substituted with deuterium, a methyl group, an ethyl group, an iso-propyl group, a tert-butyl group, a nitrile group, a phenyl group, a trimethylsilyl group or a trimethylgermanium group.

According to one embodiment of the present specification, R100 and R101 are the same as or different from each other, and each independently a phenyl group unsubstituted or substituted with a trimethylgermanium group.

According to one embodiment of the present specification, R100 is a phenyl group.

According to one embodiment of the present specification, R101 is a phenyl group substituted with a trimethylgermanium group.

According to one embodiment of the present specification, Chemical Formula 5 may be selected from among the following compounds.

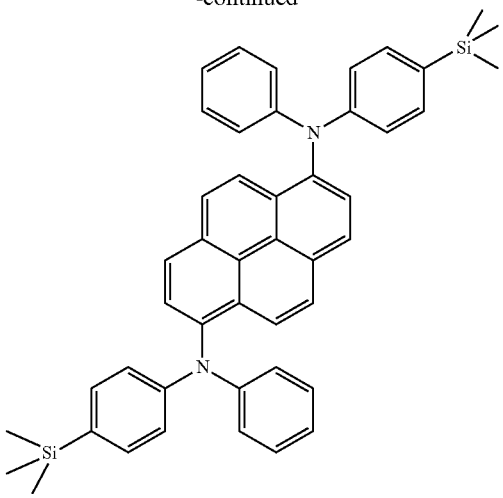

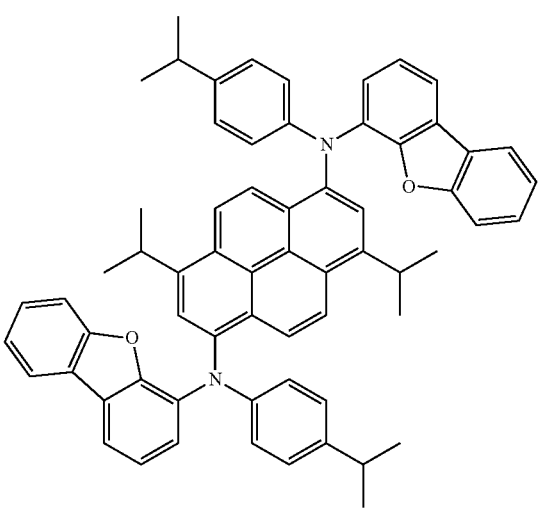

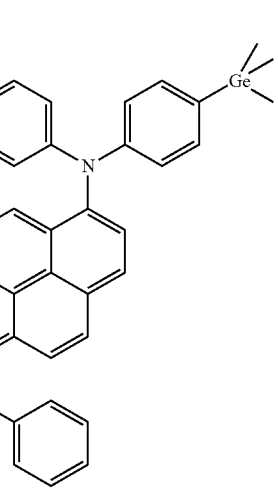

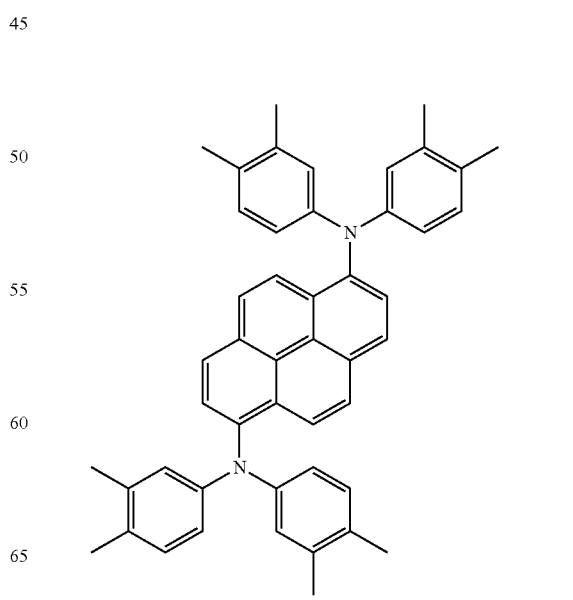

73
-continued
74
-continued
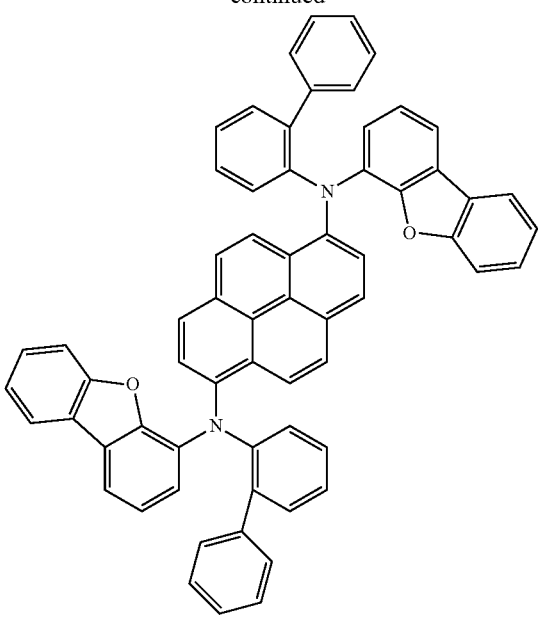
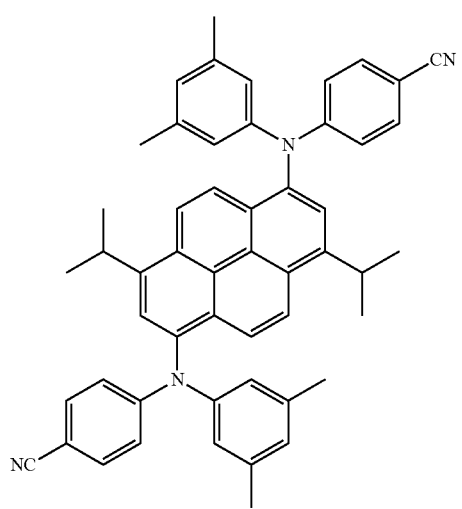
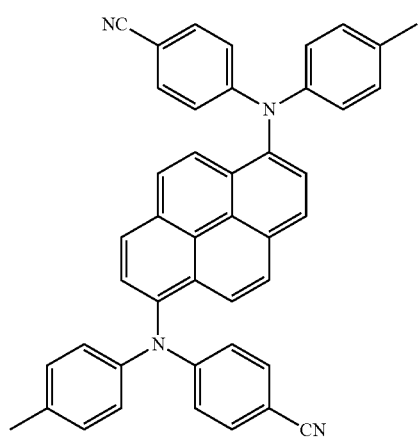
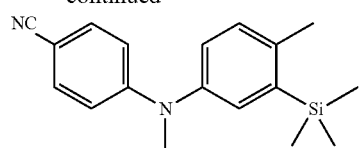
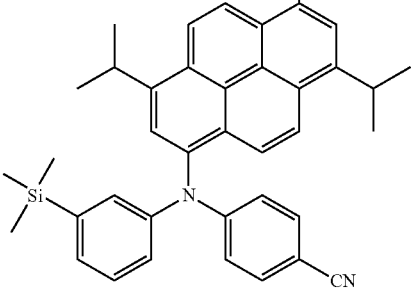
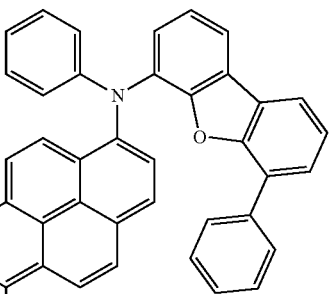
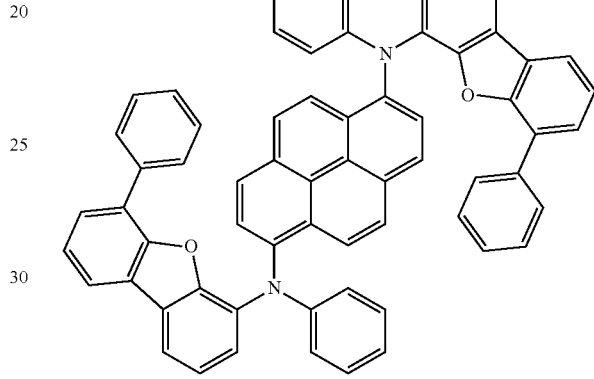
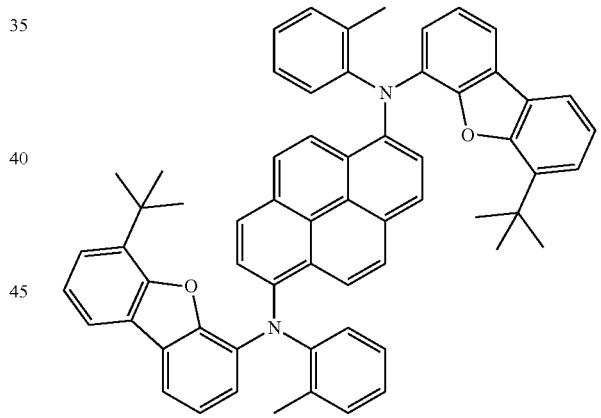
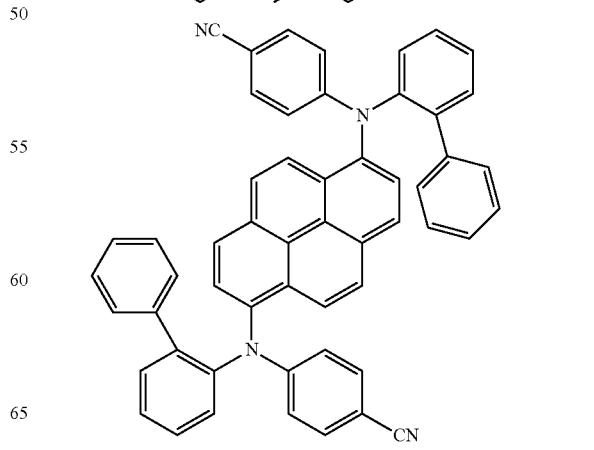

-continued

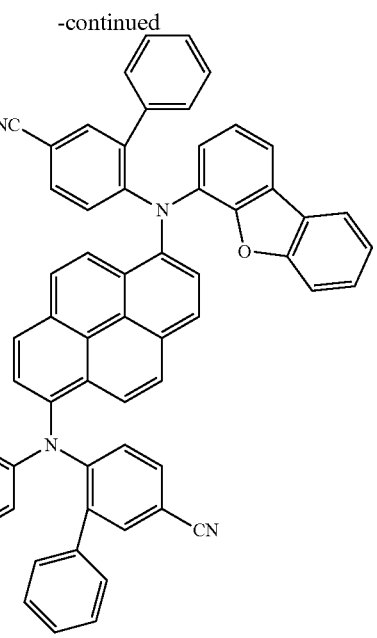

According to one embodiment of the present specification, the organic material layer includes a light emitting layer, and the light emitting layer may include a compound represented by the following Chemical Formula 6.

[Chemical Formula 6]

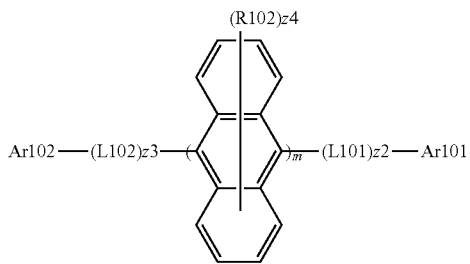

In Chemical Formula 6,

Ar101 and Ar102 are the same as or different from each other, and each independently a substituted or unsubstituted aryl group; or a substituted or unsubstituted heterocyclic group, L101 and L102 are the same as or different from each other, and each independently a direct bond; a substituted or unsubstituted arylene group; or a substituted or unsubstituted heteroarylene group, R102 is hydrogen; deuterium; a halogen group; a nitrile group; a nitro group; a hydroxyl group; a carbonyl group; an ester group; an imide group; a substituted or unsubstituted amine group; a substituted or unsubstituted silyl group; a substituted or unsubstituted boron group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted aralkyl group; a substituted or unsubstituted aralkenyl group; a substituted or unsubstituted alkylaryl group; a substituted or unsubstituted alkylamine group; a substituted or unsubstituted aralkylamine group; a substituted or unsubstituted heteroarylamine group; a substituted or unsubstituted arylamine group; a substituted or unsubstituted arylheteroarylamine group; a substituted or unsubstituted arylphosphine group; a substituted or unsubstituted phosphine oxide group; a substituted or unsubstituted aryl group; or a substituted or unsubstituted heterocyclic group, z2 and z3 are the same as or different from each other and each independently an integer of 1 or 2, z4 is an integer of 0 to 8, and when z2 to z4 are 2 or greater, substituents in the parentheses are the same as or different from each other, m is an integer of 1 or greater, and when m is an integer of 2 or greater, substituents in the parentheses are the same as or different from each other.

According to one embodiment of the present specification, the light emitting layer includes the compound represented by Chemical Formula 6 as a host of the light emitting layer.

According to one embodiment of the present specification, Ar101 and Ar102 are the same as or different from each other, and each independently a substituted or unsubstituted aryl group having 6 to 60 carbon atoms; or a substituted or unsubstituted heterocyclic group having 2 to 60 carbon atoms.

According to one embodiment of the present specification, Ar101 and Ar102 are the same as or different from each other, and each independently an aryl group having 6 to 60 carbon atoms unsubstituted or substituted with an alkyl group, an aryl group or a heterocyclic group; or a heterocyclic group having 2 to 60 carbon atoms unsubstituted or substituted with an alkyl group, an aryl group or a heterocyclic group.

According to one embodiment of the present specification, Ar101 and Ar102 are the same as or different from each other, and each independently a phenyl group unsubstituted or substituted with an aryl group or a heterocyclic group; a biphenyl group unsubstituted or substituted with an aryl group or a heterocyclic group; a terphenyl group unsubstituted or substituted with an aryl group or a heterocyclic group; a naphthyl group unsubstituted or substituted with an aryl group or a heterocyclic group; a fluorene group unsubstituted or substituted with an alkyl group, an aryl group or a heterocyclic group; a phenanthrene group unsubstituted or substituted with an aryl group or a heterocyclic group; or a triphenylene group unsubstituted or substituted with an aryl group or a heterocyclic group.

According to one embodiment of the present specification, Ar101 and Ar102 are the same as or different from each other, and each independently a phenyl group; a biphenyl group; a terphenyl group; a naphthyl group; a fluorene group unsubstituted or substituted with a methyl group or a phenyl group; a phenanthrene group; or a triphenylene group.

According to one embodiment of the present specification, Ar101 is a 2-naphthyl group.

According to one embodiment of the present specification, Ar102 is a 1-naphthyl group.

According to one embodiment of the present specification, L101 and L102 are the same as or different from each other, and each independently a direct bond; a phenylene group; or a naphthylene group.

According to one embodiment of the present specification, L101 is a phenylene group.

According to one embodiment of the present specification, L102 is a direct bond.

According to one embodiment of the present specification, R102 is hydrogen.

According to one embodiment of the present specification, z2 is 1.

According to one embodiment of the present specification, m is 1.

According to one embodiment of the present specification, m is 2.

According to one embodiment of the present specification, Chemical Formula 6 may be selected from among the following compounds.

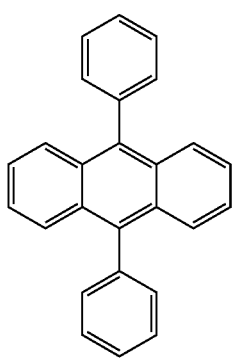

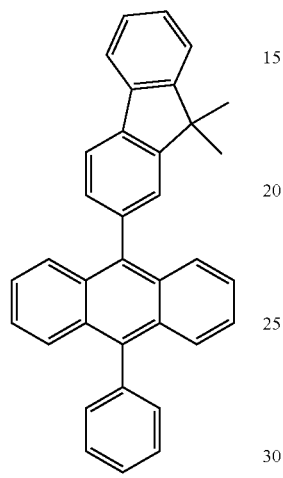

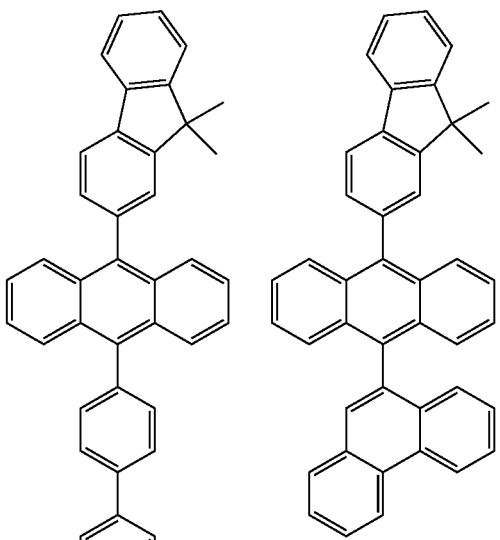

-continued

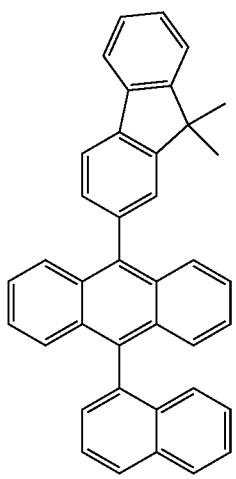

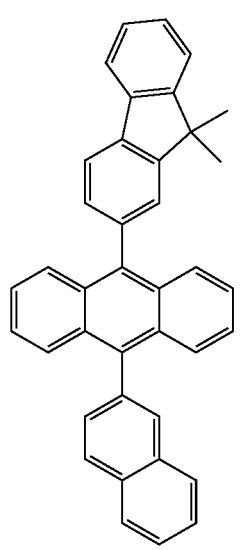

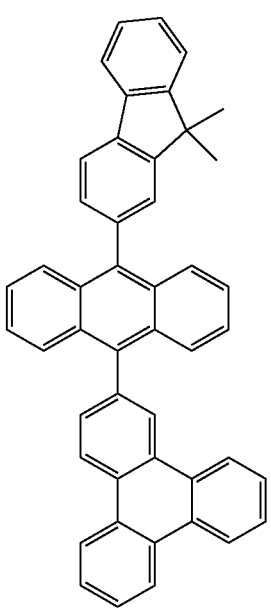

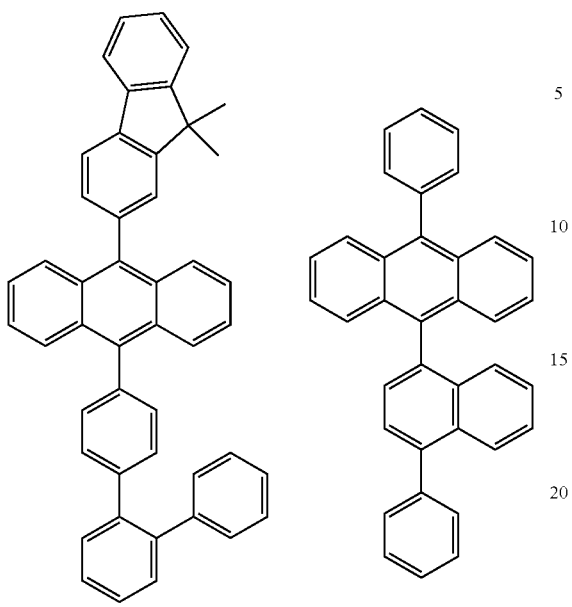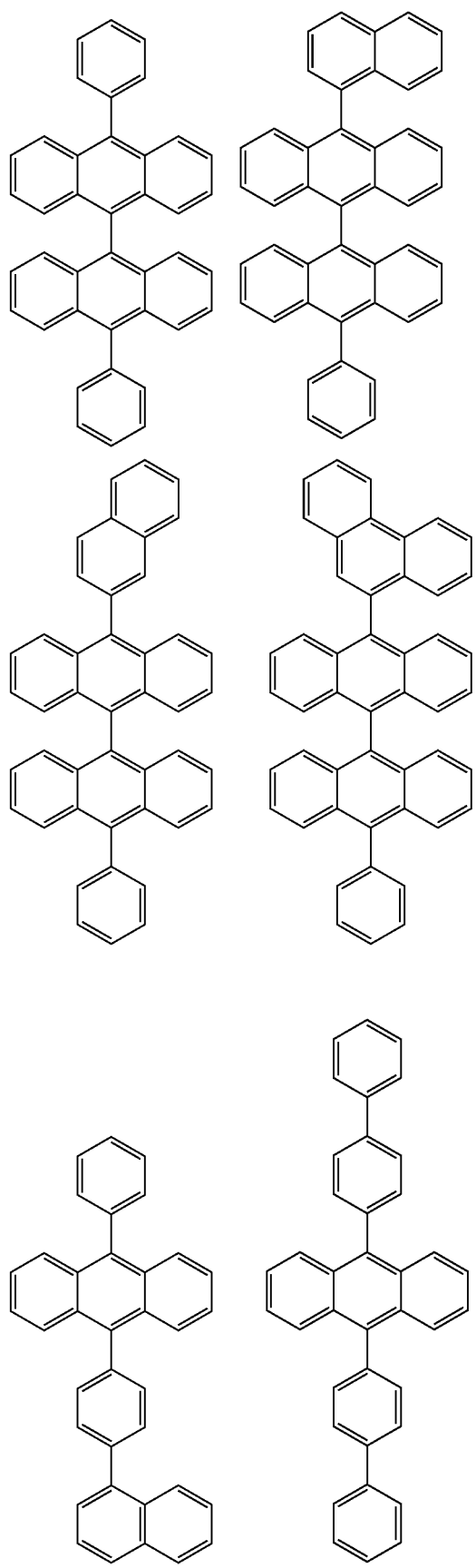

-continued
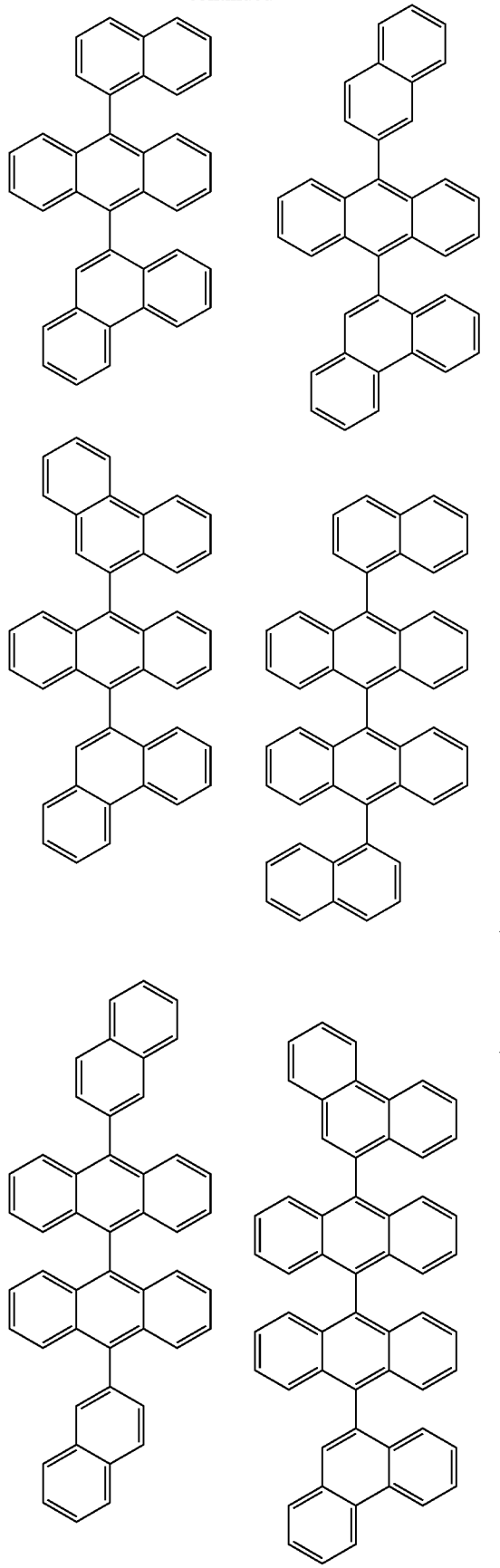
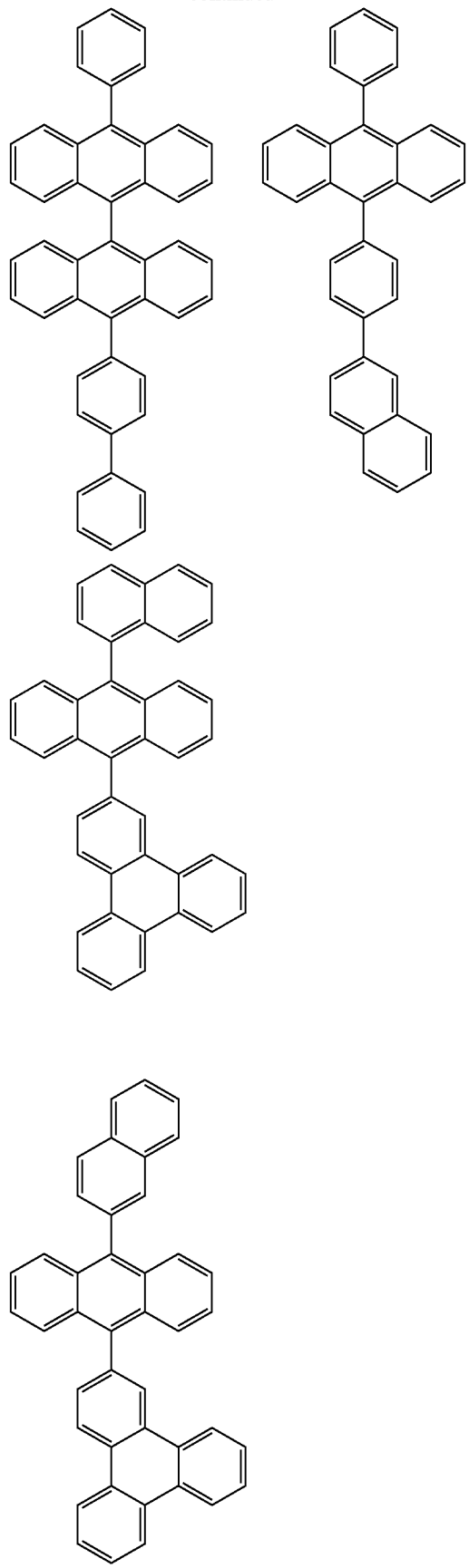

83
-continued
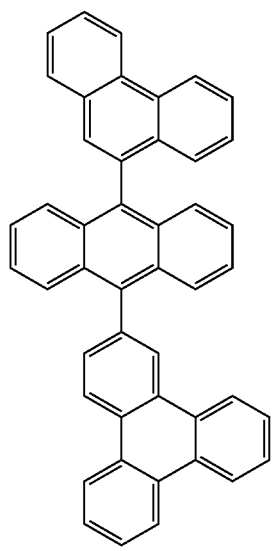
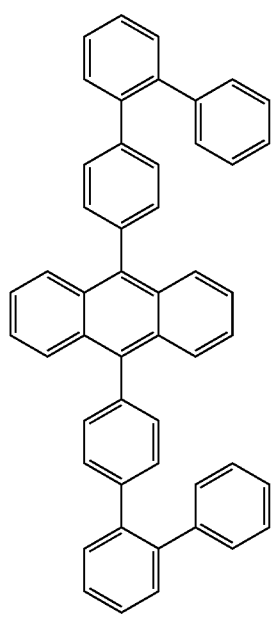
84
-continued
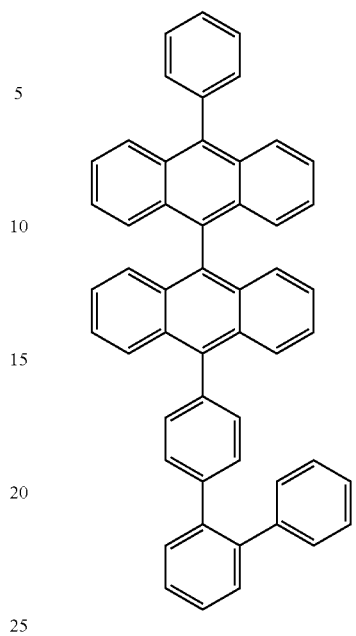
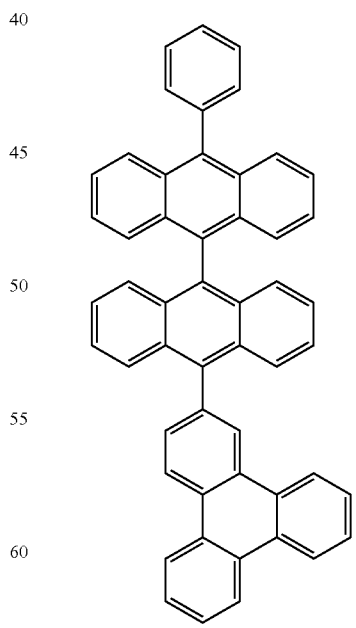

85
-continued
86
-continued
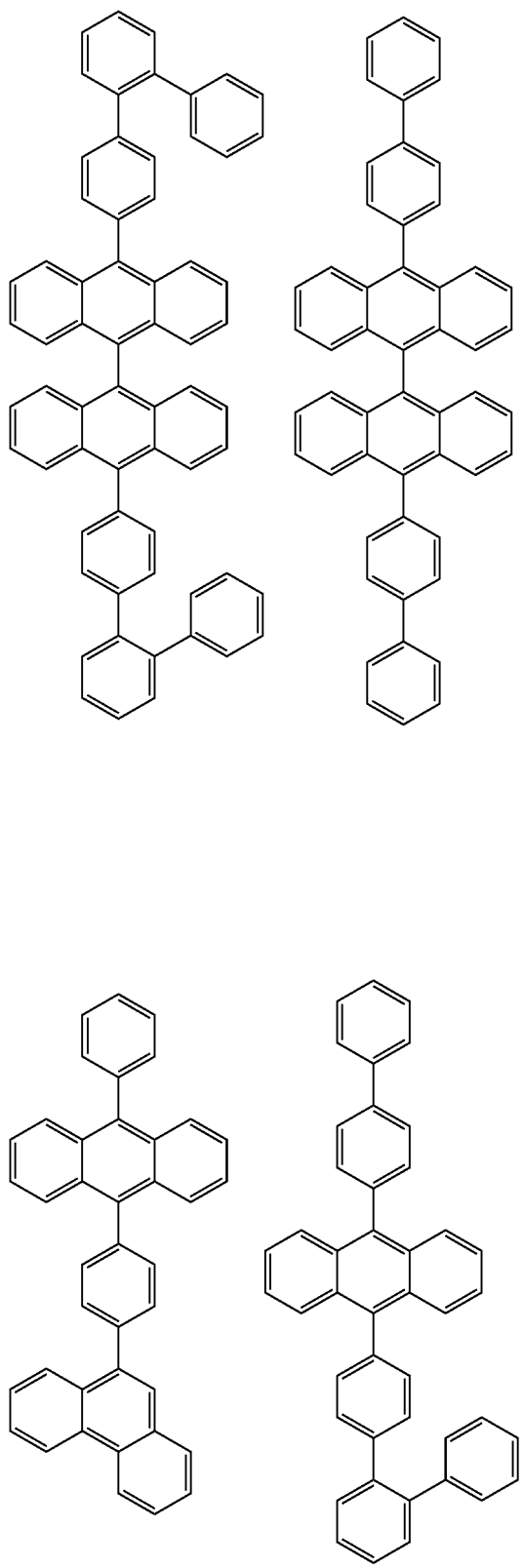

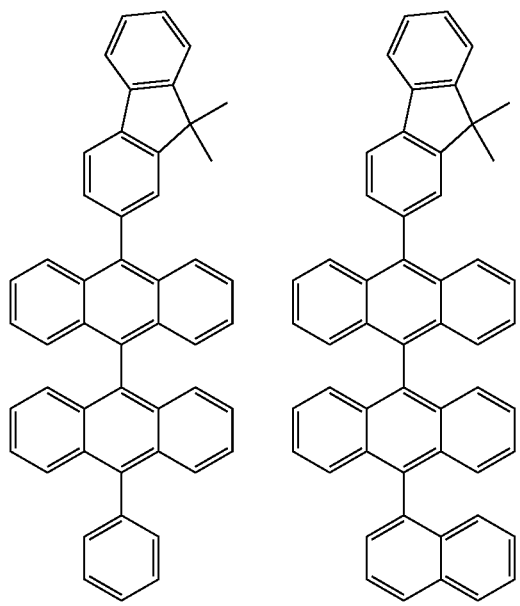
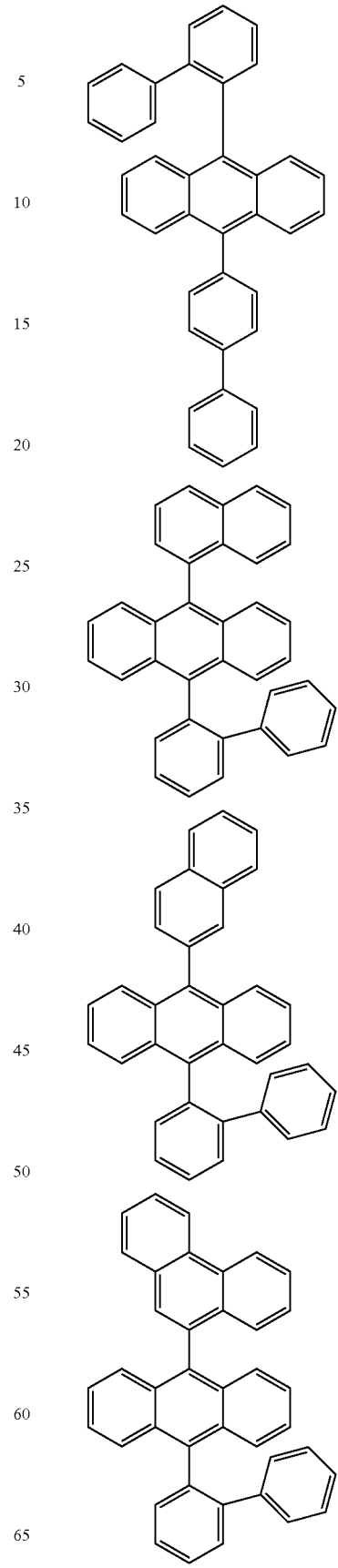

89
-continued
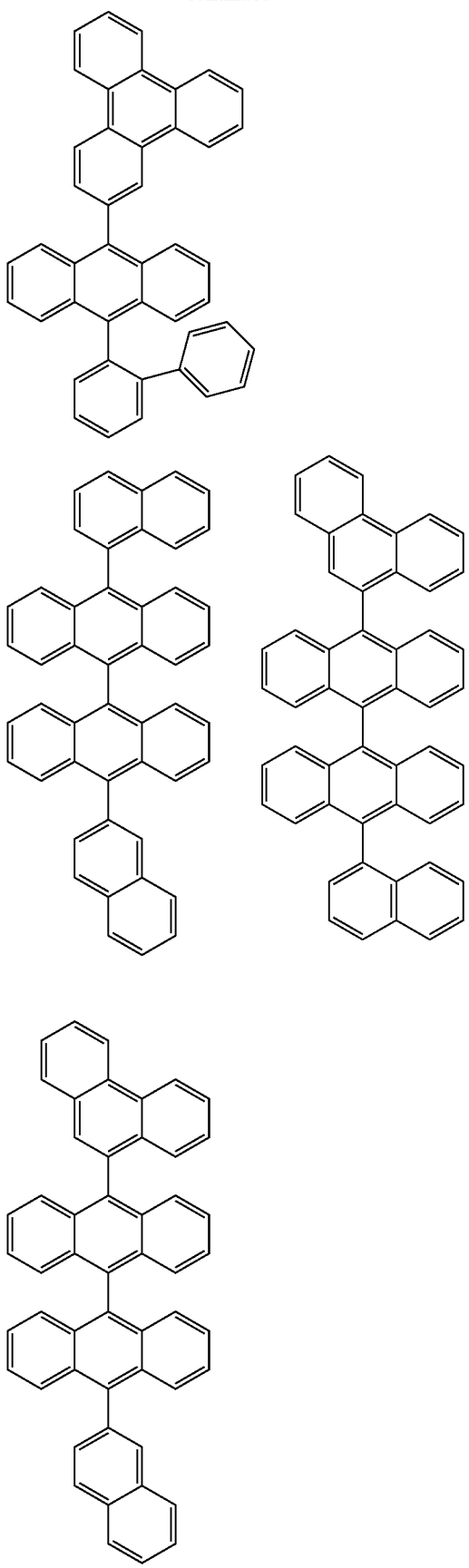
90
-continued
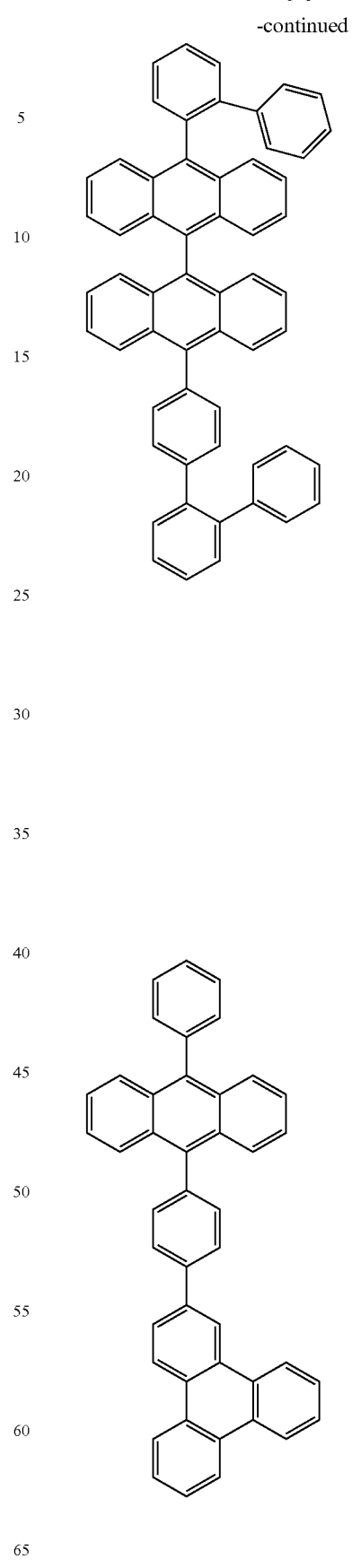

91
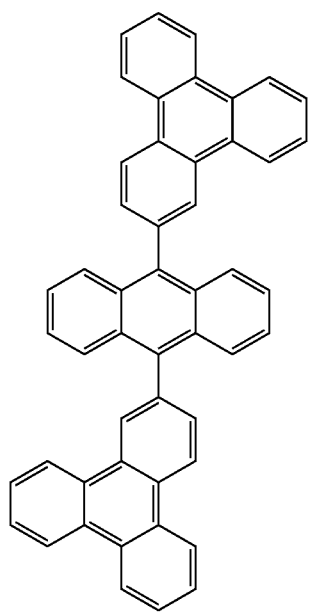
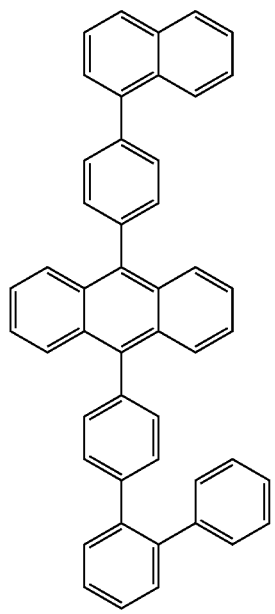
92
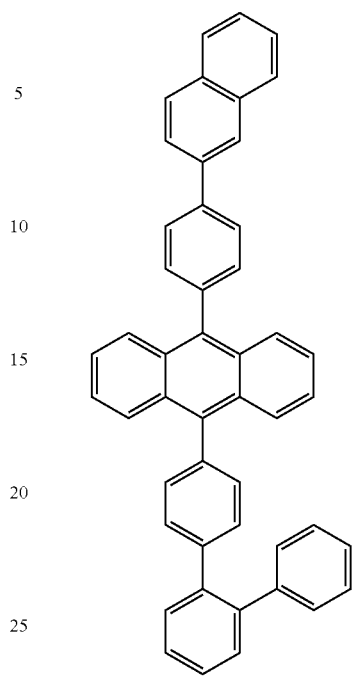
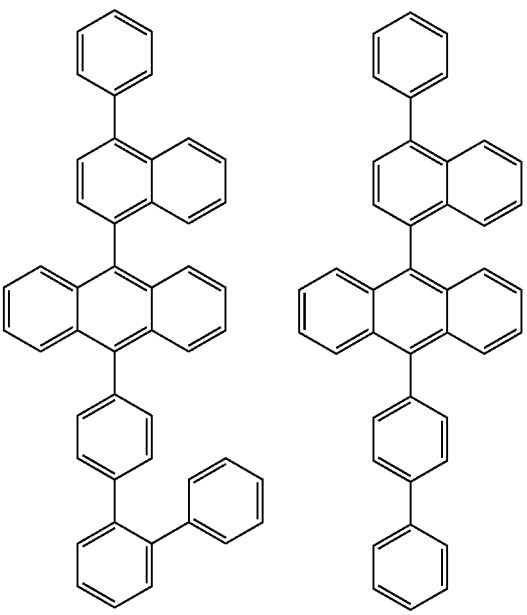

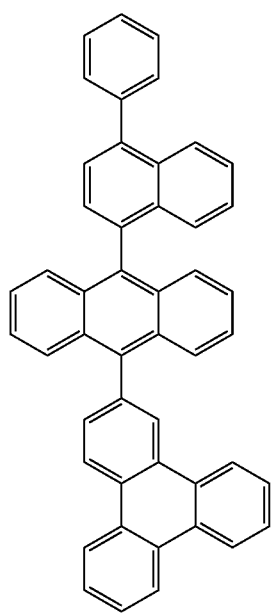
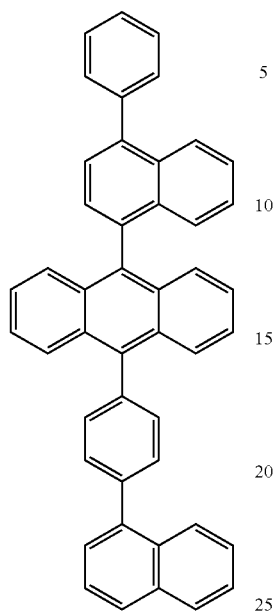
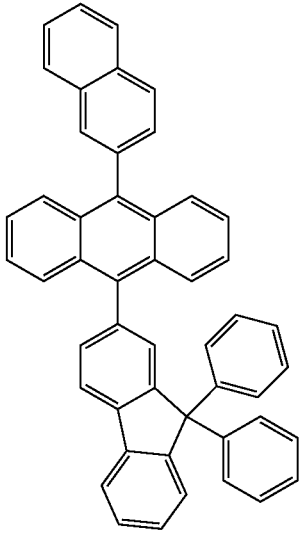
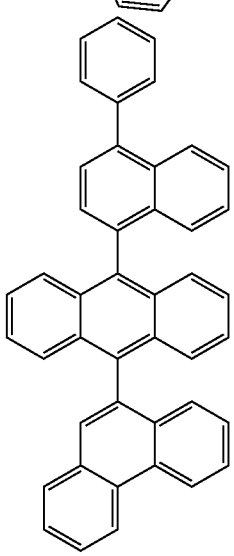
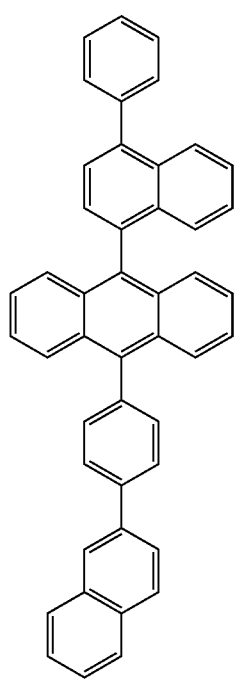
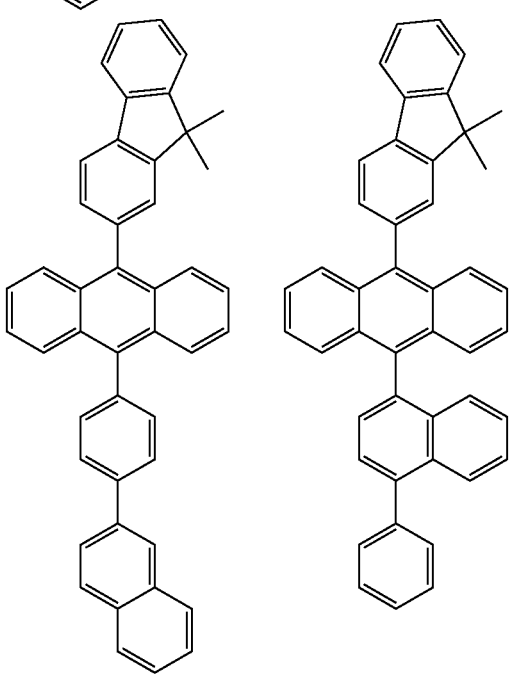

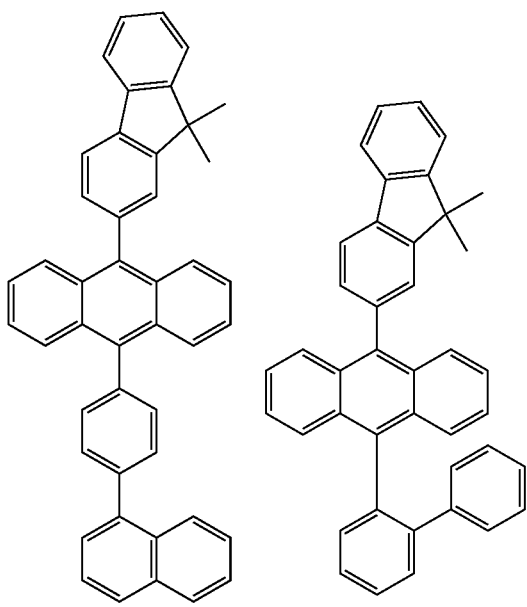
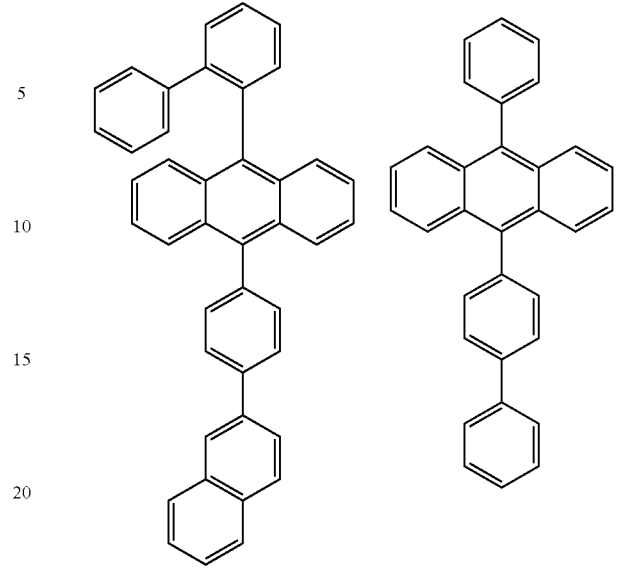
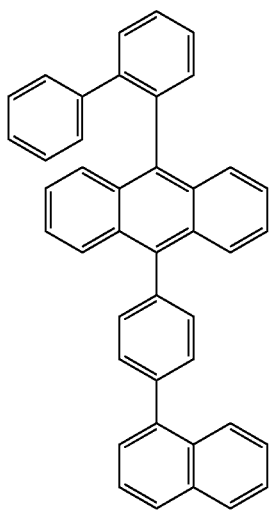
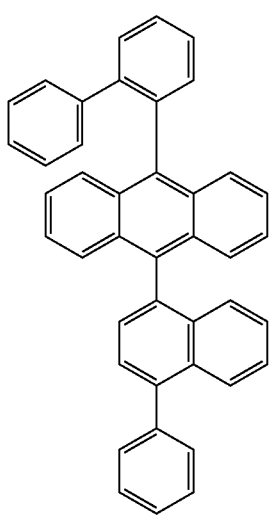

According to one embodiment of the present specification, the organic material layer includes a light emitting layer, and the light emitting layer includes the compound represented by Chemical Formula 5 as a dopant of the light emitting layer and includes the compound represented by Chemical Formula 6 as a host of the light emitting layer.

The organic light emitting device of the present specification may be manufactured using materials and methods known in the art, except that one or more layers of the organic material layers include the compound of the present specification, that is, the compound of Chemical Formula 1.

When the organic light emitting device includes a plurality of organic material layers, the organic material layers may be formed with materials the same as or different from each other.

For example, the organic light emitting device of the present specification may be manufactured by consecutively laminating a first electrode, an organic material layer and a second electrode on a substrate. Herein, the organic light emitting device may be manufactured by forming an anode on a substrate by depositing a metal, a metal oxide having conductivity, or an alloy thereof using a physical vapor deposition (PVD) method such as sputtering or e-beam evaporation, and forming an organic material layer including a hole injection layer, a hole transfer layer, a light emitting layer and an electron transfer layer thereon, and then depositing a material capable of being used as a cathode thereon. In addition to such a method, the organic light emitting device may also be manufactured by consecutively depositing a cathode material, an organic material layer and an anode material on a substrate.

In addition, the compound of Chemical Formula 1 may be formed into the organic material layer using a solution coating method as well as a vacuum deposition method when manufacturing the organic light emitting device. Herein, the solution coating method means spin coating, dip coating, doctor blading, inkjet printing, screen printing, a spray method, roll coating and the like, but is not limited thereto.

In addition to such a method, the organic light emitting device may be manufactured by consecutively depositing a cathode material, an organic material layer and an anode material on a substrate (International Patent Application Laid-Open Publication No. 2003/012890). However, the manufacturing method is not limited thereto.

In one embodiment of the present specification, the first electrode is an anode, and the second electrode is a cathode.

In another embodiment, the first electrode is a cathode, and the second electrode is an anode.

As the anode material, materials having large work function are normally preferable so that hole injection to an organic material layer is smooth. Specific examples of the anode material capable of being used in the present disclosure include metals such as vanadium, chromium, copper, zinc and gold, or alloys thereof; metal oxides such as zinc oxide, indium oxide, indium tin oxide (ITO) and indium zinc oxide (IZO); combinations of metals and oxides such as $ZnO:Al$ or $SnO_2:Sb$; conductive polymers such as poly(3-methylthiophene), poly[3,4-(ethylene-1,2-dioxy)thiophene] (PEDOT), polypyrrole and polyaniline, but are not limited thereto.

As the cathode material, materials having small work function are normally preferable so that electron injection to an organic material layer is smooth. Specific examples of the cathode material capable of being used in the present disclosure include metals such as magnesium, calcium, sodium, potassium, titanium, indium, yttrium, lithium, gadolinium, aluminum, silver, tin and lead, or alloys thereof; multilayer structure materials such as LiF/Al or $LiO_2$/Al, and the like, but are not limited thereto.

The hole injection layer is a layer that injects holes from an electrode, and the hole injection material is preferably a compound that has an ability to transfer holes, therefore, has a hole injection effect in an anode, has an excellent hole injection effect for a light emitting layer or a light emitting material, prevents excitons generated in the light emitting layer from moving to an electron injection layer or an electron injection material, and in addition, has an excellent thin film forming ability. The highest occupied molecular orbital (HOMO) of the hole injection material is preferably in between the work function of an anode material and the HOMO of surrounding organic material layers. Specific examples of the hole injection material include metal porphyrins, oligothiophene, arylamine-based organic materials, hexanitrile hexaazatriphenylene-based organic materials, quinacridone-based organic materials, perylene-based organic materials, anthraquinone, and polyaniline- and polythiophene-based conductive polymers, and the like, but are not limited thereto.

The hole transfer layer is a layer that receives holes from a hole injection layer and transfers the holes to a light emitting layer, and as the hole transfer material, materials capable of receiving holes from an anode or a hole injection layer, moving the holes to a light emitting layer, and having high mobility for the holes are suitable. Specific examples thereof include arylamine-based organic materials, conductive polymers, block copolymers having conjugated parts and non-conjugated parts together, and the like, but are not limited thereto.

The light emitting material is a material capable of emitting light in a visible light region by receiving holes and electrons from a hole transfer layer and an electron transfer layer, respectively, and binding the holes and the electrons, and is preferably a material having favorable quantum efficiency for fluorescence or phosphorescence. Specific examples thereof include 8-hydroxyquinoline aluminum complexes ($Alq_3$); carbazole-based compounds; dimerized styryl compounds; BAlq; 10-hydroxybenzo quinoline-metal compounds; benzoxazole-, benzthiazole- and benzimidazole-based compounds; poly(p-phenylenevinylene) (PPV)-based polymers; spiro compounds; polyfluorene, rubrene, and the like, but are not limited thereto.

The light emitting layer may include a host material and a dopant material. The host material includes fused aromatic ring derivatives, heteroring-containing compounds or the like. Specifically, the fused aromatic ring derivative includes anthracene derivatives, pyrene derivatives, naphthalene derivatives, pentacene derivatives, phenanthrene compounds, fluoranthene compounds and the like, and the heteroring-containing compound includes carbazole derivatives, dibenzofuran derivatives, ladder-type furan compounds, pyrimidine derivatives and the like, but the material is not limited thereto.

The dopant material includes aromatic amine derivatives, styrylamine compounds, boron complexes, fluoranthene compounds, metal complexes and the like. Specifically, the aromatic amine derivative is a fused aromatic ring derivative having a substituted or unsubstituted arylamine group and includes arylamine group-including pyrene, anthracene, chrysene, peryflanthene and the like, and the styrylamine compound is a compound in which substituted or unsubstituted arylamine is substituted with at least one arylvinyl group, and one, two or more substituents selected from the group consisting of an aryl group, a silyl group, an alkyl group, a cycloalkyl group and an arylamine group are substituted or unsubstituted. Specifically, styrylamine, styryldiamine, styryltriamine, styryltetramine or the like is included, but the styrylamine compound is not limited thereto. In addition, the metal complex includes iridium complexes, platinum complexes or the like, but is not limited thereto.

The electron transfer layer is a layer that receives electrons from an electron injection layer and transfers the electrons to a light emitting layer, and as the electron transfer material, materials capable of favorably receiving electrons from a cathode, moving the electrons to a light emitting layer, and having high mobility for the electrons are suitable. Specific examples thereof include Al complexes of 8-hydroxyquinoline; complexes including $Alq_3$; organic radical compounds; hydroxyflavon-metal complexes, and the like, but are not limited thereto. The electron transfer layer may be used together with any desired cathode material as used in the art. Particularly, examples of the suitable cathode material include common materials that have small work function, and in which an aluminum layer or a silver layer follows. Specifically, the cathode material includes cesium, barium, calcium, ytterbium and samarium, and in each case, an aluminum layer or a silver layer follows.

The electron injection layer is a layer that injects electrons from an electrode, and the electron injection material is preferably a compound that has an ability to transfer electrons, has an electron injection effect from a cathode, has an excellent electron injection effect for a light emitting layer or a light emitting material, prevents excitons generated in the light emitting layer from moving to a hole injection layer, and in addition, has an excellent thin film forming ability. Specific examples thereof include fluorenone, anthraquinodimethane, diphenoquinone, thiopyran dioxide, oxazole, oxadiazole, triazole, imidazole, perylene tetracarboxylic acid, fluorenylidene methane, anthrone or the like, and derivatives thereof, metal complex compounds, nitrogen-containing 5-membered ring derivatives, and the like, but are not limited thereto.

The metal complex compound includes 8-hydroxyquinolinato lithium, bis(8-hydroxyquinolinato)zinc, bis(8-hydroxyquinolinato)copper, bis(8-hydroxyquinolinato)manganese, tris(8-hydroxyquinolinato)aluminum, tris(2-methyl-8- hydroxyquinolinato)aluminum, tris(8-hydroxyquinolinato)gallium, bis(10-hydroxybenzo[h]quinolinato)berylium, bis(10-hydroxybenzo[h]quinolinato)zinc, bis(2-methyl-8-quinolinato)chlorogallium, bis(2-methyl-8-quinolinato)(o-cresolato)gallium, bis(2-methyl-8-quinolinato) (1-naphtholato)aluminum, bis(2-methyl-8-quinolinato) (2-naphtholato)gallium and the like, but is not limited thereto.

The organic light emitting device according to the present specification may be a top-emission type, a bottom-emission type or a dual-emission type depending on the materials used.

In one embodiment of the present specification, the compound of Chemical Formula 1 may be included in an organic solar cell or an organic transistor in addition to an organic light emitting device.

Preparation of the compound represented by Chemical Formula 1, and manufacture of the organic light emitting device including the same will be specifically described with reference to the following examples. However, the following examples are for illustrative purposes only, and the scope of the present specification is not limited thereto.

PREPARATION EXAMPLE 1

Compound Synthesis of the following Compound 1

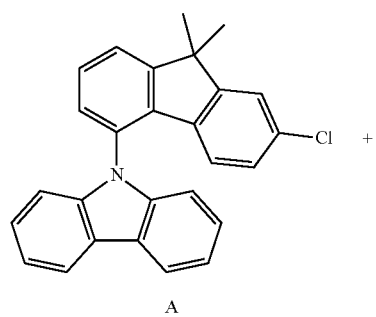

A

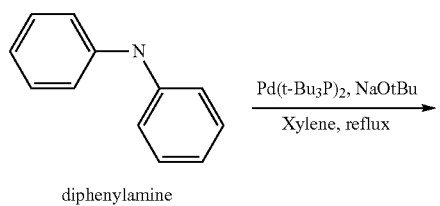

diphenylamine

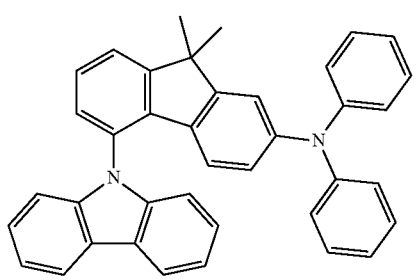

After completely dissolving Compound A (15.0 g, 38.17 mmol) and diphenylamine (7.10 g, 41.98 mmol) in 160 ml of xylene in a 500 ml round bottom flask under nitrogen atmosphere, sodium tert-butoxide (4.40 g, 45.80 mmol) and then bis(tri-tert-butylphosphine)palladium(0) (0.20 g, 0.38 mmol) were added thereto, and the result was heated and stirred for 3 hours. The result was cooled to room temperature, filtered to remove the base, and then xylene was vacuum concentrated. The result was recrystallized with 250 ml of ethyl acetate to prepare Compound 1 (14.55 g, yield: 72%).

MS[M+H]$^+$=527

PREPARATION EXAMPLE 2

Compound Synthesis of the following Compound 2

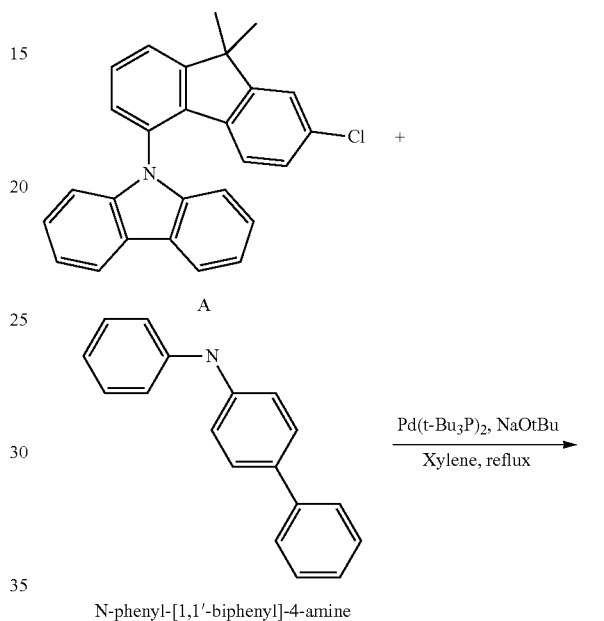

N-phenyl-[1,1'-biphenyl]-4-amine

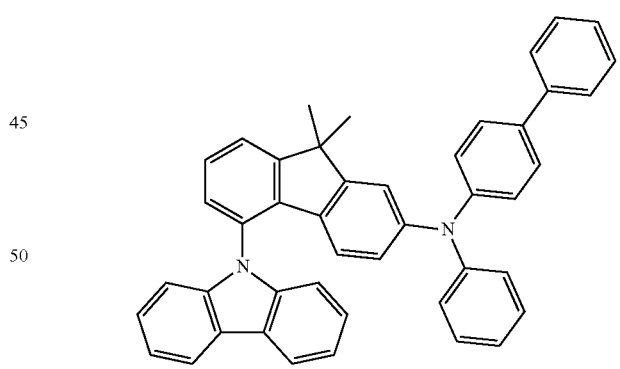

After completely dissolving Compound A (15.0 g, 38.17 mmol) and N-phenyl-[1,1'-biphenyl]-4-amine (10.29 g, 41.98 mmol) in 180 ml of xylene in a 500 ml round bottom flask under nitrogen atmosphere, sodium tert-butoxide (4.40 g, 45.80 mmol) and then bis(tri-tert-butylphosphine)palladium(0) (0.20 g, 0.38 mmol) were added thereto, and the result was heated and stirred for 8 hours. The result was cooled to room temperature, filtered to remove the base, and then xylene was vacuum concentrated. The result was recrystallized with 270 ml of ethyl acetate to prepare Compound 2 (16.17 g, yield: 70%).

MS[M+H]$^+$=603

PREPARATION EXAMPLE 3

Compound Synthesis of the following Compound 3

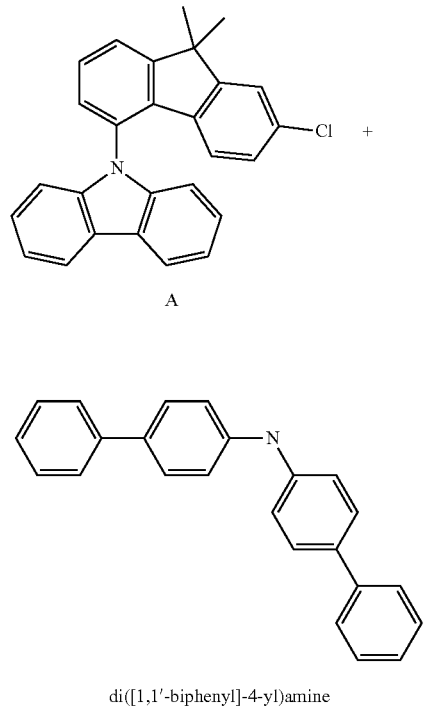

di([1,1'-biphenyl]-4-yl)amine

After completely dissolving Compound A (15.0 g, 38.17 mmol) and di([1,1'-biphenyl]-4-yl)amine (13.48 g, 41.98 mmol) in 200 ml of xylene in a 500 ml round bottom flask under nitrogen atmosphere, sodium tert-butoxide (4.40 g, 45.80 mmol) and then bis(tri-tert-butylphosphine)palladium(0) (0.20 g, 0.38 mmol) were added thereto, and the result was heated and stirred for 6 hours. The result was cooled to room temperature, filtered to remove the base, and then xylene was vacuum concentrated. The result was recrystallized with 290 ml of ethyl acetate to prepare Compound 3 (21.45 g, yield: 83%).

MS[M+H]$^+$=679

PREPARATION EXAMPLE 4

Compound Synthesis of the following Compound 4

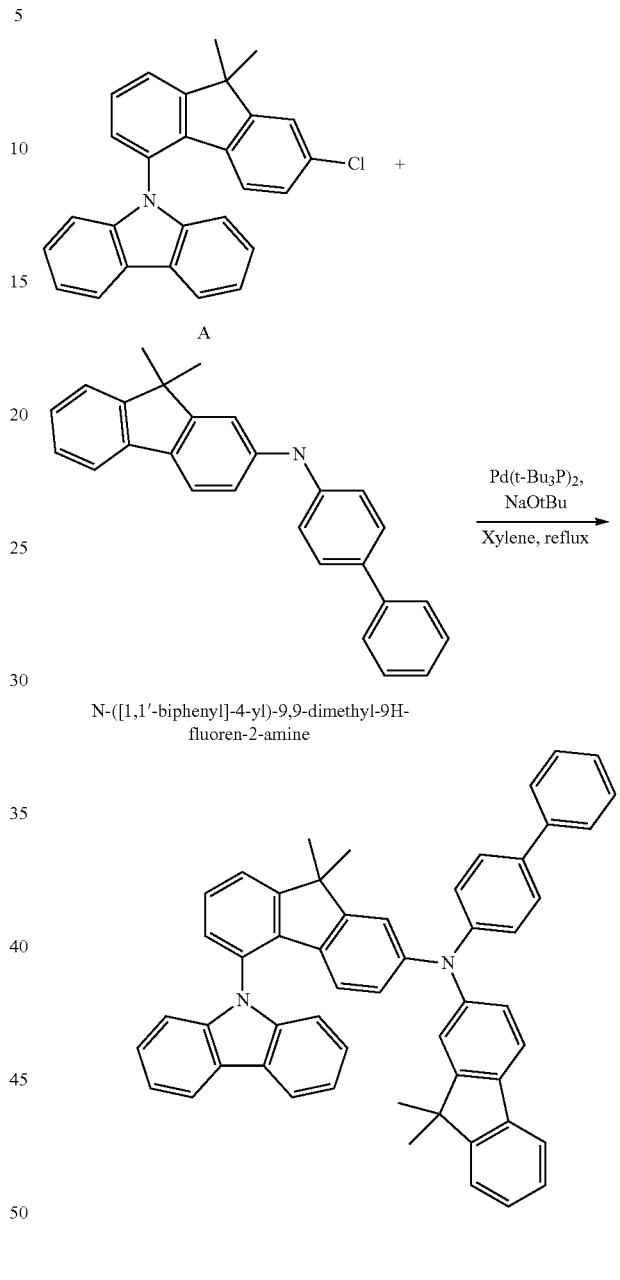

N-([1,1'-biphenyl]-4-yl)-9,9-dimethyl-9H-fluoren-2-amine

After completely dissolving Compound A (15.0 g, 38.17 mmol) and N-([1,1'-biphenyl]-4-yl)-9,9-dimethyl-9H-fluorene-2-amine (15.16 g, 41.98 mmol) in 180 ml of xylene in a 500 ml round bottom flask under nitrogen atmosphere, sodium tert-butoxide (4.40 g, 45.80 mmol) and then bis(tri-tert-butylphosphine)palladium(0) (0.20 g, 0.38 mmol) were added thereto, and the result was heated and stirred for 4 hours. The result was cooled to room temperature, filtered to remove the base, and then xylene was vacuum concentrated. The result was recrystallized with 180 ml of ethyl acetate to prepare Compound 4 (24.56 g, yield: 89%).

MS[M+H]$^+$=719

PREPARATION EXAMPLE 5

Compound Synthesis of the following Compound 5

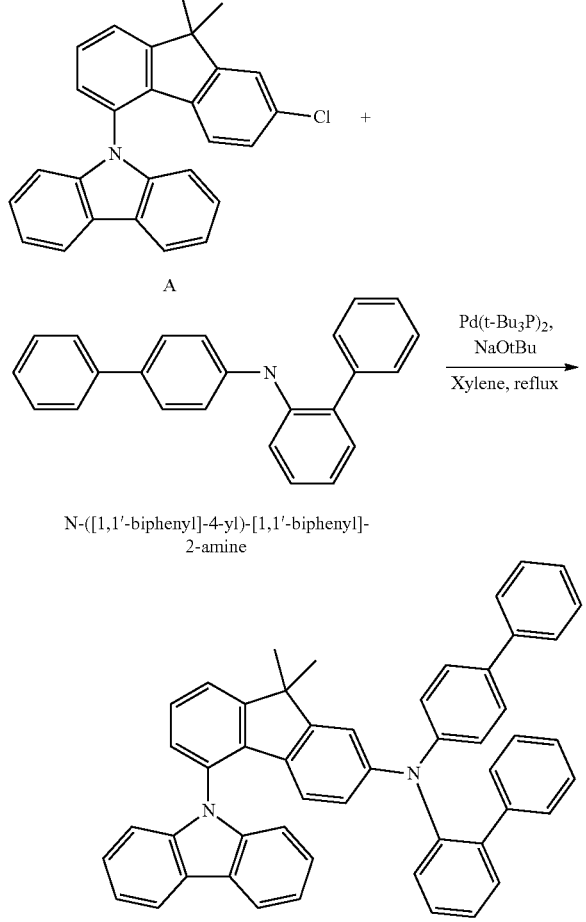

N-([1,1'-biphenyl]-4-yl)-[1,1'-biphenyl]-2-amine

After completely dissolving Compound A (15.0 g, 38.17 mmol) and N-([1,1'-biphenyl]-4-yl)-[1,1'-biphenyl]-2-amine (13.48 g, 41.98 mmol) in 200 ml of xylene in a 500 ml round bottom flask under nitrogen atmosphere, sodium tert-butoxide (4.40 g, 45.80 mmol) and then bis(tri-tert-butylphosphine)palladium(0) (0.20 g, 0.38 mmol) were added thereto, and the result was heated and stirred for 3 hours. The result was cooled to room temperature, filtered to remove the base, and then xylene was vacuum concentrated. The result was recrystallized with 230 ml of ethyl acetate to prepare Compound 5 (18.86 g, yield: 73%).

MS[M+H]$^+$=679

PREPARATION EXAMPLE 6

Compound Synthesis of the following Compound 6

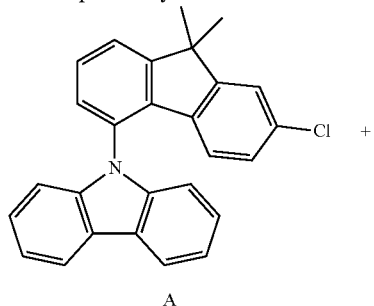

-continued

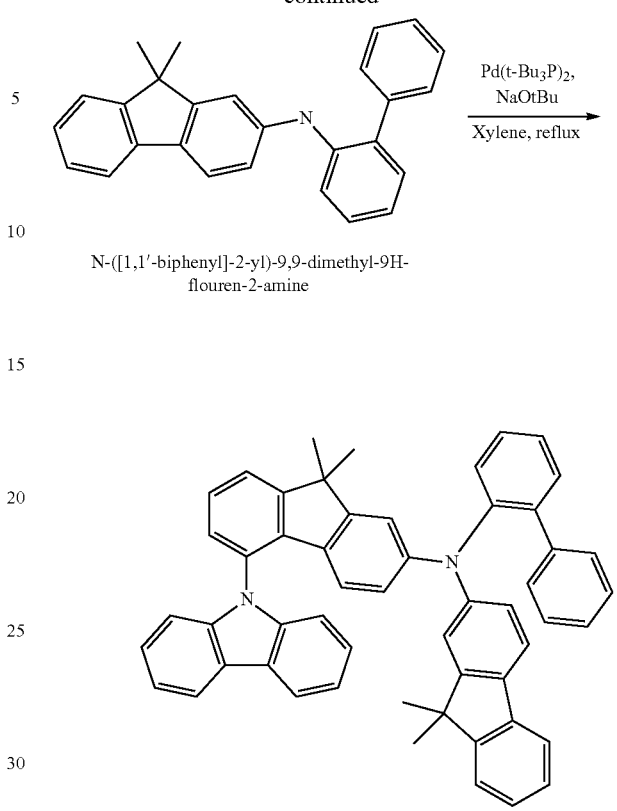

N-([1,1'-biphenyl]-2-yl)-9,9-dimethyl-9H-flouren-2-amine

After completely dissolving Compound A (15.0 g, 38.17 mmol) and N-([1,1'-biphenyl]-2-yl)-9,9-dimethyl-9H-fluorene-2-amine (15.16 g, 41.98 mmol) in 180 ml of xylene in a 500 ml round bottom flask under nitrogen atmosphere, sodium tert-butoxide (4.40 g, 45.80 mmol) and then bis(tri-tert-butylphosphine)palladium(0) (0.20 g, 0.38 mmol) were added thereto, and the result was heated and stirred for 5 hours. The result was cooled to room temperature, filtered to remove the base, and then xylene was vacuum concentrated. The result was recrystallized with 210 ml of ethyl acetate to prepare Compound 6 (23.22 g, yield: 85%).

MS[M+H]$^+$=719

PREPARATION EXAMPLE 7

Compound Synthesis of the following Compound 7

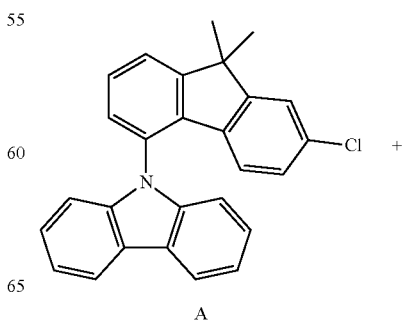

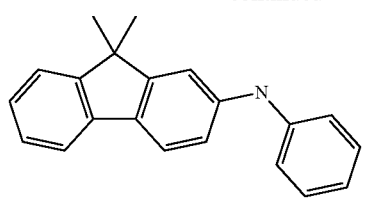

9,9-dimethyl-N-phenyl-9H-flouren-2-amine

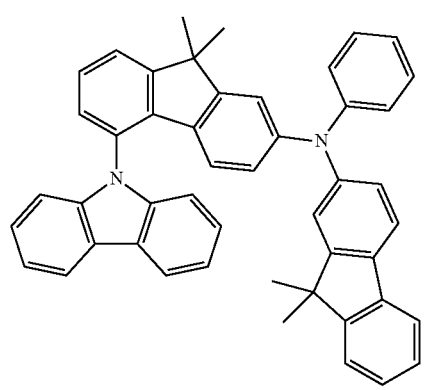

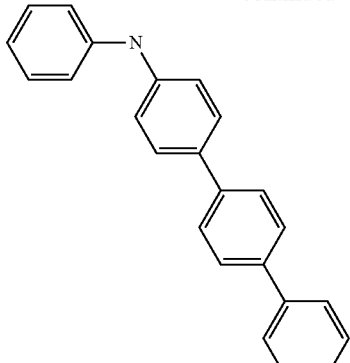

N-phenyl-[1,1':4',1''-terphenyl]-4-amine

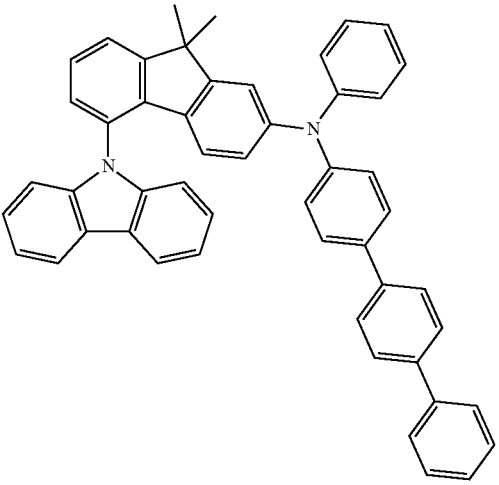

After completely dissolving Compound A (15.0 g, 38.17 mmol) and 9,9-dimethyl-N-phenyl-9H-fluorene-2-amine (15.16 g, 41.98 mmol) in 180 ml of xylene in a 500 ml round bottom flask under nitrogen atmosphere, sodium tert-butoxide (4.40 g, 45.80 mmol) and then bis(tri-tert-butylphosphine)palladium(0) (0.20 g, 0.38 mmol) were added thereto, and the result was heated and stirred for 2 hours. The result was cooled to room temperature, filtered to remove the base, and then xylene was vacuum concentrated. The result was recrystallized with 210 ml of ethyl acetate to prepare Compound 7 (21.01 g, yield: 86%).

MS[M+H]$^+$=643

PREPARATION EXAMPLE 8

Compound Synthesis of the following Compound 8

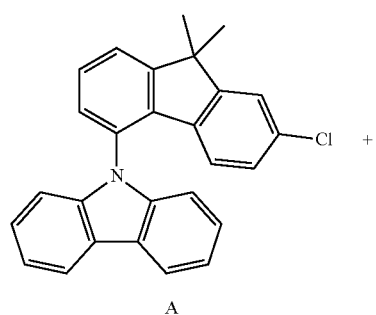

A

After completely dissolving Compound A (15.0 g, 38.17 mmol) and N-phenyl-[1,1':4',1''-terphenyl]-4-amine (13.48 g, 41.98 mmol) in 200 ml of xylene in a 500 ml round bottom flask under nitrogen atmosphere, sodium tert-butoxide (4.40 g, 45.80 mmol) and then bis(tri-tert-butylphosphine)palladium(0) (0.20 g, 0.38 mmol) were added thereto, and the result was heated and stirred for 4 hours. The result was cooled to room temperature, filtered to remove the base, and then xylene was vacuum concentrated. The result was recrystallized with 320 ml of ethyl acetate to prepare Compound 8 (22.76 g, yield: 88%).

MS[M+H]$^+$=679

PREPARATION EXAMPLE 9

Compound Synthesis of the following Compound 9

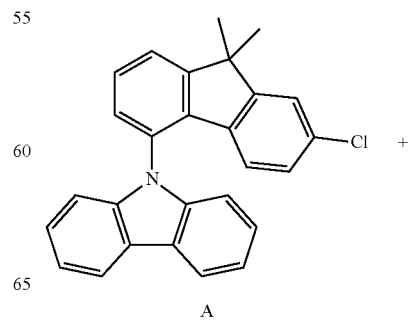

A

-continued

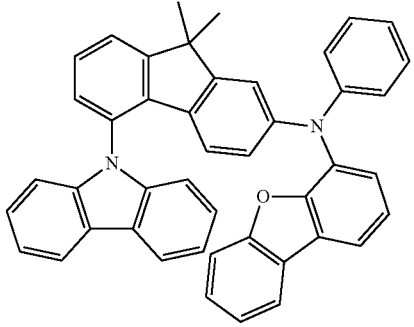

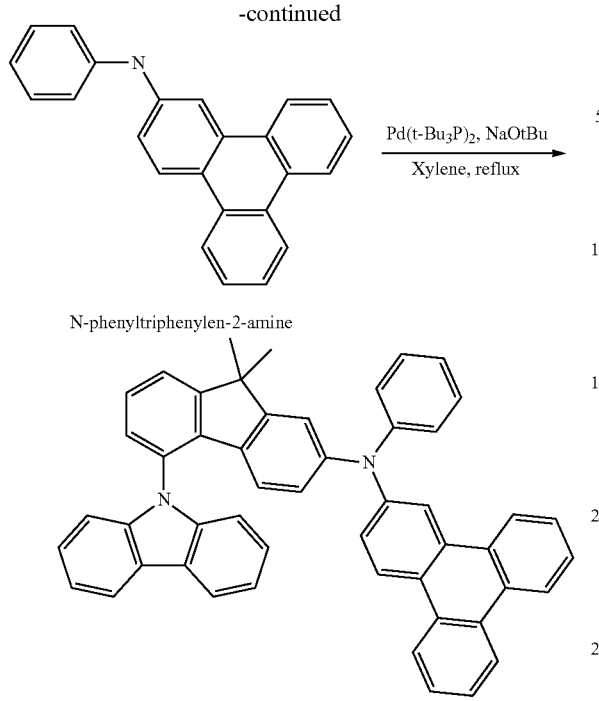

N-phenyltriphenylen-2-amine

After completely dissolving Compound A (15.0 g, 38.17 mmol) and N-phenyltriphenylene-2-amine (13.48 g, 41.98 mmol) in 200 ml of xylene in a 500 ml round bottom flask under nitrogen atmosphere, sodium tert-butoxide (4.40 g, 45.80 mmol) and then bis(tri-tert-butylphosphine)palladium (0) (0.20 g, 0.38 mmol) were added thereto, and the result was heated and stirred for 4 hours. The result was cooled to room temperature, filtered to remove the base, and then xylene was vacuum concentrated. The result was recrystallized with 320 ml of ethyl acetate to prepare Compound 9 (17.36 g, yield: 67%).

MS[M+H]⁺=677

PREPARATION EXAMPLE 10

Compound Synthesis of the following Compound 10

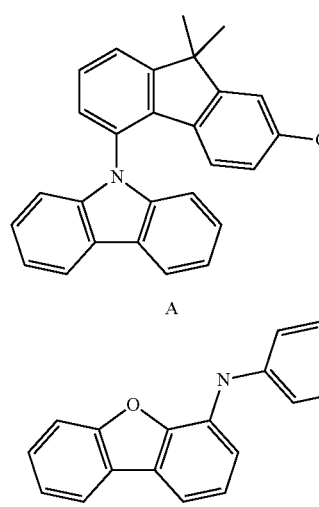

-continued

After completely dissolving Compound A (15.0 g, 38.17 mmol) and N-phenyldibenzo[b,d]furan-4-amine (10.87 g, 41.98 mmol) in 220 ml of xylene in a 500 ml round bottom flask under nitrogen atmosphere, sodium tert-butoxide (4.40 g, 45.80 mmol) and then bis(tri-tert-butylphosphine)palladium(0) (0.20 g, 0.38 mmol) were added thereto, and the result was heated and stirred for 5 hours. The result was cooled to room temperature, filtered to remove the base, and then xylene was vacuum concentrated. The result was recrystallized with 250 ml of ethyl acetate to prepare Compound 10 (16.48 g, yield: 70%).

MS[M+H]⁺=617

PREPARATION EXAMPLE 11

Compound Synthesis of the following Compound 11

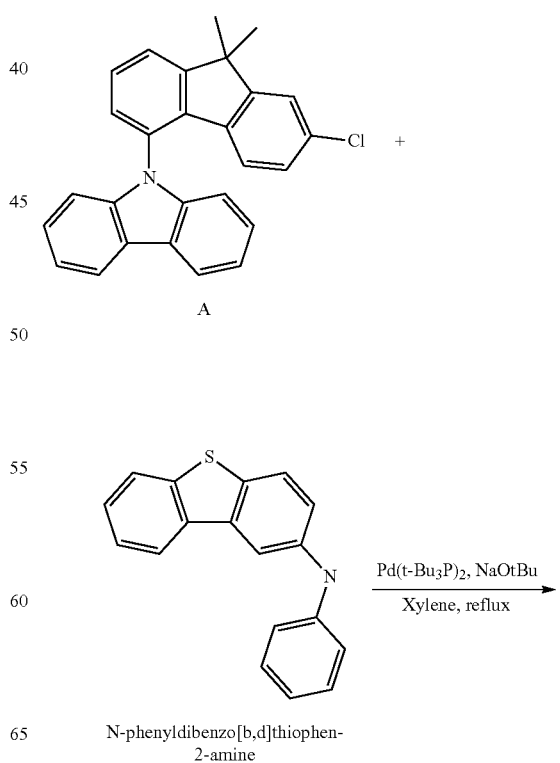

N-phenyldibenzo[b,d]thiophen-2-amine

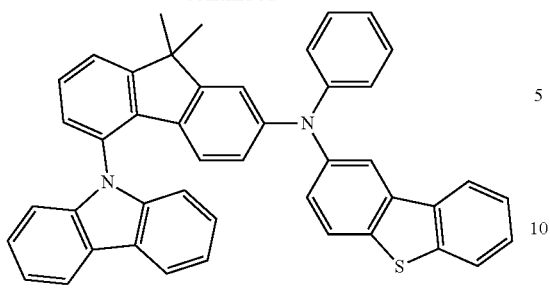

After completely dissolving Compound A (15.0 g, 38.17 mmol) and N-phenyldibenzo[b,d]thiophene-2-amine (11.55 g, 41.98 mmol) in 230 ml of xylene in a 500 ml round bottom flask under nitrogen atmosphere, sodium tert-butoxide (4.40 g, 45.80 mmol) and then bis(tri-tert-butylphosphine)palladium(0) (0.20 g, 0.38 mmol) were added thereto, and the result was heated and stirred for 7 hours. The result was cooled to room temperature, filtered to remove the base, and then xylene was vacuum concentrated. The result was recrystallized with 250 ml of ethyl acetate to prepare Compound 11 (17.72 g, yield: 73%).

MS[M+H]$^+$=633

PREPARATION EXAMPLE 12

Compound Synthesis of the following Compound 12

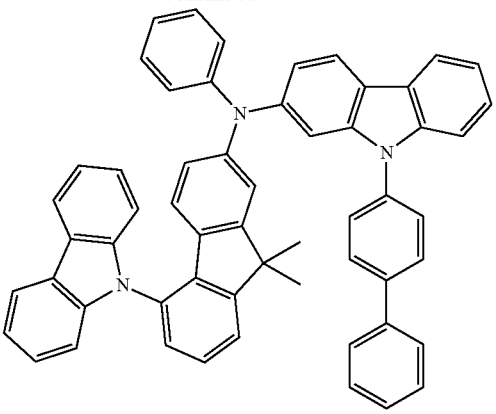

After completely dissolving Compound A (15.0 g, 38.17 mmol) and 9-([1,1'-biphenyl]-4-yl)-N-phenyl-9H-carbazole-2-amine (17.21 g, 41.98 mmol) in 230 ml of xylene in a 500 ml round bottom flask under nitrogen atmosphere, sodium tert-butoxide (4.40 g, 45.80 mmol) and then bis(tri-tert-butylphosphine)palladium(0) (0.20 g, 0.38 mmol) were added thereto, and the result was heated and stirred for 4 hours. The result was cooled to room temperature, filtered to remove the base, and then xylene was vacuum concentrated. The result was recrystallized with 230 ml of ethyl acetate to prepare Compound 12 (15.44 g, yield: 64%).

MS[M+H]$^+$=768

PREPARATION EXAMPLE 13 TO PREPARATION EXAMPLE 24

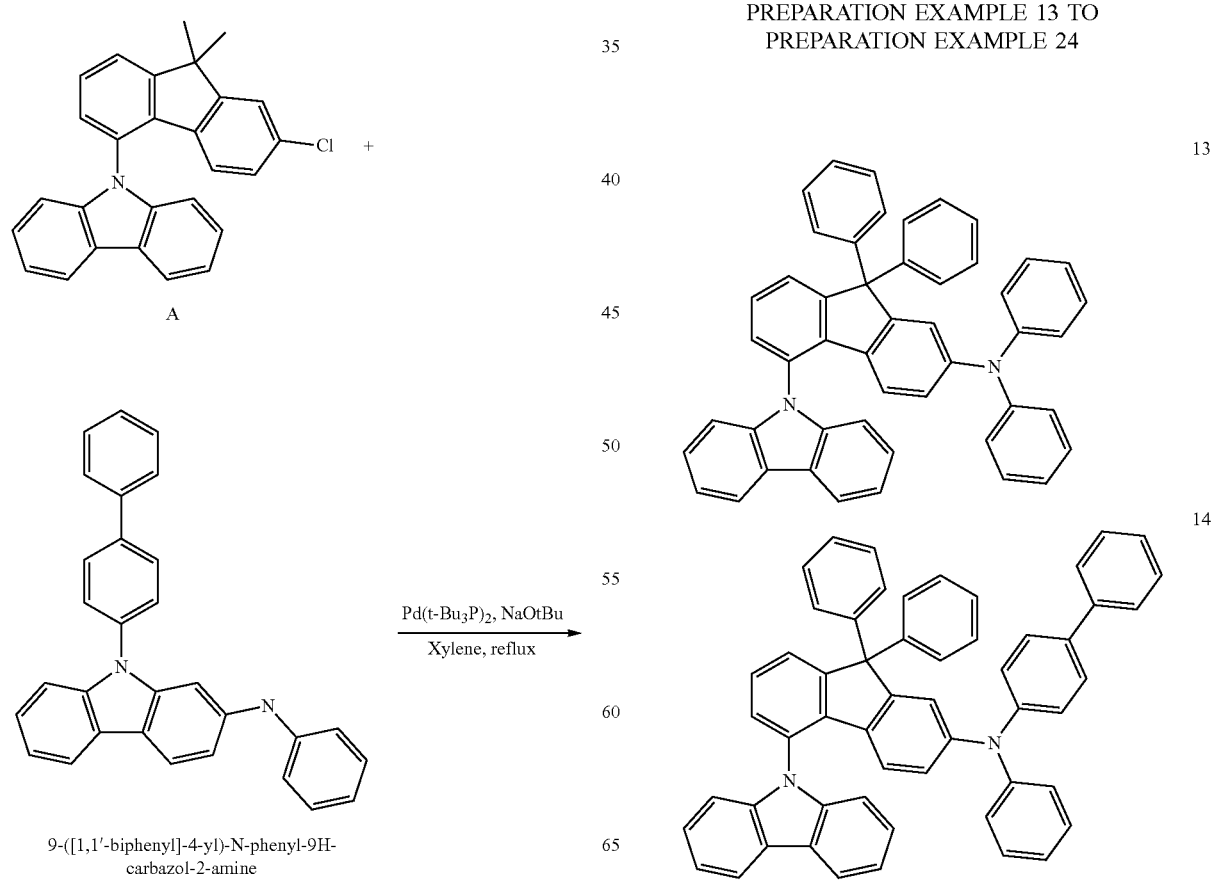

15
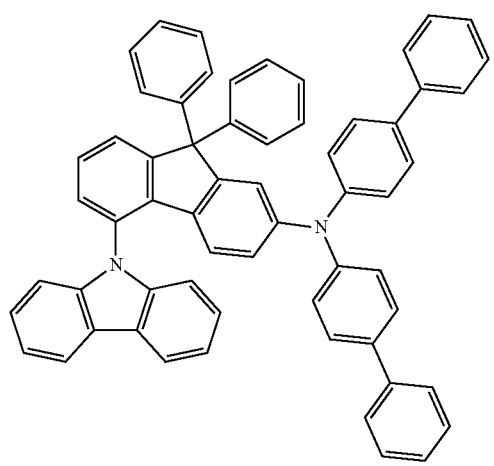
16
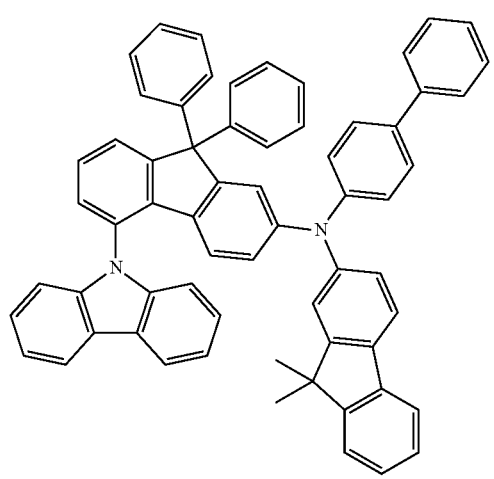
17
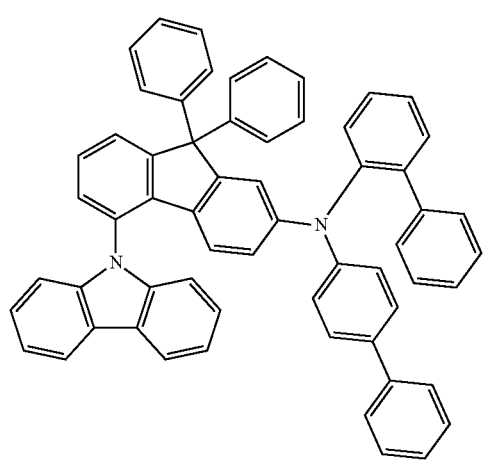
18
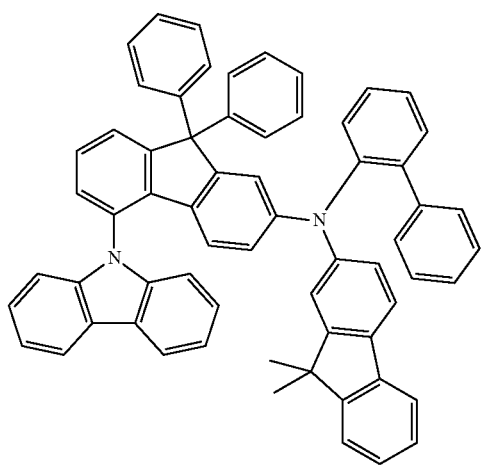
19
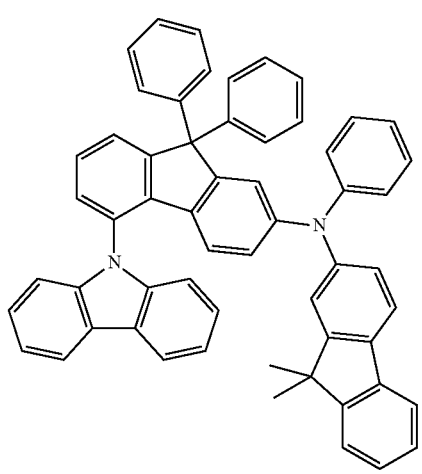
20
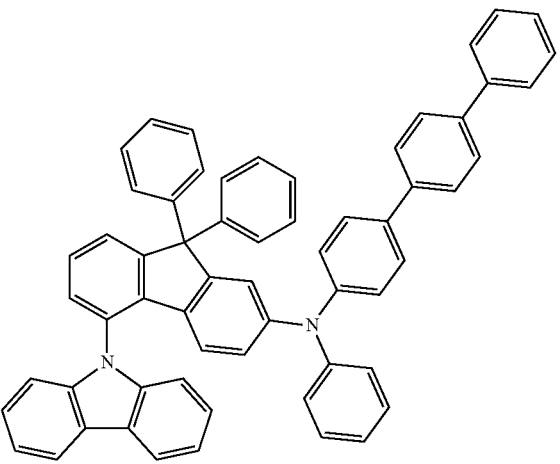

21
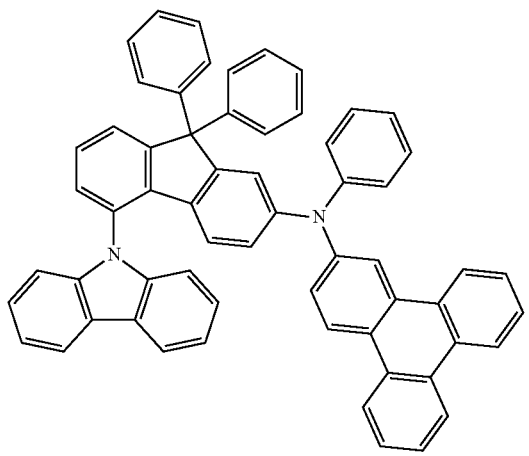
22
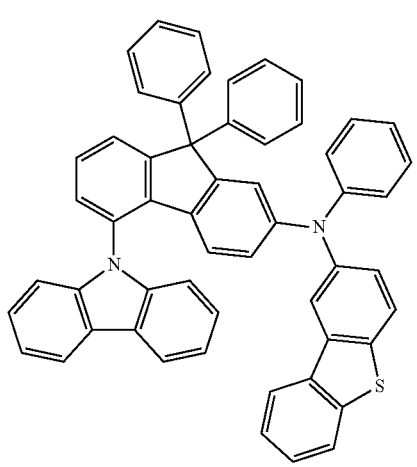
23
24
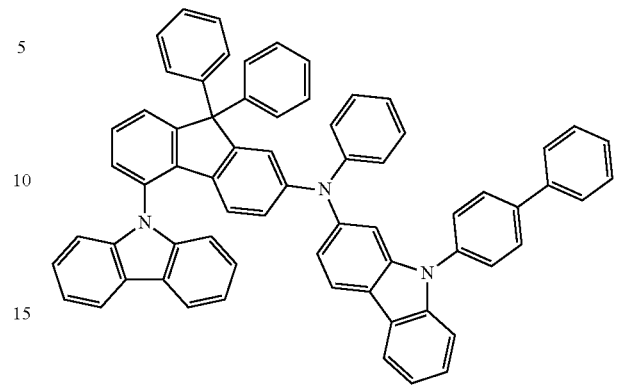
Compound 13 to Compound 24 were prepared in the same manner as in Preparation Example 1 to Preparation Example 12 except that Compound B was used as the staring material instead of Compound A. MS values of Compound 13 to Compound 24 are listed in the following Table 1.
TABLE 1
| Compound | MS [M + H]+ |
|---|---|
| 13 | 651 |
| 14 | 727 |
| 15 | 804 |
| 16 | 844 |
| 17 | 804 |
| 18 | 844 |
| 19 | 767 |
| 20 | 804 |
| 21 | 802 |
| 22 | 841 |
| 23 | 757 |
| 24 | 893 |
PREPARATION EXAMPLE 25 TO
PREPARATION EXAMPLE 36
25
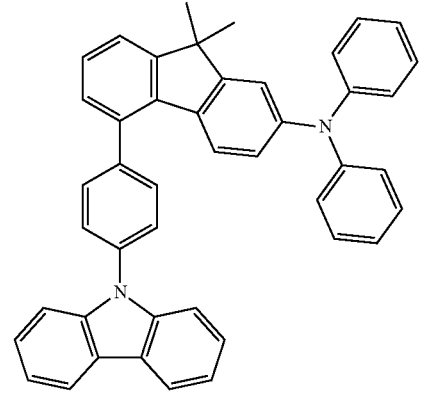

26
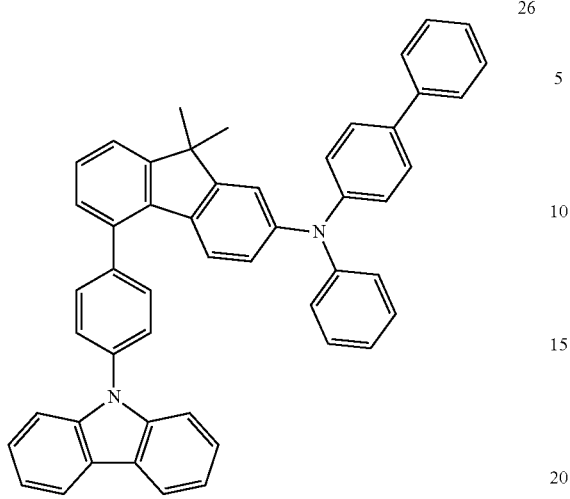
29
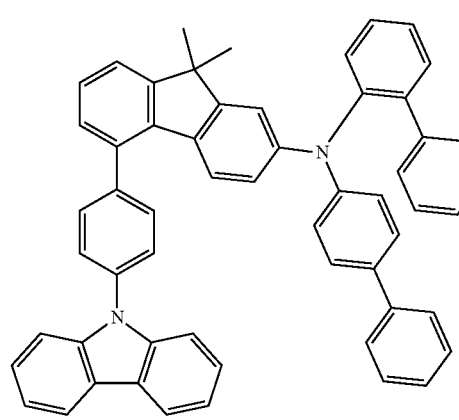
27
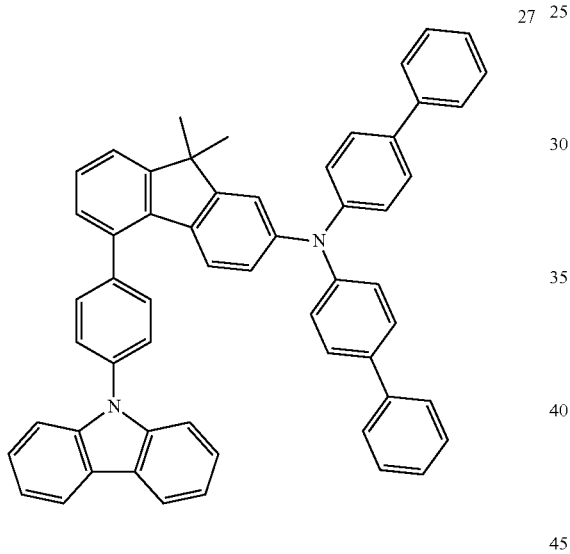
30
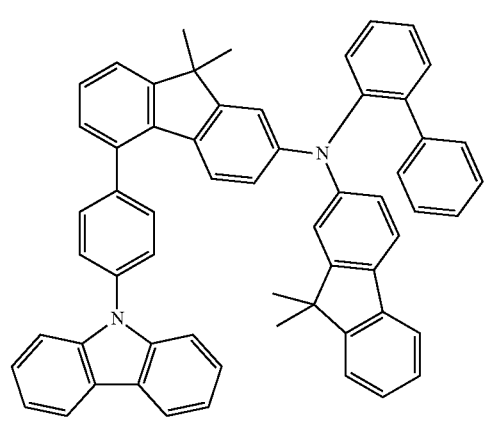
28
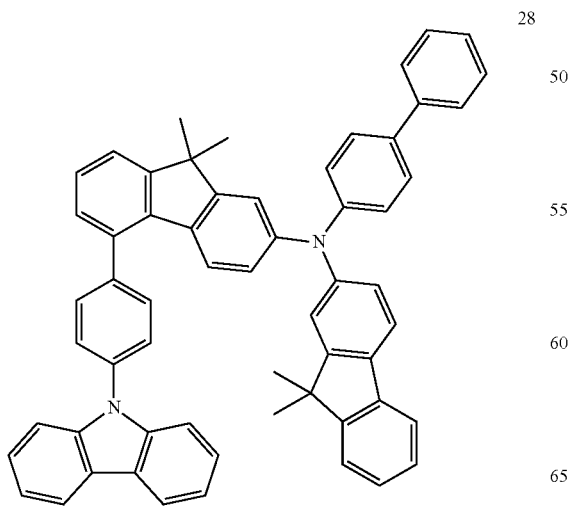
31
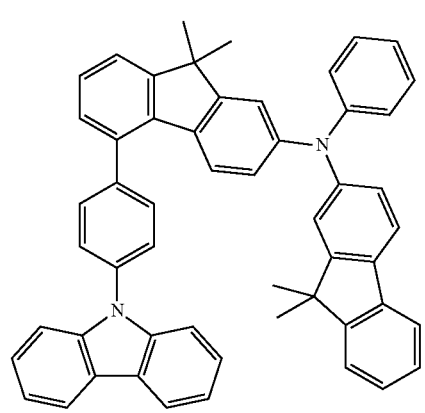

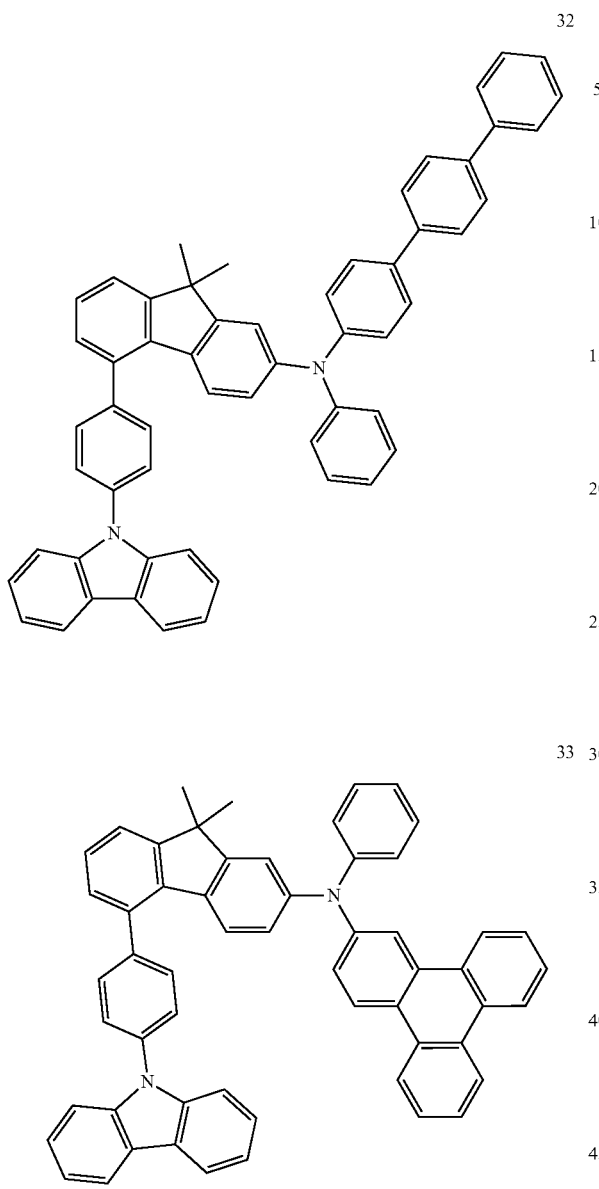
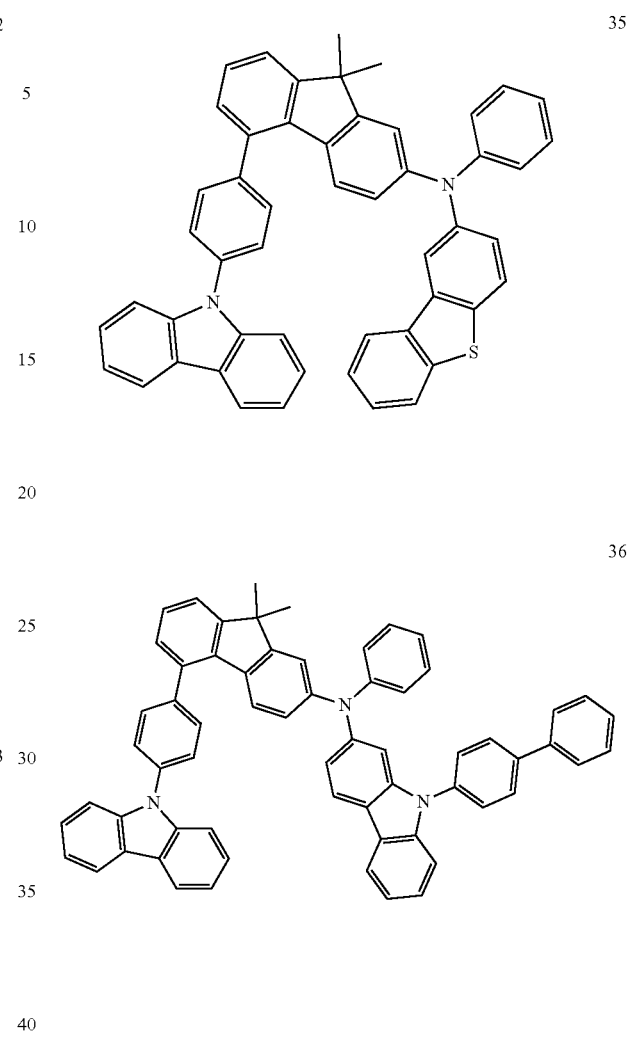
Compound 25 to Compound 36 were prepared in the same manner as in Preparation Example 1 to Preparation Example 12 except that Compound C was used as the staring material instead of Compound A. MS values of Compound 25 to Compound 36 are listed in the following Table 2.
TABLE 2
| Compound | MS $[M + H]^+$ |
|---|---|
| 25 | 603 |
| 26 | 679 |
| 27 | 756 |
| 28 | 796 |
| 29 | 756 |
| 30 | 796 |
| 31 | 719 |
| 32 | 756 |
| 33 | 754 |
| 34 | 693 |
| 35 | 709 |
| 36 | 845 |

PREPARATION EXAMPLE 37 TO
PREPARATION EXAMPLE 48
37
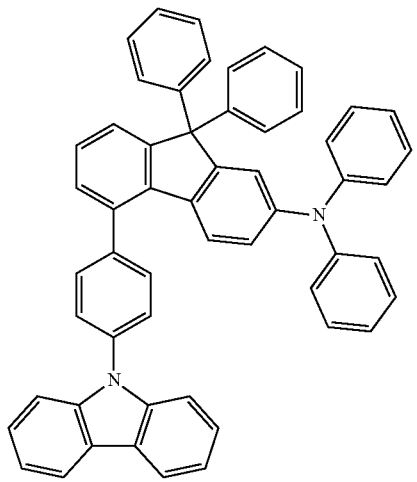
38
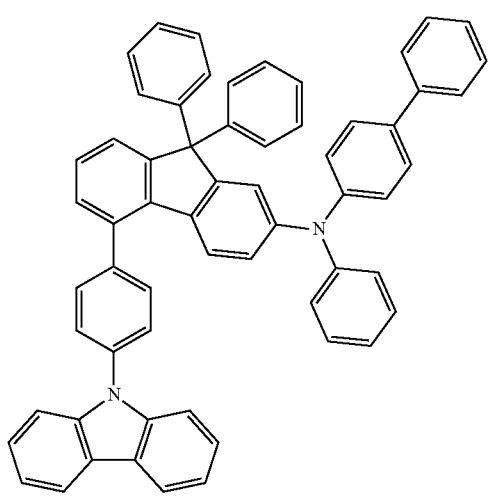
39
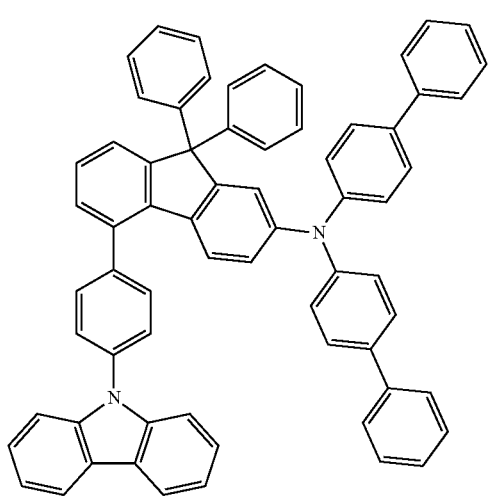
-continued
40
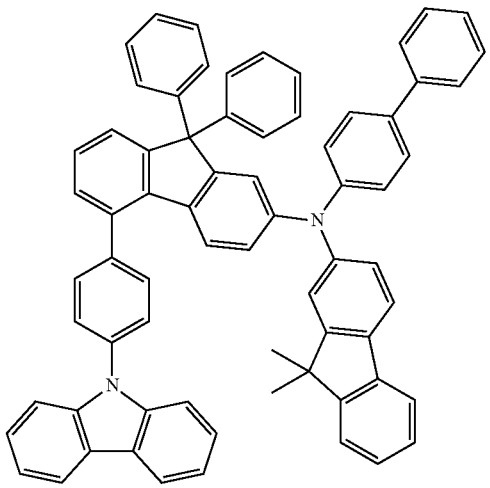
41
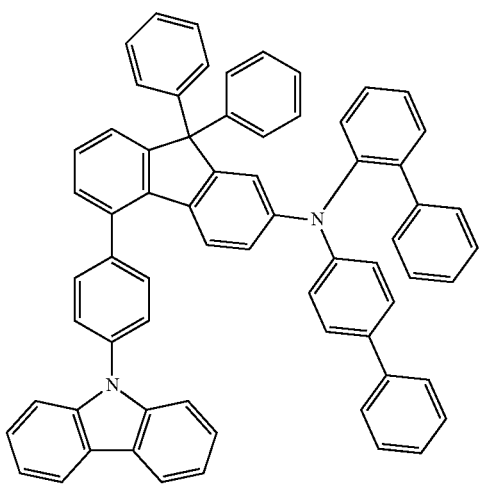
42
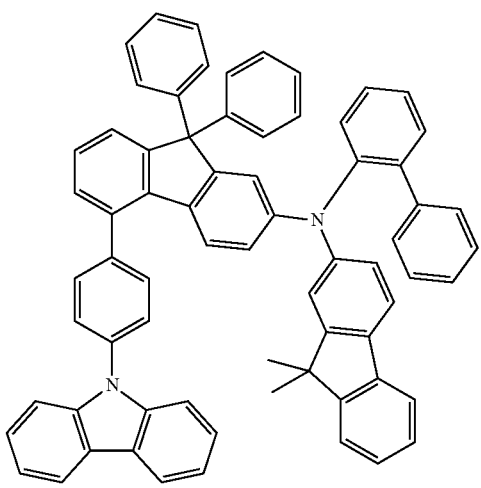

43
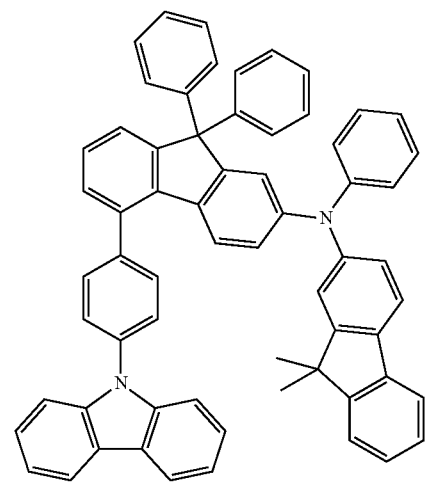
44
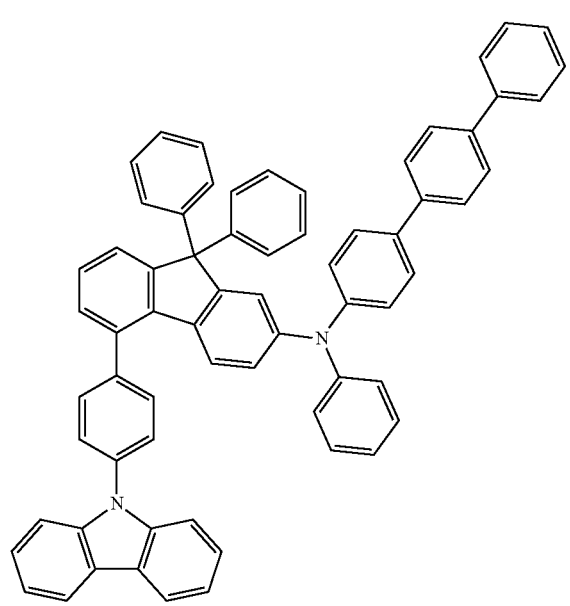
45
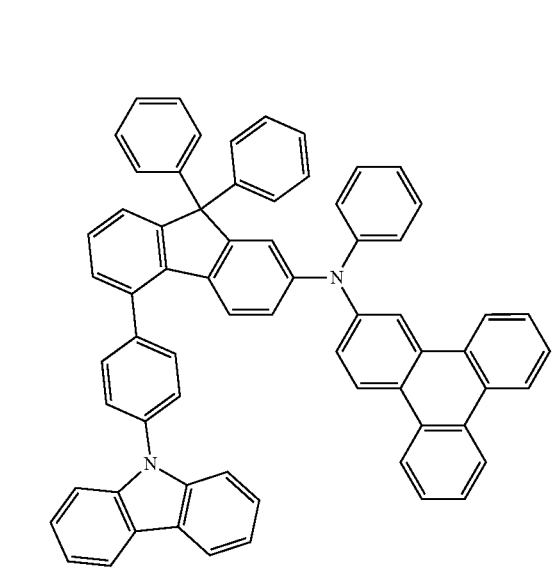
46
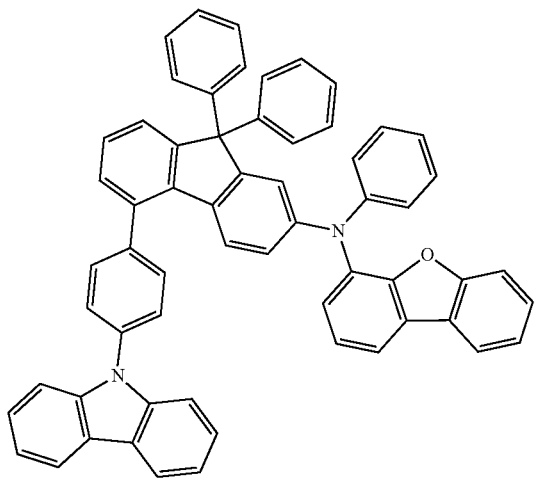
47
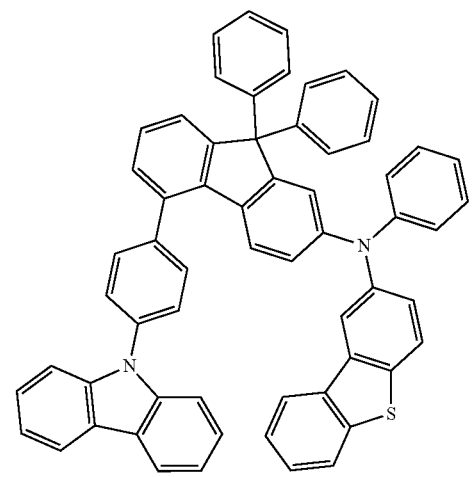
48
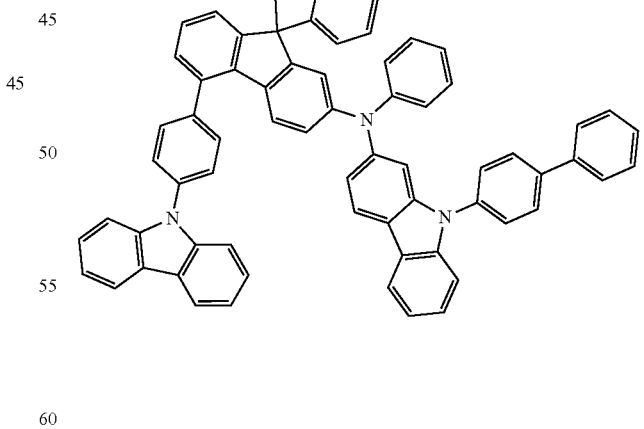
Compound 37 to Compound 48 were prepared in the same manner as in Preparation Example 1 to Preparation Example 12 except that Compound D was used as the staring material instead of Compound A. MS values of Compound 37 to Compound 48 are listed in the following Table 3.

TABLE 3

| Compound | MS [M + H]+ |
| --- | --- |
| 37 | 727 |
| 38 | 804 |
| 39 | 880 |
| 40 | 920 |
| 41 | 880 |
| 42 | 920 |
| 43 | 844 |
| 44 | 880 |
| 45 | 878 |
| 46 | 818 |
| 47 | 834 |
| 48 | 969 |

EXAMPLE 1

A glass substrate on which indium tin oxide (ITO) was coated as a thin film to a thickness of 1,000 Å was placed in detergent-dissolved distilled water and ultrasonic cleaned. Herein, a product of Fischer Co. was used as the detergent, and as the distilled water, distilled water filtered twice with a filter manufactured by Millipore Co. was used. After the ITO was cleaned for 30 minutes, ultrasonic cleaning was repeated twice using distilled water for 10 minutes. After the cleaning with distilled water was finished, the substrate was ultrasonic cleaned with solvents of isopropyl alcohol, acetone and methanol, then dried, and then transferred to a plasma cleaner. In addition, the substrate was cleaned for 5 minutes using oxygen plasma, and then transferred to a vacuum depositor.

On the transparent ITO electrode prepared as above, a hole injection layer was formed by thermal vacuum depositing hexanitrile hexaazatriphenylene (HAT) of the following chemical formula to a thickness of 500 Å.

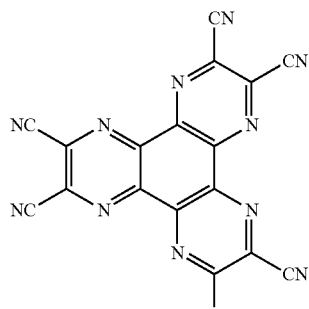

[HAT]

A hole transfer layer was formed on the hole injection layer by vacuum depositing the following compound 4-4'-bis[N-(1-naphthyl)-N-phenylamino]biphenyl (NPB) (300 Å), a material transferring holes.

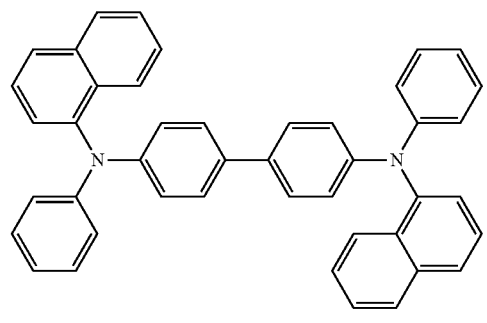

[NPB]

Subsequently, an electron suppression layer was formed on the hole transfer layer to a film thickness of 100 Å by vacuum depositing the following Compound 1.

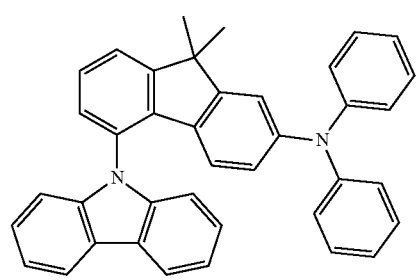

[Compound 1]

Next, a light emitting layer was formed on the electron suppression layer to a film thickness of 300 Å by vacuum depositing BH and BD shown below in a weight ratio of 25:1.

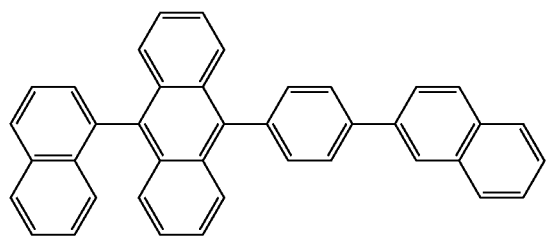

[BH]

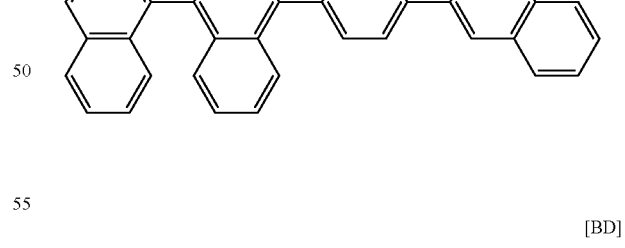

[BD]

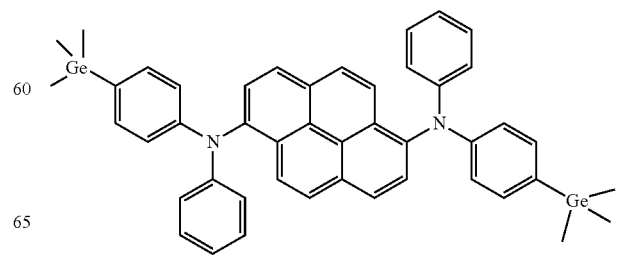

-continued

[ET1]

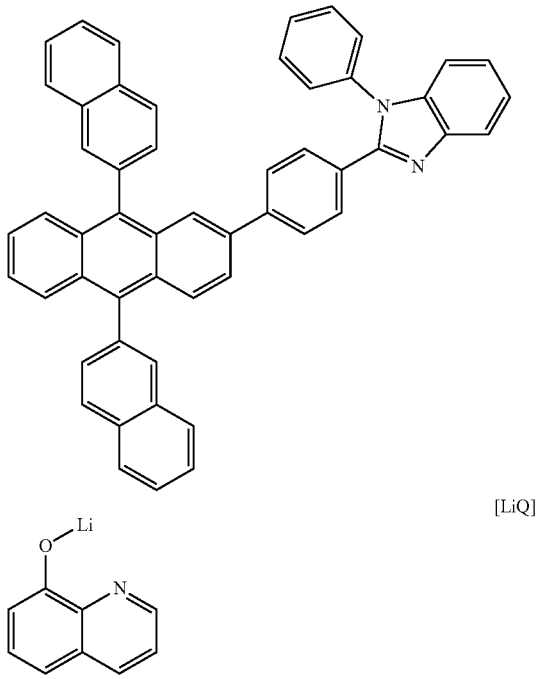

[LiQ]

An electron injection and transfer layer was formed on the light emitting layer to a thickness of 300 Å by vacuum depositing the compound ET1 and the compound lithium quinolate (LiQ) in a weight ratio of 1:1. A cathode was formed on the electron injection and transfer layer by depositing lithium fluoride (LiF) to a thickness of 12 Å and aluminum to a thickness of 2,000 Å in consecutive order.

An organic light emitting device was manufactured by maintaining, in the above-mentioned processes, the deposition rates of the organic materials at 0.4 Å/sec to 0.7 Å/sec, the deposition rates of the lithium fluoride and the aluminum of the cathode at 0.3 Å/sec and 2 Å/sec, respectively, and the degree of vacuum during the deposition at $2 \times 10^7$ torr to $5 \times 10^{-6}$ torr.

EXAMPLE 1-1

An organic light emitting device was manufactured in the same manner as in Example 1 except that Compound 2 was used instead of Compound 1.

EXAMPLE 1-2

An organic light emitting device was manufactured in the same manner as in Example 1 except that Compound 3 was used instead of Compound 1.

EXAMPLE 1-3

An organic light emitting device was manufactured in the same manner as in Example 1 except that Compound 4 was used instead of Compound 1.

EXAMPLE 1-4

An organic light emitting device was manufactured in the same manner as in Example 1 except that Compound 5 was used instead of Compound 1.

EXAMPLE 1-5

An organic light emitting device was manufactured in the same manner as in Example 1 except that Compound 6 was used instead of Compound 1.

EXAMPLE 1-6

An organic light emitting device was manufactured in the same manner as in Example 1 except that Compound 7 was used instead of Compound 1.

EXAMPLE 1-7

An organic light emitting device was manufactured in the same manner as in Example 1 except that Compound 8 was used instead of Compound 1.

EXAMPLE 1-8

An organic light emitting device was manufactured in the same manner as in Example 1 except that Compound 9 was used instead of Compound 1.

EXAMPLE 1-9

An organic light emitting device was manufactured in the same manner as in Example 1 except that Compound 10 was used instead of Compound 1.

EXAMPLE 1-10

An organic light emitting device was manufactured in the same manner as in Example 1 except that Compound 11 was used instead of Compound 1 다.

EXAMPLE 1-11

An organic light emitting device was manufactured in the same manner as in Example 1 except that Compound 12 was used instead of Compound 1.

EXAMPLE 1-12

An organic light emitting device was manufactured in the same manner as in Example 1 except that Compound 14 was used instead of Compound 1.

EXAMPLE 1-13

An organic light emitting device was manufactured in the same manner as in Example 1 except that Compound 15 was used instead of Compound 1.

EXAMPLE 1-14

An organic light emitting device was manufactured in the same manner as in Example 1 except that Compound 16 was used instead of Compound 1.

EXAMPLE 1-15

An organic light emitting device was manufactured in the same manner as in Example 1 except that Compound 17 was used instead of Compound 1.

EXAMPLE 1-16

An organic light emitting device was manufactured in the same manner as in Example 1 except that Compound 18 was used instead of Compound 1.

EXAMPLE 1-17

An organic light emitting device was manufactured in the same manner as in Example 1 except that Compound 19 was used instead of Compound 1.

EXAMPLE 1-18

An organic light emitting device was manufactured in the same manner as in Example 1 except that Compound 26 was used instead of Compound 1.

EXAMPLE 1-19

An organic light emitting device was manufactured in the same manner as in Example 1 except that Compound 27 was used instead of Compound 1.

EXAMPLE 1-20

An organic light emitting device was manufactured in the same manner as in Example 1 except that Compound 28 was used instead of Compound 1.

EXAMPLE 1-21

An organic light emitting device was manufactured in the same manner as in Example 1 except that Compound 29 was used instead of Compound 1.

EXAMPLE 1-22

An organic light emitting device was manufactured in the same manner as in Example 1 except that Compound 30 was used instead of Compound 1.

EXAMPLE 1-23

An organic light emitting device was manufactured in the same manner as in Example 1 except that Compound 31 was used instead of Compound 1.

COMPARATIVE EXAMPLE 1

An organic light emitting device was manufactured in the same manner as in Example 1 except that the following compound of EB1 was used instead of Compound 1.

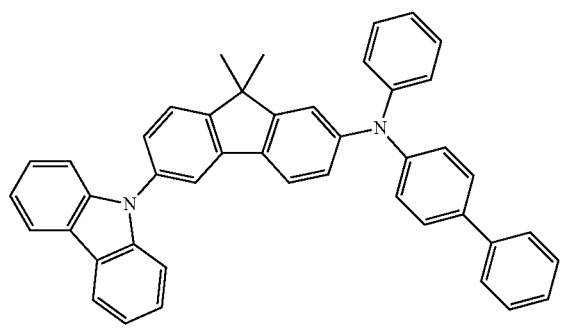

[EB1]

COMPARATIVE EXAMPLE 2

An organic light emitting device was manufactured in the same manner as in Example 1 except that the following compound of EB2 was used instead of Compound 1.

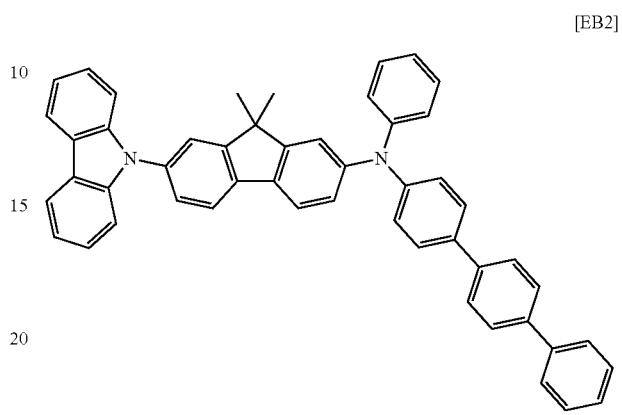

[EB2]

COMPARATIVE EXAMPLE 3

An organic light emitting device was manufactured in the same manner as in Example 1 except that the following compound of EB3 was used instead of Compound 1.

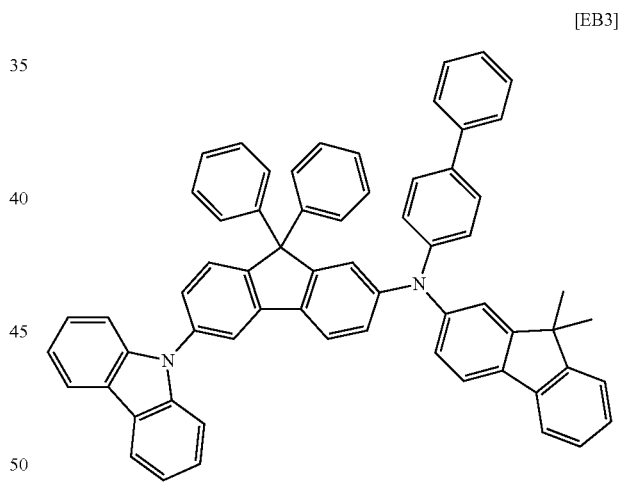

[EB3]

When a current was applied to the organic light emitting devices manufactured in Example 1, Examples 1-1 to 1-23, and Comparative Examples 1 to 3, results of the following Table 4 were obtained.

TABLE 4

| | Compound (Electron Suppression Layer) | Voltage (V@10 mA/cm$^2$) | Efficiency (cd/A@10 mA/cm$^2$) | Color Coordinate (x, y) |
|---|---|---|---|---|
| Example 1 | Compound 1 | 3.79 | 6.55 | (0.138, 0.127) |
| Example 1-1 | Compound 2 | 3.84 | 6.45 | (0.139, 0.122) |

TABLE 4-continued

| | Compound (Electron Suppression Layer) | Voltage (V@10 mA/cm$^2$) | Efficiency (cd/A@10 mA/cm$^2$) | Color Coordinate (x, y) |
|---|---|---|---|---|
| Example 1-2 | Compound 3 | 3.75 | 6.56 | (0.138, 0.126) |
| Example 1-3 | Compound 4 | 3.86 | 6.41 | (0.138, 0.127) |
| Example 1-4 | Compound 5 | 3.83 | 6.42 | (0.137, 0.125) |
| Example 1-5 | Compound 6 | 3.72 | 6.57 | (0.136, 0.125) |
| Example 1-6 | Compound 7 | 3.60 | 6.61 | (0.136, 0.127) |
| Example 1-7 | Compound 8 | 3.77 | 6.55 | (0.136, 0.125) |
| Example 1-8 | Compound 9 | 3.76 | 6.54 | (0.137, 0.125) |
| Example 1-9 | Compound 10 | 3.75 | 6.51 | (0.138, 0.125) |
| Example 1-10 | Compound 11 | 3.75 | 6.53 | (0.136, 0.125) |
| Example 1-11 | Compound 12 | 3.61 | 6.62 | (0.137, 0.125) |
| Example 1-12 | Compound 14 | 3.79 | 6.50 | (0.136, 0.125) |
| Example 1-13 | Compound 15 | 3.79 | 6.50 | (0.138, 0.126) |
| Example 1-14 | Compound 16 | 3.64 | 6.62 | (0.137, 0.125) |
| Example 1-15 | Compound 17 | 3.60 | 6.60 | (0.136, 0.127) |
| Example 1-16 | Compound 18 | 3.61 | 6.65 | (0.135, 0.127) |
| Example 1-17 | Compound 19 | 3.64 | 6.61 | (0.138, 0.127) |
| Example 1-18 | Compound 26 | 3.68 | 6.69 | (0.137, 0.125) |
| Example 1-19 | Compound 27 | 3.64 | 6.66 | (0.137, 0.125) |
| Example 1-20 | Compound 28 | 3.78 | 6.52 | (0.136, 0.125) |
| Example 1-21 | Compound 29 | 3.79 | 6.56 | (0.138, 0.126) |
| Example 1-22 | Compound 30 | 3.61 | 6.64 | (0.137, 0.125) |
| Example 1-23 | Compound 31 | 3.75 | 6.50 | (0.136, 0.127) |
| Comparative Example 1 | EB1 | 4.19 | 5.81 | (0.136, 0.127) |
| Comparative Example 2 | EB2 | 4.23 | 5.97 | (0.136, 0.127) |
| Comparative Example 3 | EB3 | 4.15 | 5.84 | (0.135, 0.125) |

As seen from Table 4, the organic light emitting devices manufactured using the compounds of the present disclosure as an electron suppression layer exhibited excellent properties in terms of efficiency, driving voltage and/or stability of the organic light emitting device when compared to using the materials of Comparative Examples 1 to 3 in which a substituent is linked at the number 2 or number 3 position of the carbazole, since the compounds of the present disclosure performed an electron blocking role.

Examples 1-1 to 1-23 exhibited properties of a voltage decrease by 10% to 12% and an efficiency increase by 10% or greater compared to such comparative examples.

As shown from the results of Table 4, it was identified that the compounds according to the present disclosure had an excellent electron blocking ability, and therefore, are capable of being used in an organic light emitting device.

EXAMPLE 2 AND EXAMPLE 2-1 TO EXAMPLE 2-23

Experiments were carried out in the same manner as in Example 1 except that the following TCTA material was used as the electron suppression layer, and the compounds used as the electron suppression layer in Example 1, and Examples 1-1 to 1-23 were used as the hole transfer layer instead of NPB.

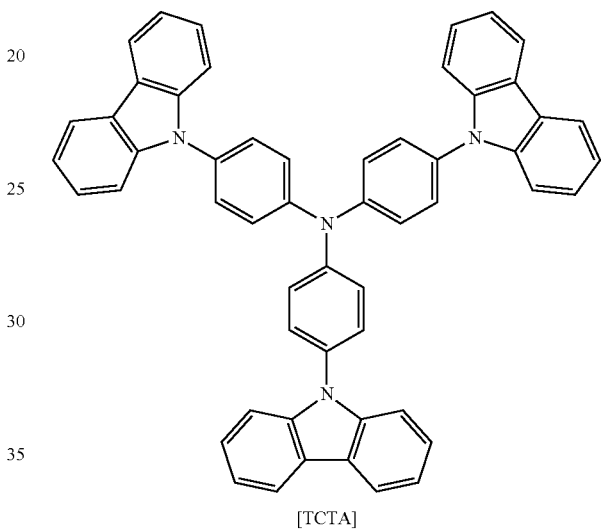

[TCTA]

COMPARATIVE EXAMPLE 4 TO COMPARATIVE EXAMPLE 6

Experiments were carried out in the same manner as in Example 2 except that the following compounds of HT1, HT2 and HT3 were each used instead of Compound 1 as the material of the hole transfer layer.

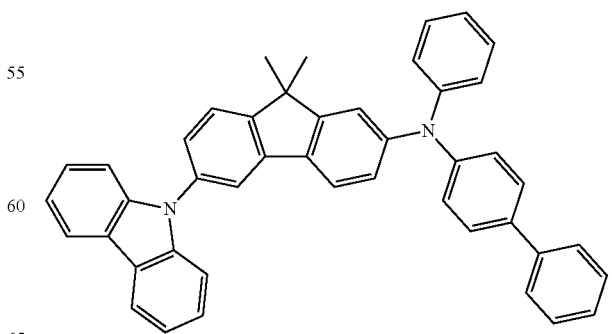

[HT1]

[HT2]

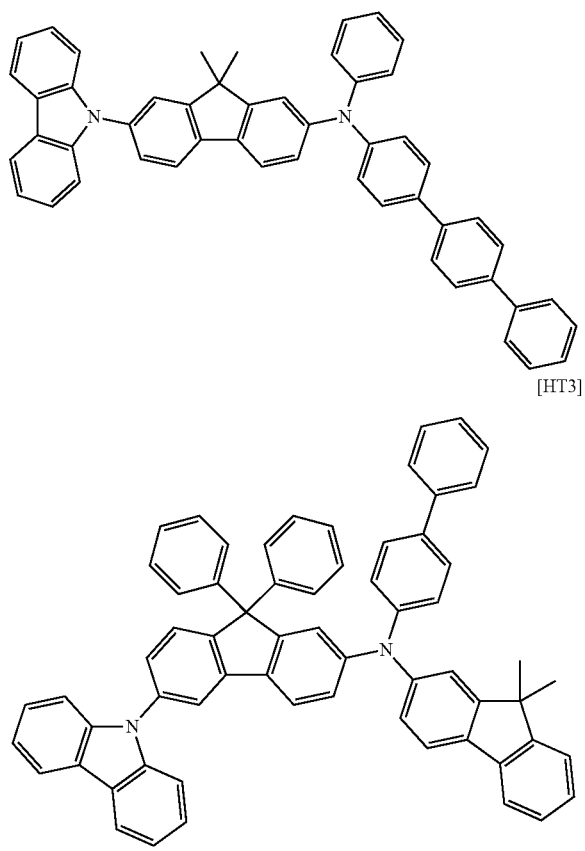

[HT3]

When a current was applied to the organic light emitting devices manufactured in Example 2, Examples 2-1 to 2-23, and Comparative Examples 4 to 6, results of the following Table 5 were obtained.

TABLE 5

| | Compound (Hole Transfer Layer) | Voltage (V@10 mA/cm$^2$) | Efficiency (cd/A@10 mA/cm$^2$) | Color Coordinate (x, y) |
| --- | --- | --- | --- | --- |
| Example 2 | Compound 1 | 4.45 | 5.45 | (0.138, 0.127) |
| Example 2-1 | Compound 2 | 4.52 | 5.35 | (0.139, 0.122) |
| Example 2-2 | Compound 3 | 4.48 | 5.36 | (0.138, 0.126) |
| Example 2-3 | Compound 4 | 4.59 | 5.39 | (0.138, 0.127) |
| Example 2-4 | Compound 5 | 4.55 | 5.42 | (0.137, 0.125) |
| Example 2-5 | Compound 6 | 4.46 | 5.47 | (0.136, 0.125) |
| Example 2-6 | Compound 7 | 4.48 | 5.51 | (0.136, 0.127) |
| Example 2-7 | Compound 8 | 4.53 | 5.35 | (0.136, 0.125) |
| Example 2-8 | Compound 9 | 4.49 | 5.34 | (0.137, 0.125) |
| Example 2-9 | Compound 10 | 4.52 | 5.38 | (0.138, 0.125) |
| Example 2-10 | Compound 11 | 4.54 | 5.46 | (0.136, 0.125) |
| Example 2-11 | Compound 12 | 4.46 | 5.36 | (0.137, 0.125) |
| Example 2-12 | Compound 14 | 4.41 | 5.31 | (0.136, 0.125) |
| Example 2-13 | Compound 15 | 4.50 | 5.50 | (0.138, 0.126) |
| Example 2-14 | Compound 16 | 4.43 | 5.52 | (0.137, 0.125) |
| Example 2-15 | Compound 17 | 4.57 | 5.58 | (0.136, 0.127) |
| Example 2-16 | Compound 18 | 4.56 | 5.55 | (0.135, 0.127) |
| Example 2-17 | Compound 19 | 4.44 | 5.51 | (0.138, 0.127) |
| Example 2-18 | Compound 26 | 4.41 | 5.59 | (0.137, 0.125) |
| Example 2-19 | Compound 27 | 4.58 | 5.46 | (0.137, 0.125) |
| Example 2-20 | Compound 28 | 4.49 | 5.45 | (0.136, 0.125) |
| Example 2-21 | Compound 29 | 4.57 | 5.46 | (0.138, 0.126) |
| Example 2-22 | Compound 30 | 4.52 | 5.44 | (0.137, 0.125) |
| Example 2-23 | Compound 31 | 4.43 | 5.40 | (0.136, 0.127) |
| Comparative Example 4 | HT1 | 5.06 | 4.91 | (0.136, 0.127) |
| Comparative Example 5 | HT2 | 5.11 | 4.95 | (0.136, 0.127) |
| Comparative Example 6 | HT3 | 5.18 | 4.52 | (0.135, 0.125) |

As seen from Table 5, the organic light emitting devices manufactured using the compounds of the present disclosure as a hole transfer layer exhibited excellent properties in terms of efficiency, driving voltage and/or stability of the organic light emitting device when compared to using the materials of Comparative Examples 4 to 6 in which a substituent is linked at the number 2 or number 3 position of the carbazole, since the compounds of the present disclosure performed a hole transferring role.

Specifically, Examples 2, and 2-1 to 2-23 exhibited properties of a voltage decrease by 10% or greater and an efficiency increase by 7% to 10% compared to such comparative examples.

As shown from the results of Table 4 and Table 5, it was identified that the compounds according to the present disclosure had an excellent hole transferring ability as well as an electron blocking ability, and are capable of being used in an organic light emitting device.

Hereinbefore, preferred embodiments of the present disclosure (electron suppression layer, hole transfer layer) have been described, however, the present disclosure is not limited thereto, and various modifications may be made within the scope of the claims and the detailed descriptions, and the modifications are also included in the scope of the present disclosure.

The invention claimed is:

1. A compound of the following Chemical Formula 1:

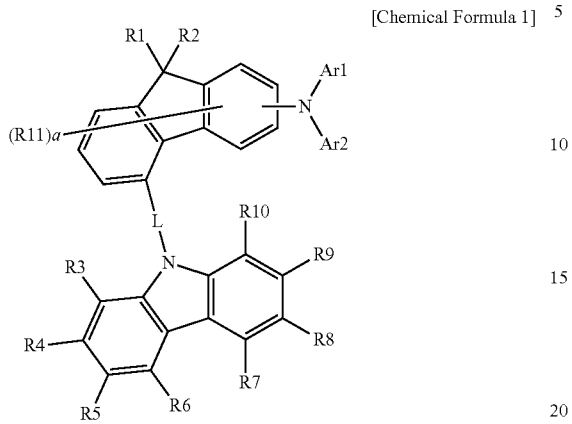

[Chemical Formula 1]

wherein, in Chemical Formula 1,

R1 and R2 are the same as or different from each other, and each independently a substituted or unsubstituted alkyl group; or a substituted or unsubstituted aryl group, Ar1 and Ar2 are the same as or different from each other, and each independently a substituted or unsubstituted aryl group; or a substituted or unsubstituted heterocyclic group, or bond to each other to form a substituted or unsubstituted ring, L is a direct bond, or a substituted or unsubstituted arylene group, and R3 to R11 are the same as or different from each other, and each independently hydrogen; deuterium; a halogen group; a nitrile group; a nitro group; a hydroxyl group; a carbonyl group; an ester group; an imide group; a substituted or unsubstituted amine group; a substituted or unsubstituted silyl group; a substituted or unsubstituted boron group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted aralkyl group; a substituted or unsubstituted aralkenyl group; a substituted or unsubstituted alkylaryl group; a substituted or unsubstituted alkylamine group; a substituted or unsubstituted aralkylamine group; a substituted or unsubstituted heteroarylamine group; a substituted or unsubstituted arylamine group; a substituted or unsubstituted arylheteroarylamine group; a substituted or unsubstituted arylphosphine group; a substituted or unsubstituted phosphine oxide group; a substituted or unsubstituted aryl group; or a substituted or unsubstituted heterocyclic group, or bond to an adjacent group to form a substituted or unsubstituted ring, a is an integer of 0 to 6, and when a is an integer of 2 or greater, R11 s are the same as or different from each other.

2. The compound of claim 1, wherein Chemical Formula 1 is represented by the following Chemical Formula 2:

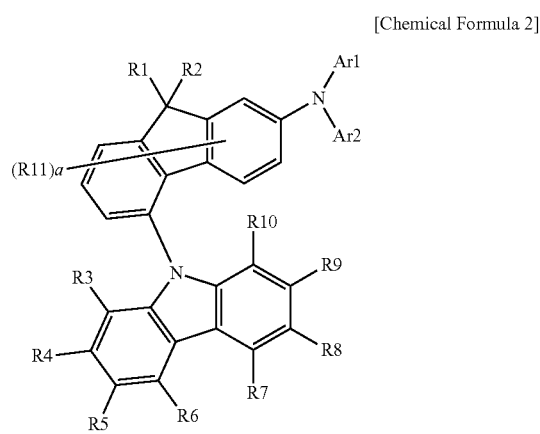

[Chemical Formula 2]

wherein, in Chemical Formula 2, definitions of substituents are the same as in Chemical Formula 1.

3. The compound of claim 1, wherein Chemical Formula 1 is represented by the following Chemical Formula 3:

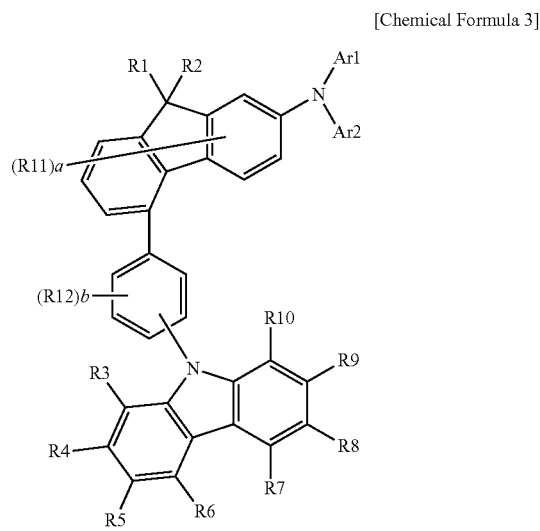

[Chemical Formula 3]

wherein, in Chemical Formula 3, definitions of R1 to R11, a, Ar1 and Ar2 are the same as in Chemical Formula 1, R12 is the same as or different from R11, has the same definition as R11, b is an integer of 0 to 4, and when b is an integer of 2 or greater, R12s are the same as or different from each other.

4. The compound of claim 3, wherein Chemical Formula 3 is represented by the following Chemical Formula 4:

[Chemical Formula 4]

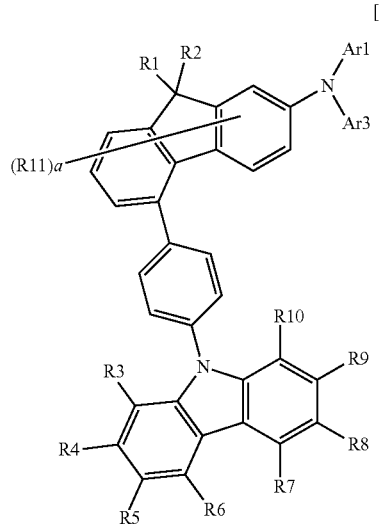

wherein, in Chemical Formula 4, definitions of substituents are the same as in Chemical Formula 1.

5. The compound of claim 1, wherein, in Chemical Formula 1, Ar1 and Ar2are the same as or different from each other, and each independently a substituted or unsubstituted phenyl group; a substituted or unsubstituted biphenyl group; a substituted or unsubstituted terphenyl group; a substituted or unsubstituted quaterphenyl group; a substituted or unsubstituted naphthyl group; a substituted or unsubstituted fluorenyl group; a substituted or unsubstituted phenanthrenyl group; a substituted or unsubstituted carbazole group; a substituted or unsubstituted benzocarbazole group; a substituted or unsubstituted dibenzofuran group; or a substituted or unsubstituted dibenzothiophene group.

6. The compound of claim 1, wherein, in Chemical Formula 1, Ar1 and Ar2are the same as or different from each other, and each independently selected from among the following structural formulae:

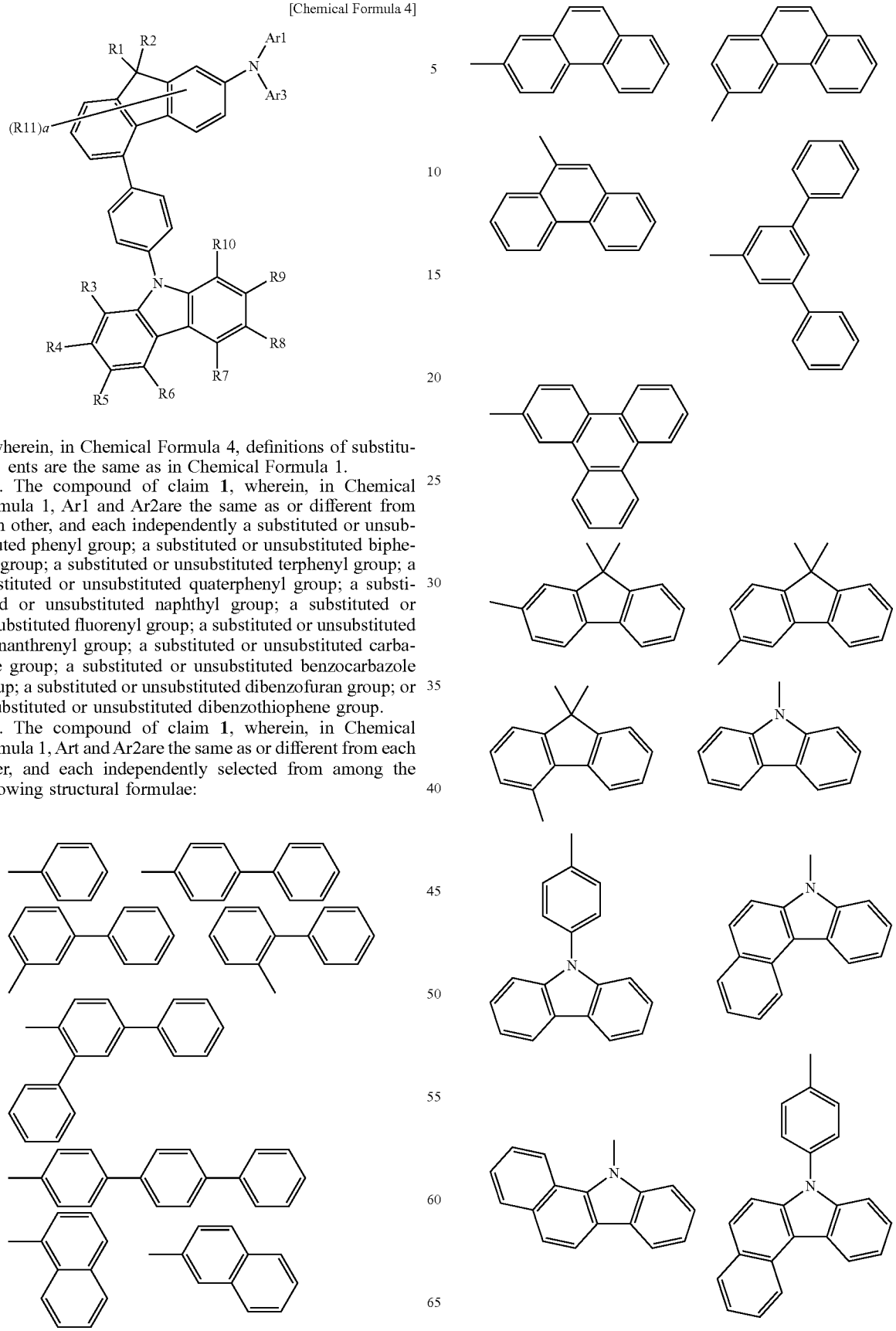

137
-continued

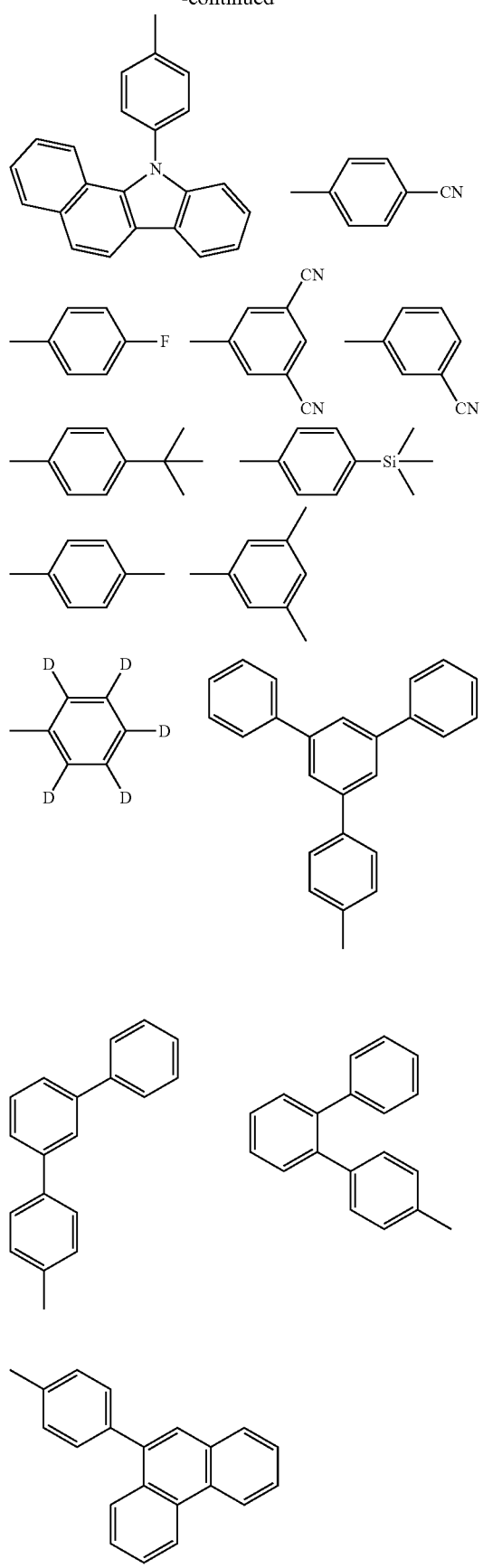

138
-continued

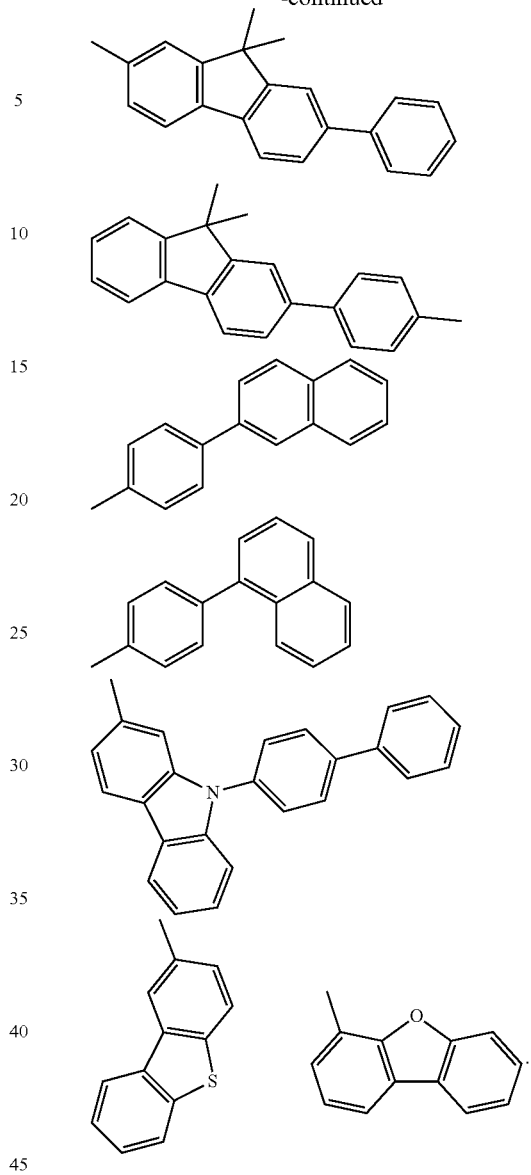

7. The compound of claim 1, wherein, in Chemical Formula 1, Ar1 and Ar2 are the same as or different from each other, each independently a substituted or unsubstituted aryl group, and bond to each other.

8. The compound of claim 1, wherein, in Chemical Formula 1, Ar1 and Ar2 are the same as or different from each other, each independently a substituted or unsubstituted phenyl group; a substituted or unsubstituted biphenyl group; or a substituted or unsubstituted naphthyl group, and bond to each other to form a substituted or unsubstituted carbazole structure; a substituted or unsubstituted benzocarbazole structure, or a substituted or unsubstituted dibenzocarbazole structure.

9. The compound of claim 1, wherein R1 and R2 are an alkyl group; an aryl group; or an aryl group substituted with an alkyl group.

10. The compound of claim 1, wherein R3 and R4 bond to each other to form a substituted or unsubstituted benzene ring, and
wherein R5 and R6 bond to each other to form a substituted or unsubstituted benzene ring.

11. The compound of claim 1, wherein Chemical Formula 1 is selected from among the following structural formulae:
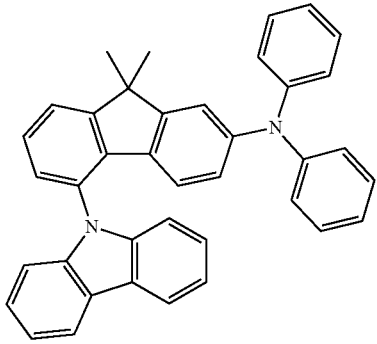
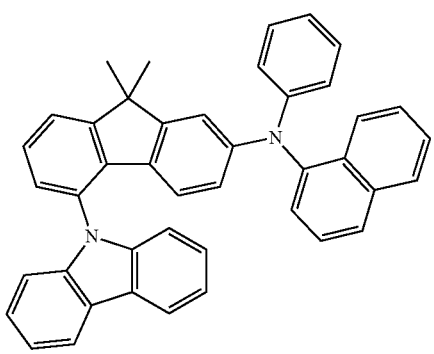
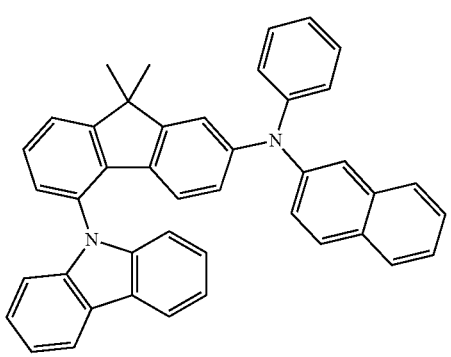
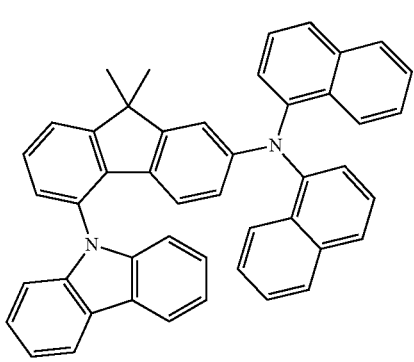
-continued
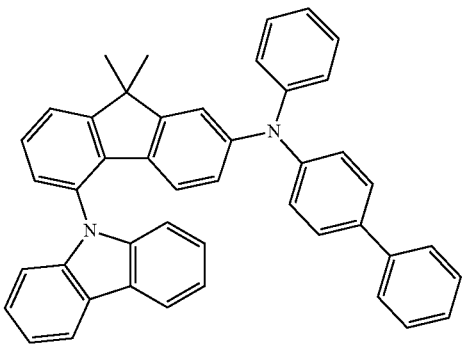
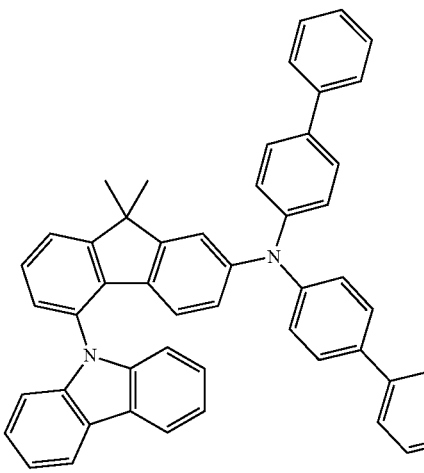
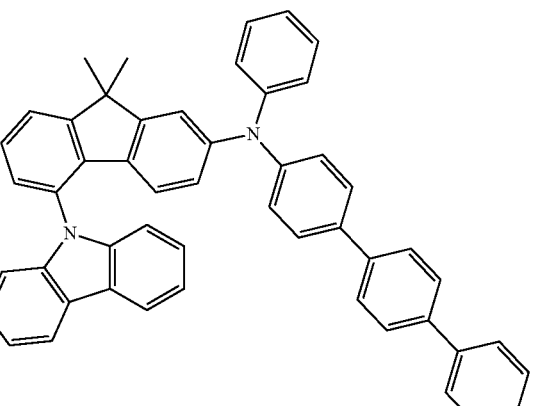
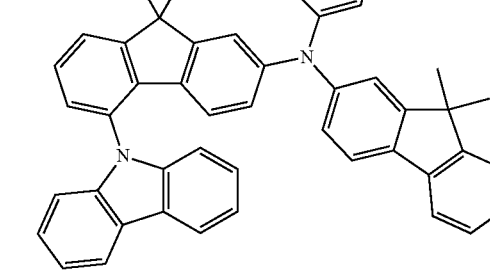

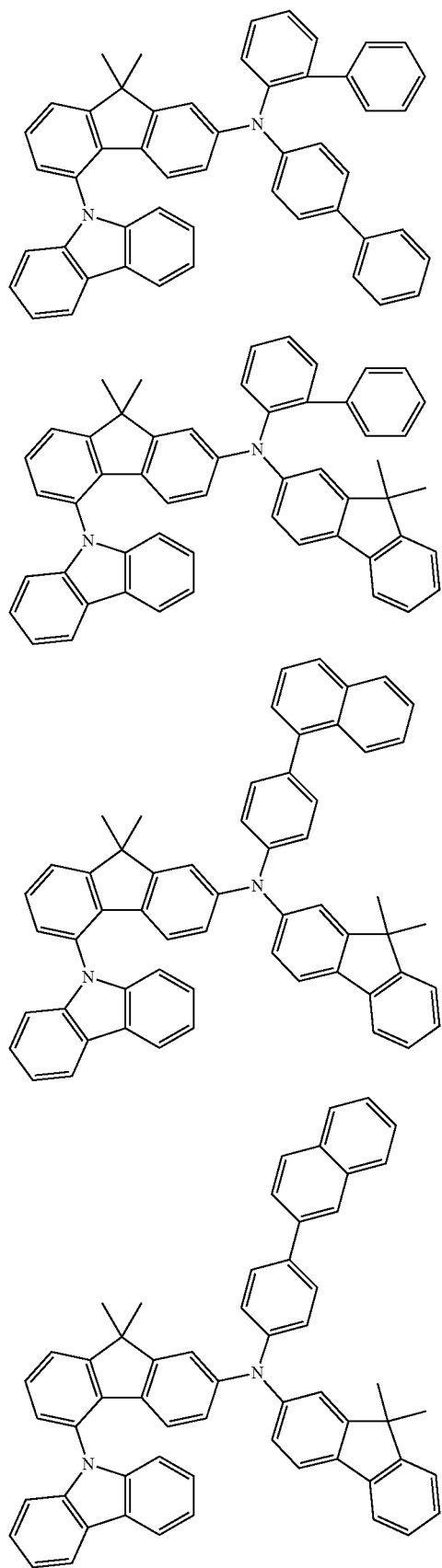
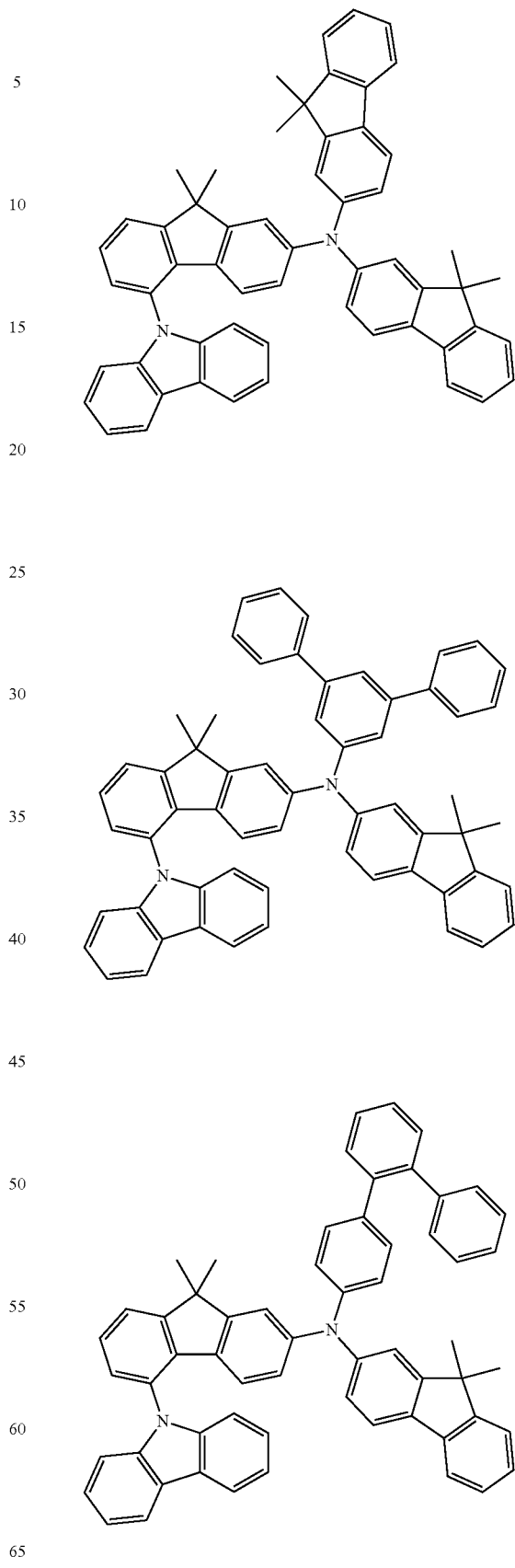

-continued
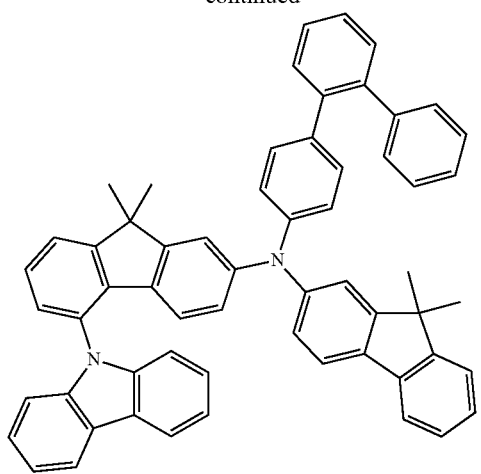
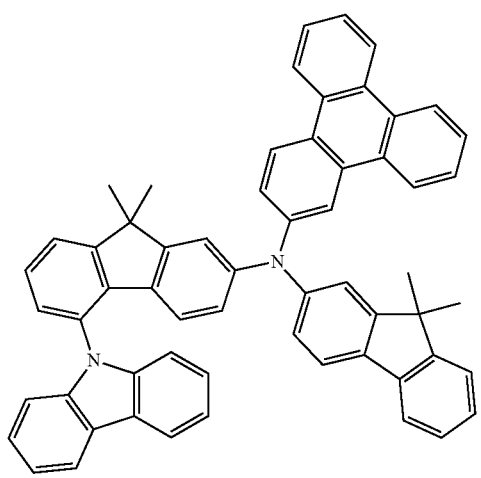
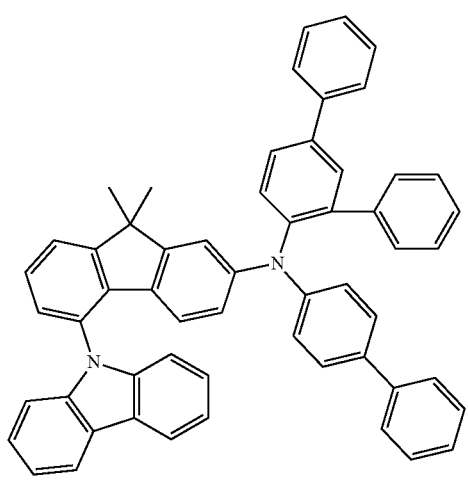
-continued
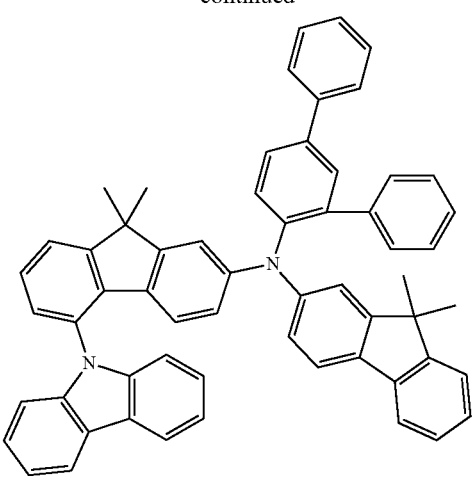
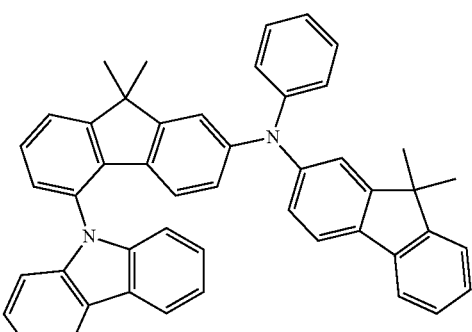
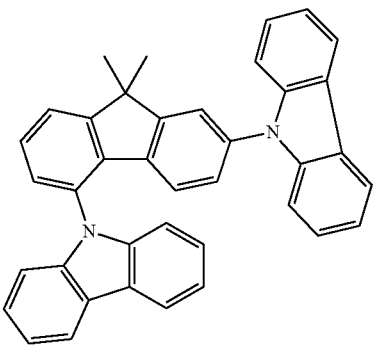
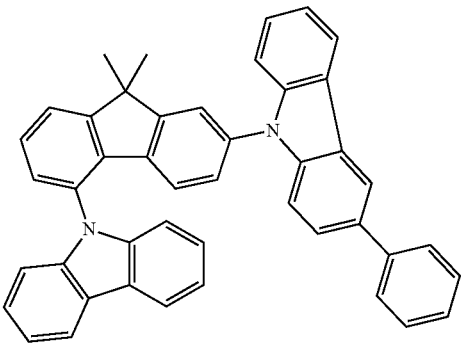

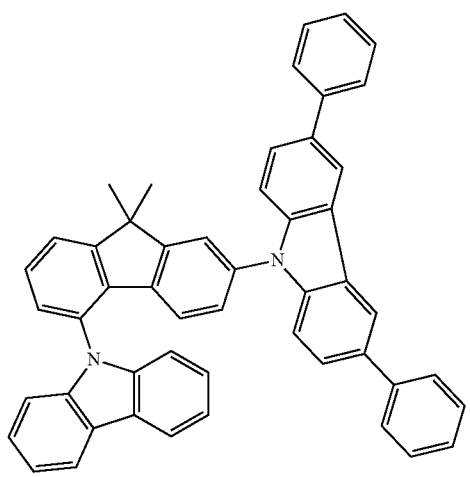
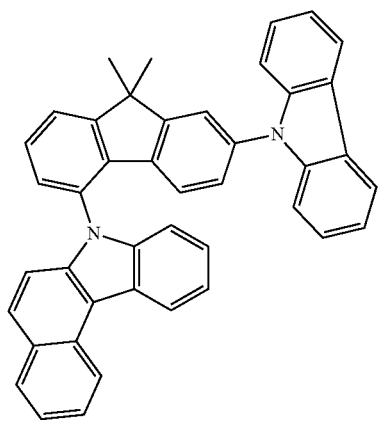
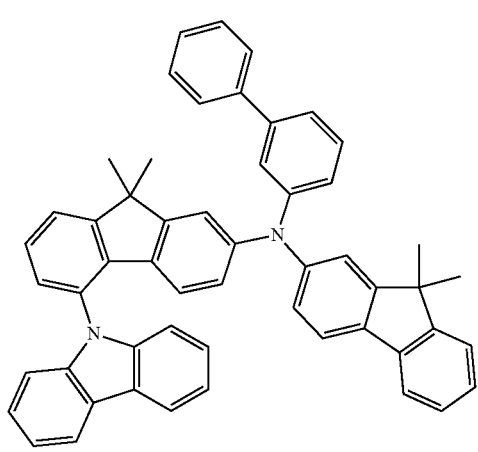
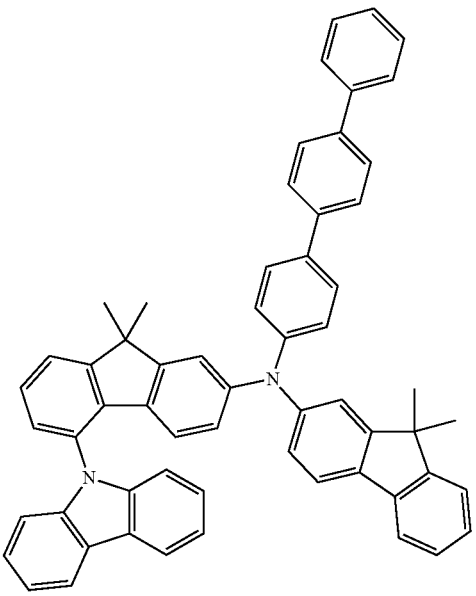
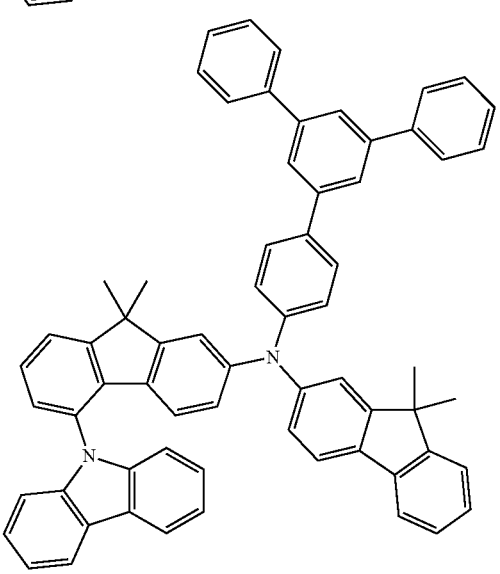
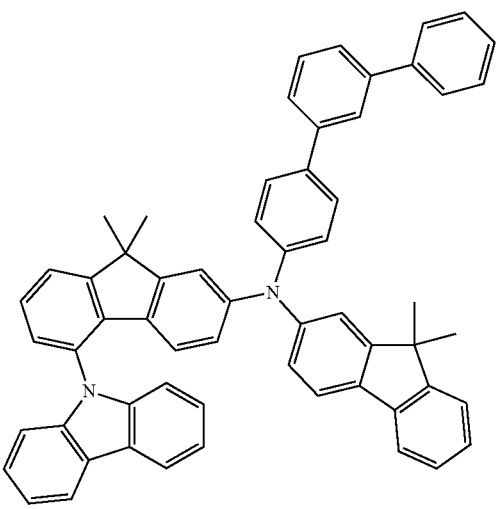

-continued
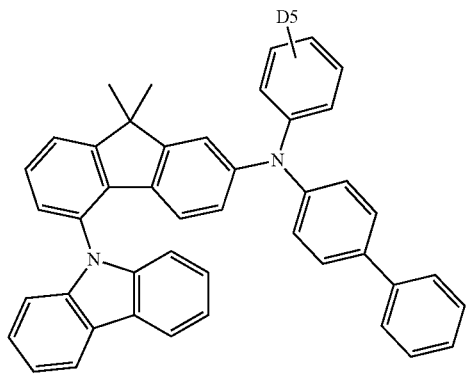
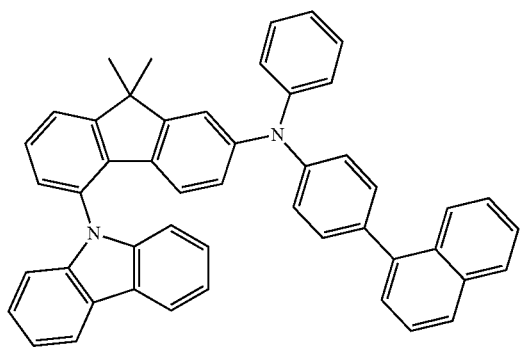
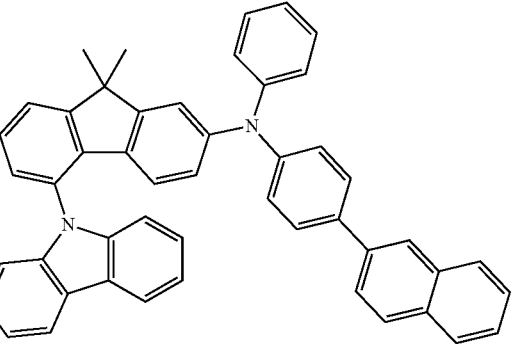
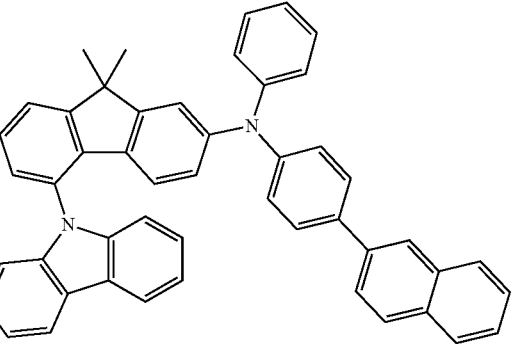
-continued
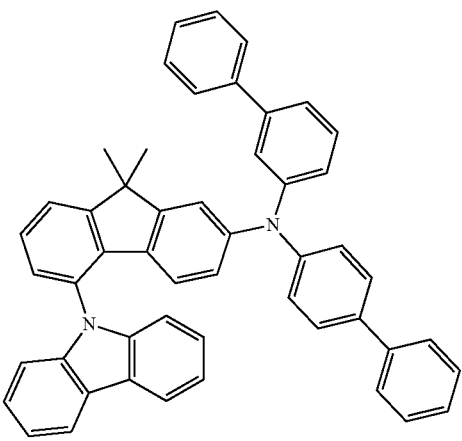
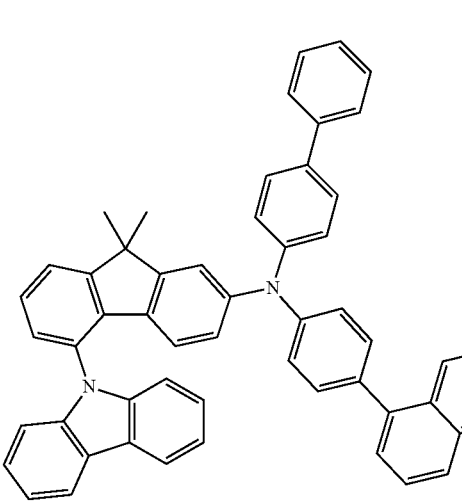
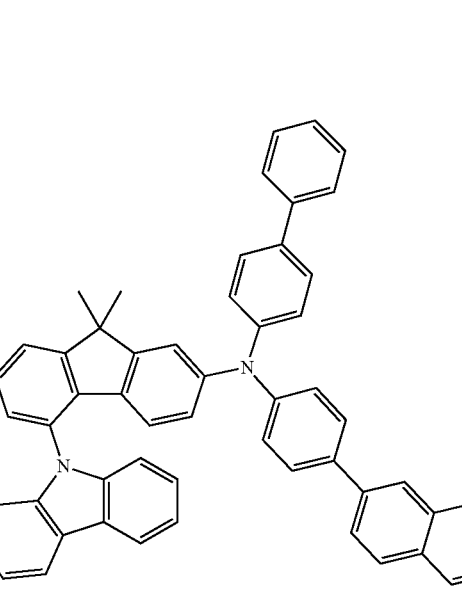

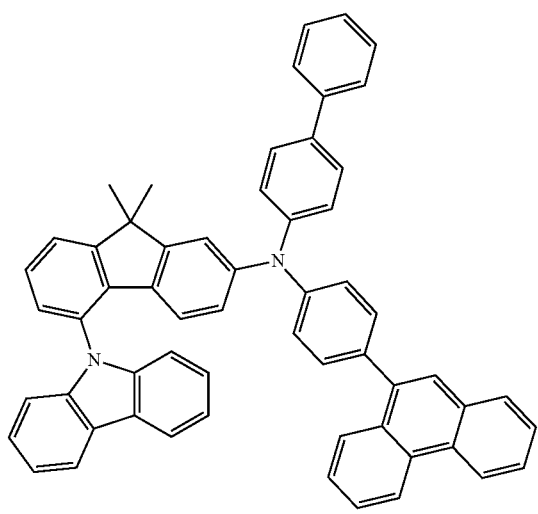
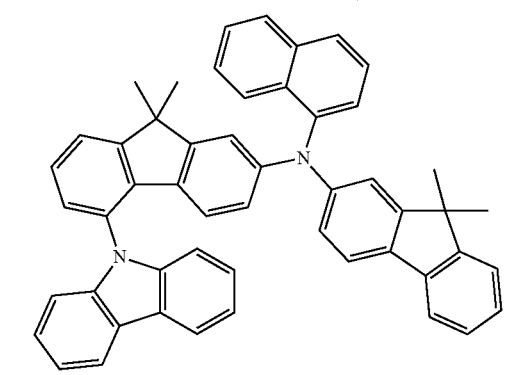
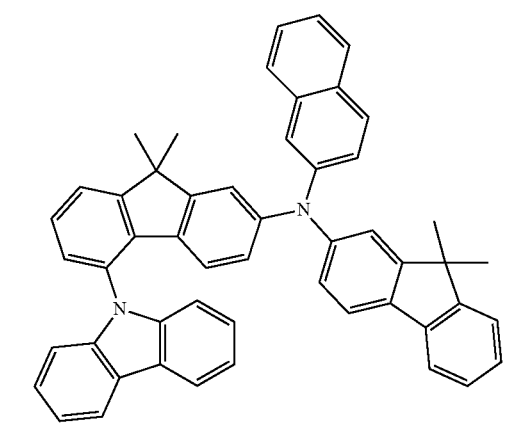
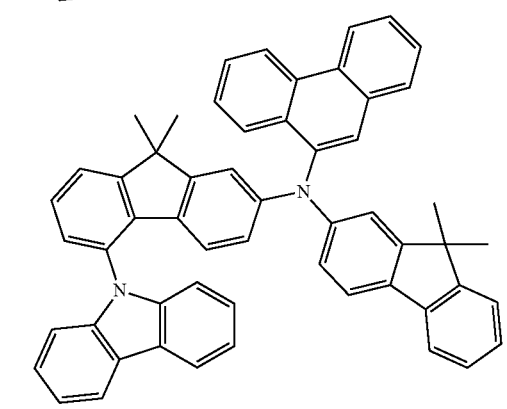
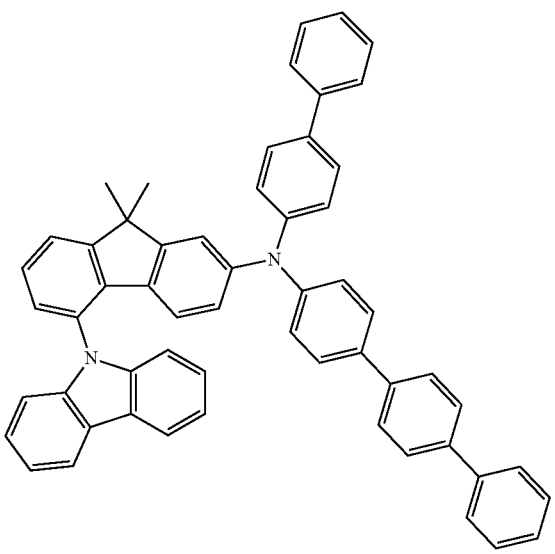
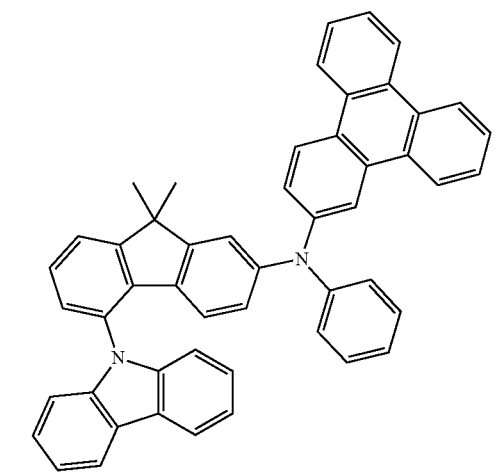
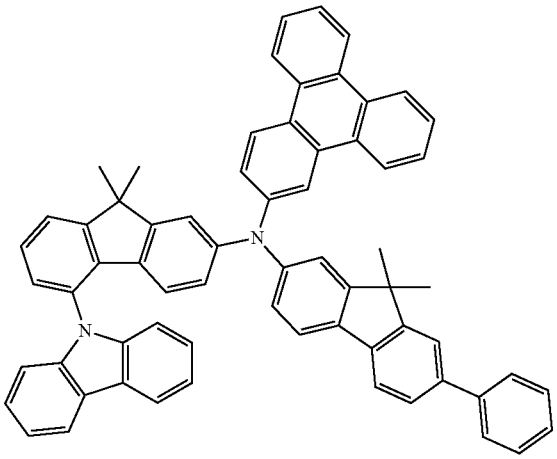

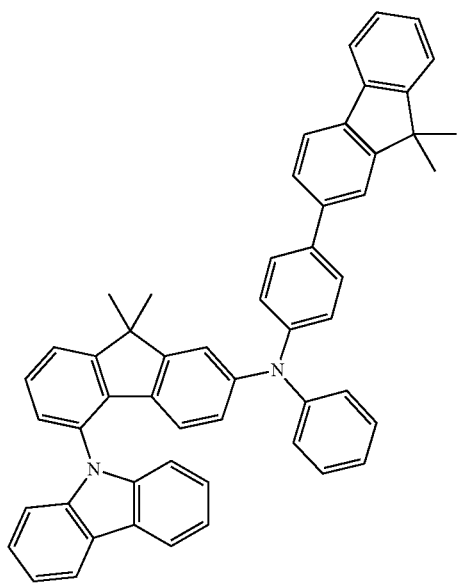
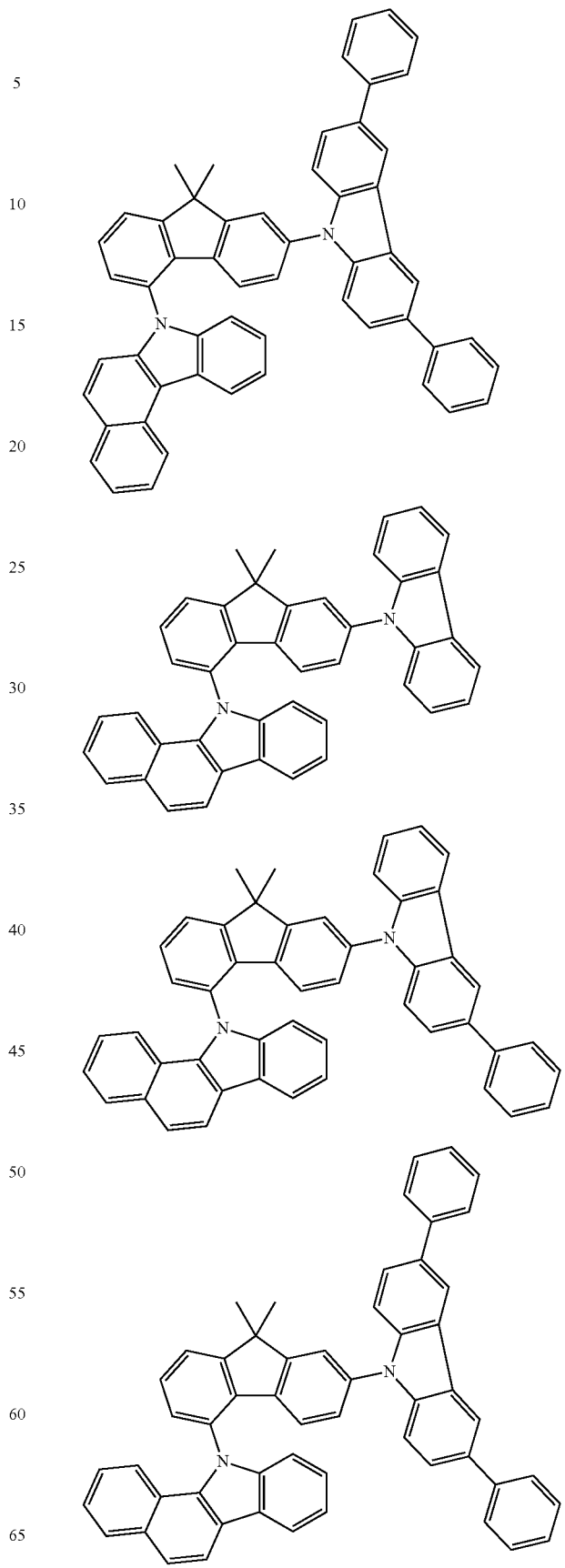

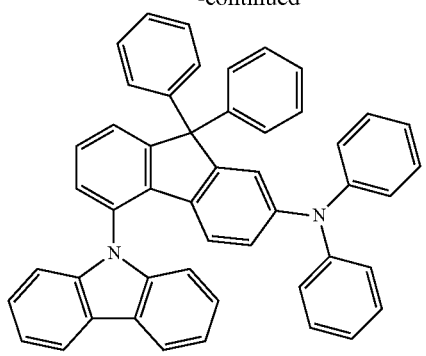
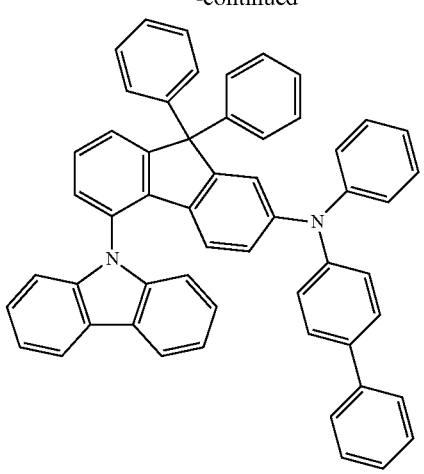
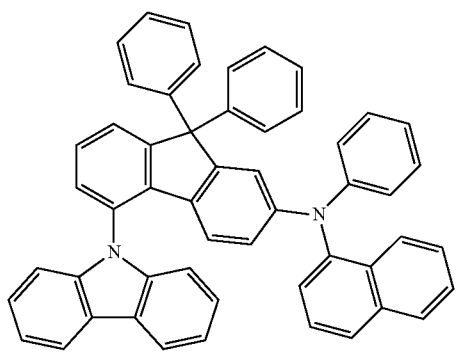
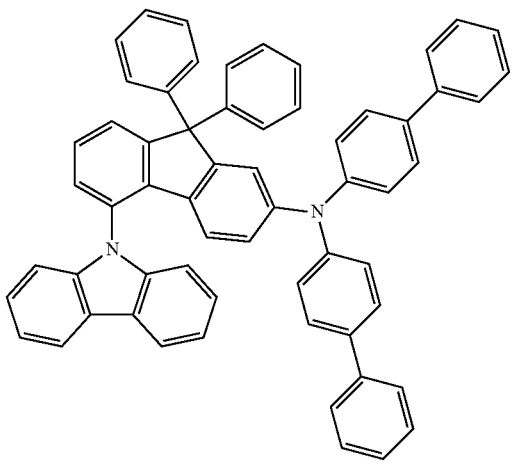
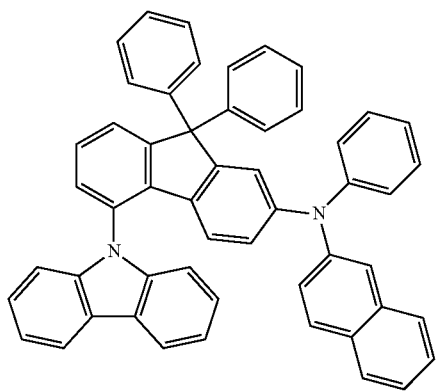
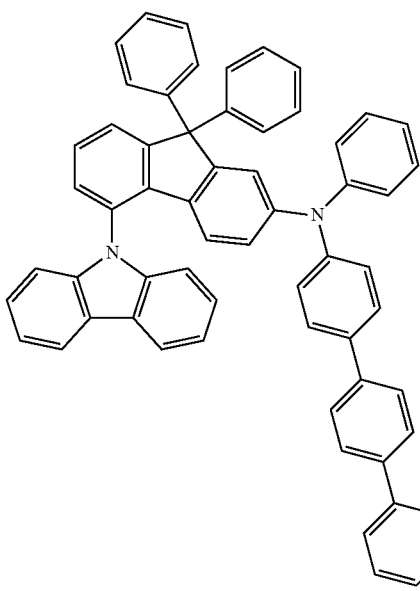
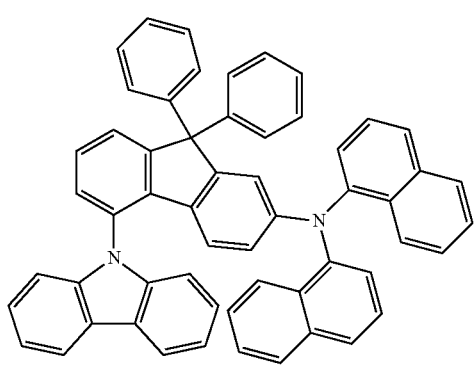

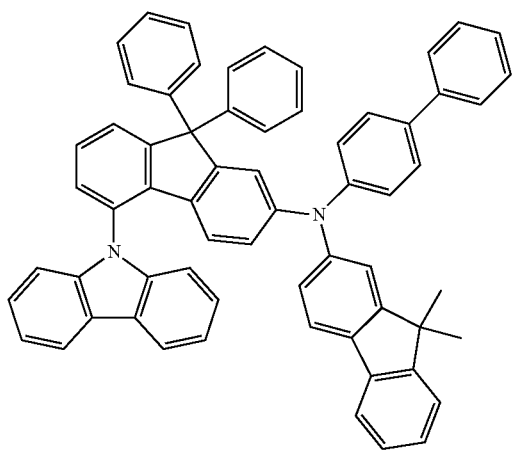
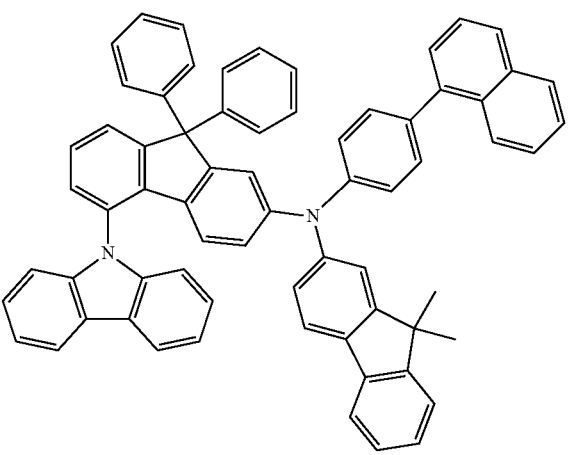
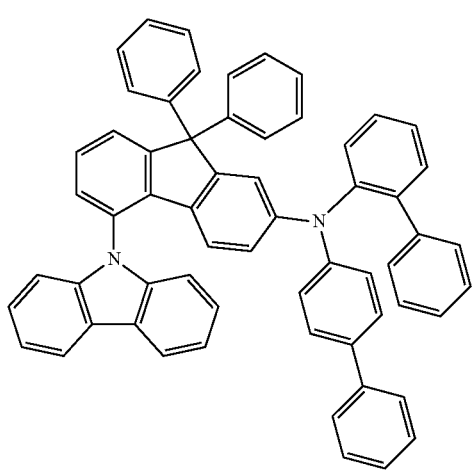
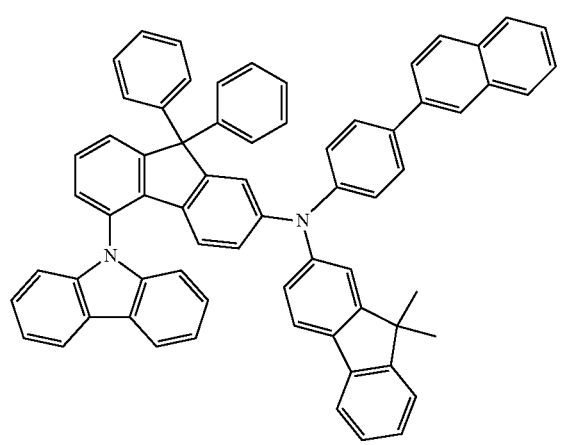
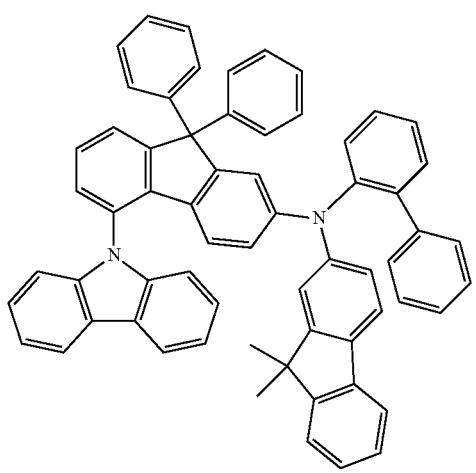
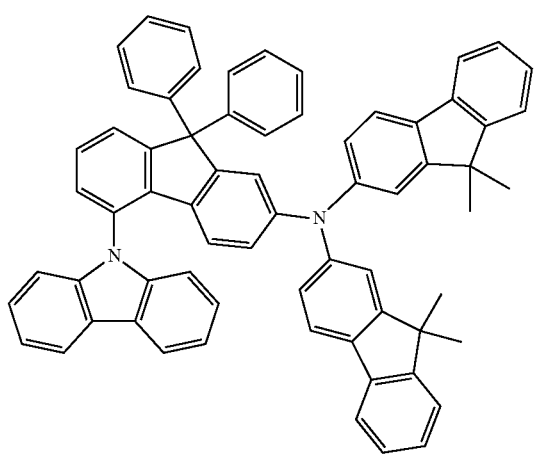

157
-continued
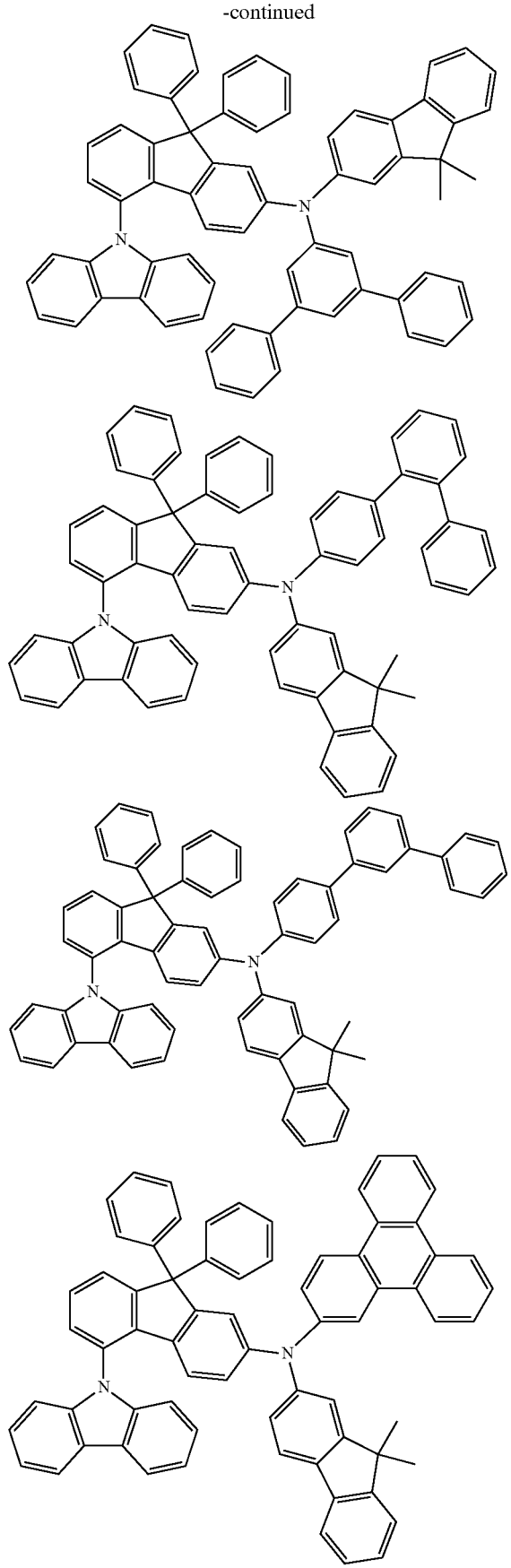
158
-continued
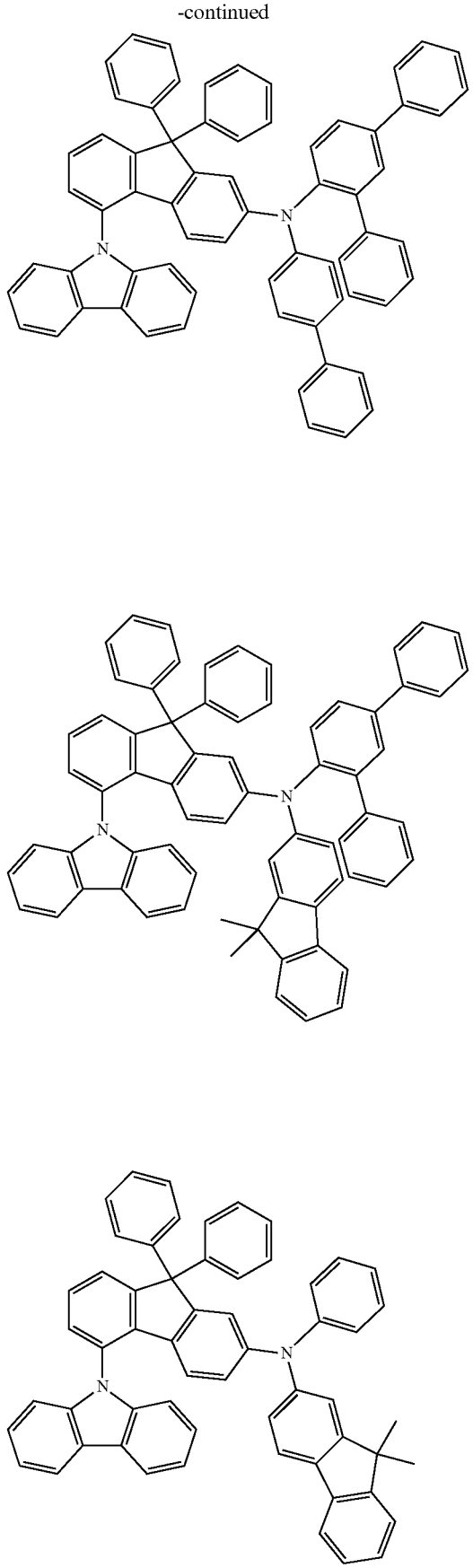

159
-continued
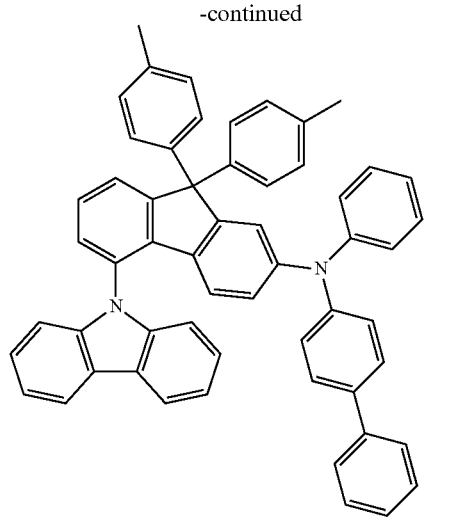
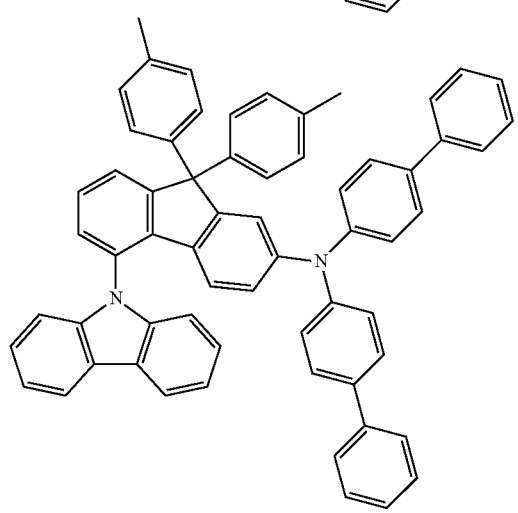
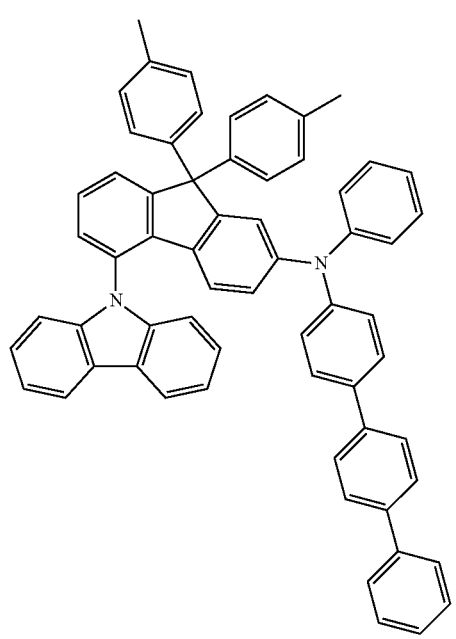
160
-continued
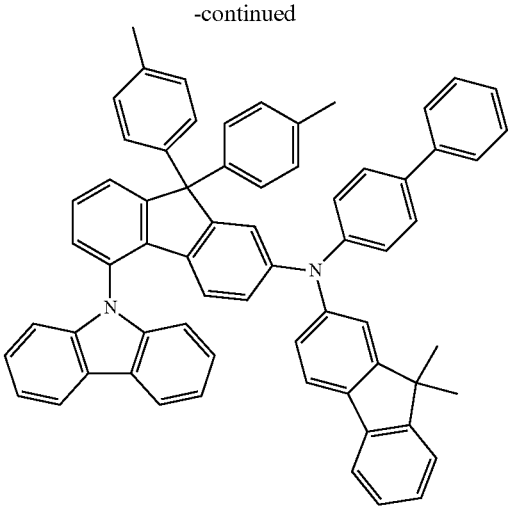
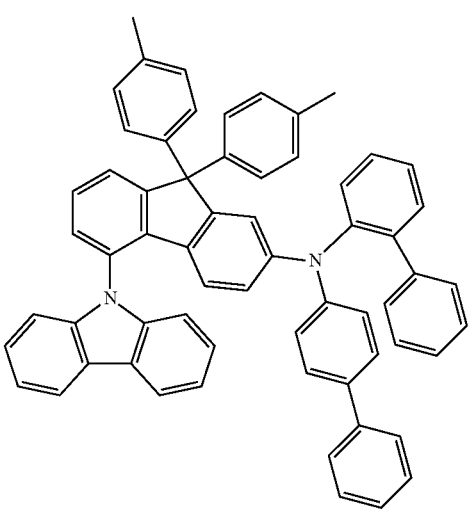
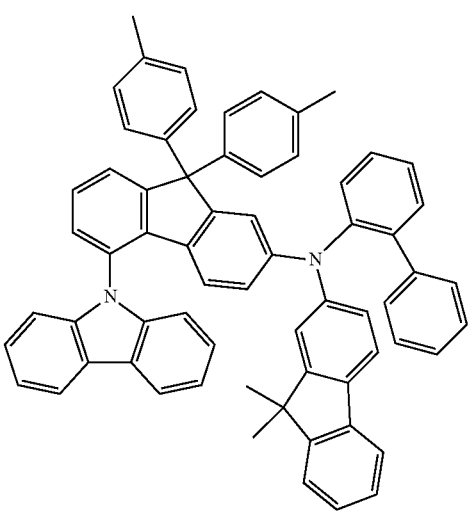

161
-continued
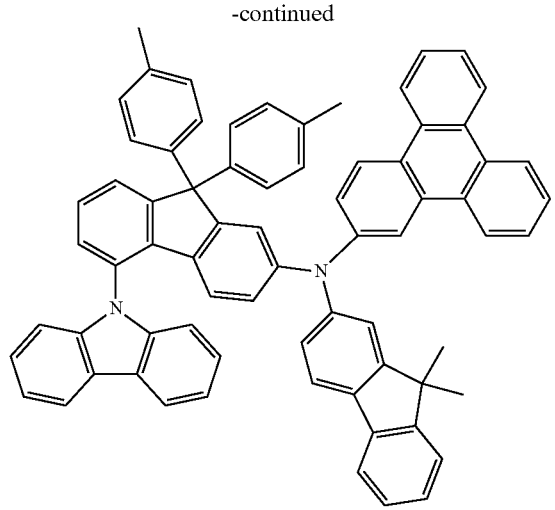
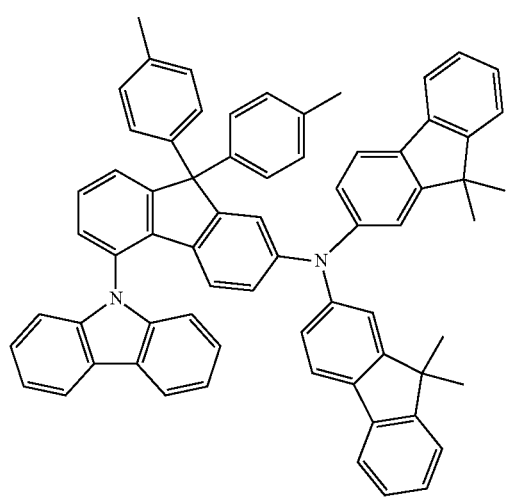
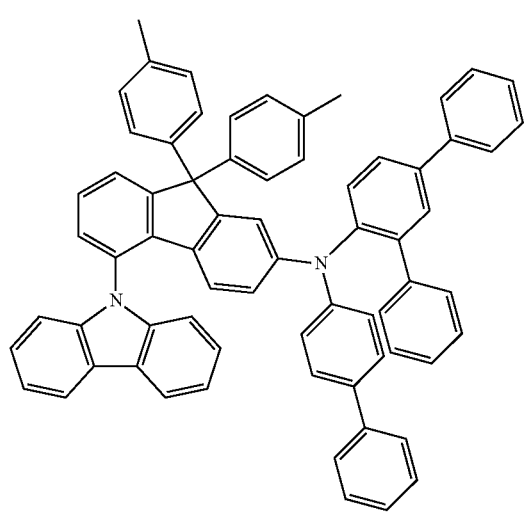
162
-continued
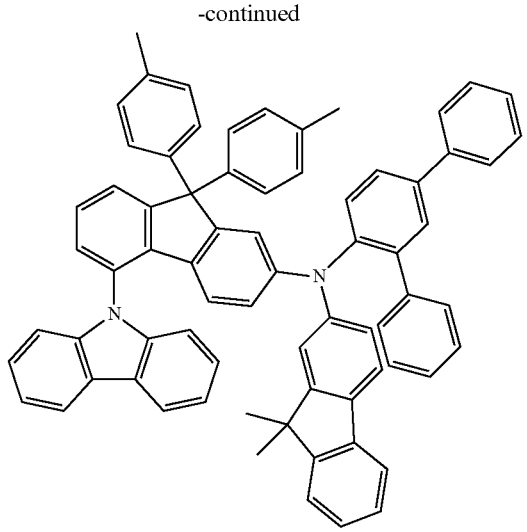
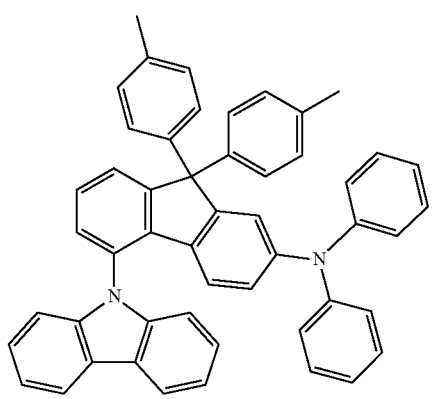
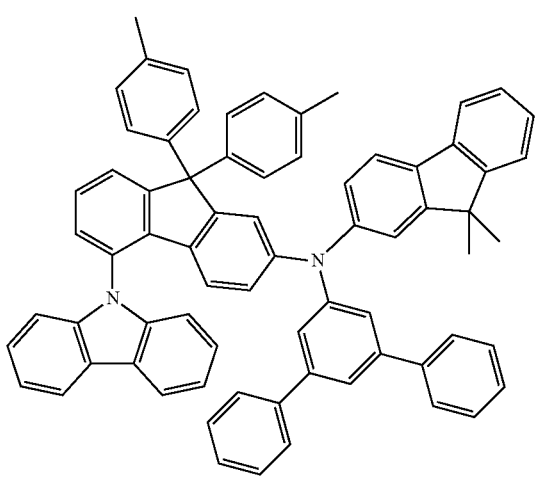

163
-continued
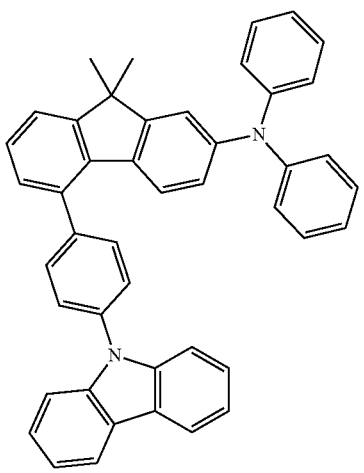
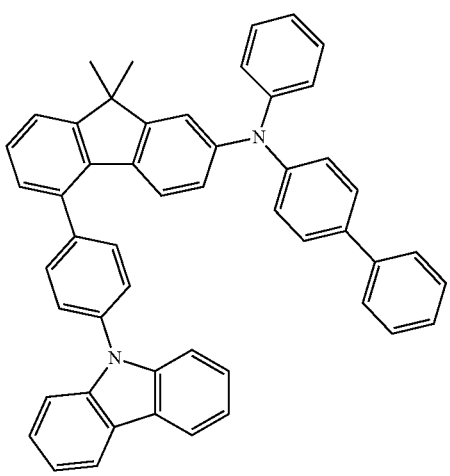
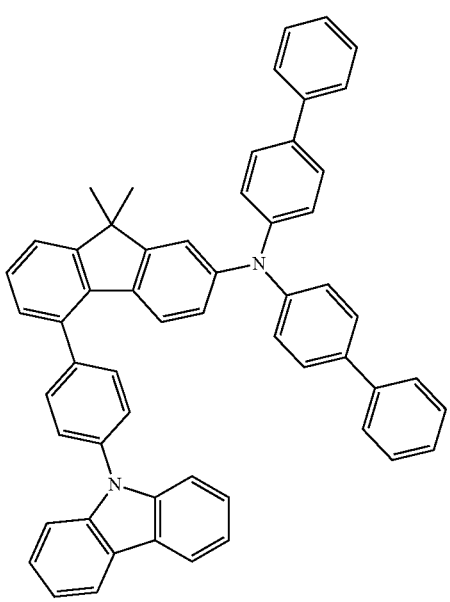
164
-continued
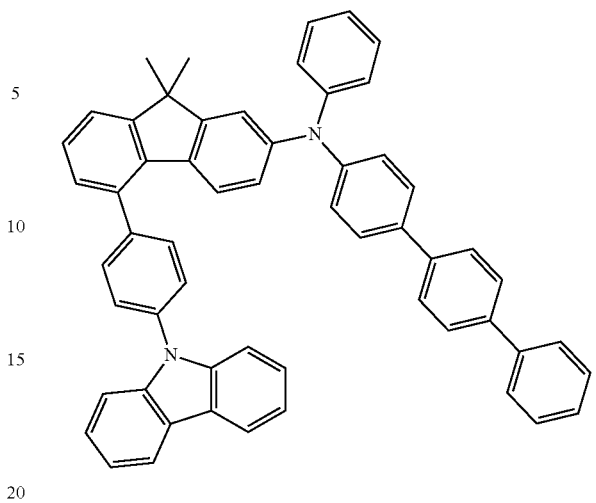
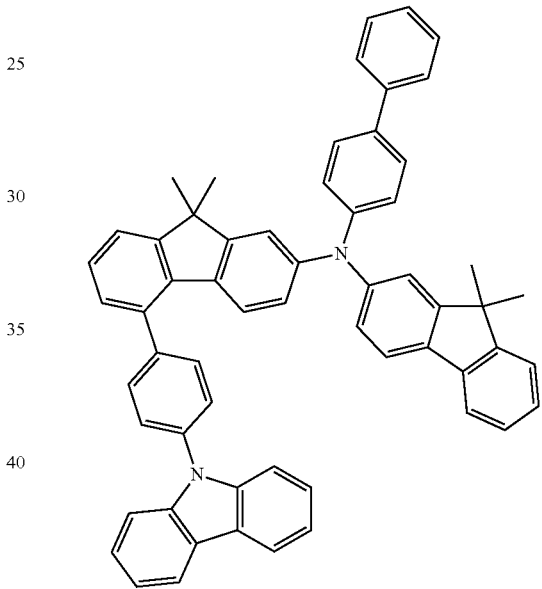
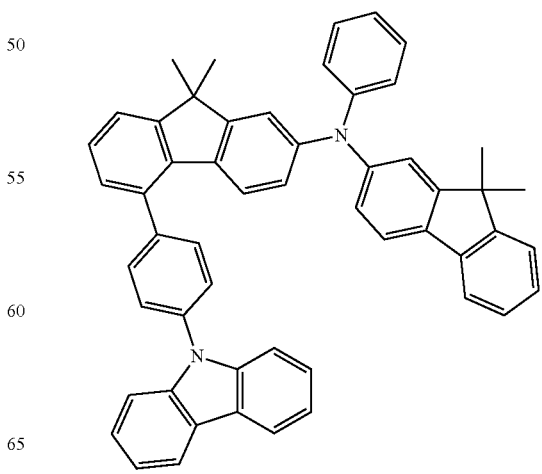

165
-continued
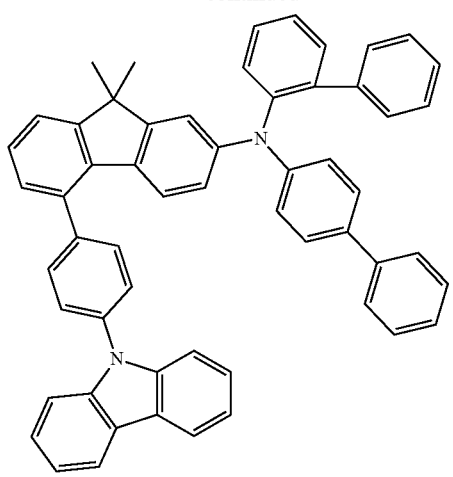
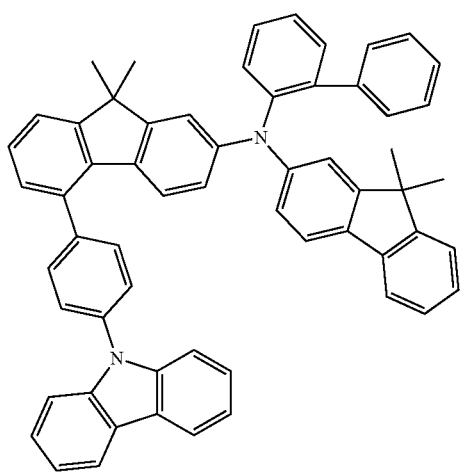
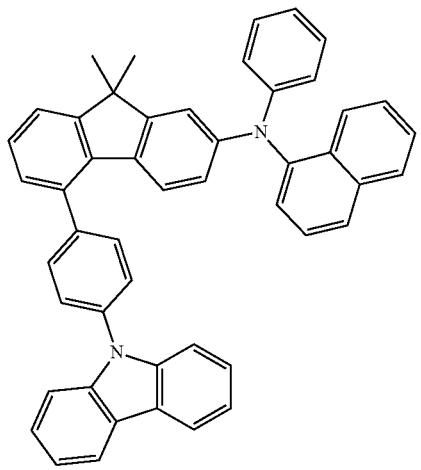
166
-continued
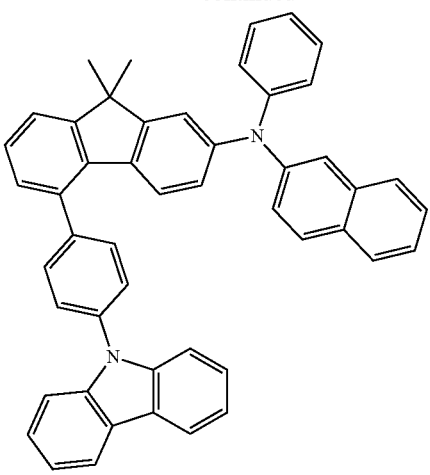
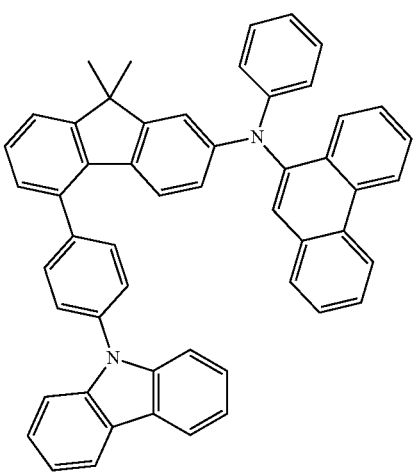
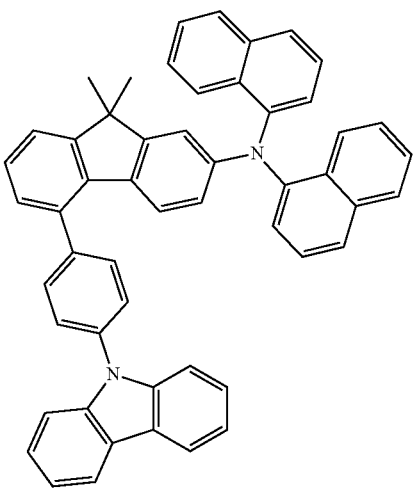

167
-continued
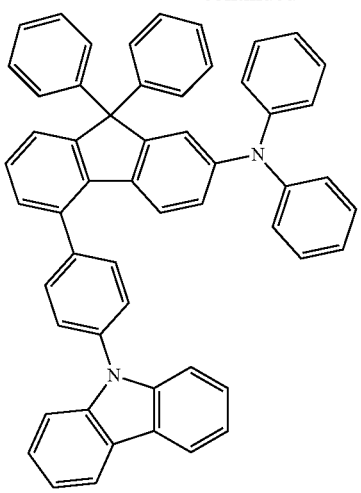
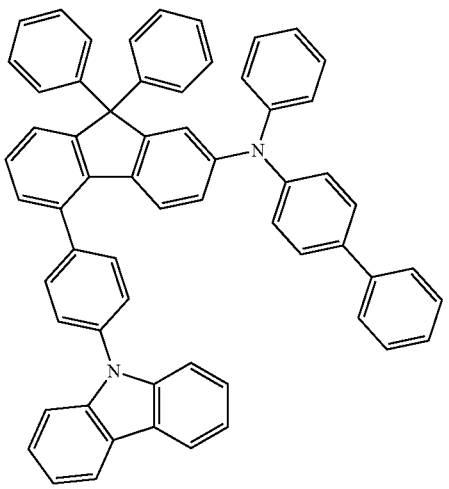
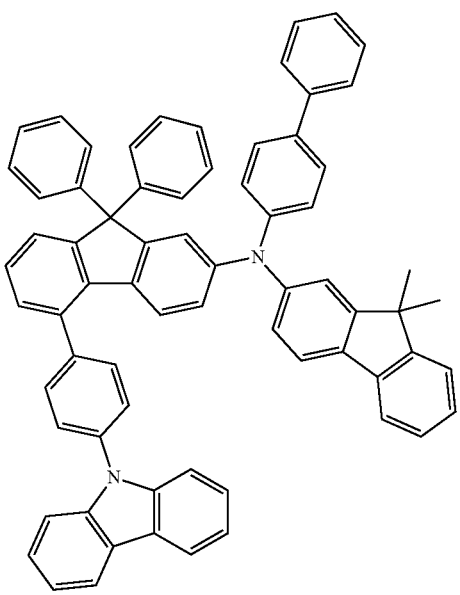
168
-continued
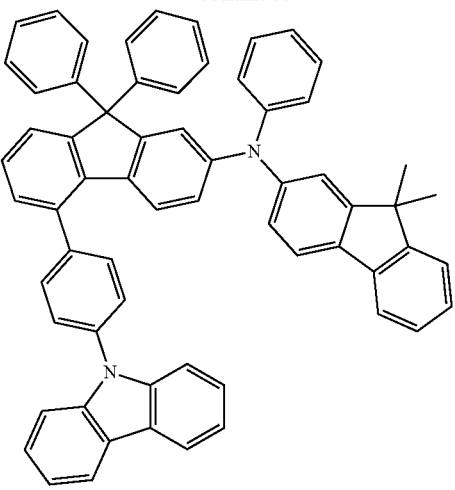
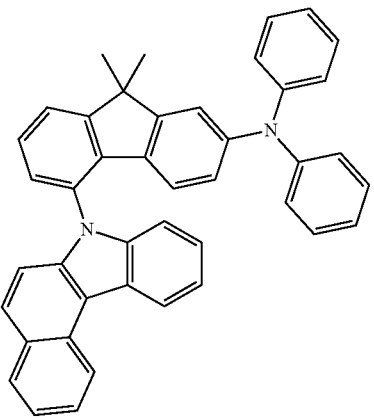
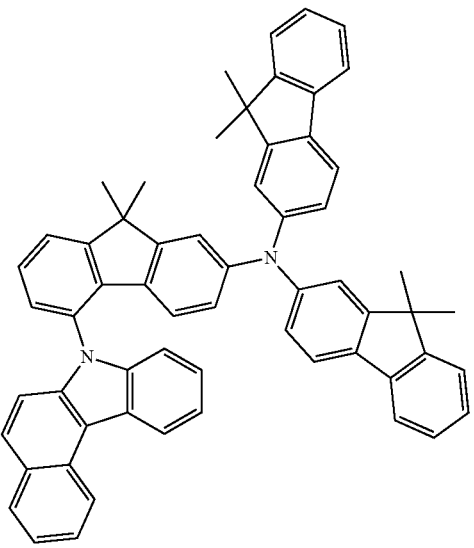

169
-continued
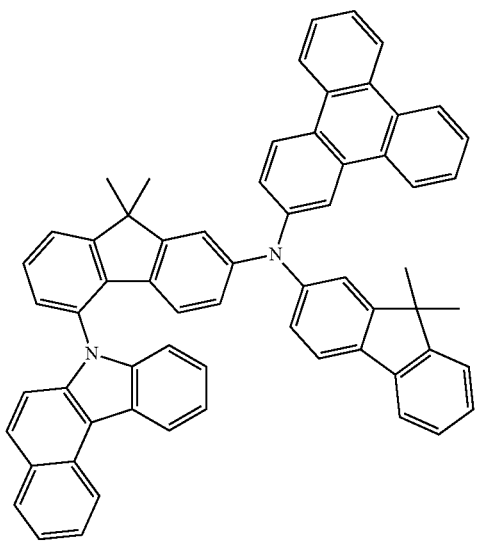
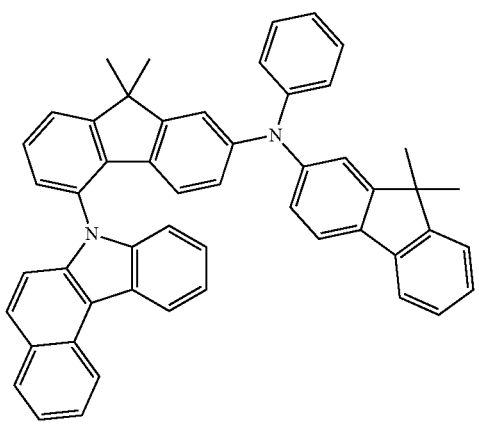
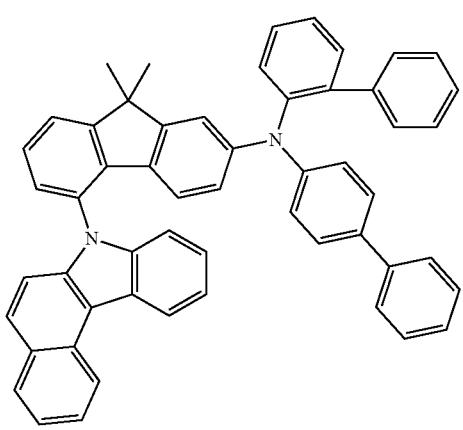
170
-continued
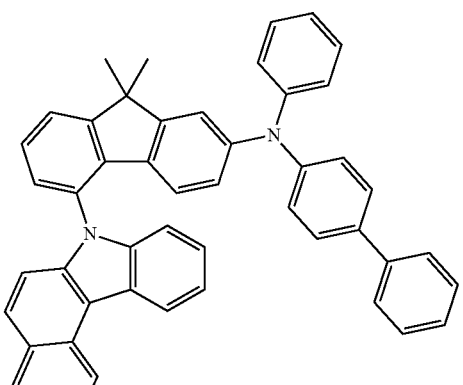
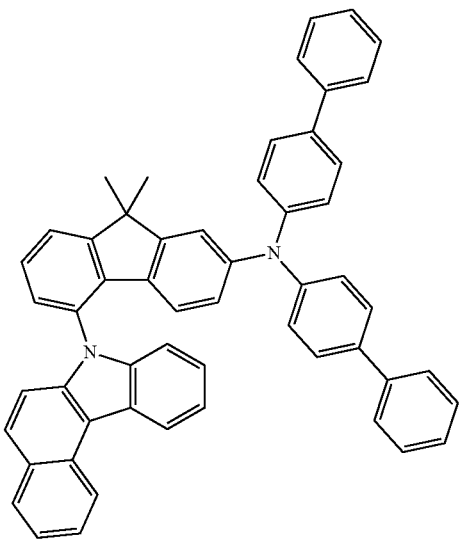
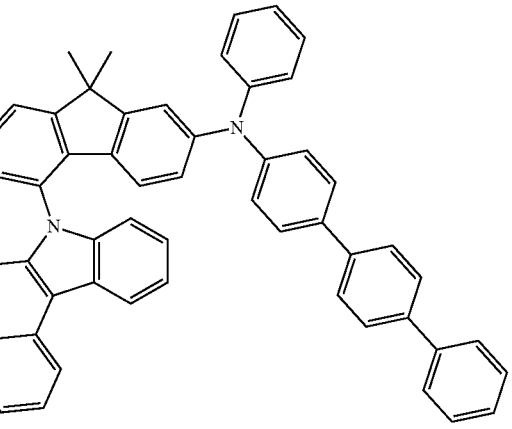

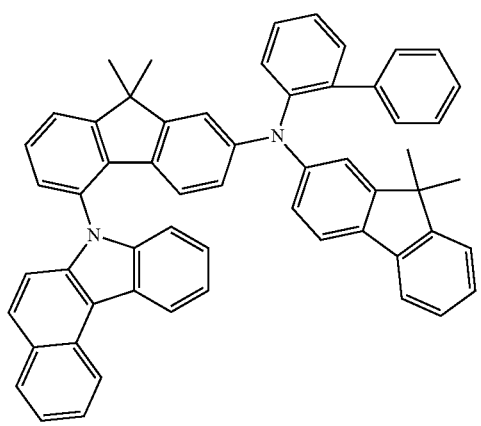
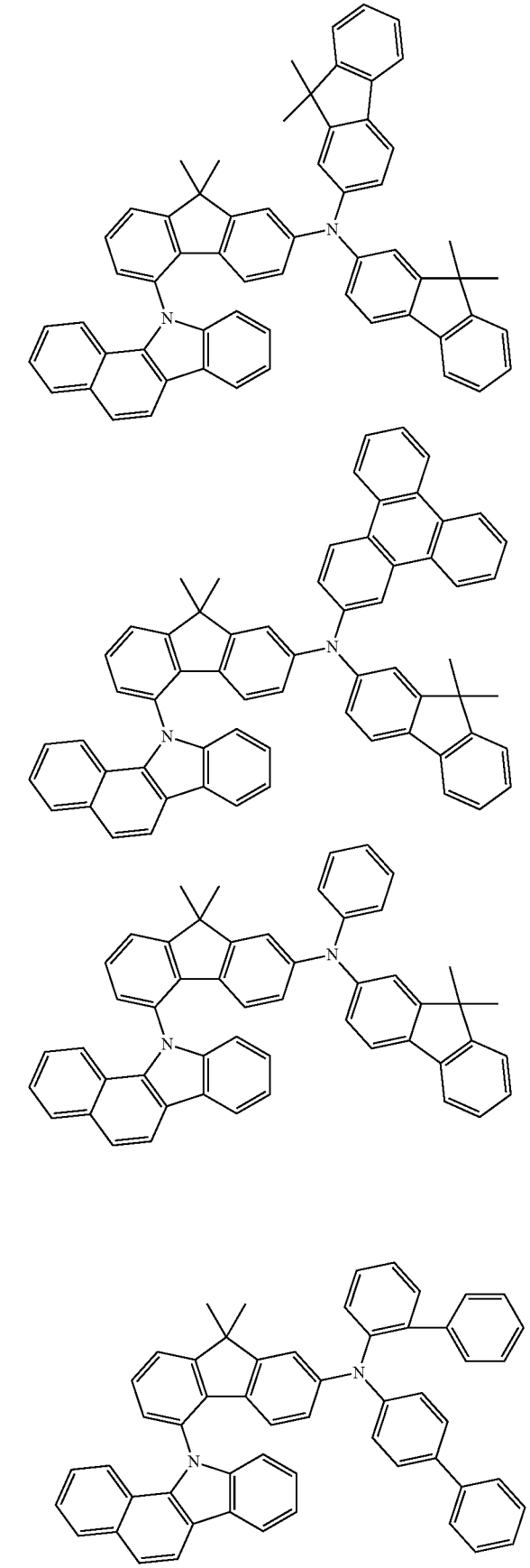

173
-continued
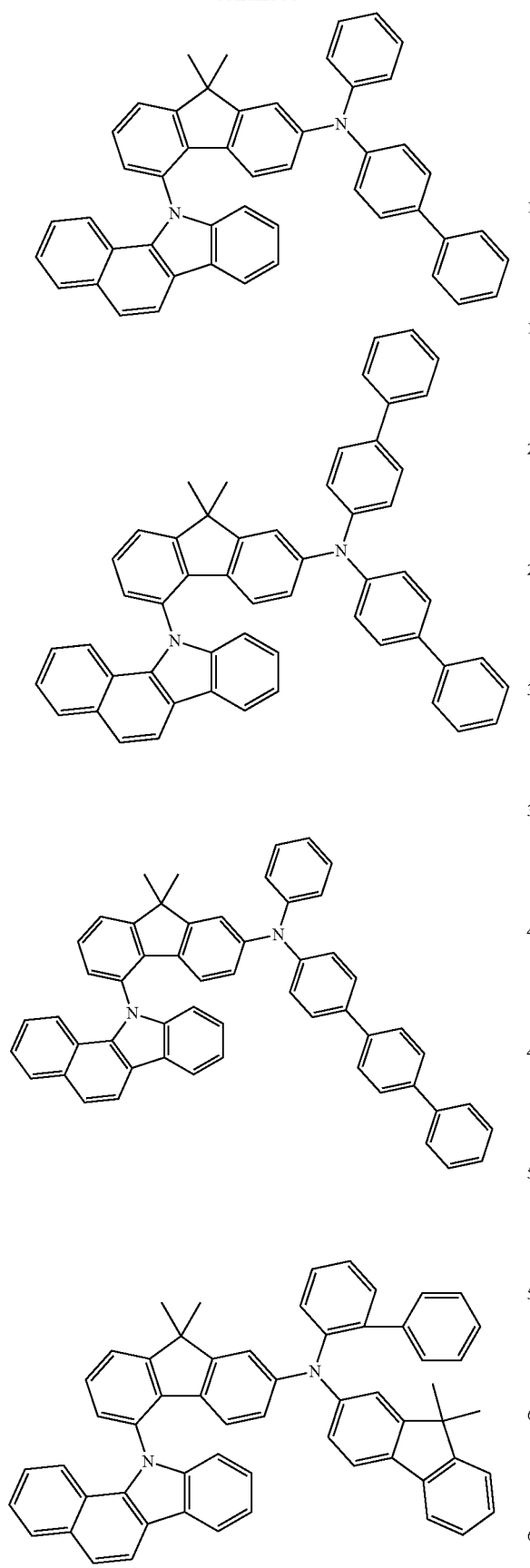
174
-continued
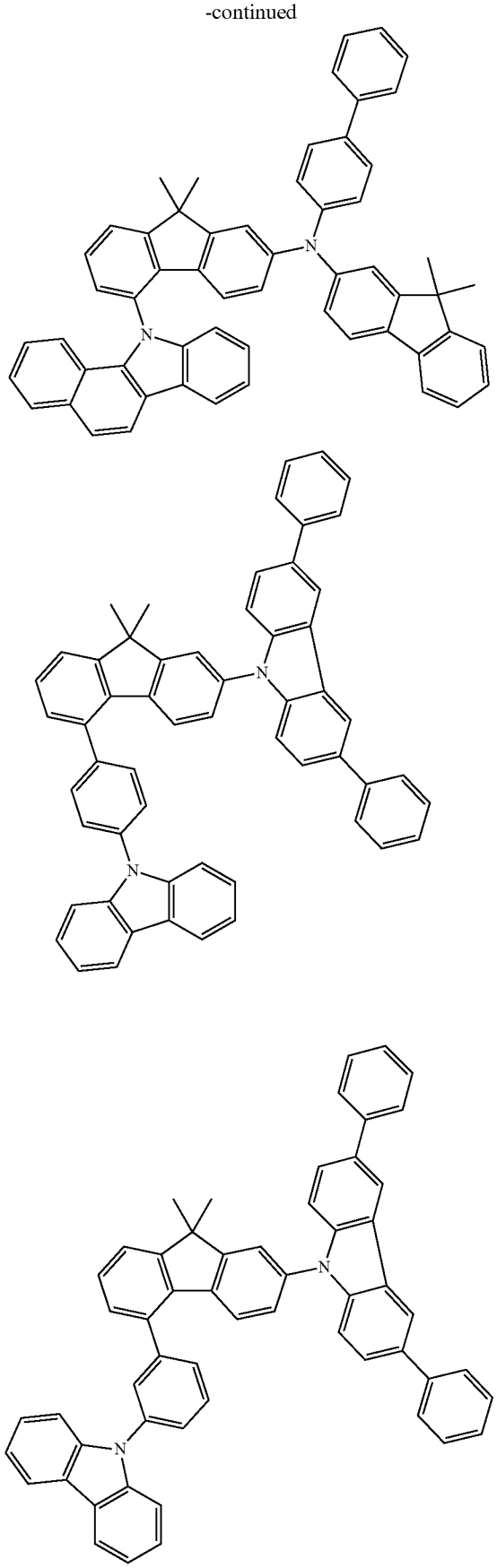

175
-continued
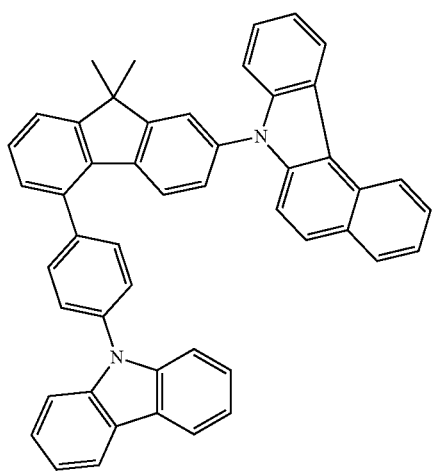
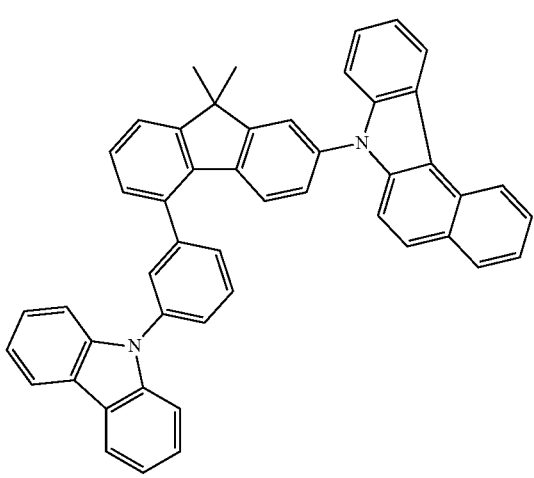
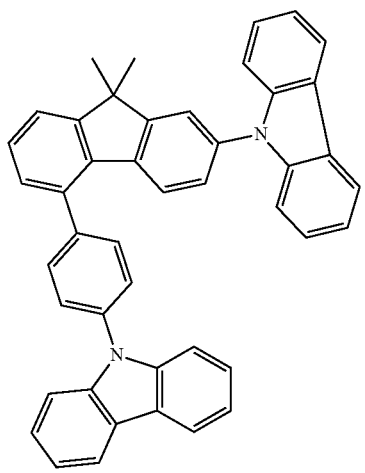
176
-continued
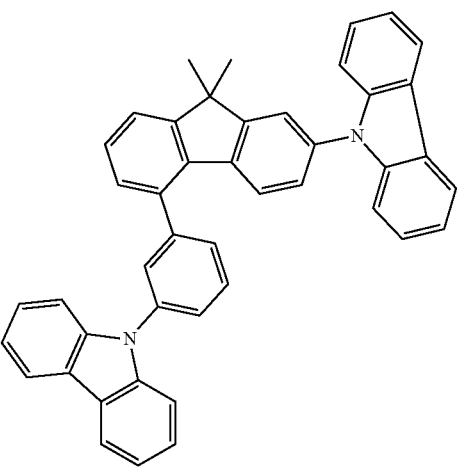
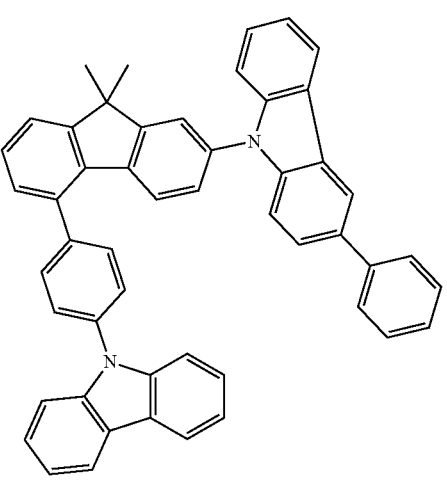
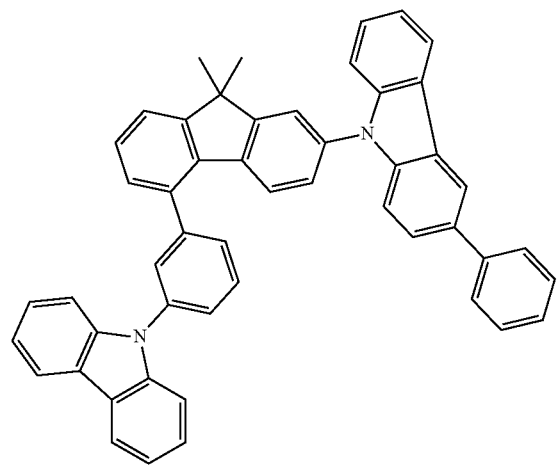

177
-continued
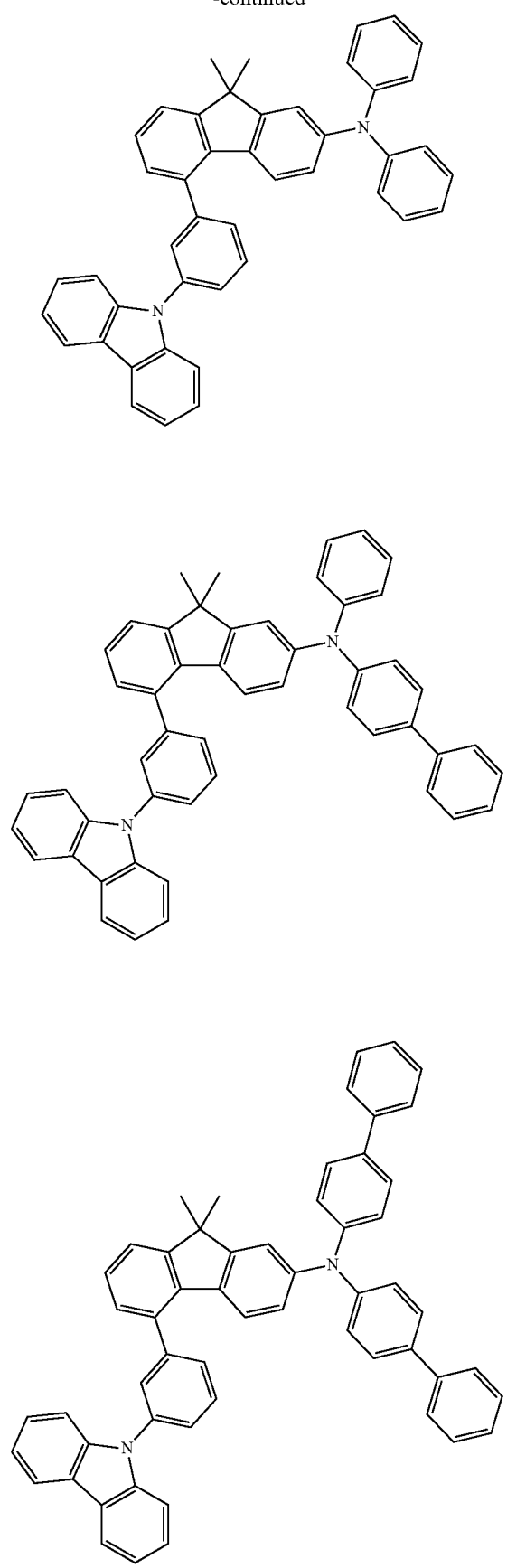
178
-continued
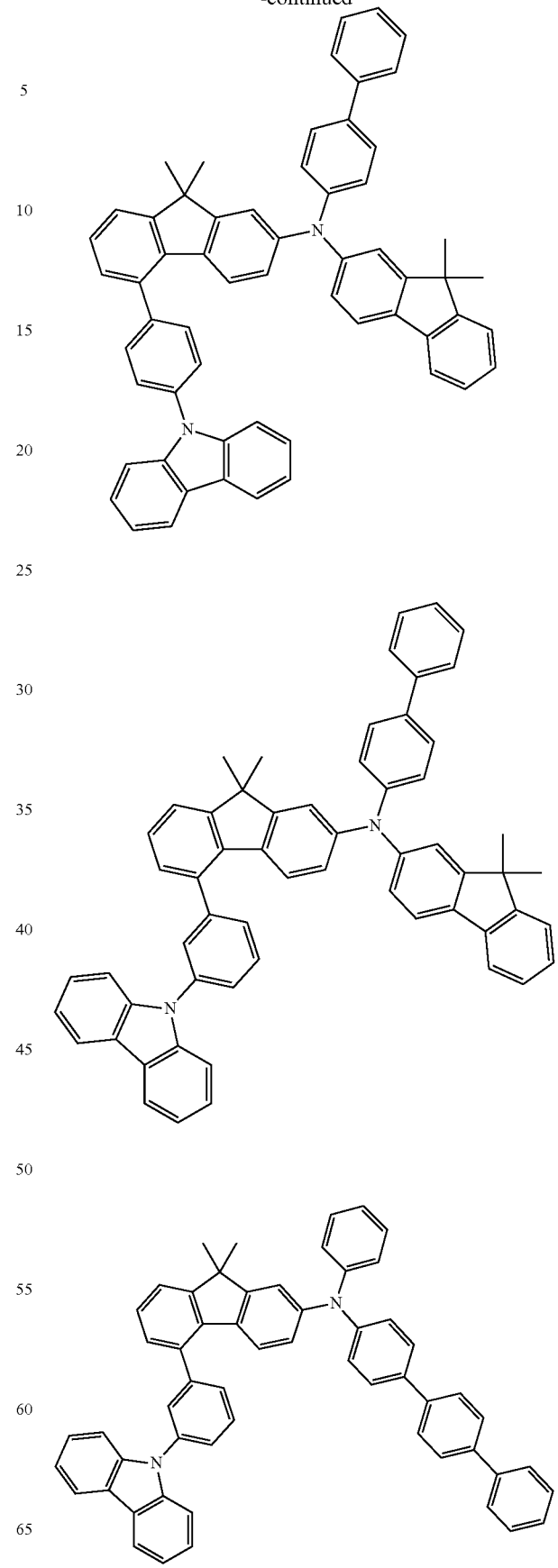

179
-continued
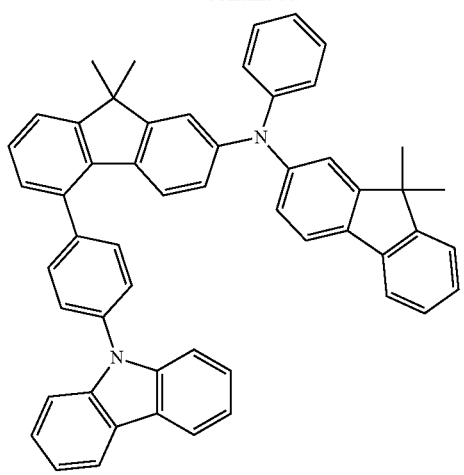
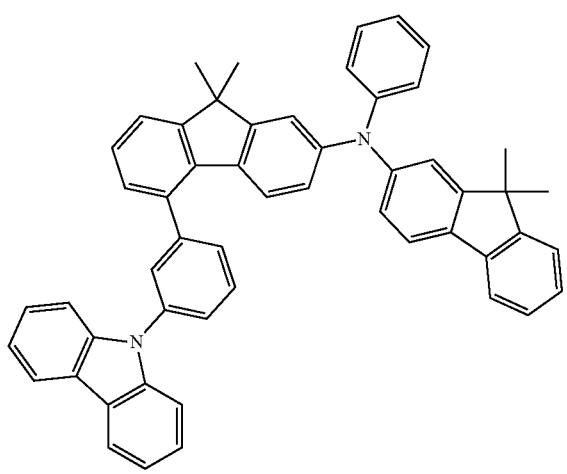
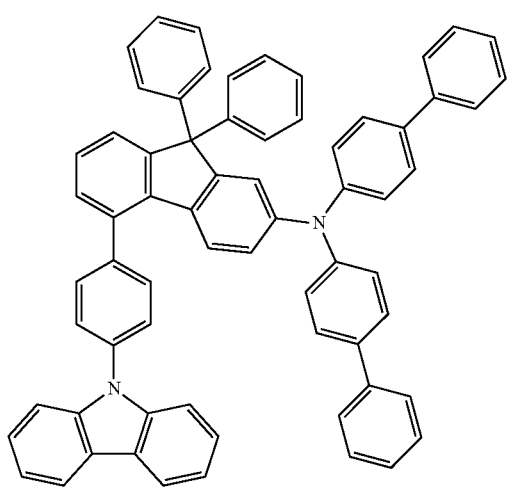
180
-continued
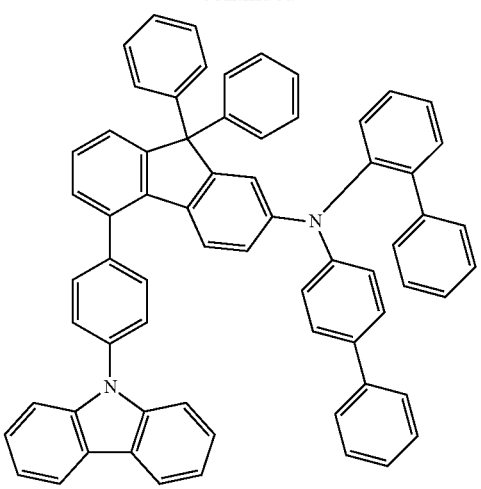
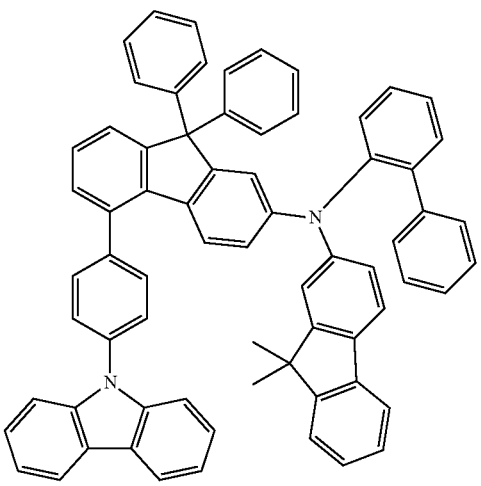
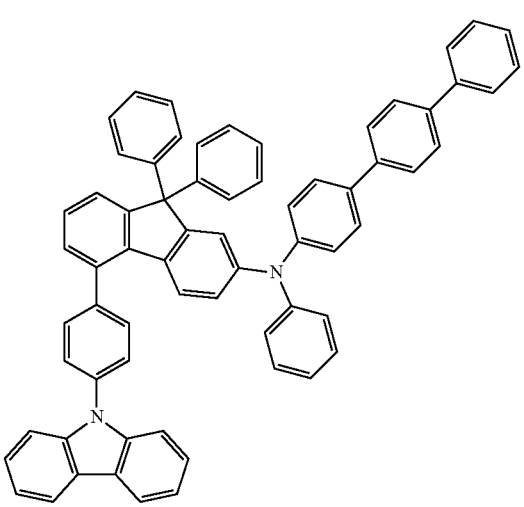

181
-continued
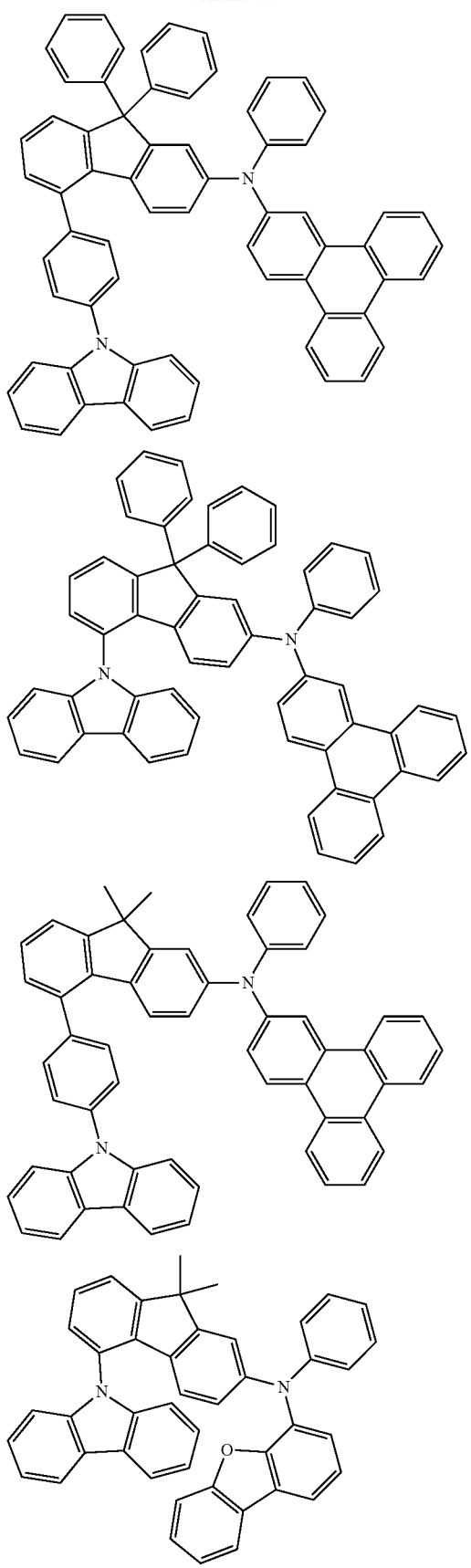
182
-continued
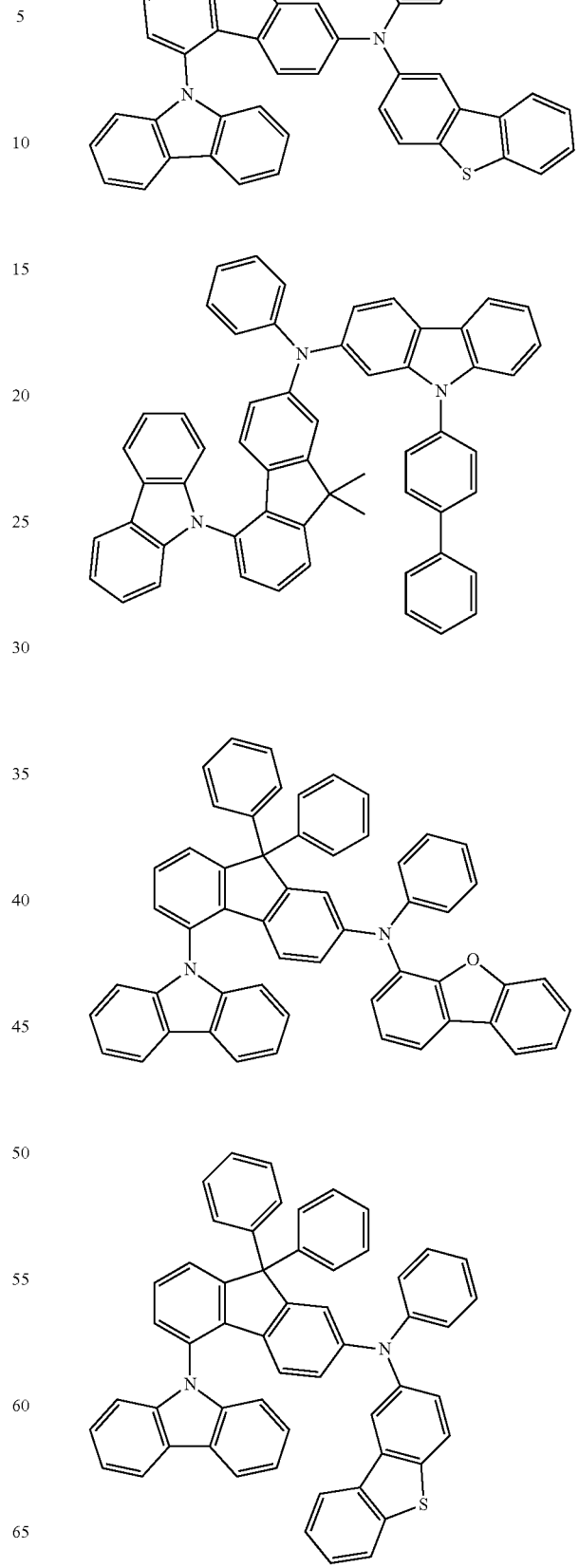

-continued

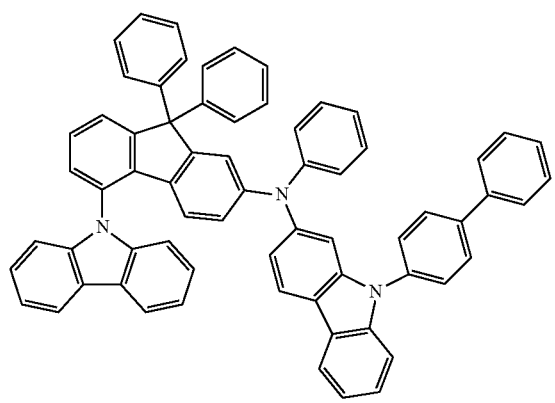

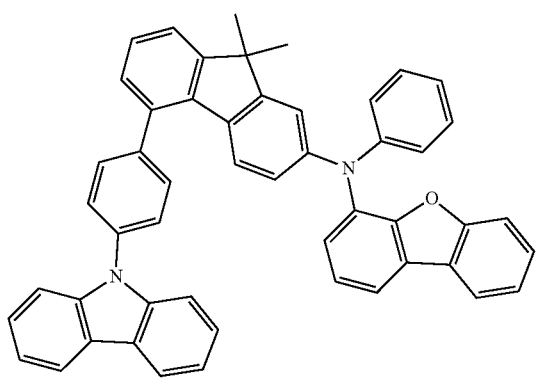

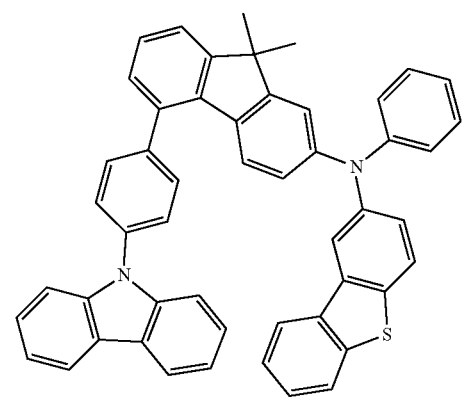

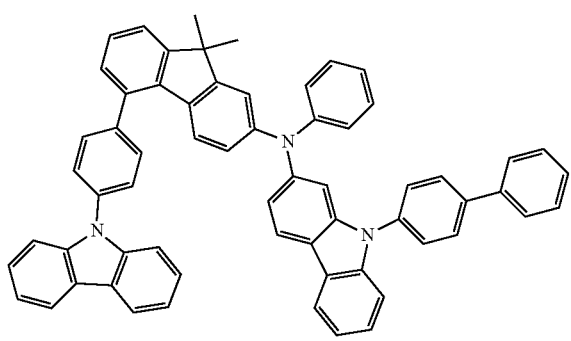

-continued

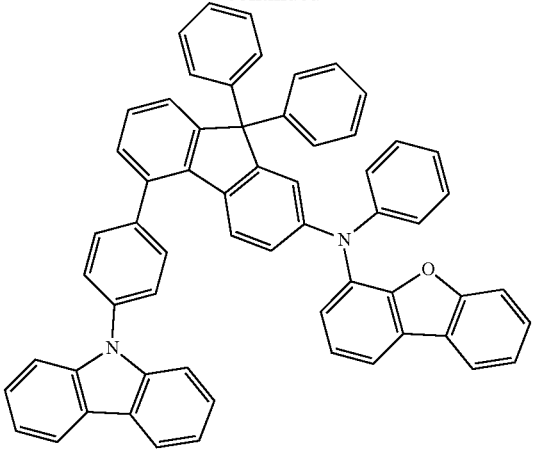

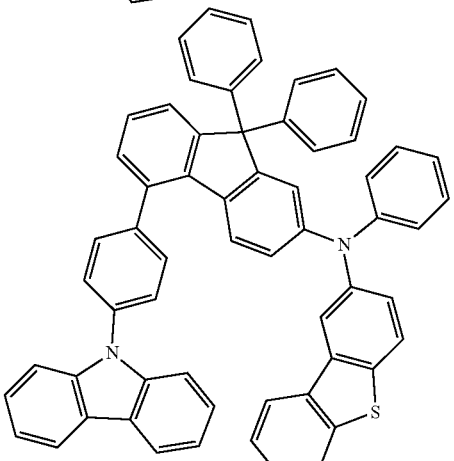

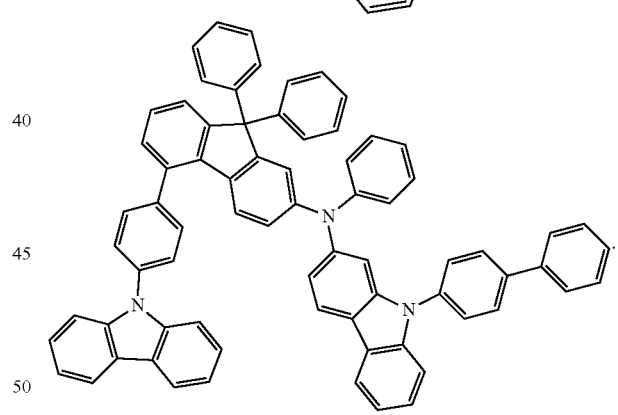

12. An organic light emitting device comprising:
a first electrode;
a second electrode provided opposite to the first electrode; and
one or more organic material layers provided between the first electrode and the second electrode,
wherein one or more layers of the organic material layers include the compound of claim 1.

13. The organic light emitting device of claim 12, wherein the organic material layer includes a hole transfer layer, and the hole transfer layer includes the compound.

14. The organic light emitting device of claim 12, wherein the organic material layer includes a hole injection layer or a layer carrying out hole injection and hole transfer at the same time, and the hole injection layer or the layer carrying out hole injection and hole transfer at the same time includes the compound.

15. The organic light emitting device of claim 12, wherein the organic material layer includes an electron suppression layer, and the electron suppression layer includes the compound.

16. The organic light emitting device of claim 12, wherein the organic material layer includes a light emitting layer, and the light emitting layer includes a compound represented by the following Chemical Formula 5:

[Chemical Formula 5]

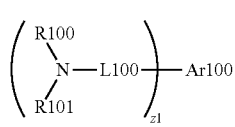

wherein, in Chemical Formula 5,
z1 is an integer of 1 or greater, and when z1 is an integer of 2 or greater, structures in the parentheses are the same as or different from each other,
Ar100 is a substituted or unsubstituted monovalent or higher benzofluorene group; a substituted or unsubstituted monovalent or higher fluoranthene group; a substituted or unsubstituted monovalent or higher pyrene group; or a substituted or unsubstituted monovalent or higher chrysene group,
L100 is a direct bond; a substituted or unsubstituted arylene group; or a substituted or unsubstituted heteroarylene group, and
R100 and R101 are the same as or different from each other, and each independently a substituted or unsubstituted aryl group; a substituted or unsubstituted alkyl group; a substituted or unsubstituted silyl group; a substituted or unsubstituted arylalkyl group; or a substituted or unsubstituted heterocyclic group, or bond to each other to form a substituted or unsubstituted ring.

17. The organic light emitting device of claim 16, wherein z1 is 2, Ar100 is a divalent pyrene group, L100 is a direct bond, and R100 and R101 are the same as or different from each other and each independently an aryl group unsubstituted or substituted with an alkylgermanium group.

18. The organic light emitting device of claim 12, wherein the organic material layer includes a light emitting layer, and the light emitting layer includes a compound represented by the following Chemical Formula 6:

[Chemical Formula 6]

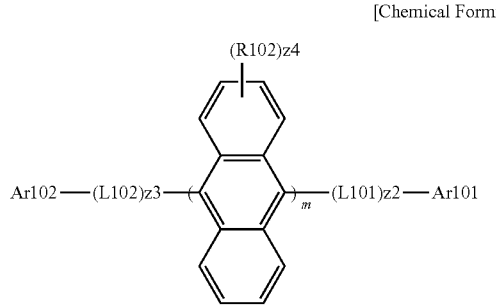

wherein, in Chemical Formula 6,
Ar101 and Ar102 are the same as or different from each other, and each independently a substituted or unsubstituted aryl group; or a substituted or unsubstituted heterocyclic group, L101 and L102 are the same as or different from each other, and each independently a direct bond; a substituted or unsubstituted arylene group; or a substituted or unsubstituted heteroarylene group,
R102 is hydrogen; deuterium; a halogen group; a nitrile group; a nitro group; a hydroxyl group; a carbonyl group; an ester group; an imide group; a substituted or unsubstituted amine group; a substituted or unsubstituted silyl group; a substituted or unsubstituted boron group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted aralkyl group; a substituted or unsubstituted aralkenyl group; a substituted or unsubstituted alkylaryl group; a substituted or unsubstituted alkylamine group; a substituted or unsubstituted aralkylamine group; a substituted or unsubstituted heteroarylamine group; a substituted or unsubstituted arylamine group; a substituted or unsubstituted arylheteroarylamine group; a substituted or unsubstituted arylphosphine group; a substituted or unsubstituted phosphine oxide group; a substituted or unsubstituted aryl group; or a substituted or unsubstituted heterocyclic group,
z2 and z3 are the same as or different from each other and each independently an integer of 1 or 2, z4 is an integer of 0 to 8, and when z2 to z4 are 2 or greater, substituents in the parentheses are the same as or different from each other, and
m is an integer of 1 or greater, and when m is an integer of 2 or greater, substituents in the parentheses are the same as or different from each other.

19. The organic light emitting device of claim 18, wherein Ar101 is a 2-naphthyl group, Ar102 is a 1-naphthyl group, L101 is a phenylene group, L102 is a direct bond, z2 is 1, R102 is hydrogen, and m is 1.

20. The organic light emitting device of claim 16, wherein the light emitting layer includes a compound represented by the following Chemical Formula 6:

[Chemical Formula 6]

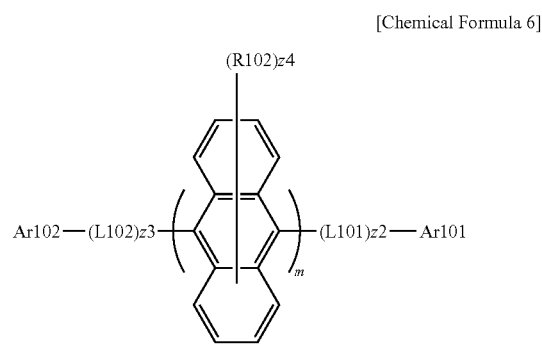

wherein, in Chemical Formula 6,
Ar101 and Ar102 are the same as or different from each other, and each independently a substituted or unsubstituted aryl group; or a substituted or unsubstituted heterocyclic group, L101 and L102 are the same as or different from each other, and each independently a direct bond; a substituted or unsubstituted arylene group; or a substituted or unsubstituted heteroarylene group, R102 is hydrogen; deuterium; a halogen group; a nitrile group; a nitro group; a hydroxyl group; a carbonyl group; an ester group; an imide group; a substituted or unsubstituted amine group;

a substituted or unsubstituted silyl group; a substituted or unsubstituted boron group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted aralkyl group; a substituted or unsubstituted aralkenyl group; a substituted or unsubstituted alkylaryl group; a substituted or unsubstituted alkylamine group; a substituted or unsubstituted aralkylamine group; a substituted or unsubstituted heteroarylamine group; a substituted or unsubstituted arylamine group; a substituted or unsubstituted arylheteroarylamine group; a substituted or unsubstituted arylphosphine group; a substituted or unsubstituted phosphine oxide group; a substituted or unsubstituted aryl group; or a substituted or unsubstituted heterocyclic group, z2 and z3 are the same as or different from each other and each independently an integer of 1 or 2, z4 is an integer of 0 to 8, and when z2 to z4 are 2 or greater, substituents in the parentheses are the same as or different from each other, and m is an integer of 1 or greater, and when m is an integer of 2 or greater, substituents in the parentheses are the same as or different from each other.

* * * * *